(12) United States Patent
Griffioen et al.

(10) Patent No.: US 10,562,869 B2
(45) Date of Patent: Feb. 18, 2020

(54) OXADIAZOLE COMPOUNDS

(71) Applicant: REMYND NV, Heverlee (BE)

(72) Inventors: Gerard Griffioen, Linden (BE); Bart De Taeye, Kessel-Lo (BE); Katrien Princen, Heverlee (BE); Koen De Witte, Ukkel (BE); Emilie Blanche, Heverlee (BE); Hasane Ratni, Habsheim (FR); Matthias Nettekoven, Grenzach-Wyhlen (DE); Mark Rogers-Evans, Bottmingen (CH)

(73) Assignee: REMYND NV, Heverlee (BE)

( * ) Notice: Subject to any disclaimer, the term of this patent is extended or adjusted under 35 U.S.C. 154(b) by 0 days.

(21) Appl. No.: 15/122,959

(22) PCT Filed: Mar. 17, 2015

(86) PCT No.: PCT/EP2015/055488
§ 371 (c)(1),
(2) Date: Sep. 1, 2016

(87) PCT Pub. No.: WO2015/140130
PCT Pub. Date: Sep. 24, 2015

(65) Prior Publication Data
US 2017/0073319 A1 Mar. 16, 2017

(30) Foreign Application Priority Data
Mar. 17, 2014 (EP) ..................... 14160354

(51) Int. Cl.
*C07D 271/07* (2006.01)
*A61K 31/496* (2006.01)
*C07D 413/12* (2006.01)
*C07D 471/10* (2006.01)

(52) U.S. Cl.
CPC ......... *C07D 271/07* (2013.01); *C07D 413/12* (2013.01); *C07D 471/10* (2013.01)

(58) Field of Classification Search
CPC .................................................. C07D 271/07
See application file for complete search history.

(56) References Cited

U.S. PATENT DOCUMENTS

| | | | |
|---|---|---|---|
| 4,177,272 A | 12/1979 | Canevari et al. |
| 2004/0067930 A1 | 4/2004 | Bhatti et al. |
| 2004/0235913 A1 | 11/2004 | Cuny et al. |
| 2005/0272739 A1 | 12/2005 | Bhatti et al. |
| 2006/0217406 A1 | 9/2006 | Bhatti et al. |
| 2007/0213359 A1 | 9/2007 | Burstein et al. |
| 2007/0249648 A1 | 10/2007 | Bladh et al. |
| 2008/0214591 A1 | 9/2008 | Bhatti et al. |
| 2009/0233918 A1 | 9/2009 | Fukunaga et al. |
| 2011/0105548 A1 | 5/2011 | Bhatti et al. |
| 2012/0220561 A1 | 8/2012 | Bartolozzi et al. |
| 2012/0252815 A1 | 10/2012 | Stieber et al. |

| | | | |
|---|---|---|---|
| 2014/0011816 A1 | 1/2014 | Biscoff et al. |
| 2014/0128404 A1 | 5/2014 | Griffioen et al. |
| 2014/0206699 A1 | 7/2014 | Griffioen et al. |

FOREIGN PATENT DOCUMENTS

| | | |
|---|---|---|
| WO | 02/083863 A2 | 10/2002 |
| WO | 2004/005293 A2 | 1/2004 |
| WO | 2005/040167 A1 | 5/2005 |
| WO | 2007/079239 A2 | 7/2007 |
| WO | 2007/090617 A2 | 8/2007 |
| WO | 2008/050200 A1 | 5/2008 |
| WO | 2011/082732 A1 | 7/2011 |
| WO | 2012/024150 A1 | 2/2012 |

(Continued)

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Lamberto et al. Journal of Biological Chemistry, vol. 286, p. 32036-32044 (2011).*
GreenPharma/Ambinter Product Guide downloaded from the internet at http://www.ambinter.com/libraries on Jun. 30, 2018. (Year: 2018).*
PCT International Search Report and Written Opinion dated Jun. 5, 2015 for PCT International Patent Application PCT/EP2015/055488, 31 pages.
Database HCAPLUS [Online] ACS; XP002731825, retrieved from STN Database accession No. 157:438666, abstract, 4 pages.
Database Registry [Online] Chemical Abstracts Service, Dec. 25, 2008, XP002731826, retrieved from STN Database accession No. 1090038-17-7, 1 page.

(Continued)

*Primary Examiner* — Emily A Bernhardt
(74) *Attorney, Agent, or Firm* — Amster, Rothstein & Ebenstein LLP

(57) ABSTRACT

The present invention relates to a compound of formula (I) or (II) or a stereoisomer, enantiomer, racemic, or tautomer thereof, (I) (II) wherein $R^1$, $R^2$, $R^3$, $L^1$, $L^2$, $L^3$, $L^4$, $L^5$ and n, have the same meaning as that defined in the claims and the description. The present invention also relates to compositions, in particular pharmaceuticals, comprising such compounds, and to uses of such compounds and compositions for the prevention and/or treatment of metabolic disorders and/or neurodegenerative diseases, and/or protein misfolding disorders.

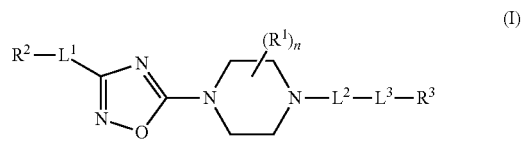

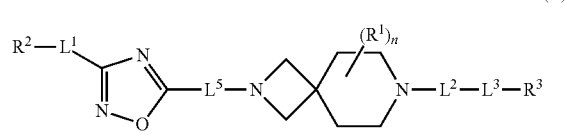

9 Claims, 1 Drawing Sheet

(56) References Cited

FOREIGN PATENT DOCUMENTS

| WO | 2012115118 A1 | 8/2012 |
|----|---------------|--------|
| WO | 2012/126984 A1 | 9/2012 |
| WO | 2013/004642 A1 | 1/2013 |
| WO | 2013/024168 A1 | 2/2013 |
| WO | 2014077532 A2 | 5/2014 |
| WO | 2014/105664 A1 | 7/2014 |

OTHER PUBLICATIONS

Database Registry [Online] Chemical Abstracts Service, Mar. 14, 2013, XP002731827, retrieved from STN Database accession No. 1423669-60-6, 1 page.
Database Registry [Online] Chemical Abstracts Service, Mar. 17, 2013, XP002735162, retrieved from STN Database accession No. 1424534-93-9, 1 page.
Database Registry [Online] Chemical Abstracts Service, Jun. 9, 2013, XP002735163, retrieved from STN Database accession No. 1436210-46-6, 1 page.
Database Registry [Online] Chemical Abstracts Service, Jul. 24, 2014, XP002735164, retrieved from STN Database accession No. 1616790-91-0, 8 pages.
Siebert C D, entitled Das Bioisosterie-Konzept: Arzneistoffentwicklung, Chemie In Unserer Zeit, vol. 38, No. 5, Oct. 2004, pp. 320-324.
Thornber C W, entitled "Isosterism and Molecular Modification in Drug Design," Chemical Society Reviews, vol. 8, No. 4, 1979, pp. 563-580, XP000953019.
PCT Notification Concerning Transmittal of International Preliminary Report on Patentability and Written Opinion of the International Searching Authority, dated Sep. 29, 2016 in connection with PCT International Patent Application No. PCT/EP2015/055488, 21 pages.

* cited by examiner

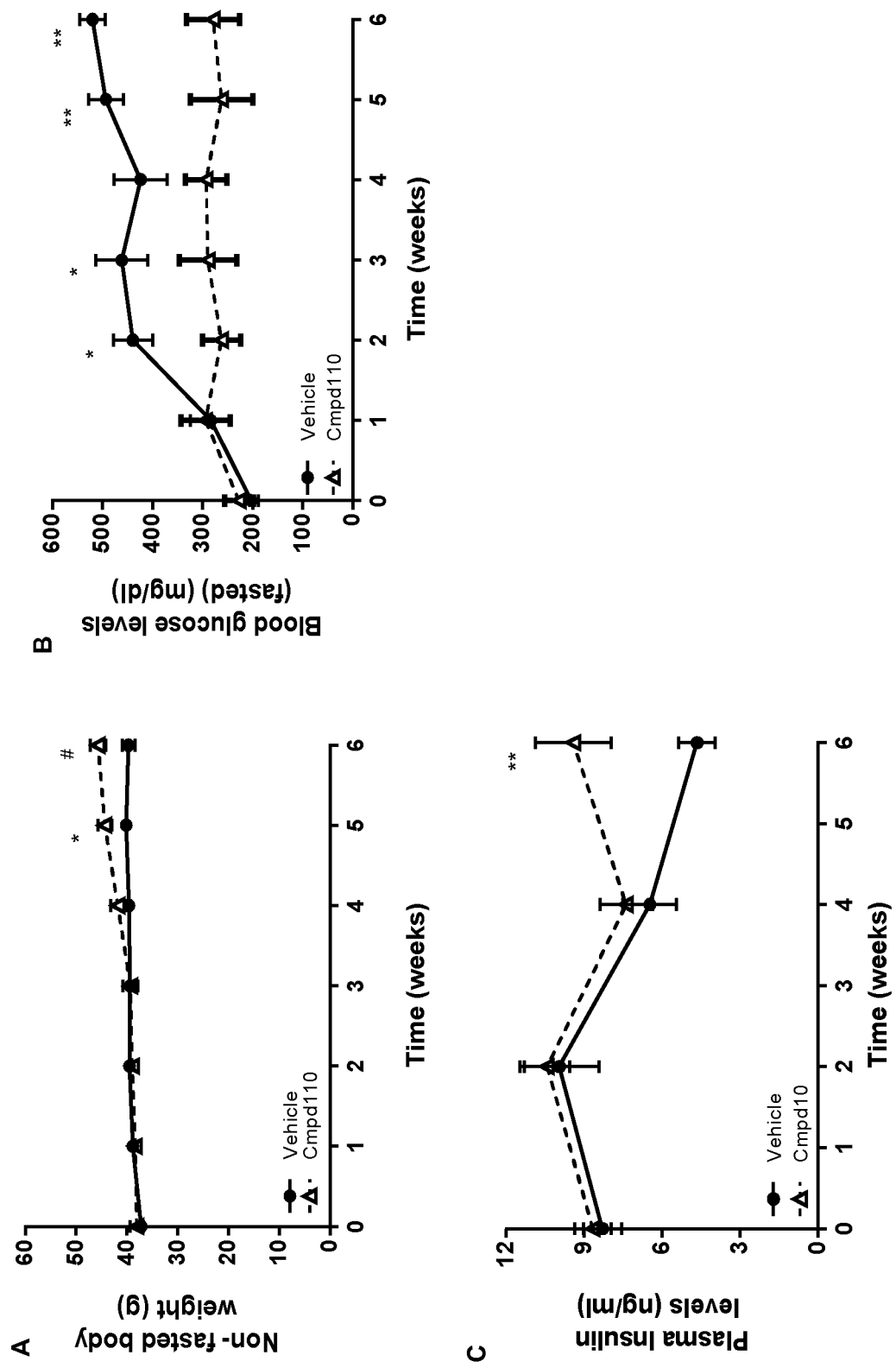

OXADIAZOLE COMPOUNDS

CROSS-REFERENCE TO RELATED APPLICATIONS

This application is a U.S. national stage entry under 35 U.S.C. § 371 of PCT International Patent Application No. PCT/EP2015/055488, filed Mar. 17, 2015, which claims priority to European Patent Application No. 14160354.8, filed Mar. 17, 2014, the contents of which are incorporated herein by reference in their entirety.

FIELD OF THE INVENTION

The present invention relates to oxadiazole derivative compounds, or pharmaceutically acceptable salts thereof, as defined herein, that are useful for treating diseases related to protein misfolding and in particular neurodegenerative diseases or diabetes.

BACKGROUND OF THE INVENTION

Several human disorders referred to as amyloidoses entail the accumulation and/or aggregation of misfolded proteins as a pathological characteristic and are therefore also referred to as protein-misfolding diseases. Most notably, Alzheimer's disease, Parkinson's disease and type 2 diabetes are common diseases which involve aberrant aggregation of amyloid-β (Aβ) and tau, alpha-synuclein and Islet Amyloid Polypeptide Precursor (IAPP), respectively. [*Misfolded Proteins in Alzheimer's Disease and Type II Diabetes*, DeToma et al., 2012, *Chem. Soc. Rev.*, 608-621]

The process or processes which lead to protein misfolding and aggregation is/are generally believed to be cytotoxic and as such may contribute to degeneration or failure of target cells such as neurons in the case of brain disorders such as Alzheimer's and Parkinson's disease or beta-cell function in the case of type 2 diabetes.

Although neurodegenerative diseases such as Alzheimer's disease and Parkinson's disease and metabolic disorders such as type 2 diabetes affect different tissues (respectively brain and pancreas), they have been shown to share similar risk factors [Janson J, Laedtke T, Parisi J E, O'Brien P, Petersen R C, Butler P C. *Diabetes*. 2004; 53:474-481]. Also the mechanism underlying the protein aggregation itself, despite the fact that it involves different proteins across different indications, has common denominators. [*Common Structure of Soluble Amyloid Oligomers Implies Common Mechanism of Pathogenesis*; Rakez Kayed1, Elizabeth Head2, Jennifer L. Thompson1, Theresa M. McIntire3, Saskia C. Milton1, Carl W. Cotman2, Charles G. Glabe1; *Science* 18 Apr. 2003: Vol. 300 no. 5618 pp. 486-489;]. These observed mechanistic commonalities between protein misfolding disorders indicate that therapeutic interventions aimed to preserve cellular integrity are expected to be efficacious over a variety of disorders which involve protein aggregation. However, the precise mechanism as to the pathways and processes involved in cellular degeneration and protein aggregation is/are still highly elusive. Therefore, in the absence of detailed mechanistic insights as to the molecular mechanism involved, the use of phenotypic assays to identify small molecules which preserve cellular integrity in cellular and animal models of amyloidosis is relevant to find effective treatments for patients suffering amyloidoses such as Alzheimer's, Parkinson's disease and diabetes. Importantly, such treatments will alter fundamentally the course of the disease as these preserve cellular integrity of the target cells such as neurons and beta-cells and thus are expected to be disease-modifying. As such these treatments are not merely reducing temporarily disease symptoms and therefore address an important current medical need.

To date, beyond diet management, medication for type 2 diabetes is focused on minimizing diabetic complications using oral hypoglycemic agents and at a later stage of the disease, insulin replacement therapy. These medications belong to four main classes:

Sulfonylureas stimulate insulin release by pancreatic β-cells. They are cheap and show little side effect, but they induce weight gain and risk of hypoglycemia and are thought to precipitate failure of insulin-producing β-cells Biguanides (of which metformin is the reference) decrease insulin resistance and triglyceride levels. They are however inducing gastrointestinal problems and are counter-indicated for people with kidney disease or heart problems.

Alpha-glucosidase inhibitors reduce glucose absorbance by small intestine. It is however an expensive treatment with inconvenient dosing, which can induce gastrointestinal problems.

Thiazolidinediones reduce insulin resistance by activating PPAR-γ in fat and muscle. They are however expensive and associated with weight gain, increased risk of heart failure, anemia and edema.

GLP-1 analogues stimulate insulin release by pancreatic β-cells in a glucose-dependent manner, inhibit glucagon release by α-cells and slow down gastric emptying. They are expensive, need to be injected and lead to nausea.

DPP-4 inhibitors increase endogenous GLP-1 levels and exert effects similar to GLP-1 analogues. There are suggestions of an increased risk of pancreatitis and pancreatic cancer associated with the use of these drugs.

SGLT-2 inhibitors increase glucose clearance through the kidney/urine. Of this class, canagliflozin recently entered the market but is associated with side effects such as an increased desire to urinate and also associated with higher risk of vaginal yeast infections and urinary tract infections.

Regarding neurodegenerative diseases, treatments are focused on delaying the onset, or reduce the existing symptoms. For example, cholinesterase inhibitors and/or Memantine are given to Alzheimer's patients to delay the onset of cognitive symptoms. Levodopa is given to Parkinson's patients to temporarily diminish motor symptoms.

There is therefore a great need for treatments which preserve and/or refunctionalize cells affected in amyloidoses to prevent the development of associated symptoms in patients.

SUMMARY OF THE INVENTION

The present invention provides compounds which decrease cytotoxicity in models of protein-misfolding disorders and were shown to decrease disease symptoms in-vivo.

According to a first aspect of the present invention, a compound of formula (I) or (II), or a stereoisomer, enantiomer, racemic, or tautomer thereof is provided,

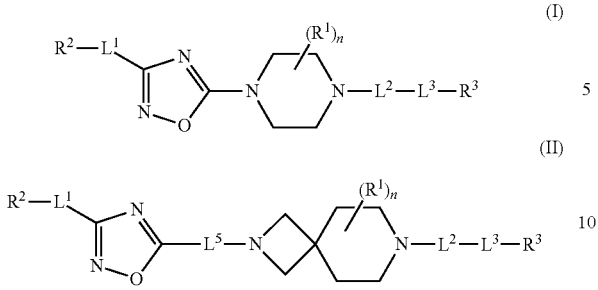

wherein, n is an integer selected from 0, 1, 2 or 3;

$R^1$ is selected from the group consisting of $C_{1-6}$alkyl, halo, halo$C_{1-6}$alkyl, and halo$C_{1-6}$alkyloxy;

$R^2$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{15}$, —$SR^{16}$, halo$C_{1-6}$alkyl, halo$C_{1-6}$alkyloxy, amino, —$NR^{17}R^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{15}$, —$SR^{16}$, halo$C_{1-6}$alkyl, halo$C_{1-6}$alkyloxy, —$NR^{17}R^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl $C_{6-12}$aryl can be unsubstituted or substituted with one or more $Z^2$;

$L^1$ is a single bond, or is a group of formula (i);

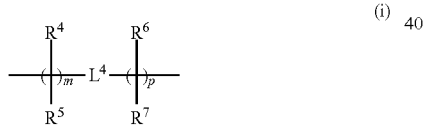

wherein the left side of the group of formula (i) is attached to $R^2$ and the right side thereof is attached to the oxadiazole ring; and wherein, m is an integer selected from 0, 1, 2, 3 or 4;

p is an integer selected from 0, 1, 2, 3 or 4;

$L^4$ is a single bond, or is selected from the group consisting of —O—, and —$NR^8$—;

$R^4$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

$R^5$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

or $R^4$ and $R^5$ together with the carbon atom to which they are attached form a saturated or unsaturated 3-, 4-, 5-, 6- or 7-membered ring;

$R^6$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

$R^7$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

or $R^6$ and $R^7$ together with the carbon atom to which they are attached form a saturated or unsaturated 3-, 4-, 5-, 6- or 7-membered ring;

$R^8$ is selected from the group consisting of hydrogen, and $C_{1-6}$alkyl;

$L^2$ is a single bond or is selected from the group consisting of —$SO_2$—, —$PO_4$—, —$PO_3$—, and —$(CR^9R^{10})_q$—; wherein, q is an integer selected from 1, 2 or 3;

$R^9$ is selected from the group consisting of hydrogen, $C_{1-6}$alkyl, halo, hydroxyl, —$OR^{15}$, —$SR^{16}$ halo$C_{1-6}$alkyl, and halo$C_{1-6}$alkyloxy;

$R^{10}$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

or $R^9$ and $R^{10}$ together with the carbon atom to which they are attached form a saturated or unsaturated 3-, 4-, 5-, 6- or 7-membered ring;

$L^3$ is a single bond or is selected from the group consisting of —$(CR^{11}R^{12})_r$—, —O—, and —$NR^{13}$—; wherein, r is an integer selected from 1, 2 or 3;

$R^{11}$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

$R^{12}$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy;

or $R^{11}$ and $R^{12}$ together with the carbon atom to which they are attached form a saturated or unsaturated 3-, 4-, 5-, 6- or 7-membered ring;

$R^{13}$ is selected from the group consisting of hydrogen, and $C_{1-6}$alkyl;

wherein at least one of $L^2$, $L^3$ is not a single bond;

$L^5$ is a single bond or —CO—;

each $R^{15}$ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{3-8}$cycloalkyl$C_{1-6}$alkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^1$;

and wherein at least one carbon atom or heteroatom of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{16}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^2$;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{17}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

each $R^{18}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

or wherein $R^{17}$ and $R^{18}$ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or $S(O)_2$;

each $R^{19}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl can be oxidized to form at least one C=O, C=S, N=O, N=S, S=O or $S(O)_2$;

each $R^{21}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene$C_{1-6}$alkylene*; wherein * represents where $R^{21}$ is bound to —CO—;

and wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, C=S, N=O, N=S, S=O or $S(O)_2$;

each $Z^1$ is independently selected from the group consisting of halo, hydrogen, $C_{1-6}$alkyl, halo$C_{1-6}$alkyl, halo$C_{1-6}$ alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —$OR^{15}$, —$SR^{16}$, cyano, amino, —$NR^{17}R^{18}$, —$CO_2R^{19}$, —$C(O)NR^{17}R^{18}$, —$C(O)R^{19}$, —$S(O)R^{19}$, —$S(O)_2R^{19}$, —$SO_2NR^{17}R^{18}$, nitro, —$NR^{20}C(O)R^{19}$, —$R^{21}$—$C(O)NR^{17}R^{18}$, —$NR^{20}S(O)_2R^{19}$, and $NR^{20}C(O)NR^{17}R^{18}$; and wherein two $Z^1$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, C=S, N=O, N=S, S=O or $S(O)_2$;

each $Z^2$ is independently selected from the group consisting of halo, hydrogen, $C_{1-6}$alkyl, halo$C_{1-6}$alkyl, halo$C_{1-6}$ alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —$OR^{15}$, —$SR^{16}$, cyano, amino, —$NR^{17}R^{18}$, —$CO_2R^{19}$, —$C(O)NR^{17}R^{18}$, —$C(O)R^{19}$, —$S(O)R^{19}$, —$S(O)_2R^{19}$, —$SO_2NR^{17}R^{18}$, nitro, —$NR^{20}C(O)R^{19}$, —$R^{21}$—$C(O)NR^{17}R^{18}$, —$NR^{20}S(O)_2R^{19}$, and —$NR^{20}C(O)NR^{17}R^{18}$; and wherein two $Z^2$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$ alkyl can be oxidized to form at least one C=O, C=S, N=O, N=S, S=O or $S(O)_2$;

and with the proviso that for a compound of formula (I) when $R^2$ is $C_{6-12}$aryl; $L^3$ is a single bond, —$(CR^{11}R^{12})_r$—, —O—, or —$NR^{13}$—; then $R^3$ is not hydrogen, $C_{1-6}$alkyl, hydroxyl, or —$OR^{15}$;

and with the proviso that for a compound of formula (I) when L is a single bond, $R^2$ is not hydrogen;

and with the proviso that said compound is not 5-(4-((3-methylpyridin-2-yl)methyl)piperazin-1-yl)-3-phenyl-1,2,4-oxadiazole;

5-(4-(3-fluorobenzyl)piperazin-1-yl)-3-phenyl-1,2,4-oxadiazole;

3-(4-bromophenyl)-5-(4-(4-fluorophenethyl)piperazin-1-yl)-1,2,4-oxadiazole;

3-(3,5-dichlorophenyl)-5-(4-(pyridin-2-ylmethyl)piperazin-1-yl)-1,2,4-oxadiazole;

1-(7-methyl-1-(3-(4-(3-(pyridin-3-yl)-1,2,4-oxadiazol-5-yl)piperazin-1-yl)propyl)-1H-indol-3-yl)ethanone;

5-(4-((2-methoxypyrimidin-5-yl)methyl)piperazin-1-yl)-3-phenyl-1,2,4-oxadiazole;

2-((4-(3-phenyl-1,2,4-oxadiazol-5-yl)piperazin-1-yl)methyl)benzoic acid;

5-(4-((2-ethyl-4-methyl-1H-imidazol-5-yl)methyl)piperazin-1-yl)-3-phenyl-1,2,4-oxadiazole;

3-phenyl-5-(4-((2-phenylthiazol-4-yl)methyl)piperazin-1-yl)-1,2,4-oxadiazole;

5-(4-benzylpiperazin-1-yl)-3-(3-methoxyphenyl)-1,2,4-oxadiazole;

5-(4-benzylpiperazin-1-yl)-3-(2,3-dimethoxyphenyl)-1,2,4-oxadiazole;

5-(4-(benzo[d][1,3]dioxol-5-ylmethyl)piperazin-1-yl)-3-phenyl-1,2,4-oxadiazole;

5-(4-(benzo[d][1,3]dioxol-5-ylmethyl)piperazin-1-yl)-3-(3,4-dimethoxyphenyl)-1,2,4-oxadiazole;

5-(4-(benzo[d][1,3]dioxol-5-ylmethyl)piperazin-1-yl)-3-(4-methoxyphenyl)-1,2,4-oxadiazole;

5-(4-(benzo[d][1,3]dioxol-5-ylmethyl)piperazin-1-yl)-3-(2-fluorophenyl)-1,2,4-oxadiazole;

5-(4-benzylpiperazin-1-yl)-3-phenyl-1,2,4-oxadiazole;

5-(4-benzylpiperazin-1-yl)-3-(4-methoxyphenyl)-1,2,4-oxadiazole;
5-(4-(benzo[d][1,3]dioxol-5-ylmethyl)piperazin-1-yl)-3-(3-methoxyphenyl)-1,2,4-oxadiazole;
5-(4-(benzo[d][1,3]dioxol-5-ylmethyl)piperazin-1-yl)-3-(2,3-dimethoxyphenyl)-1,2,4-oxadiazole;
3-(4-methoxyphenyl)-5-(4-(2,3,4-trimethoxybenzyl)piperazin-1-yl)-1,2,4-oxadiazole;
3-(3,4-dimethoxyphenyl)-5-(4-(2,3,4-trimethoxybenzyl)piperazin-1-yl)-1,2,4-oxadiazole;
3-(2,3-dimethoxyphenyl)-5-(4-(2,3,4-trimethoxybenzyl)piperazin-1-yl)-1,2,4-oxadiazole;
3-(2-fluorophenyl)-5-(4-(2,3,4-trimethoxybenzyl)piperazin-1-yl)-1,2,4-oxadiazole;
5-(4-benzylpiperazin-1-yl)-3-(2-fluorophenyl)-1,2,4-oxadiazole;
3-phenyl-5-(4-(2,3,4-trimethoxybenzyl)piperazin-1-yl)-1,2,4-oxadiazole;
5-(4-benzylpiperazin-1-yl)-3-(3,4-dimethoxyphenyl)-1,2,4-oxadiazole;
5-(4-((2,3-dihydrobenzo[b][1,4]dioxin-6-yl)methyl)piperazin-1-yl)-3-methyl-1,2,4-oxadiazole;
5-(4-(benzo[d][1,3]dioxol-5-ylmethyl)piperazin-1-yl)-3-methyl-1,2,4-oxadiazole;
3-(4-bromophenyl)-5-(4-(4-isopropoxyphenethyl)piperazin-1-yl)-1,2,4-oxadiazole;
3-(4-bromophenyl)-5-(4-phenethylpiperazin-1-yl)-1,2,4-oxadiazole;
5-(4-(benzo[b][1,4]dioxin-6-ylmethyl)piperazin-1-yl)-1,2,4-oxadiazole;
5-(4-isobutylpiperazin-1-yl)-3-isopropyl-1,2,4-oxadiazole;
N,N,2,2-tetramethyl-3-[4-(3-phenyl-1,2,4-oxadiazol-5-yl)piperazin-1-yl]propan-1-amine;
3-(4-bromophenyl)-5-[4-(2-nitrophenyl)sulfonylpiperazin-1-yl]-1,2,4-oxadiazole;
5-(4-benzylsulfonylpiperazin-1-yl)-3-cyclopropyl-1,2,4-oxadiazole;
5-[4-(4-methoxyphenyl)sulfonylpiperazin-1-yl]-3-phenyl-1,2,4-oxadiazole;
or a solvate, hydrate, pharmaceutically acceptable salt, or prodrug thereof.

In some embodiments, said compound is not
2[[(2R)-4-(3-cyclopropyl-1,2,4-oxadiazol-5-yl)-2-methylpiperazin-1-yl]methyl]-7-methoxy-[1,2,4]triazolo[1,5-c]quinazolin-5-amine;
2[[(2R)-4-(3-rwer-butyl-1,2,4-oxadiazol-5-yl)-2-methylpiperazin-1-yl]methyl]-7-methoxy-[1,2,4]triazolo[1,5-c]quinazolin-5-amine.

According to a second aspect, the present invention also encompasses a pharmaceutical composition comprising one or more pharmaceutically excipients and a therapeutically effective amount of a compound according to the first aspect of the invention; or a therapeutically effective amount of a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine, 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof.

According to a third aspect, the present invention also encompasses a compound according to the first aspect of the invention, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to the second aspect of the invention, for use as a medicament.

According to a fourth aspect, the present invention also encompasses a compound according to the first aspect of the invention, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to the second aspect of the invention, for use as a medicine for the prevention and/or treatment of metabolic disorders and/or neurodegenerative diseases and/or protein misfolding disorders.

According to a fifth aspect, the present invention also encompasses a compound according to the first aspect of the invention, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole;

N,N,2,2-tetramethyl-3-[4-(3-phenyl-1,2,4-oxadiazol-5-yl) piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to the second aspect of the invention, for use as a medicine for the prevention and/or treatment of diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension.

The present invention also encompasses method for the preparation of the compounds according to the first aspect of the invention.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The independent and dependent claims set out particular and preferred features of the invention. Features from the dependent claims may be combined with features of the independent or other dependent claims as appropriate.

BRIEF DESCRIPTION OF THE FIGURES

FIG. 1 represents in Section (A) a graph plotting the non-fasted body weight of db/db mice treated with compound 110 (Cmpd 110) of the invention, as a function of duration of treatment in weeks. Section (B) is a graph plotting the blood glucose levels of fasted db/db mice treated with compound Cmpd 110 of the invention, as a function of duration of treatment in weeks. Section (C) is a graph plotting the plasma insulin levels of db/db mice treated with compound Cmpd 110 of the invention, as a function of duration of treatment in weeks.

DETAILED DESCRIPTION OF THE INVENTION

Before the present invention is described, it is to be understood that this invention is not limited to particular processes, methods, and compounds described, as such processes, methods, and compounds may, of course, vary. It is also to be understood that the terminology used herein is not intended to be limiting, since the scope of the present invention will be limited only by the appended claims.

When describing the compounds and processes of the invention, the terms used are to be construed in accordance with the following definitions, unless a context dictates otherwise.

As used in the specification and the appended claims, the singular forms "a", "an," and "the" include both singular and plural referents unless the context clearly dictates otherwise. By way of example, "a compound" means one compound or more than one compound.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

When describing the present invention, the terms used are to be construed in accordance with the following definitions, unless a context dictates otherwise.

The terms described above and others used in the specification are well understood to those in the art.

Whenever the term "substituted" is used herein, it is meant to indicate that one or more hydrogen atoms on the atom indicated in the expression using "substituted" is replaced with a selection from the indicated group, provided that the indicated atom's normal valence is not exceeded, and that the substitution results in a chemically stable compound, i.e. a compound that is sufficiently robust to survive isolation from a reaction mixture.

Where groups can be substituted, such groups may be substituted with one or more, and preferably one, two or three substituents. Preferred substituents may be selected from but not limited to, for example, the group comprising halo, hydroxyl, $C_{1-6}$alkyl, $C_{1-6}$alkoxy, halo$C_{1-6}$alkyl, halo$C_{1-6}$alkyloxy, $C_{3-12}$cycloalkyl, $C_{6-12}$aryl, $C_{6-12}$aryl$C_{1-6}$alkyl, heterocyclyl, heteroaryl, $C_{1-6}$alkylthio, cyano, amino, nitro, carboxyl, aminocarbonyl, hydroxycarbonyl$C_{1-6}$alkyl, $C_{1-6}$alkyloxycarbonyl, mono- or di$C_{1-6}$alkylamino, mono- or di$C_{1-6}$alkylaminocarbonyl, $C_{1-6}$alkylcarbonyl, —S(O)$C_{1-6}$ alkyl, —S(O)$_2C_{1-6}$alkyl, $C_{1-6}$alkylcarbonylamino, and mono or di-$C_{1-6}$alkylaminocarbonyl$C_{1-6}$alkyl.

The terminology regarding a chemical group "wherein at least one carbon atom or heteroatom of said group can be oxidized to form at least one C=O, C=S, N=O, N=S, S=O or S(O)$_2$" as used herein, refers to a group where two or more hydrogen atoms on a carbon atom or heteroatom of said group are taken together to form C=O, C=S, N=O, N=S, S=O or S(O)$_2$. As an example, the terminology "an alkyl wherein a carbon atom or heteroatom of said alkyl can oxidized to form a C=O, C=S, N=O, N=S, S=O or S(O)$_2$", includes among other examples CH$_3$—C(O)—CH$_2$—, CH$_3$—C(O)—, CH$_3$—C(S)—CH$_2$— and (CH$_3$)$_2$—CH$_2$—C(O)—CH$_2$—CH$_2$—. For example, the terminology "a 5-, 6-, or 7-membered heterocyclyl wherein a carbon atom or heteroatom of said heterocyclyl can be oxidized to form a C=O, C=S, N=O, N=S, S=O or S(O)$_2$", includes among other examples 6-oxo-1H-pyridin-3-yl, 2-oxo-1H-pyridin-4yl, 6-thioxo-1H-pyridin-3-yl and 2-thioxo-1H-pyridin-4yl.

The term "halo" or "halogen" as a group or part of a group is generic for fluoro, chloro, bromo, iodo.

The term "amino" refers to the group —NH$_2$.

The term "hydroxyl" or "hydroxy" as used herein refers to the group —OH.

The term "thiol" or "sulfuhydryl" refers to the group —SH.

The term "oxo" as used herein refers to the group =O.

The term "nitro" as used herein refers to the group —NO$_2$.

The term "cyano" as used herein refers to the group —CN.

The term "carboxy" or "carboxyl" or "hydroxycarbonyl" as used herein refers to the group —CO$_2$H.

The term "aminocarbonyl" as used herein refers to the group —CO—NH$_2$.

The term "alkyl" by itself or as part of another substituent refers to a hydrocarbyl group of formula $C_nH_{2n+1}$ wherein n is a number greater than or equal to 1. Alkyl groups may be linear or branched and may be substituted as indicated herein. Generally, alkyl groups of this invention comprise from 1 to 6 carbon atoms, preferably from 1 to 5 carbon atoms, preferably from 1 to 4 carbon atoms, more preferably from 1 to 3 carbon atoms, still more preferably 1 to 2 carbon atoms. When a subscript is used herein following a carbon atom, the subscript refers to the number of carbon atoms that the named group may contain. For example, the term "$C_{1-6}$alkyl", as a group or part of a group, refers to a hydrocarbyl group of formula —$C_nH_{2n+1}$ wherein n is a number ranging from 1 to 6. Thus, for example, "$C_{1-6}$alkyl" includes all linear or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers. For example, "$C_{1-5}$alkyl" includes all includes all linear or branched alkyl groups with between 1 and 5 carbon atoms, and thus includes methyl, ethyl, n-propyl, i-propyl, butyl and its isomers (e.g. n-butyl, i-butyl and t-butyl); pentyl and its isomers. For example, "$C_{1-4}$alkyl" includes all linear or branched alkyl groups with between 1 and 4 carbon atoms, and thus includes methyl, ethyl, n-propyl, i-propyl, butyl and its isomers (e.g. n-butyl, i-butyl and t-butyl). For example "$C_{1-3}$alkyl" includes all linear or branched alkyl groups with between 1 and 3 carbon atoms, and thus includes methyl, ethyl, n-propyl, i-propyl. A "substituted $C_{1-6}$alkyl" refers to a $C_{1-6}$alkyl group substituted with one or more substituent(s) (for example 1 to 3 substituent(s), for example 1, 2, or 3 substituent(s)) at any available point of attachment.

When the suffix "ene" is used in conjunction with an alkyl group, i.e. "alkylene", this is intended to mean the alkyl group as defined herein having two single bonds as points of attachment to other groups. As used herein, the term "$C_{1-6}$alkylene", by itself or as part of another substituent, refers to $C_{1-6}$alkyl groups that are divalent, i.e., with two single bonds for attachment to two other groups. Alkylene groups may be linear or branched and may be substituted as indicated herein. Non-limiting examples of alkylene groups include methylene (—CH$_2$—), ethylene (—CH$_2$—CH$_2$—), methylmethylene (—CH(CH$_3$)—), 1-methyl-ethylene (—CH(CH$_3$)—CH$_2$—), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and its chain isomers, hexylene and its chain isomers.

When the term "alkyl" is used as a suffix following another term, as in "hydroxyalkyl," this is intended to refer to an alkyl group, as defined above, being substituted with one or two (preferably one) substituent(s) selected from the other, specifically-named group, also as defined herein. The term "hydroxy$C_{1-6}$alkyl" therefore refers to a —R$^a$—OH group wherein R$^a$ is $C_{1-6}$alkylene as defined herein.

The term "halo$C_{1-6}$alkyl" as a group or part of a group, refers to a $C_{1-6}$alkyl group having the meaning as defined above wherein one, two, or three hydrogen atoms are each replaced with a halogen as defined herein. Non-limiting examples of such halo$C_{1-6}$alkyl groups include chloromethyl, 1-bromoethyl, fluoromethyl, difluoromethyl, trifluoromethyl, 1,1,1-trifluoroethyl, trichloromethyl, tribromomethyl, and the like.

The term "trihalomethyl" as a group or part of a group, refers to a $C_1$ alkyl group (methyl) having the meaning as defined above wherein three hydrogen atoms are each replaced with a halogen as defined herein. Non-limiting examples of such trihalomethyl groups include trichloromethyl, tribromomethyl, and the like.

The term "$C_{1-6}$alkoxy" or "$C_{1-6}$alkyloxy", as a group or part of a group, refers to a group having the formula —OR$^b$ wherein R$^b$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "haloC$_{1-6}$alkoxy", as a group or part of a group, refers to a group of formula —O—R$^c$ wherein R$^c$ is haloC$_{1-6}$ alkyl as defined herein. Non-limiting examples of suitable haloC$_{1-6}$alkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The term "alkenyl" as a group or part of a group, refers to an unsaturated hydrocarbyl group, which may be linear, or branched, comprising one or more carbon-carbon double bonds. When a subscript is used herein following a carbon atom, the subscript refers to the number of carbon atoms that the named group may contain. For example, the term "C$_{2-6}$alkenyl" refers to an unsaturated hydrocarbyl group, which may be linear, or branched comprising one or more carbon-carbon double bonds and comprising from 2 to 6 carbon atoms. For example, C$_{2-4}$alkenyl includes all linear, or branched alkenyl groups having 2 to 4 carbon atoms. Examples of C$_{2-6}$alkenyl groups are ethenyl, 2-propenyl, 2-butenyl, 3-butenyl, 2-pentenyl and its isomers, 2-hexenyl and its isomers, 2,4-pentadienyl. and the like.

Where alkenyl groups as defined herein are divalent groups having single bonds for attachment to two other groups, they are termed "alkenylene". As used herein, the term "C$_{2-6}$alkenylene", by itself or as part of another substituent, refers to C$_{2-6}$alkenyl groups that are divalent, i.e., with two single bonds for attachment to two other groups.

The term "C$_{2-6}$alkenyloxy", as a group or part of a group, refers to a group having the formula —OR$^d$ wherein R$^d$ is C$_{2-6}$alkenyl as defined herein above.

The term "alkynyl" by itself or as part of another substituent, refers to an unsaturated hydrocarbyl group, which may be linear, or branched, comprising one or more carbon-carbon triple bonds. When a subscript is used herein following a carbon atom, the subscript refers to the number of carbon atoms that the named group may contain. For example, the term "C$_{2-6}$alkynyl" refers to an unsaturated hydrocarbyl group, which may be linear, or branched comprising one or more carbon-carbon triple bonds and comprising from 2 to 6 carbon atoms. For example, C$_{2-4}$alkynyl includes all linear, or branched alkynyl groups having 2 to 4 carbon atoms. Non limiting examples of C$_{2-6}$alkynyl groups include ethynyl, 2-propynyl, 2-butynyl, 3-butynyl, 2-pentynyl and its chain isomers, 2-hexynyl and its chain isomers, and the like.

Where alkynyl groups as defined herein are divalent groups having single bonds for attachment to two other groups, they are termed "alkynylene". As used herein, the term "C$_{2-6}$alkynylene", by itself or as part of another substituent, refers to C$_{2-6}$alkynyl groups that are divalent, i.e., with two single bonds for attachment to two other groups.

The term "C$_{2-6}$alkynyloxy", as a group or part of a group, refers to a group having the formula —OR$^e$ wherein R$^e$ is C$_{2-6}$alkynyl as defined herein above.

The term "cycloalkyl", as a group or part of a group, refers to a cyclic alkyl group, that is a monovalent, saturated, hydrocarbyl group having 1 or more cyclic structure, and comprising from 3 to 12 carbon atoms, more preferably from 3 to 9 carbon atoms, more preferably from 3 to 7 carbon atoms; more preferably from 3 to 6 carbon atoms. Cycloalkyl includes all saturated hydrocarbon groups containing 1 or more rings, including monocyclic or bicyclic groups. The further rings of multi-ring cycloalkyls may be either fused, bridged and/or joined through one or more spiro atoms. When a subscript is used herein following a carbon atom, the subscript refers to the number of carbon atoms that the named group may contain. For example, the term "C$_{3-8}$cycloalkyl", a cyclic alkyl group comprising from 3 to 8 carbon atoms. For example, the term "C$_{3-6}$cycloalkyl", a cyclic alkyl group comprising from 3 to 6 carbon atoms. Examples of C$_{3-12}$cycloalkyl groups include but are not limited to cyclopropyl, cyclobutyl, cyclopentyl, cyclohexyl, cycloheptyl, cyclooctyl, bicycle[2.2.1]heptan-2yl, (1S,4R)-norbornan-2-yl, (1R,4R)-norbornan-2-yl, (1 S,4S)-norbornan-2-yl, (1R,4S)-norbornan-2-yl.

When the suffix "ene" is used in conjunction with a cycloalkyl group, i.e. cycloalkylene, this is intended to mean the cycloalkyl group as defined herein having two single bonds as points of attachment to other groups. Non-limiting examples of "C$_{3-8}$cycloalkylene" include 1,2-cyclopropylene, 1,1-cyclopropylene, 1,1-cyclobutylene, 1,2-cyclobutylene, 1,3-cyclopentylene, 1,1-cyclopentylene, and 1,4-cyclohexylene.

Where an alkylene or cycloalkylene group is present, connectivity to the molecular structure of which it forms part may be through a common carbon atom or different carbon atom. To illustrate this applying the asterisk nomenclature of this invention, a C$_3$alkylene group may be for example *—CH$_2$CH$_2$CH$_2$—*, CH(—CH$_2$CH$_3$)—* or *—CH$_2$CH (—CH$_3$)—*. Likewise a C$_3$cycloalkylene group may be

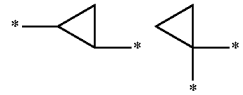

The term "C$_{6-12}$cycloalkyloxy", as a group or part of a group, refers to a group having the formula —OR$^f$ wherein R$^f$ is C$_{3-12}$cycloalkyl as defined herein above.

The term "C$_{6-12}$aryl", as a group or part of a group, refers to a polyunsaturated, aromatic hydrocarbyl group having a single ring (i.e. phenyl) or multiple aromatic rings fused together (e.g. naphthyl), or linked covalently, typically containing 6 to 12 atoms; preferably 6 to 10, wherein at least one ring is aromatic. The aromatic ring may optionally include one to two additional rings (either cycloalkyl, heterocyclyl or heteroaryl) fused thereto. Examples of suitable aryl include C$_{6-10}$aryl, more preferably C$_{6-8}$aryl. Non-limiting examples of C$_{6-12}$aryl comprise phenyl, biphenylyl, biphenylenyl, or 1- or 2-naphthanelyl; 1-, 2-, 3-, 4-, 5- or 6-tetralinyl (also known as "1,2,3,4-tetrahydronaphtalene); 1-, 2-, 3-, 4-, 5-, 6-, 7- or 8-azulenyl, 4-, 5-, 6 or 7-indenyl; 4- or 5-indanyl; 5-, 6-, 7- or 8-tetrahydronaphthyl; 1,2,3,4-tetrahydronaphthyl; and 1,4-dihydronaphthyl; 1-, 2-, 3-, 4- or 5-pyrenyl. A "substituted C$_{6-12}$aryl" refers to a C$_{6-12}$aryl group having one or more substituent(s) (for example 1, 2 or 3 substituent(s), or 1 to 2 substituent(s)), at any available point of attachment.

As used herein, the term "spiro atom" refers to the atom that connects two cyclic structures in a spiro compound. Non limiting examples of spiro atoms include quaternary carbon atoms. As used herein, the term "spiro compound" refers to a bicyclic compound wherein the two rings are connected through one atom.

When the suffix "ene" is used in conjunction with an aryl group; i.e. arylene, this is intended to mean the aryl group as defined herein having two single bonds as points of attachment to other groups. Suitable "C$_{6-12}$arylene" groups include 1,4-phenylene, 1,2-phenylene, 1,3-phenylene, biphenylylene, naphthylene, indenylene, 1-, 2-, 5- or 6-tetralinylene, and the like. Where a carbon atom in an aryl group is replaced with a heteroatom, the resultant ring is referred to herein as a heteroaryl ring.

The term "$C_{6-12}$aryloxy", as a group or part of a group, refers to a group having the formula —$OR^g$ wherein $R^g$ is $C_{6-12}$aryl as defined herein above.

The term "$C_{6-12}$aryl$C_{1-6}$alkyl", as a group or part of a group, means a $C_{1-6}$alkyl as defined herein, wherein at least one hydrogen atom is replaced by at least one $C_{6-12}$aryl as defined herein. Non-limiting examples of $C_{6-12}$aryl$C_{1-6}$alkyl group include benzyl, phenethyl, dibenzylmethyl, methylphenylmethyl, 3-(2-naphthyl)-butyl, and the like.

The term "$C_{6-12}$aryl$C_{1-6}$alky$C_{6-12}$aryl$C_6$", as a group or part of a group, means a $C_{6-12}$aryl, wherein at least one hydrogen atom is replaced by at least one $C_{6-12}$aryl$C_{1-6}$alkyl as defined herein.

The term "$C_{6-12}$arylene$C_{1-6}$alkylene", as a group or part of a group, refers to a group having the formula —$R^h$—$R^a$ wherein $R^h$ is $C_{6-12}$arylene as defined herein and $R^a$ is $C_{1-6}$alkylene as defined herein.

The term "$C_{6-12}$aryl$C_{1-6}$alkyloxy", as a group or part of a group, refers to a group having the formula —O—$R^a$—$R^g$ wherein $R^g$ is $C_{6-12}$aryl, and $R^a$ is $C_{1-6}$alkylene as defined herein above.

The terms "heterocyclyl" or "heterocycloakyl" or "heterocyclo", as a group or part of a group, refer to non-aromatic, fully saturated or partially unsaturated cyclic groups (for example, 3 to 7 member monocyclic, 7 to 11 member bicyclic, or comprising a total of 3 to 10 ring atoms) which have at least one heteroatom in at least one carbon atom-containing ring; wherein said ring may be fused to an aryl, cycloalkyl, heteroaryl or heterocyclyl ring. Each ring of the heterocyclyl group containing a heteroatom may have 1, 2, 3 or 4 heteroatoms selected from N, O and/or S, where the N and S heteroatoms may optionally be oxidized and the N heteroatoms may optionally be quaternized, and wherein at least one carbon atom of heterocyclyl can be oxidized to form at least one C=O. The heterocyclic group may be attached at any heteroatom or carbon atom of the ring or ring system, where valence allows. The rings of multi-ring heterocycles may be fused, bridged and/or joined through one or more spiro atoms.

Non limiting exemplary heterocyclic groups include aziridinyl, oxiranyl, thiiranyl, piperidinyl, azetidinyl, oxetanyl, pyrrolidinyl, thietanyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, chromanyl (also known as 3,4-dihydrobenzo[b]pyranyl), isoindolinyl, 2H-pyrrolyl, 1-pyrrolinyl, 2-pyrrolinyl, 3-pyrrolinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl. The term "aziridinyl" as used herein includes aziridin-1-yl and aziridin-2-yl. The term "oxyranyl" as used herein includes oxyranyl-2-yl. The term "thiiranyl" as used herein includes thiiran-2-yl. The term "azetidinyl" as used herein includes azetidin-1-yl, azetidin-2-yl and azetidin-3-yl. The term "oxetanyl" as used herein includes oxetan-2-yl and oxetan-3-yl. The term "thietanyl" as used herein includes thietan-2-yl and thietan-3-yl. The term "pyrrolidinyl" as used herein includes pyrrolidin-1-yl, pyrrolidin-2-yl and pyrrolidin-3-yl. The term "tetrahydrofuranyl" as used herein includes tetrahydrofuran-2-yl and tetrahydrofuran-3-yl. The term "tetrahydrothiophenyl" as used herein includes tetrahydrothiophen-2-yl and tetrahydrothiophen-3-yl. The term "succinimidyl" as used herein includes succinimid-1-yl and succininmid-3-yl. The term "dihydropyrrolyl" as used herein includes 2,3-dihydropyrrol-1-yl, 2,3-dihydro-1H-pyrrol-2-yl, 2,3-dihydro-1H-pyrrol-3-yl, 2,5-dihydropyrrol-1-yl, 2,5-dihydro-1H-pyrrol-3-yl and 2,5-dihydropyrrol-5-yl. The term "2H-pyrrolyl" as used herein includes 2H-pyrrol-2-yl, 2H-pyrrol-3-yl, 2H-pyrrol-4-yl and 2H-pyrrol-5-yl. The term "3H-pyrrolyl" as used herein includes 3H-pyrrol-2-yl, 3H-pyrrol-3-yl, 3H-pyrrol-4-yl and 3H-pyrrol-5-yl. The term "dihydrofuranyl" as used herein includes 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,5-dihydrofuran-4-yl and 2,5-dihydrofuran-5-yl. The term "dihydrothiophenyl" as used herein includes 2,3-dihydrothiophen-2-yl, 2,3-dihydrothiophen-3-yl, 2,3-dihydrothiophen-4-yl, 2,3-dihydrothiophen-5-yl, 2,5-dihydrothiophen-2-yl, 2,5-dihydrothiophen-3-yl, 2,5-dihydrothiophen-4-yl and 2,5-dihydrothiophen-5-yl. The term "imidazolidinyl" as used herein includes imidazolidin-1-yl, imidazolidin-2-yl and imidazolidin-4-yl. The term "pyrazolidinyl" as used herein includes pyrazolidin-1-yl, pyrazolidin-3-yl and pyrazolidin-4-yl. The term "imidazolinyl" as used herein includes imidazolin-1-yl, imidazolin-2-yl, imidazolin-4-yl and imidazolin-5-yl. The term "pyrazolinyl" as used herein includes 1-pyrazolin-3-yl, 1-pyrazolin-4-yl, 2-pyrazolin-1-yl, 2-pyrazolin-3-yl, 2-pyrazolin-4-yl, 2-pyrazolin-5-yl, 3-pyrazolin-1-yl, 3-pyrazolin-2-yl, 3-pyrazolin-3-yl, 3-pyrazolin-4-yl and 3-pyrazolin-5-yl. The term "dioxolanyl" also known as "1,3-dioxolanyl" as used herein includes dioxolan-2-yl, dioxolan-4-yl and dioxolan-5-yl. The term "dioxolyl" also known as "1,3-dioxolyl" as used herein includes dioxol-2-yl, dioxol-4-yl and dioxol-5-yl. The term "oxazolidinyl" as used herein includes oxazolidin-2-yl, oxazolidin-3-yl, oxazolidin-4-yl and oxazolidin-5-yl. The term "isoxazolidinyl" as used herein includes isoxazolidin-2-yl, isoxazolidin-3-yl, isoxazolidin-4-yl and isoxazolidin-5-yl. The term "oxazolinyl" as used herein includes 2-oxazolinyl-2-yl, 2-oxazolinyl-4-yl, 2-oxazolinyl-5-yl, 3-oxazolinyl-2-yl, 3-oxazolinyl-4-yl, 3-oxazolinyl-5-yl, 4-oxazolinyl-2-yl, 4-oxazolinyl-3-yl, 4-oxazolinyl-4-yl and 4-oxazolinyl-5-yl. The term "isoxazolinyl" as used herein includes 2-isoxazolinyl-3-yl, 2-isoxazolinyl-4-yl, 2-isoxazolinyl-5-yl, 3-isoxazolinyl-3-yl, 3-isoxazolinyl-4-yl, 3-isoxazolinyl-5-yl, 4-isoxazolinyl-2-yl, 4-isoxazolinyl-3-yl, 4-isoxazolinyl-4-yl and 4-isoxazolinyl-5-yl. The term "thiazolidinyl" as used herein includes thiazolidin-2-yl, thiazolidin-3-yl, thiazolidin-4-yl and thiazolidin-5-yl. The term "isothiazolidinyl" as used herein includes isothiazolidin-2-yl, isothiazolidin-3-yl, isothiazolidin-4-yl and isothiazolidin-5-yl. The term "chromanyl" as used herein includes chroman-2-yl, chroman-3-yl, chroman-4-yl, chroman-5-yl, chroman-6-yl, chroman-7-yl and chroman-8-yl. The term "thiazolinyl" as used herein includes 2-thiazolinyl-2-yl, 2-thiazolinyl-4-yl, 2-thiazolinyl-5-yl, 3-thiazolinyl-2-yl, 3-thiazolinyl-4-yl, 3-thiazolinyl-5-yl, 4-thiazolinyl-2-yl, 4-thiazolinyl-3-yl, 4-thiazolinyl-4-yl and 4-thiazolinyl-5-yl. The term "isothiazolinyl" as used herein includes 2-isothiazolinyl-3-yl, 2-isothiazolinyl-4-yl, 2-isothiazolinyl-5-yl, 3-isothiazolinyl-3-yl, 3-isothiazolinyl-4-yl, 3-isothiazolinyl-5-yl, 4-isothiazolinyl-2-yl, 4-isothiazolinyl-3-yl, 4-isothiazolinyl-4-yl and 4-isothiazolinyl-5-yl. The term "piperidyl" also known as "piperidinyl" as used herein includes piperid-1-yl, piperid-2-yl, piperid-3-yl and piperid-4-yl. The term "dihydropyridinyl" as used herein includes 1,2-dihydropyridin-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,4-dihydropyridin-1-yl, 1,4-dihydropyridin-2-yl, 1,4-dihydropyridin-3-yl, 1,4-dihydropyridin-4-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 3,4-dihydropyridin-2-yl, 3,4-dihydropyridin-3-yl, 3,4-dihydropyridin-4-yl, 3,4-dihydropyridin-5-yl and 3,4-dihydropyridin-6-yl. The term "tetrahydropyridinyl" as used herein includes 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl, 1,2,3,4-tetrahydropyridin-5-yl, 1,2,3,4-tetrahydropyridin-6-yl, 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl, 1,2,3,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl and 2,3,4,5-tetrahydropyridin-6-yl. The term "tetrahydropyranyl" also known as "oxanyl" or "tetrahydro-2H-pyranyl", as used herein includes tetrahydropyran-2-yl, tetrahydropyran-3-yl and tetrahydropyran-4-yl. The term "2H-pyranyl" as used herein includes 2H-pyran-2-yl, 2H-pyran-3-yl, 2H-pyran-4-yl, 2H-pyran-5-yl and 2H-pyran-6-yl. The term "4H-pyranyl" as used herein includes 4H-pyran-2-yl, 4H-pyran-3-yl and 4H-pyran-4-yl. The term "3,4-dihydro-2H-pyranyl" as used herein includes 3,4-dihydro-2H-pyran-2-yl, 3,4-dihydro-2H-pyran-3-yl, 3,4-dihydro-2H-pyran-4-yl, 3,4-dihydro-2H-pyran-5-yl and 3,4-dihydro-2H-pyran-6-yl. The term "3,6-dihydro-2H-pyranyl" as used herein includes 3,6-dihydro-2H-pyran-2-yl, 3,6-dihydro-2H-pyran-3-yl, 3,6-dihydro-2H-pyran-4-yl, 3,6-dihydro-2H-pyran-5-yl and 3,6-dihydro-2H-pyran-6-yl. The term "tetrahydrothiophenyl", as used herein includes tetrahydrothiophen-2-yl, tetrahydrothiophenyl-3-yl and tetrahydrothiophenyl-4-yl. The term "2H-thiopyranyl" as used herein includes 2H-thiopyran-2-yl, 2H-thiopyran-3-yl, 2H-thiopyran-4-yl, 2H-thiopyran-5-yl and 2H-thiopyran-6-yl. The term "4H-thiopyranyl" as used herein includes 4H-thiopyran-2-yl, 4H-thiopyran-3-yl and 4H-thiopyran-4-yl. The term "3,4-dihydro-2H-thiopyranyl" as used herein includes 3,4-dihydro-2H-thiopyran-2-yl, 3,4-dihydro-2H-thiopyran-3-yl, 3,4-dihydro-2H-thiopyran-4-yl, 3,4-dihydro-2H-thiopyran-5-yl and 3,4-dihydro-2H-thiopyran-6-yl. The term "3,6-dihydro-2H-thiopyranyl" as used herein includes 3,6-dihydro-2H-thiopyran-2-yl, 3,6-dihydro-2H-thiopyran-3-yl, 3,6-dihydro-2H-thiopyran-4-yl, 3,6-dihydro-2H-thiopyran-5-yl and 3,6-dihydro-2H-thiopyran-6-yl. The term "piperazinyl" also known as "piperazidinyl" as used herein includes piperazin-1-yl and piperazin-2-yl.

The term "morpholinyl" as used herein includes morpholin-2-yl, morpholin-3-yl and morpholin-4-yl. The term "thiomorpholinyl" as used herein includes thiomorpholin-2-yl, thiomorpholin-3-yl and thiomorpholin-4-yl. The term "dioxanyl" as used herein includes 1,2-dioxan-3-yl, 1,2-dioxan-4-yl, 1,3-dioxan-2-yl, 1,3-dioxan-4-yl, 1,3-dioxan-5-yl and 1,4-dioxan-2-yl. The term "dithianyl" as used herein includes 1,2-dithian-3-yl, 1,2-dithian-4-yl, 1,3-dithian-2-yl, 1,3-dithian-4-yl, 1,3-dithian-5-yl and 1,4-dithian-2-yl. The term "oxathianyl" as used herein includes oxathian-2-yl and oxathian-3-yl. The term "trioxanyl" as used herein includes 1,2,3-trioxan-4-yl, 1,2,3-trioxay-5-yl, 1,2,4-trioxay-3-yl, 1,2,4-trioxay-5-yl, 1,2,4-trioxay-6-yl and 1,3,4-trioxay-2-yl. The term "azepanyl" as used herein includes azepan-1-yl, azepan-2-yl, azepan-1-yl, azepan-3-yl and azepan-4-yl. The term "homopiperazinyl" as used herein includes homopiperazin-1-yl, homopiperazin-2-yl, homopiperazin-3-yl and homopiperazin-4-yl.

The term "indolinyl" as used herein includes indolin-1-yl, indolin-2-yl, indolin-3-yl, indolin-4-yl, indolin-5-yl, indolin-6-yl, and indolin-7-yl. The term "quinolizinyl" as used herein includes quinolizidin-1-yl, quinolizidin-2-yl, quinolizidin-3-yl and quinolizidin-4-yl. The term "isoindolinyl" as used herein includes isoindolin-1-yl, isoindolin-2-yl, isoindolin-3-yl, isoindolin-4-yl, isoindolin-5-yl, isoindolin-6-yl, and isoindolin-7-yl. The term "3H-indolyl" as used herein includes 3H-indol-2-yl, 3H-indol-3-yl, 3H-indol-4-yl, 3H-indol-5-yl, 3H-indol-6-yl, and 3H-indol-7-yl. The term "quinolizinyl" as used herein includes quinolizidin-1-yl, quinolizidin-2-yl, quinolizidin-3-yl and quinolizidin-4-yl. The term "quinolizinyl" as used herein includes quinolizidin-1-yl, quinolizidin-2-yl, quinolizidin-3-yl and quinolizidin-4-yl. The term "tetrahydroquinolinyl" as used herein includes tetrahydroquinolin-1-yl, tetrahydroquinolin-2-yl, tetrahydroquinolin-3-yl, tetrahydroquinolin-4-yl, tetrahydroquinolin-5-yl, tetrahydroquinolin-6-yl, tetrahydroquinolin-7-yl and tetrahydroquinolin-8-yl. The term "tetrahydroisoquinolinyl" as used herein includes tetrahydroisoquinolin-1-yl, tetrahydroisoquinolin-2-yl, tetrahydroisoquinolin-3-yl, tetrahydroisoquinolin-4-yl, tetrahydroisoquinolin-5-yl, tetrahydroisoquinolin-6-yl, tetrahydroisoquinolin-7-yl and tetrahydroisoquinolin-8-yl. The term "1H-pyrrolizine" as used herein includes 1H-pyrrolizin-1-yl, 1H-pyrrolizin-2-yl, 1H-pyrrolizin-3-yl, 1H-pyrrolizin-5-yl, 1H-pyrrolizin-6-yl and 1H-pyrrolizin-7-yl.

The term "3H-pyrrolizine" as used herein includes 3H-pyrrolizin-1-yl, 3H-pyrrolizin-2-yl, 3H-pyrrolizin-3-yl, 3H-pyrrolizin-5-yl, 3H-pyrrolizin-6-yl and 3H-pyrrolizin-7-yl.

When the suffix "ene" is used in conjunction with a heterocyclyl group, i.e. "heterocyclylene", this is intended to mean the heterocyclyl group as defined herein having two single bonds as points of attachment to other groups.

The term "heterocyclyloxy", as a group or part of a group, refers to a group having the formula —O—$R^i$ wherein $R^i$ is heterocyclyl as defined herein above.

The term "heterocyclyl$C_{1-6}$alkyloxy", as a group or part of a group, refers to a group having the formula —O—$R^a$—$R^i$ wherein $R^i$ is heterocyclyl, and $R^a$ is $C_{1-6}$alkylene as defined herein above.

The term "heterocyclyl$C_{1-6}$alkyl", as a group or part of a group, means a $C_{1-6}$alkyl as defined herein, wherein at least one hydrogen atom is replaced by at least one heterocyclyl as defined herein.

The term "heterocyclylene$C_{1-6}$alkylene", as a group or part of a group, refers to a group having the formula —$R^j$—$R^a$ wherein $R^j$ is heterocyclylene as defined herein and $R^a$ is $C_{1-6}$alkylene as defined herein.

The term "heteroaryl" as a group or part of a group, refers but is not limited to 5 to 12 carbon-atom aromatic rings or ring systems containing 1 or 2 rings which can be fused together or linked covalently, typically containing 5 to 6 atoms; at least one of which is aromatic in which one or more carbon atoms in one or more of these rings can be replaced by N, O and/or S atoms where the N and S heteroatoms may optionally be oxidized and the N heteroatoms may optionally be quaternized, and wherein at least one carbon atom of said heteroaryl can be oxidized to form at least one C=O. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, thienopyridinyl, purinyl, imidazo[1,2-a]pyridinyl, 6-oxopyridazin-1(6H)-yl, 2-oxopyridin-1(2H)-yl, 6-oxopyridazin-1(6H)-yl, 2-oxopyridin-1(2H)-yl, 1,3-benzodioxolyl, quinolinyl, isoquinolinyl, cinnolinyl, quinazolinyl, quinoxalinyl; preferably said heteroaryl group is selected from the group consisting of pyridyl, 1,3-benzodioxolyl, benzo[d]oxazol-2(3H)-one, 2,3-dihydro-benzofuranyl, pyrazinyl, pyrazolyl, pyrrolyl, isoxazolyl, thiophenyl, imidazolyl, benzimidazolyl, pyrimidinyl, triazolyl and thiazolyl.

The term "pyrrolyl" (also called azolyl) as used herein includes pyrrol-1-yl, pyrrol-2-yl and pyrrol-3-yl.

The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl, oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, -indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl.

The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol-4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quinazolin-4-yl, quinazolin-5-yl, quinazolin-6-yl, quinazolin-7-yl and quinazolin-8-yl. The term "quinoxalinyl" as used herein includes quinoxalin-2-yl, quinoxalin-5-yl, and quinoxalin-6-yl.

When the suffix "ene" is used in conjunction with a heteroaryl group, i.e. "heteroarylene", this is intended to mean the heteroaryl group as defined herein having two single bonds as points of attachment to other groups.

The term "heteroaryloxy", as a group or part of a group, refers to a group having the formula —O—$R^k$ wherein $R^k$ is heteroaryl as defined herein above.

The term "heteroaryl$C_{1-6}$alkyl", as a group or part of a group, means a $C_{1-6}$alkyl as defined herein, wherein at least one hydrogen atom is replaced by at least one heteroaryl as defined herein.

The term "heteroaryl$C_{1-6}$alkyloxy", as a group or part of a group, refers to a group having the formula —O—$R^a$—$R^k$ wherein $R^k$ is heteroaryl, and $R^a$ is $C_{1-6}$alkylene as defined herein above.

The term "heteroarylene$C_{1-6}$alkylene", as a group or part of a group, refers to a group having the formula —$R^m$—$R^a$— wherein $R^m$ is heteroarylene as defined herein and $R^a$ is $C_{1-6}$alkylene as defined herein.

The term "cyano$C_{1-6}$alkyl" as a group or part of a group, refers to a $C_{1-6}$alkyl group having the meaning as defined above wherein at least one hydrogen atom is replaced with at least one cyano group as defined herein. Non-limiting examples of such cyano$C_{1-6}$alkyl groups include cyanomethyl, 1-cyanoethyl, 1-cyanopropyl and the like.

The term "cyano$C_{1-6}$alkyloxy", as a group or part of a group, refers to a group having the formula —O—$R^n$ wherein $R^a$ is cyano$C_{1-6}$alkyl as defined herein above.

The term "$C_{1-6}$alkylthio", as a group or part of a group, refers to a group having the formula —S—$R^b$ wherein $R^b$ is $C_{1-6}$alkyl as defined herein above. Non-limiting examples of $C_{1-6}$alkylthio groups include methylthio (—$SCH_3$), ethylthio (—$SCH_2CH_3$), n-propylthio, isopropylthio, n-butylthio, isobutylthio, sec-butylthio, tert-butylthio and the like.

The term "$C_{2-6}$alkenylthio", as a group or part of a group, refers to a group having the formula —S—$R^d$ wherein $R^d$ is $C_{2-6}$alkenyl as defined herein above.

The term "$C_{2-6}$alkynylthio", as a group or part of a group, refers to a group having the formula —S—$R^e$ wherein $R^e$ is $C_{2-6}$alkynyl as defined herein above.

The term "$C_{6-12}$arylthio", as a group or part of a group, refers to a group having the formula —S—$R^g$ wherein $R^g$ is $C_{6-12}$aryl as defined herein above.

The term "$C_{3-12}$cycloalkylthio", as a group or part of a group, refers to a group having the formula —S—$R^f$ wherein $R^f$ is $C_{3-12}$cycloalkyl as defined herein above.

The term "$C_{6-12}$aryl$C_{1-6}$alkylthio", as a group or part of a group, refers to a group having the formula —S—$R^a$—$R^g$ wherein $R^a$ is $C_{1-6}$alkylene and $R^g$ is $C_{6-12}$aryl as defined herein above.

The term "heterocyclylthio", as a group or part of a group, refers to a group having the formula —S—$R^i$ wherein $R^i$ is heterocyclyl as defined herein above.

The term "heteroarylthio", as a group or part of a group, refers to a group having the formula —S—$R^k$ wherein $R^k$ is heteroaryl as defined herein above.

The term "heterocyclyl$C_{1-6}$alkylthio", as a group or part of a group, refers to a group having the formula —S—$R^a$—$R^g$ k wherein $R^a$ is $C_{1-6}$alkylene and $R^k$ is heterocyclyl as defined herein above.

The term "heteroaryl$C_{1-6}$alkylthio", as a group or part of a group, refers to a group having the formula —S—$R^a$—$R^k$ wherein $R^a$ is $C_{1-6}$alkylene and $R^k$ is heteroaryl as defined herein above.

The term "cyano$C_{1-6}$alkylthio", as a group or part of a group, refers to a group having the formula —S—$R^n$ wherein $R^a$ is cyano$C_{1-6}$alkyl as defined herein above.

The term "mono- or di-$C_{1-6}$alkylamino", as a group or part of a group, refers to a group of formula —N($R^o$)($R^p$) wherein $R^o$ and $R^p$ are each independently selected from hydrogen, or $C_{1-6}$alkyl, wherein at least one of $R^o$ or $R^p$ is $C_{1-6}$alkyl. Thus, alkylamino include mono-alkyl amino group (e.g. mono-$C_{1-6}$alkylamino group such as methylamino and ethylamino), and di-alkylamino group (e.g. di-$C_{1-6}$alkylamino group such as dimethylamino and diethylamino). Non-limiting examples of suitable mono- or di-$C_{1-6}$alkylamino groups include n-propylamino, isopropylamino, n-butylamino, i-butylamino, sec-butylamino, t-butylamino, pentylamino, n-hexylamino, di-n-propylamino, di-i-propylamino, ethylmethylamino, methyl-n-propylamino, methyl-i-propylamino, n-butylmethylamino, i-butylmethylamino, t-butylmethylamino, ethyl-n-propylamino, ethyl-i-propylamino, n-butylethylamino, i-butylethylamino, t-butylethylamino, di-n-butylamino, di-i-butylamino, methylpentylamino, methylhexylamino, ethylpentylamino, ethylhexylamino, propylpentylamino, propylhexylamino, and the like.

The term "mono- or di-$C_{6-12}$arylamino", as a group or part of a group, refers to a group of formula —N($R^q$)($R^r$) wherein $R^q$ and $R^r$ are each independently selected from hydrogen, $C_{6-12}$aryl, or $C_{1-6}$alkyl, wherein at least one of $R^q$ or $R^r$ is $C_{6-12}$aryl.

The term "mono- or di-$C_{3-8}$cycloalkylamino", as a group or part of a group, refers to a group of formula —N($R^s$)($R^t$) wherein $R^s$ and $R^t$ are each independently selected from hydrogen, $C_{3-8}$cycloalkyl, or $C_{1-6}$alkyl, wherein at least one of $R^s$ or $R^t$ is $C_{3-8}$cycloalkyl.

The term "amino$C_{1-6}$alkyl", as a group or part of a group, refers to a group of formula —$R^a$—NR$^o$R$^p$ wherein $R^a$ is $C_{1-6}$alkylene, $R^o$ is hydrogen or $C_{1-6}$alkyl as defined herein, and $R^p$ is hydrogen or $C_{1-6}$alkyl as defined herein.

The term "mono- or di-heteroarylamino", as a group or part of a group, refers to a group of formula —N($R^u$)($R^v$) wherein $R^u$ and $R^v$ are each independently selected from hydrogen, heteroaryl, or $C_{1-6}$alkyl, wherein at least one of $R^u$ or $R^v$ is heteroaryl as defined herein.

The term "mono- or di-heterocyclylamino", as a group or part of a group, refers to a group of formula —N($R^w$)($R^x$) wherein $R^w$ and $R^x$ are each independently selected from hydrogen, heterocyclyl, or $C_{1-6}$alkyl, wherein at least one of $R^w$ or $R^x$ is heterocyclyl as defined herein.

The term "hydroxycarbonyl$C_{1-6}$alkyl", as a group or part of a group, refers to a group of formula —$R^a$—COOH, wherein $R^a$ is $C_{1-6}$alkylene as defined herein.

The term "$C_{1-6}$alkyloxycarbonyl", as a group or part of a group, refers to a group of formula —COO—$R^b$, wherein $R^b$ is $C_{1-6}$alkyl as defined herein.

The term "mono- or di$C_{1-6}$alkylaminocarbonyl", as a group or part of a group, refers to a group of formula —CONR$^o$R$^p$ wherein R$^o$R$^p$ are each independently selected from hydrogen, or $C_{1-6}$alkyl, wherein at least one of $R^o$ or $R^p$ is $C_{1-6}$alkyl.

The term "$C_{1-6}$alkylcarbonyl", as a group or part of a group, refers to a group of formula —CO—$R^b$, wherein $R^b$ is $C_{1-6}$alkyl as defined herein.

The term "$C_{1-6}$alkylcarbonylamino", as a group or part of a group, refers to a group of formula —NR$^o$—CO—$R^b$, wherein $R^o$ is selected from hydrogen, or $C_{1-6}$alkyl and $R^b$ is $C_{1-6}$alkyl as defined herein.

The term "mono or di-$C_{1-6}$alkylaminocarbonyl$C_{1-6}$alkyl", as a group or part of a group, refers to a group of formula —$R^a$—CONR$^o$R$^p$ wherein R$^o$R$^p$ are each independently selected from hydrogen, or $C_{1-6}$alkyl, wherein at least one of $R^o$ or $R^p$ is $C_{1-6}$alkyl, and $R^a$ is $C_{1-6}$alkylene as defined herein.

The term "leaving group" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a trihalomethyl group (e.g. $CCl_3$, $CI_3$, $CBr_3$).

The term "a saturated or unsaturated 3-, 4-, 5-, 6- or 7-membered ring" as used herein encompasses saturated or unsaturated carbon only membered rings, as well as saturated or unsaturated heteroatoms containing rings. The term "a saturated 3-, 4-, 5-, 6- or 7-carbon membered ring" as used herein refers to saturated carbon only membered ring such as $C_{3-7}$cycloalkyl and $C_{3-7}$cycloalkylene.

Whenever used in the present invention the term "compounds of the invention" or a similar term is meant to include the compounds of general formula (I) or (II) and any subgroup thereof. This term also refers to the compounds as depicted in Table 1 and their derivatives, N-oxides, salts, solvates, hydrates, stereoisomeric forms, racemic mixtures, tautomeric forms, optical isomers, analogues, pro-drugs, esters and metabolites, as well as their quaternized nitrogen analogues. The N-oxide forms of said compounds are meant to comprise compounds wherein one or several nitrogen atoms are oxidized to the so-called N-oxide.

Preferred statements (features) and embodiments of the compounds and processes of this invention are now set forth. Each statements and embodiments of the invention so defined may be combined with any other statement and/or embodiments unless clearly indicated to the contrary. In particular, any feature indicated as being preferred or advantageous may be combined with any other feature or features indicated as being preferred or advantageous.

Numbered statements of this invention are:

1. A compound of formula (I) or (II); or a stereoisomer, enantiomer, racemic, or tautomer thereof,

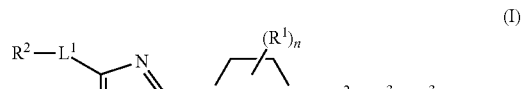

(I)

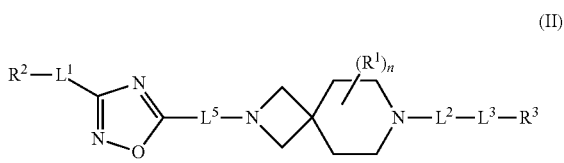

(II)

wherein n is an integer selected from 0, 1, 2 or 3;

$R^1$ is selected from the group consisting of $C_{1-6}$alkyl, halo, halo$C_{1-6}$alkyl, and halo$C_{1-6}$alkyloxy;

$R^2$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —OR$^{15}$, —SR$^{16}$, halo$C_{1-6}$alkyl, halo$C_{1-6}$alkyloxy, amino, —NR$^{17}$R$^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —OR$^{15}$, —SR$^{16}$, halo$C_{1-6}$alkyl, halo$C_{1-6}$alkyloxy, —NR$^{17}$R$^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$;

L¹ is a single bond, or is a group of formula (i);

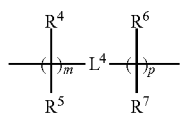

wherein the left side of the group of formula (i) is attached to R² and the right side thereof is attached to the oxadiazole ring; and wherein, m is an integer selected from 0, 1, 2, 3 or 4;
p is an integer selected from 0, 1, 2, 3 or 4;
L⁴ is a single bond, or is selected from the group consisting of —O—, and —NR⁸—;
R⁴ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
R⁵ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
or R⁴ and R⁵ together with the carbon atom to which they are attached form a saturated or unsaturated 3-, 4-, 5-, 6- or 7-membered ring;
R⁶ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
R⁷ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
or R⁶ and R⁷ together with the carbon atom to which they are attached form a saturated or unsaturated 3-, 4-, 5-, 6- or 7-membered ring;
R⁸ is selected from the group consisting of hydrogen, and $C_{1-6}$alkyl;
L² is a single bond or is selected from the group consisting of —SO₂—, —PO₄—, —PO₃—, and —(CR⁹R¹⁰)$_q$—; wherein,
q is an integer selected from 1, 2 or 3;
R⁹ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
R¹⁰ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
or R⁹ and R¹⁰ together with the carbon atom to which they are attached form a saturated or unsaturated 3-, 4-, 5-, 6- or 7-membered ring;
L³ is a single bond or is selected from the group consisting of —(CR¹¹R¹²)$_r$—, —O—, and —NR¹³—; wherein,
r is an integer selected from 1, 2 or 3;
R¹¹ is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
R¹² is selected from the group consisting of hydrogen, $C_{1-6}$alkyl, halo, hydroxyl, —OR¹⁵, —SR¹⁶, halo$C_{1-6}$alkyl, and halo$C_{1-6}$alkyloxy;
or R¹¹ and R¹² together with the carbon atom to which they are attached form a saturated or unsaturated 3-, 4-, 5-, 6- or 7-membered ring;
R¹³ is selected from the group consisting of hydrogen, and $C_{1-6}$alkyl;
wherein at least one of L², L³ is not a single bond;

L⁵ is a single bond or —CO—;
each R¹⁵ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{3-8}$cycloalkyl$C_{1-6}$alkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more Z¹;
and wherein at least one carbon atom or heteroatom of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or S(O)₂;
each R¹⁶ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more Z²;
and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or S(O)₂;
each R¹⁷ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;
and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or S(O)₂;
each R¹⁸ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;
and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or S(O)₂;
or wherein R¹⁷ and R¹⁸ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or S(O)₂;
each R¹⁹ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;
wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or S(O)$_2$, each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl can be oxidized to form at least one C=O, C=S, N=O, N=S, S=O or S(O)$_2$;

each $R^{21}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene$C_{1-6}$alkylene*; wherein * represents where $R^{21}$ is bound to —CO—;

and wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, C=S, N=O, N=S, S=O or S(O)$_2$;

each $Z^1$ is independently selected from the group consisting of halo, hydrogen, $C_{1-6}$alkyl, halo$C_{1-6}$alkyl, halo$C_{1-6}$ alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —OR$^{15}$, —SR$^{16}$, cyano, amino, —NR$^{17}$R$^{18}$, —CO$_2$R$^{19}$, —C(O)NR$^{17}$R$^{18}$, —C(O)R$^{19}$, —S(O)R$^{19}$, —S(O)$_2$R$^{19}$, —SO$_2$NR$^{17}$R$^{18}$, nitro, —NR$^{20}$C(O)R$^{19}$, —R$^{21}$—C(O)NR$^{17}$R$^{18}$, —NR$^{20}$S(O)$_2$R$^{19}$, and NR$^{20}$C(O)NR$^{17}$R$^{18}$; and wherein two $Z^1$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, C=S, N=O, N=S, S=O or S(O)$_2$;

each $Z^2$ is independently selected from the group consisting of halo, hydrogen, $C_{1-6}$alkyl, halo$C_{1-6}$alkyl, halo$C_{1-6}$ alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —OR$^{15}$, —SR$^{16}$, cyano, amino, —NR$^{17}$R$^{18}$, —CO$_2$R$^{19}$, —C(O)NR$^{17}$R$^{18}$, —C(O)R$^{19}$, —S(O)R$^{19}$, —S(O)$_2$R$^{19}$, —SO$_2$NR$^{17}$R$^{18}$, nitro, —NR$^{20}$C(O)R$^{19}$, —R$^{21}$—C(O)NR$^{17}$R$^{18}$, —NR$^{20}$S(O)$_2$R$^{19}$, and —NR$^{20}$C(O)NR$^{17}$R$^{18}$; and wherein two $Z^2$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$ alkyl can be oxidized to form at least one C=O, C=S, N=O, N=S, S=O or S(O)$_2$;

and with the proviso that for a compound of formula (I) when $R^2$ is $C_{6-12}$aryl; $L^3$ is a single bond, —(CR$^{11}$R$^{12}$)$_r$—, —O—, or —NR$^{13}$—; then $R^3$ is not hydrogen, $C_{1-6}$alkyl, hydroxyl, or —OR$^{15}$;

and with the proviso that for a compound of formula (I) when L is a single bond, $R^2$ is not hydrogen;

and with the proviso that said compound is not 5-(4-((3-methylpyridin-2-yl)methyl)piperazin-1-yl)-3-phenyl-1,2,4-oxadiazole;
5-(4-(3-fluorobenzyl)piperazin-1-yl)-3-phenyl-1,2,4-oxadiazole;
3-(4-bromophenyl)-5-(4-(4-fluorophenethyl)piperazin-1-yl)-1,2,4-oxadiazole;
3-(3,5-dichlorophenyl)-5-(4-(pyridin-2-ylmethyl)piperazin-1-yl)-1,2,4-oxadiazole;
1-(7-methyl-1-(3-(4-(3-(pyridin-3-yl)-1,2,4-oxadiazol-5-yl)piperazin-1-yl)propyl)-1H-indol-3-yl)ethanone;
5-(4-((2-methoxypyrimidin-5-yl)methyl)piperazin-1-yl)-3-phenyl-1,2,4-oxadiazole;
2-((4-(3-phenyl-1,2,4-oxadiazol-5-yl)piperazin-1-yl)methyl)benzoic acid;
5-(4-((2-ethyl-4-methyl-1H-imidazol-5-yl)methyl)piperazin-1-yl)-3-phenyl-1,2,4-oxadiazole;
3-phenyl-5-(4-((2-phenylthiazol-4-yl)methyl)piperazin-1-yl)-1,2,4-oxadiazole;
5-(4-benzylpiperazin-1-yl)-3-(3-methoxyphenyl)-1,2,4-oxadiazole;
5-(4-benzylpiperazin-1-yl)-3-(2,3-dimethoxyphenyl)-1,2,4-oxadiazole;
5-(4-(benzo[d][1,3]dioxol-5-ylmethyl)piperazin-1-yl)-3-phenyl-1,2,4-oxadiazole;
5-(4-(benzo[d][1,3]dioxol-5-ylmethyl)piperazin-1-yl)-3-(3,4-dimethoxyphenyl)-1,2,4-oxadiazole;
5-(4-(benzo[d][1,3]dioxol-5-ylmethyl)piperazin-1-yl)-3-(4-methoxyphenyl)-1,2,4-oxadiazole;
5-(4-(benzo[d][1,3]dioxol-5-ylmethyl)piperazin-1-yl)-3-(2-fluorophenyl)-1,2,4-oxadiazole;
5-(4-benzylpiperazin-1-yl)-3-phenyl-1,2,4-oxadiazole;
5-(4-benzylpiperazin-1-yl)-3-(4-methoxyphenyl)-1,2,4-oxadiazole;
5-(4-(benzo[d][1,3]dioxol-5-ylmethyl)piperazin-1-yl)-3-(3-methoxyphenyl)-1,2,4-oxadiazole;
5-(4-(benzo[d][1,3]dioxol-5-ylmethyl)piperazin-1-yl)-3-(2,3-dimethoxyphenyl)-1,2,4-oxadiazole;
3-(4-methoxyphenyl)-5-(4-(2,3,4-trimethoxybenzyl)piperazin-1-yl)-1,2,4-oxadiazole;
3-(3,4-dimethoxyphenyl)-5-(4-(2,3,4-trimethoxybenzyl)piperazin-1-yl)-1,2,4-oxadiazole;
3-(2,3-dimethoxyphenyl)-5-(4-(2,3,4-trimethoxybenzyl)piperazin-1-yl)-1,2,4-oxadiazole;
3-(2-fluorophenyl)-5-(4-(2,3,4-trimethoxybenzyl)piperazin-1-yl)-1,2,4-oxadiazole;
5-(4-benzylpiperazin-1-yl)-3-(2-fluorophenyl)-1,2,4-oxadiazole;
3-phenyl-5-(4-(2,3,4-trimethoxybenzyl)piperazin-1-yl)-1,2,4-oxadiazole;
5-(4-benzylpiperazin-1-yl)-3-(3,4-dimethoxyphenyl)-1,2,4-oxadiazole;
5-(4-((2,3-dihydrobenzo[b][1,4]dioxin-6-yl)methyl)piperazin-1-yl)-3-methyl-1,2,4-oxadiazole;
5-(4-(benzo[d][1,3]dioxol-5-ylmethyl)piperazin-1-yl)-3-methyl-1,2,4-oxadiazole;
3-(4-bromophenyl)-5-(4-(4-isopropoxyphenethyl)piperazin-1-yl)-1,2,4-oxadiazole;
3-(4-bromophenyl)-5-(4-phenethylpiperazin-1-yl)-1,2,4-oxadiazole;
5-(4-(benzo[b][1,4]dioxin-6-ylmethyl)piperazin-1-yl)-1,2,4-oxadiazole;
5-(4-isobutylpiperazin-1-yl)-3-isopropyl-1,2,4-oxadiazole;
N,N,2,2-tetramethyl-3-[4-(3-phenyl-1,2,4-oxadiazol-5-yl)piperazin-1-yl]propan-1-amine;
3-(4-bromophenyl)-5-[4-(2-nitrophenyl)sulfonylpiperazin-1-yl]-1,2,4-oxadiazole;

5-(4-benzylsulfonylpiperazin-1-yl)-3-cyclopropyl-1,2,4-oxadiazole;

5-[4-(4-methoxyphenyl)sulfonylpiperazin-1-yl]-3-phenyl-1,2,4-oxadiazole;

or a solvate, hydrate, pharmaceutically acceptable salt, or prodrug thereof.

2. The compound according to statement 1, having structural formula (IA) or (IIA),

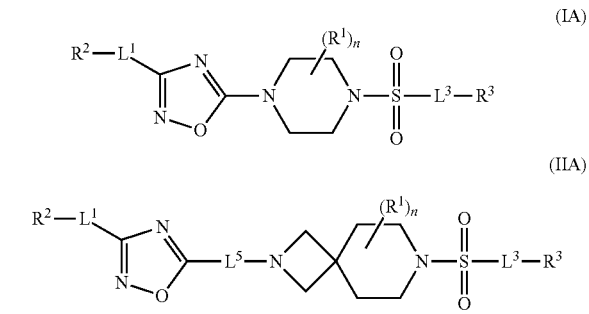

wherein $L^1$, $L^3$, $L^5$, n, $R^1$, $R^2$ and $R^3$ have the same meaning as that defined in statement 1.

3. The compound according to statements 1 or 2, having structural formula (IB) or (IIB),

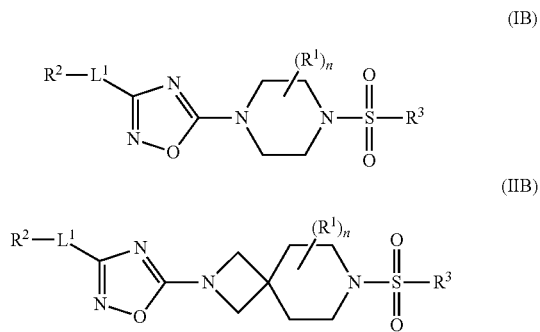

wherein, $L^1$, n, $R^1$, $R^2$ and $R^3$ have the same meaning as that defined in statements 1 or 2.

4. The compound according to any one of statements 1 to 3, wherein $R^2$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, halo$C_{1-6}$alkyloxy, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, halo$C_{1-6}$alkyloxy, mono or di-$C_{1-6}$alkylamino, mono or di-$C_{6-12}$arylamino, mono or di-$C_{3-8}$cycloalkylamino, mono or di-heterocyclylamino, or mono or di-heteroarylamino, can be unsubstituted or substituted with—one, two, or three $Z^1$.

5. The compound according to any one of statements 1 to 4, wherein $R^2$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, $C_{1-6}$alkyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, halo$C_{1-6}$alkyl, halo$C_{1-6}$alkyloxy, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, $C_{1-6}$alkyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, $C_{1-6}$alkylthio, halo$C_{1-6}$alkyl, halo$C_{1-6}$alkyloxy, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, can be unsubstituted or substituted with one, two, or three $Z^1$.

6. The compound according to any one of statements 1 to 5, wherein $R^2$ is selected from the group consisting of $C_{6-12}$aryl, hydrogen, $C_{1-6}$alkyl, $C_{3-12}$cycloalkyl, heterocyclyl, heteroaryl, halo, hydroxyl, $C_{1-6}$alkyloxy, thiol, $C_{1-6}$alkylthio, halo$C_{1-6}$alkyl, halo$C_{1-6}$alkyloxy, amino, mono or di-$C_{1-6}$alkylamino, mono or di-$C_{6-12}$arylamino, mono or di-$C_{3-8}$cycloalkylamino, and cyano; and wherein said $C_{6-12}$aryl, $C_{1-6}$alkyl, $C_{3-12}$cycloalkyl, heterocyclyl, heteroaryl, $C_{1-6}$alkyloxy, $C_{1-6}$alkylthio, halo$C_{1-6}$alkyl, halo$C_{1-6}$alkyloxy, mono or di-$C_{1-6}$alkylamino, mono or di-$C_{6-12}$arylamino, mono or di-$C_{3-8}$cycloalkylamino, can be unsubstituted or substituted with one, two, or three $Z^1$.

7. The compound according to any one of statements 1 to 6, wherein $R^2$ is selected from the group consisting of $C_{6-12}$aryl, hydrogen, $C_{1-6}$alkyl, $C_{3-12}$cycloalkyl, heterocyclyl, heteroaryl, halo, hydroxyl, $C_{1-6}$alkyloxy, thiol, $C_{1-6}$alkylthio, halo$C_{1-6}$alkyl, halo$C_{1-6}$alkyloxy, and cyano; and wherein said $C_{6-12}$aryl, $C_{1-6}$alkyl, $C_{3-12}$cycloalkyl, heterocyclyl, heteroaryl, $C_{1-6}$alkyloxy, $C_{1-6}$alkylthio, halo$C_{1-6}$alkyl, or halo$C_{1-6}$alkyloxy can be unsubstituted or substituted with one, two, or three $Z^1$.

8. The compound according to any one of statements 1 to 7, wherein $R^2$ is selected from the group consisting of $C_{6-12}$aryl, hydrogen, $C_{1-6}$alkyl, $C_{3-12}$cycloalkyl, heterocyclyl, heteroaryl, halo, hydroxyl, $C_{1-6}$alkyloxy, halo$C_{1-6}$alkyl, and cyano; and wherein said $C_{6-12}$aryl, $C_{1-6}$alkyl, $C_{3-12}$cycloalkyl, heterocyclyl, heteroaryl, $C_{1-6}$alkyloxy, or halo$C_{1-6}$alkyl, can be unsubstituted or substituted one, two, or three $Z^1$.

9. The compound according to any one of statements 1 to 8, having structural formula (IC) or (IIC),

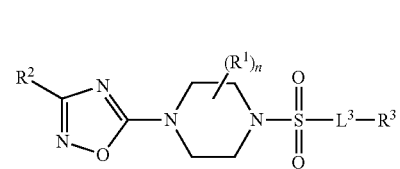
(IC)

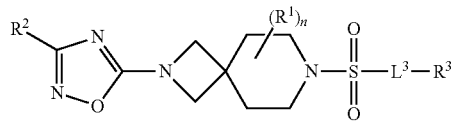
(IIC)

wherein, $L^3$, n, $R^1$, $R^2$ and $R^3$ have the same meaning as defined in any one of statements 1 to 8.

10. The compound according to any one of statements 1 to 8, having structural formula (ID) or (IIID),

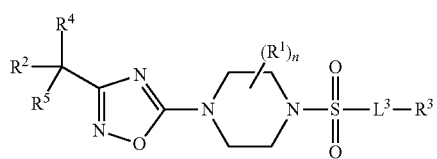
(ID)

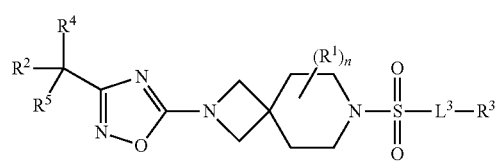
(IIID)

wherein, $L^3$, n, $R^1$, $R^2$, $R^3$, $R^4$, and $R^5$, have the same meaning as defined in any one of statements 1 to 8.

11. The compound according to any one of statements 1 to 8, having structural formula (IE) or (IIIE),

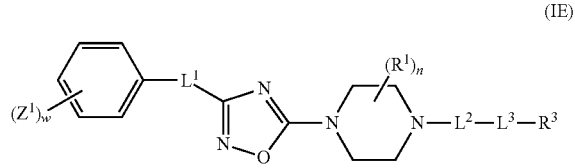
(IE)

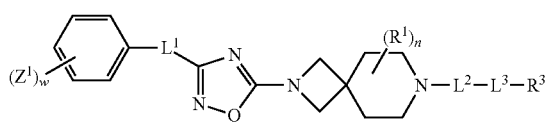
(IIIE)

wherein, $L^3$, $L^2$, $L^3$, $L^5$, n, $R^1$, $R^2$, $R^3$, and $Z^1$ have the same meaning as that defined in any one of statements 1 to 8, and wherein, w is an integer selected from 1, 2, or 3.

12. The compound according to any one of statements 1 to 8 and 11, having structural formula (IF) or (IIIF),

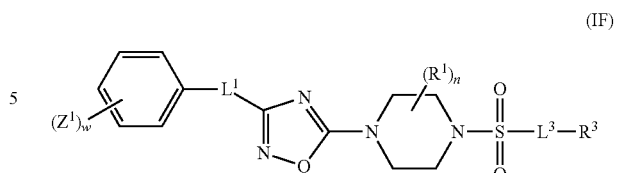
(IF)

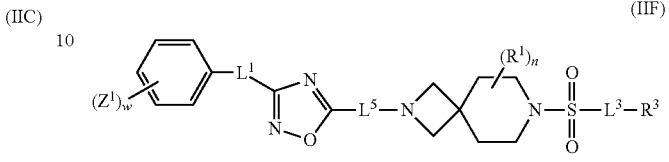
(IIIF)

wherein, $L^1$, $L^3$, $L^5$, n, $R^1$, $R^3$, and $Z^1$ have the same meaning as that defined in any one of statements 1 to 8 and 11, and wherein, w is an integer selected from 1, 2, or 3.

13. The compound according to any one of statements 1 to 11, having structural formula (IG) or (IIG),

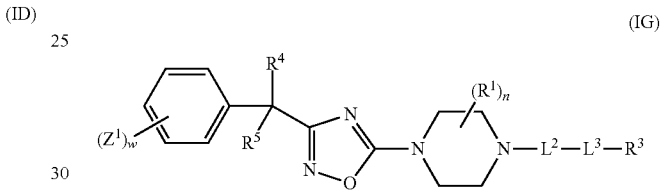
(IG)

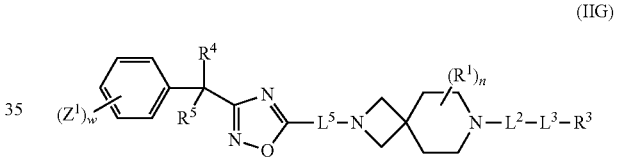
(IIG)

wherein, $L^2$, $L^3$, $L^5$, n, $R^1$, $R^3$, $R^4$, $R^5$, and $Z^1$ have the same meaning as defined in any one of statements 1 to 11, and wherein, w is an integer selected from 1, 2, or 3.

14. The compound according to any one of statements 1 to 13, wherein w is an integer selected from 1, 2, or 3;

$R^4$ is selected from the group consisting of $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$alkyloxy;

$R^5$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$alkyloxy;

or $R^4$ and $R^5$ together with the carbon atom to which they are attached form a saturated or unsaturated 3-, 4-, 5-, 6- or 7-membered ring.

15. The compound according to any one of statements 1 to 14, having structural formula (IH) or (IIH),

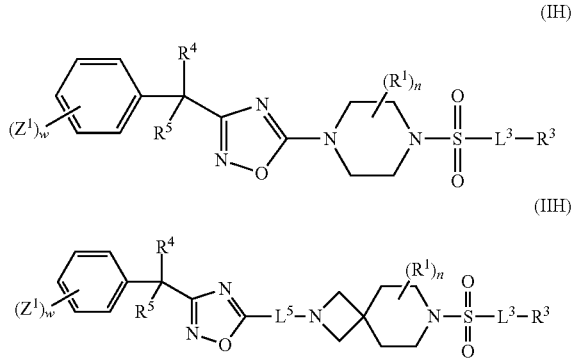

wherein, $L^3$, $L^5$, n, $R^1$, $R^3$, $R^4$, $R^5$, and $Z^1$ and w have the same meaning as defined in any one of statements 1 to 15, and wherein, w is an integer selected from 1, 2, or 3.

16. The compound according to any one of statements 1 to 15, wherein $R^4$ is selected from the group consisting of $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy; and $R^5$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.

17. The compound according to any one of statements 1 to 16, wherein $R^4$ is selected from the group consisting of $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy; and $R^5$ is selected from the group consisting of hydrogen, $C_{1-6}$alkyl, halo, hydroxyl, $C_{1-6}$alkyloxy, thiol, $C_{1-6}$alkylthio, halo$C_{1-6}$ alkyl, and halo$C_{1-6}$alkyloxy.

18. The compound according to any one of statements 1 to 17, wherein $R^4$ is selected from the group consisting of $C_{1-6}$alkyl, halo, halo$C_{1-6}$alkyl, and halo$C_{1-6}$alkyloxy; and $R^5$ is selected from the group consisting of hydrogen, $C_{1-6}$alkyl, halo, halo$C_{1-6}$alkyl, and halo$C_{1-6}$alkyloxy.

19. The compound according to any one of statements 1 to 18, wherein $R^4$ is selected from the group consisting of $C_{1-6}$alkyl, and halo.

20. The compound according to any one of statements 11 to 18, wherein w is an integer selected from 1, or 2.

21. The compound according to any one of statements 1 to 20, wherein $R^1$ is selected from the group consisting of $C_{1-6}$alkyl, and halo.

22. The compound according to any one of statements 1 to 21, wherein $R^1$ is $C_{1-6}$alkyl.

23. The compound according to any one of statements 1 to 22, wherein n is an integer selected from 0 or 1.

24. The compound according to any one of statements 1 to 23, wherein n is 0.

25. The compound according to any one of statements 1 to 24, wherein R is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, halo$C_{1-6}$alkyloxy, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-2}$aryl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$ alkyloxy, heteroaryl$C_{1-6}$alkyloxy, cyano$C_{1-6}$alkyloxy, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$ alkyl, halo$C_{1-6}$alkyloxy, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, can be unsubstituted or substituted with one, two, or three $Z^2$.

26. The compound according to any one of statements 1 to 25, wherein $R^3$ is selected from the group consisting of $C_{6-12}$aryl, hydrogen, $C_{1-6}$alkyl, $C_{3-12}$cycloalkyl, heterocyclyl, heteroaryl, halo, hydroxyl, $C_{1-6}$alkyloxy, $C_{6-12}$aryloxy, cyano$C_{1-6}$alkyloxy, thiol, $C_{1-6}$alkylthio, halo$C_{1-6}$alkyl, halo$C_{1-6}$alkyloxy, amino, mono or di-$C_{1-6}$alkylamino, mono or di-$C_{6-12}$arylamino, and mono or di-$C_{3-8}$cycloalkylamino; and wherein said $C_{6-12}$aryl, $C_{1-6}$alkyl, $C_{3-12}$cycloalkyl, heterocyclyl, heteroaryl, $C_{1-6}$alkyloxy, $C_{6-12}$aryloxy, cyano$C_{1-6}$alkyloxy, $C_{1-6}$alkylthio, halo$C_{1-6}$ alkyl, halo$C_{1-6}$alkyloxy, mono or di-$C_{1-6}$alkylamino, mono or di-$C_{6-12}$arylamino, mono or di-$C_{3-8}$cycloalkylamino, can be unsubstituted or substituted with one, two, or three $Z^2$.

27. The compound according to any one of statements 1 to 26, wherein $R^3$ is selected from the group consisting of $C_{6-12}$aryl, hydrogen, $C_{1-6}$alkyl, $C_{3-12}$cycloalkyl, heterocyclyl, heteroaryl, halo, halo$C_{1-6}$alkyl, halo$C_{1-6}$alkyloxy, amino, mono or di-$C_{1-6}$alkylamino, and mono or di-$C_{6-12}$arylamino; and wherein said $C_{6-12}$aryl, $C_{1-6}$alkyl, $C_{3-12}$cycloalkyl, heterocyclyl, heteroaryl, halo$C_{1-6}$alkyl, halo$C_{1-6}$alkyloxy, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, can be unsubstituted or substituted with one, two, or three $Z^2$.

28. The compound according to any one of statements 1 to 27, wherein $R^3$ is selected from the group consisting of $C_{6-12}$aryl, hydrogen, $C_{1-6}$alkyl, heterocyclyl, heteroaryl, halo, halo$C_{1-6}$alkyl, halo$C_{1-6}$alkyloxy, and mono or di $C_{1-6}$alkylamino; and wherein said $C_{6-12}$aryl, $C_{1-6}$alkyl, heterocyclyl, heteroaryl, halo$C_{1-6}$alkyl, halo$C_{1-6}$alkyloxy, mono or di-$C_{1-6}$alkylamino, can be unsubstituted or substituted with one, two, or three $Z^2$.

29. The compound according to any one of statements 1 to 28, wherein m is an integer selected from 0, 1, or 2.

30. The compound according to any one of statements 1 to 29, wherein m is an integer selected from 0, or 1.

31. The compound according to any one of statements 1 to 30, wherein m is 1.

32. The compound according to any one of statements 1 to 31, wherein p is an integer selected from 0, 1, or 2.
33. The compound according to any one of statements 1 to 32, wherein p is an integer selected from 0, or 1.
34. The compound according to any one of statements 1 to 33, wherein p is 0.
35. The compound according to any one of statements 1 to 34, wherein $L^4$ is a single bond, or is selected from the group consisting of —O—, —NH—, and —N($C_{1-6}$alkyl)-.
36. The compound according to any one of statements 1 to 35, wherein $L^4$ is a single bond, or is selected from the group consisting of —O—, and —NH—.
37. The compound according to any one of statements 1 to 36, wherein $L^4$ is a single bond.
38. The compound according to any one of statements 1 to 37, wherein $R^4$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
39. The compound according to any one of statements 1 to 38, wherein $R^4$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
40. The compound according to any one of statements 1 to 39, wherein $R^4$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
41. The compound according to any one of statements 1 to 40, wherein $R^4$ is selected from the group consisting of hydrogen, $C_{1-6}$alkyl, halo, halo$C_{1-6}$alkyl, and halo$C_{1-6}$alkyloxy.
42. The compound according to any one of statements 1 to 41, wherein $R^5$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$ alkyloxy.
43. The compound according to any one of statements 1 to 42, wherein $R^5$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
44. The compound according to any one of statements 1 to 43, wherein $R^5$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
45. The compound according to any one of statements 1 to 44, wherein $R^5$ is selected from the group consisting of hydrogen, $C_{1-6}$alkyl, halo, halo$C_{1-6}$alkyl, and halo$C_{1-6}$alkyloxy.
46. The compound according to any one of statements 1 to 45, wherein $R^4$ and $R^5$ together with the carbon atom to which they are attached form a $C_{3-7}$cycloalkyl or a $C_{5-7}$cycloalkylene.
47. The compound according to any one of statements 1 to 43, wherein $R^4$ and $R^5$ together with the carbon atom to which they are attached form a $C_{3-6}$cycloalkyl or a $C_{5-6}$cycloalkylene.
48. The compound according to any one of statements 1 to 47, wherein $R^4$ and $R^5$ together with the carbon atom to which they are attached form a $C_{3-6}$cycloalkyl.
49. The compound according to any one of statements 1 to 48, wherein $R^4$ and $R^5$ together with the carbon atom to which they are attached form a $C_{3-5}$ cycloalkyl.
50. The compound according to any one of statements 1 to 49, wherein $R^6$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$ alkyloxy.
51. The compound according to any one of statements 1 to 50, wherein $R^6$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
52. The compound according to any one of statements 1 to 51, wherein $R^6$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
53. The compound according to any one of statements 1 to 52, wherein $R^6$ is selected from the group consisting of hydrogen, $C_{1-6}$alkyl, halo, halo$C_{1-6}$alkyl, and halo$C_{1-6}$alkyloxy.
54. The compound according to any one of statements 1 to 53, wherein $R^7$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$ alkyloxy.
55. The compound according to any one of statements 1 to 54, wherein $R^7$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
56. The compound according to any one of statements 1 to 55, wherein $R^7$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
57. The compound according to any one of statements 1 to 56, wherein $R^7$ is selected from the group consisting of hydrogen, $C_{1-6}$alkyl, halo, halo$C_{1-6}$alkyl, and halo$C_{1-6}$alkyloxy.
58. The compound according to any one of statements 1 to 57, wherein $R^6$ and $R^7$ together with the carbon atom to which they are attached form a $C_{3-7}$cycloalkyl or a $C_{5-7}$cycloalkylene.
59. The compound according to one of statements 1 to 58, wherein $R^6$ and $R^7$ together with the carbon atom to which they are attached form a $C_{3-6}$cycloalkyl or a $C_{5-6}$cycloalkylene.

60. The compound according to any one of statements 1 to 59, wherein $R^6$ and $R^7$ together with the carbon atom to which they are attached form a $C_{3-6}$cycloalkyl.
61. The compound according to any one of statements 1 to 60, wherein $R^6$ and $R^7$ together with the carbon atom to which they are attached form a $C_{3-5}$ cycloalkyl.
62. The compound according to any one of statements 1 to 61, wherein $R^8$ is hydrogen.
63. The compound according to any one of statements 1 to 62, wherein q is 1.
64. The compound according to any one of statements 1 to 63, wherein $R^9$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$ alkyloxy.
65. The compound according to any one of statements 1 to 64, wherein $R^9$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
66. The compound according to any one of statements 1 to 65, wherein $R^9$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
67. The compound according to any one of statements 1 to 66, wherein $R^9$ is selected from the group consisting of hydrogen, $C_{1-6}$alkyl, halo, halo$C_{1-6}$alkyl, and halo$C_{1-6}$alkyloxy.
68. The compound according to any one of statements 1 to 67, wherein $R^{10}$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$ alkyloxy.
69. The compound according to any one of statements 1 to 68, wherein $R^{10}$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
70. The compound according to any one of statements 1 to 69, wherein $R^{10}$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
71. The compound according to any one of statements 1 to 70, wherein $R^{10}$ is selected from the group consisting of hydrogen, $C_{1-6}$alkyl, halo, halo$C_{1-6}$alkyl, and halo$C_{1-6}$alkyloxy.
72. The compound according to any one of statements 1 to 71, wherein $R^9$ and $R^{10}$ together with the carbon atom to which they are attached form a $C_{3-7}$cycloalkyl or a $C_{5-7}$cycloalkylene.
73. The compound according to any one of statements 1 to 72, wherein $R^9$ and $R^{10}$ together with the carbon atom to which they are attached form a $C_{3-6}$cycloalkyl or a $C_{5-6}$cycloalkylene.
74. The compound according to any one of statements 1 to 73, wherein $R^9$ and $R^{10}$ together with the carbon atom to which they are attached form a $C_{3-6}$cycloalkyl.
75. The compound according to any one of statements 1 to 74, wherein $R^9$ and $R^{10}$ together with the carbon atom to which they are attached form a $C_{3-5}$ cycloalkyl.
76. The compound according to any one of statements 1 to 75, wherein $L^2$ is selected from the group consisting of —$SO_2$—, and —$(CR^9R^{10})_q$-.
77. The compound according to any one of statements 1 to 76, wherein $L^2$ is —$SO_2$—.
78. The compound according to any one of statements 1 to 77, wherein $L^2$ is —$(CR^9R^{10})_q$-.
79. The compound according to any one of statements 1 to 78, wherein $L^3$ is a single bond or is selected from the group consisting of —$(CR^{11}R^{12})_r$—, —O—, —NH—, and —N($C_{1-6}$alkyl)-.
80. The compound according to any one of statements 1 to 79, wherein $L^3$ is a single bond or is selected from the group consisting of —$(CR^{11}R^{12})_r$—, and —O—.
81. The compound according to any one of statements 1 to 80, wherein $L^3$ is a single bond or is —$(CR^{11}R^{12})_r$—.
82. The compound according to any one of statements 1 to 81, wherein r is 1.
83. The compound according to any one of statements 1 to 82, wherein $L^3$ is a single bond.
84. The compound according to any one of statements 1 to 83, wherein $R^{11}$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, halo$C_{1-6}$alkyl, and halo$C_{1-6}$ alkyloxy.
85. The compound according to any one of statements 1 to 84, wherein $R^1$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.
86. The compound according to any one of statements 1 to 85, wherein $R^1$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.
87. The compound according to any one of statements 1 to 86, wherein $R^1$ is selected from the group consisting of hydrogen, $C_{1-6}$alkyl, halo, halo$C_{1-6}$alkyl, and halo$C_{1-6}$alkyloxy.
88. The compound according to any one of statements 1 to 87, wherein $R^{12}$ is selected from the group consisting of hydrogen, $C_{1-6}$alkyl, halo, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, 89. The compound according to any one of statements 1 to 88, wherein $R^{12}$ is selected from the group consisting of hydrogen, $C_{1-6}$alkyl, halo, hydroxyl, $C_{1-6}$alkyloxy, $C_{6-12}$aryloxy, $C_{3-12}$cycloalkyloxy, thiol, $C_{1-6}$alkylthio, $C_{6-12}$arylthio, $C_{3-8}$cycloalkylthio, halo$C_{1-6}$alkyl, and halo$C_{1-6}$alkyloxy.

90. The compound according to any one of statements 1 to 89, wherein $R^1$ is selected from the group consisting of hydrogen, $C_{1-6}$alkyl, halo, hydroxyl, $C_{1-6}$alkyloxy, thiol, $C_{1-6}$alkylthio, halo$C_{1-6}$alkyl, and halo$C_{1-6}$alkyloxy.

91. The compound according to any one of statements 1 to 90, wherein $R^{12}$ is selected from the group consisting of hydrogen, $C_{1-6}$alkyl, halo, halo$C_{1-6}$alkyl, and halo$C_{1-6}$alkyloxy.

92. The compound according to any one of statements 1 to 91, wherein $R^{11}$ and $R^{12}$ together with the carbon atom to which they are attached form a $C_{3-7}$cycloalkyl or a $C_{5-7}$cycloalkylene.

93. The compound according to any one of statements 1 to 92, wherein $R^{11}$ and $R^{12}$ together with the carbon atom to which they are attached form a $C_{3-6}$cycloalkyl or a $C_{5-6}$cycloalkylene.

94. The compound according to any one of statements 1 to 93, wherein $R^{11}$ and $R^{12}$ together with the carbon atom to which they are attached form a $C_{3-6}$cycloalkyl.

95. The compound according to any one of statements 1 to 94, wherein $R^{11}$ and $R^{12}$ together with the carbon atom to which they are attached form a $C_{3-5}$ cycloalkyl.

96. The compound according to any one of statements 1 to 95, wherein $R^{13}$ is hydrogen.

97. The compound according to any one of statements 1 to 96, wherein each $R^{15}$ independently selected from the group consisting of $C_{1-6}$alkyl, $C_{2-6}$alkenyl, $C_{2-6}$alkynyl, $C_{6-12}$aryl, $C_{3-8}$cycloalkyl, $C_{3-8}$cycloalkyl$C_{1-6}$alkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^1$; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, or $S(O)_2$.

98. The compound according to any one of statements 1 to 97, wherein each $R^{15}$ is independently selected from the group consisting of $C_{1-6}$alkyl, $C_{2-6}$alkenyl, $C_{2-6}$alkynyl, $C_{6-12}$aryl, $C_{3-8}$cycloalkyl, $C_{3-8}$cycloalkyl$C_{1-6}$alkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^1$; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O.

99. The compound according to any one of statements 1 to 98, wherein each $R^{15}$ is independently selected from the group consisting of $C_{1-6}$alkyl, $C_{6-12}$ aryl, $C_{3-8}$cycloalkyl, $C_{3-8}$cycloalkyl$C_{1-6}$alkyl, $C_{6-12}$ aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$ aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^1$; and wherein at least one carbon atom of said $C_{1-6}$alkyl, $C_{6-12}$ aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O;

100. The compound according to any one of statements 1 to 99, wherein each $R^{15}$ is independently selected from the group consisting of $C_{1-6}$alkyl, $C_{6-12}$ aryl, $C_{3-8}$cycloalkyl$C_{1-6}$alkyl, $C_{3-8}$cycloalkyl, heterocyclyl, heteroaryl, and cyano$C_{1-6}$alkyl; and wherein said $C_{1-6}$alkyl, $C_{6-12}$ aryl, $C_{3-8}$cycloalkyl, heterocyclyl, heteroaryl, and cyano$C_{1-6}$alkyl, can be unsubstituted or substituted with one or more $Z^1$; and wherein at least one carbon atom of said $C_{1-6}$alkyl, $C_{6-12}$ aryl, $C_{3-8}$cycloalkyl, heterocyclyl, heteroaryl, or cyano$C_{1-6}$alkyl can be oxidized to form at least one C=O.

101. The compound according to any one of statements 1 to 100, wherein each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$alkyl, heterocyclyl, heteroaryl, and cyano$C_{1-6}$alkyl; and wherein said $C_{1-6}$alkyl, $C_{6-12}$aryl, $C_{3-8}$cycloalkyl, heterocyclyl, heteroaryl, and cyano$C_{1-6}$alkyl, can be unsubstituted or substituted with one or more $Z^1$; and wherein at least one carbon atom of said $C_{1-6}$alkyl, $C_{3-8}$cycloalkyl, heterocyclyl, heteroaryl, or cyano$C_{1-6}$alkyl can be oxidized to form at least one C=O.

102. The compound according to any one of statements 1 to 101, wherein each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$alkyl, heterocyclyl, heteroaryl, and cyano$C_{1-6}$alkyl; and wherein said $C_{1-6}$alkyl, $C_{6-12}$aryl, $C_{3-8}$cycloalkyl, heterocyclyl, heteroaryl, and cyano$C_{1-6}$alkyl, can be unsubstituted or substituted with one or more $Z^1$.

103. The compound according to any one of statements 1 to 102, wherein $R^{16}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^2$; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, or $S(O)_2$.

104. The compound according to any one of statements 1 to 103, wherein each $R^{16}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclylC$_{1-6}$alkyl, heteroarylC$_{1-6}$alkyl, and cyanoC$_{1-6}$alkyl, can be unsubstituted or substituted with one or more Z$^2$; and wherein at least one carbon atom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, heteroarylC$_{1-6}$alkyl, or cyanoC$_{1-6}$alkyl can be oxidized to form at least one C=O.

105. The compound according to any one of statements 1 to 104, wherein each R$^{16}$ is independently selected from the group consisting of hydrogen, C$_{1-6}$alkyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, heteroarylC$_{1-6}$alkyl, and cyanoC$_{1-6}$alkyl; and wherein said C$_{1-6}$alkyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, heteroarylC$_{1-6}$alkyl, and cyanoC$_{1-6}$alkyl, can be unsubstituted or substituted with one or more Z$^2$; and wherein at least one carbon atom of said C$_{1-6}$alkyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, heteroarylC$_{1-6}$alkyl, or cyanoC$_{1-6}$alkyl can be oxidized to form at least one C=O.

106. The compound according to any one of statements 1 to 105, wherein each R$^{16}$ is independently selected from the group consisting of hydrogen, C$_{1-6}$alkyl, C$_{6-12}$aryl, C$_{3-8}$cycloalkyl, heterocyclyl, heteroaryl, and cyanoC$_{1-6}$alkyl; and wherein said C$_{1-6}$alkyl, C$_{6-12}$aryl, C$_{3-8}$cycloalkyl, heterocyclyl, heteroaryl, and cyanoC$_{1-6}$alkyl, can be unsubstituted or substituted with one or more Z$^2$; and wherein at least one carbon atom of said C$_{1-6}$alkyl, C$_{6-12}$aryl, C$_{3-8}$cycloalkyl, heterocyclyl, heteroaryl, or cyanoC$_{1-6}$alkyl can be oxidized to form at least one C=O.

107. The compound according to any one of statements 1 to 106, wherein each R$^{16}$ is independently selected from the group consisting of hydrogen, C$_{1-6}$alkyl, heterocyclyl, heteroaryl, and cyanoC$_{1-6}$alkyl; and wherein said C$_{1-6}$alkyl, heterocyclyl, heteroaryl, and cyanoC$_{1-6}$alkyl, can be unsubstituted or substituted with one or more Z$^2$; and wherein at least one carbon atom of said C$_{1-6}$alkyl, C$_{3-8}$cycloalkyl, heterocyclyl, heteroaryl, or cyanoC$_{1-6}$alkyl can be oxidized to form at least one C=O.

108. The compound according to any one of statements 1 to 107, wherein each R$^{16}$ is independently selected from the group consisting of hydrogen, C$_{1-6}$alkyl, heterocyclyl, heteroaryl, and cyanoC$_{1-6}$alkyl; and wherein said C$_{1-6}$alkyl, heterocyclyl, and cyanoC$_{1-6}$alkyl, can be unsubstituted or substituted with one or more Z$^2$.

109. The compound according to any one of statements 1 to 108, wherein each R$^{17}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; and wherein at least one carbon atom or heteroatom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O, or S(O)$_2$.

110. The compound according to any one of statements 1 to 109, wherein each R$^{17}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; and wherein at least one carbon atom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O.

111. The compound according to any one of statements 1 to 110, wherein each R$^{17}$ is independently selected from the group consisting of hydrogen, C$_{1-6}$alkyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; and wherein at least one carbon atom of said C$_{1-6}$alkyl, C$_{6-12}$aryl, C$_{3-8}$cycloalkyl, C$_{6-12}$arylC$_{1-6}$alkyl, heterocyclyl, heteroaryl, or heterocyclylC$_1$ 6alkyl, heteroarylC$_{1-6}$alkyl can be oxidized to form at least one C=O.

112. The compound according to any one of statements 1 to 111, wherein each R$^{17}$ is independently selected from the group consisting of hydrogen, C$_{1-6}$alkyl, C$_{6-12}$aryl, C$_{3-8}$cycloalkyl, heterocyclyl, and heteroaryl; and wherein at least one carbon atom of said C$_{1-6}$alkyl, C$_{6-12}$aryl, C$_{3-8}$cycloalkyl, heterocyclyl, or heteroaryl can be oxidized to form at least one C=O.

113. The compound according to any one of statements 1 to 112, wherein each R$^{17}$ is independently selected from the group consisting of hydrogen, C$_{1-6}$alkyl, heterocyclyl, and heteroaryl; and wherein at least one carbon atom of said C$_{1-6}$alkyl, C$_{3-8}$cycloalkyl, heterocyclyl, or heteroaryl can be oxidized to form at least one C=O.

114. The compound according to any one of statements 1 to 113, wherein each R$^{17}$ is independently selected from the group consisting of hydrogen, C$_{1-6}$alkyl, heterocyclyl, and heteroaryl.

115. The compound according to any one of statements 1 to 114, wherein each R$^{18}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; and wherein at least one carbon atom or heteroatom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O, or S(O)$_2$.

116. The compound according to any one of statements 1 to 115, wherein each R$^{18}$ is independently selected from the group consisting of hydrogen, C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; and wherein at least one carbon atom of said C$_{1-6}$alkyl, C$_{2-6}$alkenyl, C$_{2-6}$alkynyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, or heteroarylC$_{1-6}$alkyl can be oxidized to form at least one C=O.

117. The compound according to any one of statements 1 to 116, wherein each R$^{18}$ is independently selected from the group consisting of hydrogen, C$_{1-6}$alkyl, C$_{6-12}$aryl, C$_{3-8}$cycloalkyl, C$_{6-12}$arylC$_{1-6}$alkyl, heterocyclyl, heteroaryl, heterocyclylC$_{1-6}$alkyl, and heteroarylC$_{1-6}$alkyl; and wherein at least one carbon atom of said C$_{1-6}$alkyl, C$_{6-12}$aryl, C$_{3-8}$cycloalkyl, C$_{6-12}$arylC$_{1-6}$alkyl, heterocyclyl, heteroaryl, or heterocyclylC$_{1-6}$alkyl, heteroarylC$_{1-6}$alkyl can be oxidized to form at least one C=O.

118. The compound according to any one of statements 1 to 117, wherein each R$^{18}$ is independently selected from the group consisting of hydrogen, C$_{1-6}$alkyl, C$_{6-12}$aryl, C$_{3-8}$cycloalkyl, heterocyclyl, and heteroaryl; and wherein at least one carbon atom of said C$_{1-6}$alkyl, C$_{6-12}$aryl, C$_{3-8}$cycloalkyl, heterocyclyl, or heteroaryl can be oxidized to form at least one C=O.

119. The compound according to any one of statements 1 to 118, wherein each R$^{18}$ is independently selected from the group consisting of hydrogen, $C_{1-6}$alkyl, heterocyclyl, and heteroaryl; and wherein at least one carbon atom of said $C_{1-6}$alkyl, $C_{3-8}$cycloalkyl, heterocyclyl, or heteroaryl can be oxidized to form at least one C=O.

120. The compound according to any one of statements 1 to 119, wherein each $R^{18}$ is independently selected from the group consisting of hydrogen, $C_{1-6}$alkyl, heterocyclyl, and heteroaryl.

121. The compound according to any one of statements 1 to 120, wherein $R^{17}$ and $R^{18}$ together with the nitrogen atom to which they are attached form a 5-, or 6-membered heterocyclyl; and wherein at least one carbon atom or heteroatom of said heterocyclyl can be oxidized to form at least one C=O, or N=O.

122. The compound according to any one of statements 1 to 121, wherein $R^{17}$ and $R^{18}$ together with the nitrogen atom to which they are attached form a 5-membered heterocyclyl; and wherein at least one carbon atom of said heterocyclyl can be oxidized to form at least one C=O.

123. The compound according to any one of statements 1 to 122, wherein each $R^{19}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, or $S(O)_2$.

124. The compound according to any one of statements 1 to 123, wherein each $R^{19}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O.

125. The compound according to any one of statements 1 to 124, wherein each $R^{19}$ is independently selected from the group consisting of hydrogen, hydroxyl, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, or heterocyclyl$C_1$ 6alkyl, heteroaryl$C_{1-6}$alkyl can be oxidized to form at least one C=O.

126. The compound according to any one of statements 1 to 125, wherein each $R^{19}$ is independently selected from the group consisting of hydrogen, hydroxyl, $C_{1-6}$alkyl, $C_{6-12}$aryl, $C_{3-8}$cycloalkyl, heterocyclyl, and heteroaryl; and wherein at least one carbon atom of said $C_{1-6}$alkyl, $C_{6-12}$aryl, $C_{3-8}$cycloalkyl, heterocyclyl, or heteroaryl can be oxidized to form at least one C=O.

127. The compound according to any one of statements 1 to 126, wherein each $R^{19}$ is independently selected from the group consisting of hydrogen, hydroxyl, $C_{1-6}$alkyl, heterocyclyl, and heteroaryl; and wherein at least one carbon atom of said $C_{1-6}$alkyl, $C_{3-8}$cycloalkyl, heterocyclyl, or heteroaryl can be oxidized to form at least one C=O.

128. The compound according to any one of statements 1 to 127, wherein each $R^{19}$ is independently selected from the group consisting of hydrogen, hydroxyl, $C_{1-6}$alkyl, heterocyclyl, and heteroaryl.

129. The compound according to any one of statements 1 to 128, wherein each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, or $S(O)_2$.

130. The compound according to any one of statements 1 to 129, wherein each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O.

131. The compound according to any one of statements 1 to 130, wherein each $R^{20}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; and wherein at least one carbon atom of said $C_{1-6}$alkyl, $C_{6-12}$aryl, $C_{3-8}$cycloalkyl, $C_{6-12}$aryl$C_{1-6}$alkyl, heterocyclyl, heteroaryl, or heterocyclyl$C_{1-6}$alkyl, heteroaryl$C_{1-6}$alkyl can be oxidized to form at least one C=O.

132. The compound according to any one of statements 1 to 131, wherein each $R^{20}$ is independently selected from the group consisting of hydrogen, $C_{1-6}$alkyl, $C_{6-12}$aryl, $C_{3-8}$cycloalkyl, heterocyclyl, and heteroaryl; and wherein at least one carbon atom of said $C_{1-6}$alkyl, $C_{6-12}$aryl, $C_{3-8}$cycloalkyl, heterocyclyl, or heteroaryl can be oxidized to form at least one C=O.

133. The compound according to any one of statements 1 to 132, wherein each $R^{20}$ is independently selected from the group consisting of hydrogen, $C_{1-6}$alkyl, heterocyclyl, and heteroaryl; and wherein at least one carbon atom of said $C_{1-6}$alkyl, $C_{3-8}$cycloalkyl, heterocyclyl, or heteroaryl can be oxidized to form at least one C=O.

134. The compound according to any one of statements 1 to 133, wherein each $R^{20}$ is independently selected from the group consisting of hydrogen, $C_{1-6}$alkyl, heterocyclyl, heteroaryl, and cyano$C_{1-6}$alkyl.

135. The compound according to any one of statements 1 to 134, wherein each $R^{21}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene$C_{1-6}$alkylene*; and wherein at least one carbon atom or heteroatom of said $C_{1-6}$alkylene, $C_{2-6}$alkenylene, $C_{2-6}$alkynylene, $C_{6-12}$aryenel, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, or $S(O)_2$, wherein * represents where $R^{21}$ is bound to CO.

136. The compound according to any one of statements 1 to 135, wherein $R^{21}$ is independently selected from the group consisting of $C_{1-6}$alkylene, $C_{6-12}$arylene, and $C_{3-8}$cycloalkylene; and wherein at least one carbon atom of said $C_{1-6}$alkylene, $C_{6-12}$arylene, $C_{3-8}$cycloalkylene can be oxidized to form at least one C=O.

137. The compound according to any one of statements 1 to 136, wherein each $R^{21}$ is independently selected from the group consisting of $C_{1-6}$alkylene, and $C_{3-8}$cycloalkylene; and wherein at least one carbon atom of said $C_{1-6}$alkylene, $C_{3-8}$cycloalkylene can be oxidized to form at least one C=O.

138. The compound according to any one of statements 1 to 137, wherein each $R^{21}$ is independently selected from the group consisting of $C_{1-6}$alkylene, and $C_{3-8}$cycloalkylene; and wherein at least one carbon atom of said $C_{1-6}$alkylene, $C_{3-8}$cycloalkylene can be oxidized to form at least one C=O.

139. The compound according to any one of statements 1 to 138, wherein each $R^{21}$ is $C_{1-6}$alkylene.

140. The compound according to any one of statements 1 to 139, wherein each $R^{21}$ is $C_{1-4}$alkylene.

141. The compound according to any one of statements 1 to 140, wherein each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, cyano, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, —$CO_2H$, —$CO_2C_{1-6}$alkyl, —$CO_2C_{2-6}$alkenyl, —$CO_2C_{2-6}$alkynyl, —$CO_2C_{6-12}$aryl, —$CO_2C_{3-8}$cycloalkyl, —$CO_2C_{6-12}$aryl$C_{1-6}$alkyl, —$CO_2$heterocyclyl, —$CO_2$heteroaryl, —$CO_2$heterocyclyl$C_{1-6}$alkyl, —$CO_2$heteroaryl$C_{1-6}$alkyl, —C(O)$NH_2$, —C(O)NH$C_{1-6}$alkyl, —C(O)NH$C_{2-6}$alkenyl, —C(O)NH$C_{2-6}$alkynyl, —C(O)NH$C_{6-12}$aryl, —C(O)NH$C_{3-8}$cycloalkyl, —C(O)NH($C_{6-12}$aryl$C_{1-6}$alkyl), —C(O)NH-heterocyclyl, —C(O)NH-heteroaryl, —C(O)NH(heterocyclyl$C_{1-6}$alkyl), —C(O)NH(heteroaryl$C_{1-6}$alkyl), —COH, —C(O)$C_{1-6}$alkyl, —C(O)$C_{2-6}$alkenyl, —C(O)$C_{2-6}$alkynyl, —C(O)$C_{6-12}$aryl, —C(O)$C_{3-8}$cycloalkyl, —C(O)heterocyclyl, —C(O)heteroaryl, —S(O)OH, —S(O)$C_{1-6}$alkyl, —S(O)$C_{2-6}$alkenyl, —S(O)$C_{2-6}$alkynyl, —S(O)$C_{6-12}$aryl, —S(O)$C_{3-8}$cycloalkyl, —S(O)heterocyclyl, —S(O)heteroaryl, —S(O)$_2$OH, —S(O)$_2C_{1-6}$alkyl, —S(O)$_2C_{2-6}$alkenyl, —S(O)$_2C_{2-6}$alkynyl, —S(O)$_2C_{6-12}$aryl, —S(O)$_2C_{3-8}$cycloalkyl, —S(O)$_2C_{6-12}$aryl$C_{1-6}$alkyl, —S(O)$_2$heterocyclyl, —S(O)$_2$ heteroaryl, —S(O)$_2$heterocyclyl$C_{1-6}$alkyl, —S(O)$_2$heteroaryl$C_{1-6}$alkyl, —S(O)$_2NH_2$, —S(O)$_2$NH$C_{1-6}$alkyl, —S(O)$_2$NH$C_{2-6}$alkenyl, —S(O)$_2$NH$C_{2-6}$alkynyl, —S(O)$_2$NH$C_{6-12}$aryl, —S(O)$_2$NH$C_{3-8}$cycloalkyl, —S(O)$_2$NH($C_{6-12}$aryl$C_{1-6}$alkyl), —S(O)$_2$NHheterocyclyl, —S(O)$_2$NHheteroaryl, —S(O)$_2$NH(heterocyclyl$C_{1-6}$alkyl), —S(O)$_2$NH(heteroaryl$C_{1-6}$alkyl), nitro, —NHC(O)H, —NHC(O)$C_{1-6}$alkyl, —NHC(O)$C_{2-6}$alkenyl, —NHC(O)$C_{2-6}$alkynyl, —NHC(O)$C_{6-12}$aryl, —NHC(O)$C_{3-8}$cycloalkyl, —NHC(O)heterocyclyl, —NHC(O)heteroaryl, —N($C_{1-6}$alkyl)C(O)H, —N($C_{1-6}$alkyl)C(O)$C_{1-6}$alkyl, —N($C_{1-6}$alkyl)C(O)$C_{6-12}$aryl, —N($C_6$alkyl)C(O)$C_{3-8}$cycloalkyl, —N($C_{1-6}$alkyl)C(O)heterocyclyl, —N($C_{1-6}$alkyl)C(O)heteroaryl, —$C_{1-6}$alkylene-C(O)$NH_2$, —$C_{1-6}$alkylene-C(O)NH$C_{1-6}$alkyl, —$C_{1-6}$ alkyleneC(O)NH$C_{2-6}$alkenyl, —$C_{1-6}$alkyleneC(O)NH$C_{2-6}$alkynyl, —$C_{1-6}$alkyleneC(O)NH$C_{6-12}$aryl, —$C_{1-6}$alkyleneC(O)NH$C_{3-8}$cycloalkyl, —$C_{1-6}$alkyleneC(O)NH$C_{6-12}$aryl$C_{1-6}$alkyl, —$C_{1-6}$alkyleneC(O)NHheterocyclyl, —$C_{1-6}$alkyleneC(O)NHheteroaryl, —$C_{1-6}$alkyleneC(O)NH-heterocyclyl$C_{1-6}$alkyl, —$C_{1-6}$alkylene-C(O)NH-heteroaryl$C_{1-6}$alkyl, —NHS(O)$_2$H, —NHS(O)$_2$OH, —NHS(O)$_2C_{1-6}$alkyl, —NHS(O)$_2C_{2-6}$alkenyl, —NHS(O)$_2C_{2-6}$alkynyl, —NHS(O)$_2C_{6-12}$aryl, —NHS(O)$_2C_{3-8}$cycloalkyl, —NHS(O)$_2C_{6-12}$aryl$C_{1-6}$alkyl, —NHS(O)$_2$heterocyclyl, —NHS(O)$_2$heteroaryl, —NHS(O)$_2$heterocyclyl$C_{1-6}$alkyl, —NHS(O)$_2$heteroaryl$C_{1-6}$alkyl, —N($C_{1-6}$alkyl)S(O)$_2$H, —N($C_{1-6}$alkyl)S(O)$_2$OH, —N($C_{1-6}$alkyl)S(O)$_2C_{1-6}$alkyl, —N($C_{1-6}$alkyl)S(O)$_2C_{2-6}$alkenyl, —N($C_{1-6}$alkyl)S(O)$_2C_{2-6}$alkynyl, —N($C_{1-6}$alkyl)S(O)$_2C_{6-12}$aryl, —N($C_{1-6}$alkyl)S(O)$_2C_{3-8}$cycloalkyl, —N($C_{1-6}$alkyl)S(O)$_2C_{6-12}$aryl$C_{1-6}$alkyl, —N($C_{1-6}$alkyl)S(O)$_2$heterocyclyl, —N($C_{1-6}$alkyl)S(O)$_2$heteroaryl, —N($C_{1-6}$alkyl)S(O)$_2$heterocyclyl$C_{1-6}$alkyl, —N($C_{1-6}$alkyl)S(O)$_2$heteroaryl$C_{1-6}$alkyl, —NHC(O)$NH_2$, —NHC(O)NH$C_{1-6}$alkyl, —NHC(O)NH$C_{2-6}$alkenyl, —NHC(O)NH$C_{2-6}$alkynyl, —NHC(O)NH$C_{6-12}$aryl, —NHC(O)NH$C_{3-8}$cycloalkyl, —NHC(O)NH$C_{6-12}$aryl$C_{1-6}$alkyl, —NHC(O)NH-heterocyclyl, —NHC(O)NH-heteroaryl, —NHC(O)NHheterocyclyl$C_{1-6}$alkyl, —NHC(O)NHheteroaryl$C_{1-6}$alkyl, —NHC(O)N$C_{1-6}$alkyl$C_{1-6}$alkyl, —NHC(O)N$C_{1-6}$alkyl$C_{6-12}$aryl, —N($C_{1-6}$alkyl)C(O)NH$C_{1-6}$alkyl, —N($C_{1-6}$alkyl)C(O)NH$C_{2-6}$alkenyl, —N($C_{1-6}$alkyl)C(O)NH$C_{2-6}$alkynyl, —N($C_{1-6}$alkyl)C(O)NH$C_{6-12}$aryl, —N($C_{1-6}$alkyl)C(O)NH$C_{3-8}$cycloalkyl, —N($C_{1-6}$alkyl)C(O)NH$C_{6-12}$aryl$C_{1-6}$alkyl, —N($C_{1-6}$alkyl)C(O)NHheterocyclyl, —N($C_{1-6}$alkyl)C(O)NHheteroaryl, —N($C_{1-6}$alkyl)C(O)NHheterocyclyl$C_{1-6}$alkyl, —N($C_{1-6}$alkyl)C(O)NHheteroaryl$C_{1-6}$alkyl; and wherein at least one carbon atom or heteroatom of said $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, or N=O.

142. The compound according to any one of statements 1 to 141, wherein each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, cyano, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, —$CO_2H$, —$CO_2C_{1-6}$alkyl, —$CO_2C_{6-12}$aryl, —$CO_2C_{3-8}$cycloalkyl, —$CO_2$heterocyclyl, —$CO_2$heteroaryl, —C(O)$NH_2$, —C(O)NH$C_{1-6}$alkyl, —C(O)NH$C_{6-12}$aryl, —C(O)NH$C_{3-8}$cycloalkyl, —C(O)NH-heterocyclyl, —C(O)NH-heteroaryl, —COH, —C(O)$C_{1-6}$alkyl, —C(O)$C_{6-12}$aryl, —C(O)$C_{3-8}$cycloalkyl, —C(O)heterocyclyl, —C(O)heteroaryl, —S(O)OH, —S(O)$C_{1-6}$alkyl, —S(O)$C_{6-12}$aryl, —S(O)$C_{3-8}$cycloalkyl, —S(O)heterocyclyl, —S(O)heteroaryl, —S(O)$_2$OH, —S(O)$_2C_{1-6}$alkyl, —S(O)$_2C_{6-12}$aryl, —S(O)$_2C_{3-8}$cycloalkyl, —S(O)$_2$heterocyclyl, —S(O)$_2$heteroaryl, —S(O)$_2$NH$_2$, —S(O)$_2$NHC$_{1-6}$alkyl, —S(O)$_2$NHC$_{6-12}$aryl, —S(O)$_2$NHC$_{3-8}$cycloalkyl, —S(O)$_2$NHheterocyclyl, —S(O)$_2$NHheteroaryl, nitro, —NHC(O)H, —NHC(O)C$_{1-6}$alkyl, —NHC(O)C$_{6-12}$aryl, —NHC(O)C$_{3-8}$cycloalkyl, —NHC(O)heterocyclyl, —NHC(O)heteroaryl, —N(C$_{1-6}$alkyl)C(O)H, —N(C$_{1-6}$alkyl)C(O)C$_{1-6}$alkyl, —N(C$_{1-6}$alkyl)C(O)C$_{6-12}$aryl, —N(C$_{1-6}$alkyl)C(O)C$_{3-8}$cycloalkyl, —N(C$_{1-6}$alkyl)C(O)heterocyclyl, —N(C$_{1-6}$alkyl)C(O)heteroaryl, —C$_{1-6}$alkylene-C(O)NH$_2$, —C$_{1-6}$alkyleneC(O)NHC$_{1-6}$alkyl, —C$_{1-6}$alkylene-C(O)NHC$_{6-12}$aryl, —C$_{1-6}$alkyleneC(O)NHC$_{3-8}$cycloalkyl, —C$_{1-6}$alkyleneC(O)NHheterocyclyl, —C$_{1-6}$alkylene-C(O)NHheteroaryl, —NHS(O)$_2$H, —NHS(O)$_2$OH, —NHS(O)$_2$C$_{1-6}$alkyl, —NHS(O)$_2$C$_{6-12}$aryl, —NHS(O)$_2$C$_{3-8}$cycloalkyl, —NHS(O)$_2$heterocyclyl, —NHS(O)$_2$heteroaryl, —NC$_{1-6}$alkylS(O)$_2$H, —NC$_{1-6}$alkylS(O)$_2$OH, —NC$_{1-6}$alkylS(O)$_2$C$_{1-6}$alkyl, —NC$_{1-6}$alkylS(O)$_2$C$_{6-12}$aryl, —NC$_{1-6}$alkylS(O)$_2$C$_{3-8}$cycloalkyl, —NC$_{1-6}$alkylS(O)$_2$heterocyclyl, —NC$_{1-6}$alkylS(O)$_2$heteroaryl, —NHC(O)NH$_2$, —NHC(O)NHC$_{1-6}$alkyl, —NHC(O)NHC$_{6-12}$aryl, —NHC(O)NHC$_{3-8}$cycloalkyl, —NHC(O)NHC$_{6-12}$arylC$_{1-6}$alkyl, —NHC(O)NH-heterocyclyl, —NHC(O)NHheteroaryl, —NC$_{1-6}$alkylC(O)NHC$_{1-6}$ alkyl, —NC$_{1-6}$alkylC(O)NHC$_{6-12}$aryl, —NC$_{1-6}$alkylC(O)NHC$_{3-8}$cycloalkyl, —NC$_{1-6}$alkylC(O)NHheterocyclyl, and —NC$_{1-6}$alkylC(O)NHheteroaryl.

143. The compound according to any one of statements 1 to 142, wherein each $Z^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{6-12}$aryl, heterocyclyl, heterocyclylC$_{1-6}$alkyl, heteroaryl, heteroarylC$_{1-6}$alkyl, hydroxyl, C$_{1-6}$alkyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{6-12}$arylthio, C$_{3-8}$cycloalkylthio, C$_{6-12}$arylC$_{1-6}$alkylthio, heterocyclylthio, heteroarylthio, heterocyclylC$_{1-6}$alkylthio, heteroarylC$_{1-6}$alkylthio, cyanoC$_{1-6}$alkylthio, cyano, amino, mono or di-C$_{1-6}$alkylamino, mono or di-C$_{6-12}$arylamino, mono or di-C$_{3-8}$cycloalkylamino, mono or di-heterocyclylamino, mono or di-heteroarylamino, —CO$_2$H, —CO$_2$C$_{1-6}$alkyl, —CO$_2$C$_{6-12}$aryl, —CO$_2$C$_{3-8}$cycloalkyl, —CO$_2$heterocyclyl, —CO$_2$heteroaryl, —C(O)NH$_2$, —C(O)NHC$_{1-6}$alkyl, —C(O)NHC$_{6-12}$aryl, —C(O)NHC$_{3-8}$cycloalkyl, —C(O)NHheterocyclyl, —C(O)NHheteroaryl, —COH, —C(O)C$_{1-6}$alkyl, —C(O)C$_{6-12}$aryl, —C(O)C$_{3-8}$cycloalkyl, —C(O)heterocyclyl, —C(O)heteroaryl, —S(O)$_2$OH, —S(O)$_2$C$_{1-6}$alkyl, —S(O)$_2$C$_{6-12}$aryl, —S(O)$_2$C$_{3-8}$cycloalkyl, —S(O)$_2$heterocyclyl, —S(O)$_2$heteroaryl, S(O)$_2$NH$_2$, —S(O)$_2$NHC$_{1-6}$alkyl, —S(O)$_2$NHC$_{6-12}$aryl, —S(O)$_2$NHC$_{3-8}$cycloalkyl, —S(O)$_2$ NHheterocyclyl, —S(O)$_2$NHheteroaryl, nitro, —NHC(O)H, —NHC(O)C$_{1-6}$alkyl, —NHC(O)C$_{6-12}$aryl, NHC(O)C$_{3-8}$cycloalkyl, —NHC(O)heterocyclyl, —NHC(O)heteroaryl, —N(C$_{1-6}$alkyl)C(O)H, N(C$_{1-6}$alkyl)C(O)C$_{1-6}$ alkyl, —N(C$_{1-6}$alkyl)C(O)C$_{6-12}$aryl, —N(C$_{1-6}$alkyl)C(O)C$_{3-8}$cycloalkyl, —N(C$_{1-6}$alkyl)C(O)heterocyclyl, —N(C$_{1-6}$alkyl)C(O)heteroaryl, —C$_{1-6}$alkyleneC(O)NH$_2$, —C$_{1-6}$alkyleneC(O)NHC$_{1-6}$alkyl, —C$_{1-6}$alkyleneC(O)NHC$_{6-12}$aryl, —C$_{1-6}$alkyleneC(O)NHC$_{3-8}$cycloalkyl, —C$_{1-6}$alkyleneC(O)NH-heterocyclyl, —C$_{1-6}$alkyleneC(O)NHheteroaryl, —NHS(O)$_2$H, —NHS(O)$_2$OH, —NHS(O)$_2$C$_{1-6}$alkyl, —NHS(O)$_2$C$_{6-12}$aryl, —NHS(O)$_2$C$_{3-8}$cycloalkyl, —NHS(O)$_2$heterocyclyl, —NHS(O)$_2$heteroaryl, —NC$_{1-6}$alkylS(O)$_2$H, —NC$_{1-6}$alkylS(O)$_2$OH, —NC$_{1-6}$alkylS(O)$_2$C$_{1-6}$alkyl, —NC$_{1-6}$alkylS(O)$_2$C$_{6-12}$aryl, —NC$_{1-6}$alkylS(O)$_2$C$_{3-8}$cycloalkyl, —NC$_{1-6}$alkylS(O)$_2$heterocyclyl, and —NC$_{1-6}$alkylS(O)$_2$heteroaryl; and wherein at least one carbon atom or heteroatom of said C$_{1-6}$alkyl, C$_{3-12}$cycloalkyl, C$_{6-12}$aryl, C$_{1-6}$alkylC$_{6-12}$aryl, heterocyclyl, heterocyclylC$_{1-6}$alkyl, heteroaryl, or heteroarylC$_{1-6}$alkyl can be oxidized to form at least one C=O, or N=O.

144. The compound according to any one of statements 1 to 143, wherein each $Z^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{6-12}$aryl, heterocyclyl, heterocyclylC$_{1-6}$alkyl, heteroaryl, heteroarylC$_{1-6}$alkyl, hydroxyl, C$_{1-6}$alkyloxy, C$_{6-12}$aryloxy, C$_{3-12}$cycloalkyloxy, C$_{6-12}$arylC$_{1-6}$alkyloxy, heterocyclyloxy, heteroaryloxy, heterocyclylC$_{1-6}$alkyloxy, heteroarylC$_{1-6}$alkyloxy, cyanoC$_{1-6}$alkyloxy, thiol, C$_{1-6}$alkylthio, C$_{6-12}$arylthio, C$_{3-8}$cycloalkylthio, cyano, amino, mono or di-C$_{1-6}$alkylamino, mono or di-C$_{6-12}$arylamino, mono or di-C$_{3-8}$cycloalkylamino, mono or di-heterocyclylamino, mono or di-heteroarylamino, —CO$_2$H, —CO$_2$C$_{1-6}$alkyl, —CO$_2$C$_{6-12}$aryl, —CO$_2$C$_{3-8}$cycloalkyl, —CO$_2$heterocyclyl, —CO$_2$heteroaryl, —C(O)NH$_2$, —C(O)NHC$_{1-6}$alkyl, —C(O)NHC$_{6-12}$aryl, —C(O)NHC$_{3-8}$cycloalkyl, —C(O)NHheterocyclyl, —C(O)NHheteroaryl, —COH, —C(O)C$_{1-6}$alkyl, —C(O)C$_{6-12}$aryl, —C(O)C$_{3-8}$cycloalkyl, —C(O)heterocyclyl, —C(O)heteroaryl, —S(O)$_2$OH, —S(O)$_2$C$_{1-6}$alkyl, —S(O)$_2$C$_{6-12}$aryl, —S(O)$_2$C$_{3-8}$cycloalkyl, —S(O)$_2$heterocyclyl, —S(O)$_2$heteroaryl, —S(O)$_2$NH$_2$, —S(O)$_2$NHC$_{1-6}$alkyl, —S(O)$_2$NHC$_{6-12}$aryl, —S(O)$_2$NHC$_{3-8}$cycloalkyl, nitro, —NHC(O)H, —NHC(O)C$_{1-6}$alkyl, —NHC(O)C$_{6-12}$aryl, —NHC(O)C$_{3-8}$cycloalkyl, —N(C$_{1-6}$alkyl)C(O)H, —N(C$_{1-6}$alkyl)C (O)$C_{1-6}$alkyl, —N($C_{1-6}$alkyl)C(O)$C_{6-12}$aryl, —N($C_{1-6}$alkyl)C(O)$C_{3-8}$cycloalkyl, —NHS(O)$_2$H, —NHS(O)$_2$OH, —NHS(O)$_2C_{1-6}$alkyl, —NHS(O)$_2C_{6-12}$aryl, —NHS(O)$_2C_{3-8}$cycloalkyl, —N$C_{1-6}$alkylS(O)$_2$H, —N$C_{1-6}$alkylS(O)$_2$OH, —N$C_{1-6}$alkylS(O)$_2C_{1-6}$alkyl, —N$C_{1-6}$alkylS(O)$_2C_{6-12}$aryl, and —N$C_{1-6}$alkylS(O)$_2C_{3-8}$cycloalkyl; and wherein at least one carbon atom or heteroatom of said $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, or N=O.

146. The compound according to any one of statements 1 to 145, wherein each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, cyano$C_{1-6}$alkyloxy, thiol, $C_{1-6}$alkylthio, cyano, amino, mono or di-$C_{1-6}$alkylamino, mono or di-$C_{6-12}$arylamino, —CO$_2$H, —CO$_2C_{1-6}$alkyl, —CO$_2C_{6-12}$aryl, —C(O)NH$_2$, —C(O)NH$C_{1-6}$alkyl, —C(O)NH$C_{6-12}$aryl, —COH, —C(O)$C_{1-6}$alkyl, —C(O)$C_{6-12}$aryl, —S(O)$_2$ OH, —S(O)$_2C_{1-6}$alkyl, —S(O)$_2C_{6-12}$aryl, —S(O)$_2$NH$_2$, —S(O)$_2$NH$C_{1-6}$alkyl, —S(O)$_2$NH$C_{6-12}$aryl, nitro, —NHC(O)H, —NHC(O)$C_{1-6}$alkyl, —NHC(O)$C_{6-12}$aryl, —N($C_{1-6}$alkyl)C(O)H, —N($C_{1-6}$alkyl)C(O)$C_{1-6}$alkyl, —N($C_{1-6}$alkyl)C(O)$C_{6-12}$aryl, —NHS(O)$_2$H, —NHS(O)$_2$ OH, —NHS(O)$_2C_{1-6}$alkyl, —NHS(O)$_2C_{6-12}$aryl, —N$C_{1-6}$alkylS(O)$_2$H, —N$C_{1-6}$alkylS(O)$_2$OH, —N$C_{1-6}$ alkylS(O)$_2C_{1-6}$alkyl, and —N$C_{1-6}$alkylS(O)$_2C_{6-12}$aryl; and wherein at least one carbon atom or heteroatom of said $C_{1-6}$alkyl, $C_{3-8}$cycloalkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, or N=O.

147. The compound according to any one of statements 1 to 146, wherein each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl$C_{1-6}$alkyl, heteroaryl, hydroxyl, $C_{1-6}$alkyloxy, cyano$C_{1-6}$alkyloxy, thiol, $C_{1-6}$alkylthio, cyano, amino, mono or di $C_{1-6}$alkylamino, —CO$_2$H, —CO$_2C_{1-6}$alkyl, —C(O)NH$_2$, —C(O)NH$C_{1-6}$alkyl, —COH, —C(O)$C_{1-6}$alkyl, —NHC(O)H, —NHC(O)$C_{1-6}$alkyl, —N($C_{1-6}$ alkyl)C(O)H, and —N($C_{1-6}$alkyl)C(O)$C_{1-6}$alkyl; and wherein at least one carbon atom of said $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O.

148. The compound according to any one of statements 1 to 147, wherein each $Z^1$ is independently selected from the group consisting of halo, hydrogen, $C_{1-6}$alkyl, halo$C_{1-6}$alkyl, halo$C_{1-6}$alkyloxy, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, cyano$C_{1-6}$alkyloxy, thiol, $C_{1-6}$alkylthio, cyano, amino, mono or di $C_{1-6}$alkylamino, —C(O)$C_{1-6}$alkyl, —NHC(O)$C_{1-6}$alkyl, and —N($C_{1-6}$alkyl)C(O)$C_{1-6}$alkyl; and wherein at least one carbon atom of said $C_{1-6}$alkyl, $C_{6-12}$aryl, $C_{1-6}$alkyl $C_{6-12}$ aryl, heterocyclyl, heterocyclyl$C_{1-6}$alkyl, heteroaryl, or heteroaryl$C_{1-6}$alkyl can be oxidized to form at least one C=O.

149. The compound according to any one of statements 1 to 148, wherein each $Z^1$ is independently selected from the group consisting of halo, hydrogen, $C_{1-6}$alkyl, halo$C_{1-6}$alkyl, halo$C_{1-6}$alkyloxy, $C_{6-12}$aryl, heterocyclyl, heteroaryl, hydroxyl, $C_{1-6}$alkyloxy, thiol, $C_{1-6}$alkylthio, cyano, amino, and mono or di-$C_{1-6}$alkylamino; and wherein at least one carbon atom of said $C_{1-6}$alkyl, $C_{6-12}$aryl, heterocyclyl, heteroaryl, can be oxidized to form at least one C=O.

150. The compound according to any one of statements 1 to 149, wherein two $Z^1$ together with the atom to which they are attached form a 5-, or 6-membered ring; and wherein at least one carbon atom of said ring can be oxidized to form at least one C=O.

151. The compound according to any one of statements 1 to 150, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{2-6}$alkenyloxy, $C_{2-6}$alkynyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{2-6}$alkenylthio, $C_{2-6}$alkynylthio, $C_{6-12}$arylthio, $C_{3-8}$cycloalkylthio, $C_{6-12}$aryl$C_{1-6}$alkylthio, heterocyclylthio, heteroarylthio, heterocyclyl$C_{1-6}$alkylthio, heteroaryl$C_{1-6}$alkylthio, cyano$C_{1-6}$alkylthio, cyano, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, —CO$_2$H, —CO$_2C_{1-6}$alkyl, —CO$_2C_{2-6}$alkenyl, —CO$_2C_{2-6}$alkynyl, —CO$_2C_{6-12}$aryl, —CO$_2C_{3-8}$cycloalkyl, —CO$_2C_{6-12}$aryl$C_{1-6}$alkyl, —CO$_2$heterocyclyl, —CO$_2$heteroaryl, —CO$_2$heterocyclyl$C_{1-6}$alkyl, —CO$_2$heteroaryl$C_{1-6}$alkyl, —C(O)NH$_2$, —C(O)NH$C_{1-6}$alkyl, —C(O)NH$C_{2-6}$alkenyl, —C(O)NH$C_{2-6}$alkynyl, —C(O)NH$C_{6-12}$aryl, —C(O)NH$C_{3-8}$cycloalkyl, —C(O)NH($C_{6-12}$aryl$C_{1-6}$alkyl), —C(O)NH-heterocyclyl, —C(O)NH-heteroaryl, —C(O)NH(heterocyclyl$C_{1-6}$alkyl), —C(O)NH(heteroaryl$C_{1-6}$alkyl), —COH, —C(O)$C_{1-6}$alkyl, —C(O)$C_{2-6}$alkenyl, —C(O)$C_{2-6}$alkynyl, —C(O)$C_{6-12}$aryl, —C(O)$C_{3-8}$cycloalkyl, —C(O)heterocyclyl, —C(O)heteroaryl, —S(O)OH, —S(O)$C_{1-6}$alkyl, —S(O)$C_{2-6}$alkenyl, —S(O)$C_{2-6}$alkynyl, —S(O)$C_{6-12}$aryl, —S(O)$C_{3-8}$cycloalkyl, —S(O)heterocyclyl, —S(O)heteroaryl, —S(O)$_2$OH, —S(O)$_2C_{1-6}$alkyl, —S(O)$_2C_{2-6}$alkenyl, —S(O)$_2C_{2-6}$alkynyl, —S(O)$_2C_{6-12}$aryl, —S(O)$_2C_{3-8}$cycloalkyl, —S(O)$_2C_{6-12}$aryl$C_{1-6}$alkyl, —S(O)$_2$heterocyclyl, —S(O)$_2$ heteroaryl, —S(O)$_2$heterocyclyl$C_{1-6}$alkyl, —S(O)$_2$heteroaryl$C_{1-6}$alkyl, —S(O)$_2$NH$_2$, —S(O)$_2$NH$C_{1-6}$alkyl, —S(O)$_2$NH$C_{2-6}$alkenyl, —S(O)$_2$NH$C_{2-6}$alkynyl, —S(O)$_2$ NH$C_{6-12}$aryl, —S(O)$_2$NH$C_{3-8}$cycloalkyl, —S(O)$_2$NH($C_{6-12}$aryl$C_{1-6}$alkyl), —S(O)$_2$NHheterocyclyl, —S(O)$_2$ NHheteroaryl, —S(O)$_2$NH(heterocyclyl$C_{1-6}$alkyl), —S(O)$_2$NH(heteroaryl$C_{1-6}$alkyl), nitro, —NHC(O)H, —NHC(O)$C_{1-6}$alkyl, —NHC(O)$C_{2-6}$alkenyl, —NHC(O)$C_{2-6}$alkynyl, —NHC(O)$C_{6-12}$aryl, —NHC(O)$C_{3-8}$cycloalkyl, —NHC(O)heterocyclyl, —NHC(O)heteroaryl, —N($C_{1-6}$alkyl)C(O)H, —N($C_{1-6}$alkyl)C(O)$C_{1-6}$alkyl, —N($C_{1-6}$alkyl)C(O)$C_{6-12}$aryl, —N($C_{1-6}$alkyl)C(O)$C_{3-8}$cycloalkyl, —N($C_{1-6}$alkyl)C(O)heterocyclyl, —N($C_{1-6}$alkyl)C(O)heteroaryl, —$C_{1-6}$alkyleneC(O)NH$_2$, —$C_{1-6}$alkyleneC(O)NH$C_{1-6}$alkyl, —$C_{1-6}$alkylene-C(O)NH$C_{2-6}$alkenyl, —$C_{1-6}$alkyleneC(O)NH$C_{2-6}$alkynyl, $C_{1-6}$alkyleneC(O)NH$C_{6-12}$aryl, $C_{1-6}$alkylene-C(O)NH$C_{3-8}$cycloalkyl, $C_{1-6}$alkyleneC(O)NH$C_{6-12}$aryl$C_{1-6}$alkyl, $C_{1-6}$alkyleneC(O)NHheterocyclyl, $C_{1-6}$alkyleneC(O)NHheteroaryl, $C_{1-6}$alkyleneC(O)NHheterocyclyl$C_{1-6}$alkyl, $C_{1-6}$alkylene-C(O)NHheteroaryl$C_{1-6}$alkyl, —NHS(O)$_2$H, —NHS(O)$_2$OH, —NHS (O)₂C₁₋₆alkyl, —NHS(O)₂C₂₋₆alkenyl, —NHS(O)₂C₂₋₆alkynyl, —NHS(O)₂C₆₋₁₂aryl, —NHS(O)₂C₃₋₈cycloalkyl, —NHS(O)₂C₆₋₁₂arylC₁₋₆alkyl, —NHS(O)₂heterocyclyl, —NHS(O)₂heteroaryl, —NHS(O)₂heterocyclylC₁₋₆alkyl, —NHS(O)₂heteroarylC₁₋₆alkyl, —NC₁₋₆alkylS(O)₂H, —NC₁₋₆alkylS(O)₂OH, —NC₁₋₆alkylS(O)₂C₁₋₆alkyl, —NC₁₋₆alkylS(O)₂C₂₋₆alkenyl, —NC₁₋₆alkylS(O)₂C₂₋₆alkynyl, —NC₁₋₆alkylS(O)₂C₆₋₁₂aryl, —NC₁₋₆alkylS(O)₂C₃₋₈cycloalkyl, —NC₁₋₆alkylS(O)₂C₆₋₁₂arylC₁₋₆alkyl, —NC₁₋₆alkylS(O)₂heterocyclyl, —NC₁₋₆alkylS(O)₂heteroaryl, —NC₁₋₆alkylS(O)₂heterocyclylC₁₋₆alkyl, —NC₁₋₆alkylS(O)₂heteroarylC₁₋₆alkyl, —NHC(O)NH₂, —NHC(O)NHC₁₋₆alkyl, —NHC(O)NHC₂₋₆alkenyl, —NHC(O)NHC₂₋₆alkynyl, —NHC(O)NHC₆₋₁₂aryl, —NHC(O)NHC₃₋₈cycloalkyl, —NHC(O)NHC₆₋₁₂arylC₁₋₆alkyl, —NHC(O)NH-heterocyclyl, —NHC(O)NH-heteroaryl, —NHC(O)NHheterocyclylC₁₋₆ alkyl, —NHC(O)NHheteroarylC₁₋₆alkyl, —NHC(O)NC₁₋₆alkylC₁₋₆alkyl, —NHC(O)NC₁₋₆alkylC₆₋₁₂aryl, —NC₁₋₆alkylC(O)NHC₁₋₆alkyl, —NC₁₋₆alkylC(O)NHC₂₋₆alkenyl, —NC₁₋₆alkylC(O)NHC₂₋₆alkynyl, —NC₁₋₆alkylC(O)NHC₆₋₁₂aryl, —NC₁₋₆alkylC(O)NHC₃₋₈cycloalkyl, —NC₁₋₆alkylC(O)NHC₆₋₁₂arylC₁₋₆alkyl, —NC₁₋₆alkylC(O)NHheterocyclyl, —NC₁₋₆alkylC(O)NHheteroaryl, —NC₁₋₆alkylC(O)NHheterocyclylC₁₋₆alkyl, and —NC₁₋₆alkylC(O)NHheteroarylC₁₋₆alkyl; and wherein at least one carbon atom or heteroatom of said ring, C₁₋₆alkyl, C₃₋₁₂cycloalkyl, C₆₋₁₂aryl, C₁₋₆alkylC₆₋₁₂aryl, heterocyclyl, heterocyclylC₁₋₆alkyl, heteroaryl, or heteroarylC₁₋₆alkyl can be oxidized to form at least one C=O, or N=O.

152. The compound according to any one of statements 1 to 151, wherein each $Z^2$ is independently selected from the group consisting of halo, hydrogen, C₁₋₆alkyl, haloC₁₋₆alkyl, haloC₁₋₆alkyloxy, C₃₋₁₂cycloalkyl, C₆₋₁₂aryl, C₁₋₆alkylC₆₋₁₂aryl, heterocyclyl, heterocyclylC₁₋₆alkyl, heteroaryl, heteroarylC₁₋₆alkyl, hydroxyl, C₁₋₆alkyloxy, C₂₋₆alkenyloxy, C₂₋₆alkynyloxy, C₆₋₁₂aryloxy, C₃₋₁₂cycloalkyloxy, C₆₋₁₂arylC₁₋₆alkyloxy, heterocyclyloxy, heteroaryloxy, heterocyclylC₁₋₆alkyloxy, heteroarylC₁₋₆alkyloxy, cyanoC₁₋₆alkyloxy, thiol, C₁₋₆alkylthio, C₂₋₆alkenylthio, C₂₋₆alkynylthio, C₆₋₁₂arylthio, C₃₋₈cycloalkylthio, C₆₋₁₂arylC₁₋₆alkylthio, heterocyclylthio, heteroarylthio, heterocyclylC₁₋₆alkylthio, heteroarylC₁₋₆alkylthio, cyanoC₁₋₆alkylthio, cyano, amino, mono or di-C₁₋₆alkylamino, mono or di-C₆₋₁₂arylamino, mono or di-C₃₋₈cycloalkylamino, mono or di-heterocyclylamino, mono or di-heteroarylamino, —CO₂H, —CO₂C₁₋₆alkyl, —CO₂C₆₋₁₂aryl, —CO₂C₃₋₈cycloalkyl, —CO₂heterocyclyl, —CO₂heteroaryl, —C(O)NH₂, —C(O)NHC₁₋₆alkyl, —C(O)NHC₆₋₁₂aryl, —C(O)NHC₃₋₈cycloalkyl, —C(O)NH-heterocyclyl, —C(O)NHheteroaryl, —COH, —C(O)C₁₋₆alkyl, —C(O)C₆₋₁₂aryl, —C(O)C₃₋₈cycloalkyl, —C(O)heterocyclyl, —C(O)heteroaryl, —S(O)OH, —S(O)C₁₋₆alkyl, —S(O)C₆₋₁₂aryl, —S(O)C₃₋₈cycloalkyl, —S(O)heterocyclyl, —S(O)heteroaryl, —S(O)₂OH, —S(O)₂C₁₋₆alkyl, —S(O)₂C₆₋₁₂aryl, —S(O)₂C₃₋₈cycloalkyl, —S(O)₂heterocyclyl, —S(O)₂heteroaryl, —S(O)₂NH₂, —S(O)₂NHC₁₋₆alkyl, —S(O)₂NHC₆₋₁₂aryl, —S(O)₂NHC₃₋₈cycloalkyl, —S(O)₂NHheterocyclyl, —S(O)₂NHheteroaryl, nitro, —NHC(O)H, —NHC(O)C₁₋₆alkyl, —NHC(O)C₆₋₁₂aryl, —NHC(O)C₃₋₈cycloalkyl, —NHC(O)heterocyclyl, —NHC(O)heteroaryl, —N(C₁₋₆alkyl)C(O)H, —N(C₁₋₆alkyl)C(O)C₁₋₆alkyl, —N(C₁₋₆alkyl)C(O)C₆₋₁₂aryl, —N(C₁₋₆alkyl)C(O)C₃₋₈cycloalkyl, —N(C₁₋₆alkyl)C(O)heterocyclyl, —N(C₁₋₆alkyl)C(O)heteroaryl, —C₁₋₆alkyleneC(O)NH₂, —C₁₋₆alkyleneC(O)NHC₁₋₆alkyl, C₁₋₆alkyleneC(O)NHC₆₋₁₂aryl, C₁₋₆alkyleneC(O)NHC₃₋₈cycloalkyl, C₁₋₆alkyleneC(O)NHheterocyclyl, C₁₋₆alkyleneC(O)NHheteroaryl, —NHS(O)₂H, —NHS(O)₂OH, —NHS(O)₂C₁₋₆alkyl, —NHS(O)₂C₆₋₁₂aryl, —NHS(O)₂C₃₋₈cycloalkyl, —NHS(O)₂heterocyclyl, —NHS(O)₂heteroaryl, —NC₁₋₆alkylS(O)₂H, —NC₁₋₆alkylS(O)₂OH, —NC₁₋₆alkylS(O)₂C₁₋₆alkyl, —NC₁₋₆alkylS(O)₂C₆₋₁₂aryl, —NC₁₋₆alkylS(O)₂C₃₋₈cycloalkyl, —NC₁₋₆alkylS(O)₂heterocyclyl, —NC₁₋₆alkylS(O)₂heteroaryl, —NHC(O)NH₂, —NHC(O)NHC₁₋₆alkyl, —NHC(O)NHC₆₋₁₂aryl, —NHC(O)NHC₃₋₈cycloalkyl, —NHC(O)NHC₆₋₁₂arylC₁₋₆alkyl, —NHC(O)NH-heterocyclyl, —NHC(O)NHheteroaryl, —NC₁₋₆alkylC(O)NHC₁₋₆alkyl, —NC₁₋₆alkylC(O)NHC₆₋₁₂aryl, —NC₁₋₆alkylC(O)NHC₃₋₈cycloalkyl, —NC₁₋₆alkylC(O)NHheterocyclyl, and —NC₁₋₆alkylC(O)NHheteroaryl; and wherein at least one carbon atom or heteroatom of said ring, C₁₋₆alkyl, C₃₋₁₂cycloalkyl, C₆₋₁₂aryl, C₁₋₆alkylC₆₋₁₂aryl, heterocyclyl, heterocyclylC₁₋₆alkyl, heteroaryl, or heteroarylC₁₋₆alkyl can be oxidized to form at least one C=O, or N=O.

153. The compound according to any one of statements 1 to 152, wherein each $Z^2$ is independently selected from the group consisting of halo, hydrogen, C₁₋₆alkyl, haloC₁₋₆alkyl, haloC₁₋₆alkyloxy, C₃₋₁₂cycloalkyl, C₆₋₁₂aryl, C₁₋₆alkylC₆₋₁₂aryl, heterocyclyl, heterocyclylC₁₋₆alkyl, heteroaryl, heteroarylC₁₋₆alkyl, hydroxyl, C₁₋₆alkyloxy, C₆₋₁₂aryloxy, C₃₋₈cycloalkyloxy, C₆₋₁₂arylC₁₋₆alkyloxy, heterocyclyloxy, heteroaryloxy, heterocyclylC₁₋₆alkyloxy, heteroarylC₁₋₆alkyloxy, cyanoC₁₋₆alkyloxy, thiol, C₁₋₆alkylthio, C₆₋₁₂arylthio, C₃₋₈cycloalkylthio, C₆₋₁₂arylC₁₋₆alkylthio, heterocyclylthio, heteroarylthio, heterocyclylC₁₋₆alkylthio, heteroarylC₁₋₆alkylthio, cyanoC₁₋₆alkylthio, cyano, amino, mono or di-C₁₋₆alkylamino, mono or di-C₆₋₁₂arylamino, mono or di-C₃₋₈cycloalkylamino, mono or di-heterocyclylamino, mono or di-heteroarylamino, CO₂H, CO₂C₁₋₆alkyl, CO₂C₆₋₁₂aryl, CO₂C₃₋₈cycloalkyl, CO₂heterocyclyl, CO₂heteroaryl, C(O)NH₂, C(O)NHC₁₋₆alkyl, C(O)NHC₆₋₁₂aryl, C(O)NHC₃₋₈cycloalkyl, C(O)NHheterocyclyl, C(O)NHheteroaryl, COH, C(O)C₁₋₆alkyl, C(O)C₆₋₁₂aryl, C(O)C₃₋₈cycloalkyl, C(O)heterocyclyl, C(O)heteroaryl, S(O)₂OH, S(O)₂C₁₋₆alkyl, S(O)₂C₆₋₁₂aryl, S(O)₂C₃₋₈cycloalkyl, S(O)₂heterocyclyl, S(O)₂heteroaryl, S(O)₂NH₂, S(O)₂NHC₁₋₆alkyl, S(O)₂NHC₆₋₁₂aryl, S(O)₂NHC₃₋₈cycloalkyl, S(O)₂NHheterocyclyl, S(O)₂NHheteroaryl, nitro, NHC(O)H, NHC(O)C₁₋₆alkyl, NHC(O)C₆₋₁₂aryl, NHC(O)C₃₋₈cycloalkyl, NHC(O)heterocyclyl, NHC(O)heteroaryl, —N(C₁₋₆alkyl)C(O)H, N(C₁₋₆alkyl)C(O)C₁₋₆alkyl, N(C₁₋₆alkyl)C(O)C₆₋₁₂aryl, N(C₁₋₆alkyl)C(O)C₃₋₈cycloalkyl, N(C₁₋₆alkyl)C(O)heterocyclyl, N(C₁₋₆alkyl)C(O)heteroaryl, C₁₋₆alkyleneC(O)NH₂, C₁₋₆alkyleneC(O)NHC₁₋₆alkyl, C₁₋₆alkyleneC(O)NHC₆₋₁₂aryl, C₁₋₆alkyleneC(O)NHC₃₋₈cycloalkyl, C₁₋₆alkyleneC(O)NHheterocyclyl, C₁₋₆alkyleneC(O)NHheteroaryl, NHS(O)₂H, NHS(O)₂OH, NHS(O)₂C₁₋₆alkyl, NHS(O)₂C₆₋₁₂aryl, NHS(O)₂C₃₋₈cycloalkyl, NHS(O)₂heterocyclyl, NHS(O)₂heteroaryl, —NC₁₋₆alkylS(O)₂H, NC₁₋₆alkylS(O)₂OH, NC₁₋₆alkylS(O)₂C₁₋₆alkyl, NC₁₋₆alkylS(O)₂C₆₋₁₂aryl, NC₁₋₆alkylS(O)₂C₃₋₈cycloalkyl, NC₁₋₆alkylS(O)₂heterocyclyl, and NC₁₋₆alkylS(O)₂heteroaryl; and wherein at least one carbon atom or heteroatom of said ring, C₁₋₆alkyl, C₃₋₁₂cycloalkyl, C₆₋₁₂aryl, C₁₋₆alkylC₆₋₁₂aryl, heterocyclyl, heterocyclylC₁₋₆alkyl, heteroaryl, or heteroarylC₁₋₆alkyl can be oxidized to form at least one C=O, or N=O.

154. The compound according to any one of statements 1 to 153, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, $C_{3-12}$cycloalkyloxy, $C_{6-12}$aryl$C_{1-6}$alkyloxy, heterocyclyloxy, heteroaryloxy, heterocyclyl$C_{1-6}$alkyloxy, heteroaryl$C_{1-6}$alkyloxy, cyano$C_{1-6}$alkyloxy, thiol, $C_{1-6}$alkylthio, $C_{6-12}$arylthio, $C_{3-8}$cycloalkylthio, cyano, amino, mono or di-$C_{1-6}$alkylamino, mono or di-$C_{6-12}$arylamino, mono or di-$C_{3-8}$cycloalkylamino, mono or di-heterocyclylamino, mono or di-heteroarylamino, $CO_2H$, $CO_2C_{1-6}$alkyl, $CO_2C_{6-12}$aryl, $CO_2C_{3-8}$cycloalkyl, $CO_2$heterocyclyl, $CO_2$heteroaryl, $C(O)NH_2$, $C(O)NHC_{1-6}$alkyl, $C(O)NHC_{6-12}$aryl, $C(O)NHC_{3-8}$cycloalkyl, $C(O)NH$-heterocyclyl, $C(O)NH$heteroaryl, $COH$, $C(O)C_{1-6}$alkyl, $C(O)C_{6-12}$aryl, $C(O)C_{3-8}$cycloalkyl, $C(O)$heterocyclyl, $C(O)$heteroaryl, $S(O)_2OH$, $S(O)_2C_{1-6}$alkyl, $S(O)_2C_{6-12}$aryl, $S(O)_2C_{3-8}$cycloalkyl, $S(O)_2$heterocyclyl, $S(O)_2$heteroaryl, $S(O)_2NH_2$, $S(O)_2NHC_{1-6}$alkyl, $S(O)_2NHC_{6-12}$aryl, $S(O)_2NHC_{3-8}$cycloalkyl, $S(O)_2NH$heterocyclyl, $S(O)_2NH$heteroaryl, nitro, $NHC(O)H$, $NHC(O)C_{1-6}$alkyl, $NHC(O)C_{6-12}$aryl, $NHC(O)C_{3-8}$cycloalkyl, $NHC(O)$heterocyclyl, $NHC(O)$heteroaryl, $N(C_{1-6}alkyl)C(O)H$, $N(C_{1-6}alkyl)C(O)C_{1-6}$alkyl, $N(C_{1-6}alkyl)C(O)C_{6-12}$aryl, $N(C_{1-6}alkyl)C(O)C_{3-8}$cycloalkyl, $N(C_{1-6}alkyl)C(O)$heterocyclyl, $N(C_{1-6}alkyl)C(O)$heteroaryl, $NHS(O)_2H$, $NHS(O)_2OH$, $NHS(O)_2C_{1-6}$alkyl, $NHS(O)_2C_{6-12}$aryl, $NHS(O)_2 C_{3-8}$cycloalkyl, $NHS(O)_2$heterocyclyl, $NHS(O)_2$heteroaryl, $NC_{1-6}alkylS(O)_2H$, $NC_{1-6}alkylS(O)_2OH$, $NC_{1-6}alkylS(O)_2C_{1-6}$alkyl, $NC_{1-6}alkylS(O)_2C_{6-12}$aryl, $NC_{1-6}alkylS(O)_2C_{3-8}$cycloalkyl, $NC_{1-6}alkylS(O)_2$heterocyclyl, and $NC_{1-6}alkylS(O)_2$heteroaryl; and wherein at least one carbon atom or heteroatom of said ring, $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, or N=O.

155. The compound according to any one of statements 1 to 154, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, heterocyclyloxy, heteroaryloxy, cyano$C_{1-6}$alkyloxy, thiol, $C_{1-6}$alkylthio, cyano, amino, mono or di-$C_{1-6}$alkylamino, mono or di-$C_{6-12}$arylamino, mono or di-$C_{3-8}$cycloalkylamino, $CO_2H$, $CO_2C_{1-6}$alkyl, $CO_2C_{6-12}$aryl, $CO_2C_{3-8}$cycloalkyl, $C(O)NH_2$, $C(O)NHC_{1-6}$alkyl, $C(O)NHC_{6-12}$aryl, $C(O)NHC_{3-8}$cycloalkyl, $COH$, $C(O)C_{1-6}$alkyl, $C(O)C_{6-12}$aryl, $C(O)C_{3-8}$cycloalkyl, $S(O)_2OH$, $S(O)_2C_{1-6}$alkyl, $S(O)_2C_{6-12}$aryl, $S(O)_2C_{3-8}$cycloalkyl, $S(O)_2NH_2$, $S(O)_2NHC_{1-6}$alkyl, $S(O)_2NHC_{6-12}$aryl, $S(O)_2NHC_{3-8}$cycloalkyl, nitro, $NHC(O)H$, $NHC(O)C_{1-6}$alkyl, $NHC(O)C_{6-12}$aryl, $NHC(O)C_{3-8}$cycloalkyl, $N(C_{1-6}alkyl)C(O)H$, $N(C_{1-6}alkyl)C(O)C_{1-6}$alkyl, $N(C_{1-6}alkyl)C(O)C_{6-12}$aryl, $N(C_6alkyl)C(O)C_{3-8}$cycloalkyl, $NHS(O)_2H$, $NHS(O)_2OH$, $NHS(O)_2C_{1-6}$alkyl, $NHS(O)_2C_{6-12}$aryl, $NHS(O)_2C_{3-8}$cycloalkyl, $NC_{1-6}alkylS(O)_2H$, $NC_{1-6}alkylS(O)_2OH$, $NC_{1-6}alkylS(O)_2C_{1-6}$alkyl, $NC_{1-6}alkylS(O)_2C_{6-12}$aryl, and $NC_{1-6}alkylS(O)_2C_{3-8}$cycloalkyl; and wherein at least one carbon atom said ring, $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O.

156. The compound according to any one of statements 1 to 155, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, $C_{6-12}$aryloxy, cyano$C_{1-6}$alkyloxy, thiol, $C_{1-6}$alkylthio, cyano, amino, mono or di-$C_{1-6}$alkylamino, mono or di-$C_{6-12}$arylamino, $CO_2H$, $CO_2C_{1-6}$alkyl, $CO_2C_{6-12}$aryl, $C(O)NH_2$, $C(O)NHC_{1-6}$alkyl, $C(O)NHC_{6-12}$aryl, $COH$, $C(O)C_{1-6}$alkyl, $C(O)C_{6-12}$aryl, $S(O)_2OH$, $S(O)_2C_{1-6}$alkyl, $S(O)_2C_{6-12}$aryl, $S(O)_2NH_2$, $S(O)_2NHC_{1-6}$alkyl, $S(O)_2NHC_{6-12}$aryl, nitro, $NHC(O)H$, $NHC(O)C_{1-6}$alkyl, $NHC(O)C_{6-12}$aryl, $N(C_{1-6}alkyl)C(O)H$, $N(C_{1-6}alkyl)C(O)C_{1-6}$alkyl, $N(C_{1-6}alkyl)C(O)C_{6-12}$aryl, $NHS(O)_2H$, $NHS(O)_2OH$, $NHS(O)_2C_{1-6}$alkyl, $NHS(O)_2C_{6-12}$aryl, $NC_{1-6}alkylS(O)_2H$, $NC_{1-6}alkylS(O)_2OH$, $NC_{1-6}alkylS(O)_2C_{1-6}$alkyl, and $NC_{1-6}alkylS(O)_2C_{6-12}$aryl; and wherein at least one carbon atom of said ring, $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O.

157. The compound according to any one of statements 1 to 156, wherein each $Z^2$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, cyano$C_{1-6}$alkyloxy, thiol, $C_{1-6}$alkylthio, cyano, amino, mono or di-$C_{1-6}$alkylamino, $CO_2H$, $CO_2C_{1-6}$alkyl, $C(O)NH_2$, $C(O)NHC_{1-6}$alkyl, $COH$, $C(O)C_{1-6}$alkyl, $NHC(O)H$, $NHC(O)C_{1-6}$alkyl, $N(C_{1-6}alkyl)C(O)H$, and $N(C_{1-6}alkyl)C(O)C_{1-6}$alkyl; and wherein at least one carbon atom of said ring, $C_{1-6}$alkyl, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O.

158. The compound according to any one of statements 1 to 157, wherein each $Z^2$ is independently selected from the group consisting of halo, hydrogen, $C_{1-6}$alkyl, halo$C_{1-6}$alkyl, halo$C_{1-6}$alkyloxy, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, $C_{1-6}$alkyloxy, thiol, $C_{1-6}$alkylthio, cyano, amino, mono or di-$C_{1-6}$alkylamino, $C(O)C_{1-6}$ alkyl, $NHC(O)C_{1-6}$alkyl, $N(C_{1-6}alkyl)C(O)C_{1-6}$alkyl.

159. The compound according to any one of statements 1 to 158, wherein two $Z^2$ together with the atom to which they are attached form a 5-, or 6-membered ring; and wherein at least one carbon atom of said ring can be oxidized to form at least one C=O.

160. The compound according to any one of statements 1 to 159, wherein $L^5$ is a single bond.

161. The compound according to any one of statements 1 to 160, wherein $L^5$ is —CO—.

162. The compound according to any one of statements 1 to 161, having structural formula (IIJ), (IIJ)

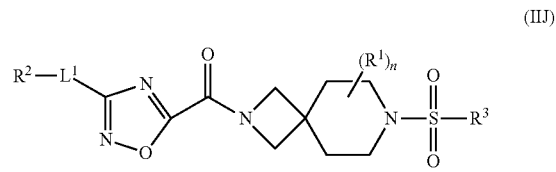

wherein, L¹, n, R¹, R², and R³ have the same meaning as defined in any one of statements 1 to 159.

163. The compound according to any one of statements 1 to 162, having structural formula (IIK),

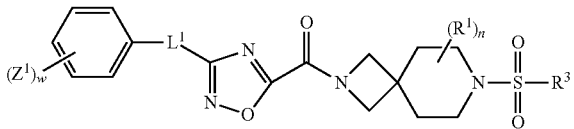

(IIK)

wherein, L¹, n, R¹, R³, and Z¹ have the same meaning as defined in any one of statements 1 to 160, and wherein, w is an integer selected from 1, 2, or 3.

164. The compound according to any one of statements 1 to 163, having structural formula (IJ) or (IIL),

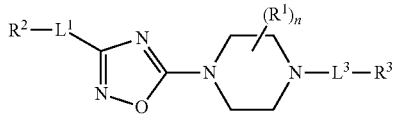

(IJ)

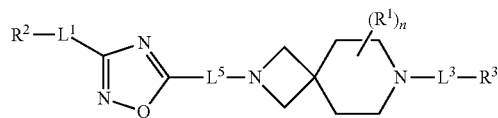

(IIL)

wherein, L¹, L³, L⁵, n, R¹, R², and R³ have the same meaning as defined in any one of statements 1 to 163.

165. The compound according to any one of statements 1 to 164, wherein L² is a single bond, and L³ is selected from the group consisting of —CH₂—, —CH₂—CH₂—, and —CH₂—CH₂—CH₂—.

166. The compound according to any one of statements 1 to 165, wherein L² is a single bond, and L³ is —CH₂—CH₂—.

167. The compound according to any one of statements 1 to 166, wherein L³ is a single bond, and L² is selected from the group consisting of —CH₂—, —CH₂—CH₂—, and —CH₂—CH₂—CH₂—.

168. The compound according to any one of statements 1 to 167, wherein L³ is a single bond, and L² is —CH₂—CH₂—.

169. The compound according to any one of statements 1 to 168, selected from the group consisting of 5-(4-(2-Chlorobenzyl)piperazin-1-yl)-3-phenyl-1,2,4-oxadiazole; 5-(4-(4-Methylbenzyl)piperazin-1-yl)-3-phenyl-1,2,4-oxadiazole; 5-(4-(4-Chlorophenethyl)piperazin-1-yl)-3-phenyl-1,2,4-oxadiazole; 5-(4-(2-(2-Methoxypyridin-4-yl)ethyl)piperazin-1-yl)-3-phenyl-1,2,4-oxadiazole; 4-(2-(4-(3-Phenyl-1,2,4-oxadiazol-5-yl)piperazin-1-yl)ethyl)morpholine; 5-(4-Isopentylpiperazin-1-yl)-3-phenyl-1,2,4-oxadiazole; 5-(4-(Benzo[d][1,3]dioxol-5-ylmethyl)piperazin-1-yl)-3-(p-tolyl)-1,2,4-oxadiazole; 5-(4-(4-Chlorobenzyl)piperazin-1-yl)-3-(p-tolyl)-1,2,4-oxadiazole; 5-(4-(3-Methoxyphenethyl)piperazin-1-yl)-3-(p-tolyl)-1,2,4-oxadiazole; 5-(4-(2-Methylbenzyl)piperazin-1-yl)-3-(p-tolyl)-1,2,4-oxadiazole; 5-(4-((4-(Oxazol-5-yl)phenyl)sulfonyl)piperazin-1-yl)-3-(p-tolyl)-1,2,4-oxadiazole; 5-(4-((4-(Difluoromethoxy)phenyl)sulfonyl)piperazin-1-yl)-3-(p-tolyl)-1,2,4-oxadiazole; 3-(p-Tolyl)-5-(4-((4-(trifluoromethoxy)phenyl)sulfonyl)piperazin-1-yl)-1,2,4-oxadiazole; 5-(4-((4-Fluorophenyl)sulfonyl)piperazin-1-yl)-3-(p-tolyl)-1,2,4-oxadiazole; 5-(4-((4-Isopropylphenyl)sulfonyl)piperazin-1-yl)-3-(p-tolyl)-1,2,4-oxadiazole; 3-(p-Tolyl)-5-(4-((4-(trifluoromethyl)phenyl)sulfonyl)piperazin-1-yl)-1,2,4-oxadiazole; 1-(4-((4-(3-(p-Tolyl)-1,2,4-oxadiazol-5-yl)piperazin-1-yl)sulfonyl)phenyl)pyrrolidin-2-one; 5-(4-((4-Methoxyphenyl)sulfonyl)piperazin-1-yl)-3-(p-tolyl)-1,2,4-oxadiazole; 5-(4-(4-Chlorophenethyl)piperazin-1-yl)-3-(4-chlorophenyl)-1,2,4-oxadiazole; 3-(4-Chlorophenyl)-5-(4-phenethylpiperazin-1-yl)-1,2,4-oxadiazole; 3-(4-Chlorophenyl)-5-(4-(3-methoxyphenethyl)piperazin-1-yl)-1,2,4-oxadiazole; 3-(4-Chlorophenyl)-5-(4-(2-methylbenzyl)piperazin-1-yl)-1,2,4-oxadiazole; 3-(4-Chlorophenyl)-5-(4-(2-(2-methoxypyridin-4-yl)ethyl)piperazin-1-yl)-1,2,4-oxadiazole; 5-(4-(4-Chlorophenethyl)piperazin-1-yl)-3-(3-chlorophenyl)-1,2,4-oxadiazole; 3-(3-Chlorophenyl)-5-(4-(2-(2-methoxypyridin-4-yl)ethyl)piperazin-1-yl)-1,2,4-oxadiazole; 3-(3-Chlorophenyl)-5-(4-(2-methylbenzyl)piperazin-1-yl)-1,2,4-oxadiazole; 5-(4-(2-Chlorobenzyl)piperazin-1-yl)-3-(3-chlorophenyl)-1,2,4-oxadiazole; 2-((4-(3-(3-Chlorophenyl)-1,2,4-oxadiazol-5-yl)piperazin-1-yl)methyl)benzonitrile; 5-(4-(2-Chlorobenzyl)piperazin-1-yl)-3-(3-fluorophenyl)-1,2,4-oxadiazole; 3-(3-Fluorophenyl)-5-(4-(4-methylbenzyl)piperazin-1-yl)-1,2,4-oxadiazole; 5-(4-(4-Chlorophenethyl)piperazin-1-yl)-3-(3-fluorophenyl)-1,2,4-oxadiazole; 3-(3-Fluorophenyl)-5-(4-(2-(2-methoxypyridin-4-yl)ethyl)piperazin-1-yl)-1,2,4-oxadiazole; 4-(2-(4-(3-(3-Fluorophenyl)-1,2,4-oxadiazol-5-yl)piperazin-1-yl)ethyl)morpholine; 3-(3-Fluorophenyl)-5-(4-isopentylpiperazin-1-yl)-1,2,4-oxadiazole; 5-(4-(2-Chlorobenzyl)piperazin-1-yl)-3-(3,4-difluorophenyl)-1,2,4-oxadiazole; 1-[2-(4-Chloro-phenyl)-ethyl]-4-[3-(3,4-difluoro-phenyl)-[1,2,4]oxadiazol-5-yl]-piperazine; 1-(3-Benzyl-[1,2,4]oxadiazol-5-yl)-4-(4-methoxy-benzenesulfonyl)-piperazine; 1-(3-Benzyl-[1,2,4]oxadiazol-5-yl)-4-(4-ethoxy-benzenesulfonyl)-piperazine; 1-(3-Benzyl-[1,2,4]oxadiazol-5-yl)-4-(4-difluoromethoxy-benzenesulfonyl)-piperazine; 1-Benzo[1,3]dioxol-5-ylmethyl-4-(3-benzyl-[1,2,4]oxadiazol-5-yl)-piperazine; 1-(3-Benzyl-[1,2,4]oxadiazol-5-yl)-4-(2-methyl-benzyl)-piperazine; 1-(3-Benzyl-[1,2,4]oxadiazol-5-yl)-4-[2-(3-methoxy-phenyl)-ethyl]-piperazine; 5-((4-(3-Benzyl-1,2,4-oxadiazol-5-yl)piperazin-1-yl)sulfonyl)benzo[d]oxazol-2(3H)-one; 5-(4-((4-Methoxyphenyl)sulfonyl)piperazin-1-yl)-3-(1-phenylpropyl)-1,2,4-oxadiazole; 1-(4-Ethoxy-benzenesulfonyl)-4-[3-(1-phenyl-propyl)-[1,2,4]oxadiazol-5-yl]-piperazine; 1-(4-Difluoromethoxy-benzenesulfonyl)-4-[3-(1-phenyl-propyl)-[1,2,4]oxadiazol-5-yl]-piperazine; 5-(4-(Benzo[d][1,3]dioxol-5-ylmethyl)piperazin-1-yl)-3-(1-phenylpropyl)-1,2,4-oxadiazole; 5-(4-(2-Methylbenzyl)piperazin-1-yl)-3-(1-phenylpropyl)-1,2,4-oxadiazole; 5-(4-(3-Methoxyphenethyl)piperazin-1-yl)-3-(1-phenylpropyl)-1,2,4-oxadiazole; 1-(4-Methoxy-benzenesulfonyl)-4-[3-((S)-1-phenyl-propyl)-[1,2,4]oxadiazol-5-yl]-piperazine; 1-(4-Methoxy-benzenesulfonyl)-4-[3-((R)-1-phenyl-propyl)-[1,2,4]oxadiazol-5-yl]-piperazine; 1-[3-(4-Chloro-benzyl)-[1,2,4]oxadiazol-5-yl]-4-(4-methoxy-benzenesulfonyl)-piperazine; 1-[3-(4-Chloro-benzyl)-[1,2,4]oxadiazol-5-yl]-4-(4-ethoxy-benzenesulfonyl)-piperazine; 1-[3-(4-Chloro-benzyl)-[1,2,4]oxadiazol-5-yl]-4-(4-difluoromethoxy-benzenesulfonyl)-piperazine;

1-Benzo[1,3]dioxol-5-ylmethyl-4-[3-(4-chloro-benzyl)-[1,2,4]oxadiazol-5-yl]-piperazine; 1-[3-(4-Chloro-benzyl)-[1,2,4]oxadiazol-5-yl]-4-[2-(3-methoxy-phenyl)-ethyl]-piperazine; 5-((4-(3-(4-Chlorobenzyl)-1,2,4-oxadiazol-5-yl)piperazin-1-yl)sulfonyl)benzo[d]oxazol-2(3H)-one; 1-[3-(4-Chloro-benzyl)-[1,2,4]oxadiazol-5-yl]-4-(2-methyl-benzyl)-piperazine; 1-[3-(4-Chloro-benzyl)-[1,2,4]oxadiazol-5-yl]-4-[2-(4-chloro-phenyl)-ethyl]-piperazine; 1-[3-(4-Chloro-benzyl)-[1,2,4]oxadiazol-5-yl]-4-[2-(6-methoxy-pyridin-3-yl)-ethyl]-piperazine; 3-(4-Chlorobenzyl)-5-(4-(2-fluorobenzyl)piperazin-1-yl)-1,2,4-oxadiazole; 1-(2-Chloro-benzyl)-4-[3-(4-chloro-benzyl)-[1,2,4]oxadiazol-5-yl]-piperazine; 1-[3-(4-Chloro-benzyl)-[1,2,4]oxadiazol-5-yl]-4-(4-methyl-benzyl)-piperazine; 4-{4-[3-(4-Chloro-benzyl)-[1,2,4]oxadiazol-5-yl]-piperazin-1-yl}-butyronitrile; 1-[3-(4-Chloro-benzyl)-[1,2,4]oxadiazol-5-yl]-4-(2-ethoxy-ethyl)-piperazine; 1-[3-(4-Chloro-benzyl)-[1,2,4]oxadiazol-5-yl]-4-propyl-piperazine; 3-(4-Chlorobenzyl)-5-(4-isopentylpiperazin-1-yl)-1,2,4-oxadiazole; 1-[3-(4-Chloro-benzyl)-[1,2,4]oxadiazol-5-yl]-4-(4,4,4-trifluoro-butyl)-piperazine; 3-(4-Chlorobenzyl)-5-(4-((tetrahydro-2H-pyran-4-yl)methyl)piperazin-1-yl)-1,2,4-oxadiazole; 4-(2-(4-(3-(4-Chlorobenzyl)-1,2,4-oxadiazol-5-yl)piperazin-1-yl)ethyl)morpholine; 3-(4-Chlorobenzyl)-5-(4-isopropylpiperazin-1-yl)-1,2,4-oxadiazole; 1-[3-(3-Chloro-benzyl)-[1,2,4]oxadiazol-5-yl]-4-(4-methoxy-benzenesulfonyl)-piperazine; 1-[3-(3-Chloro-benzyl)-[1,2,4]oxadiazol-5-yl]-4-(4-ethoxy-benzenesulfonyl)-piperazine; 1-[3-(3-Chloro-benzyl)-[1,2,4]oxadiazol-5-yl]-4-(4-difluoromethoxy-benzenesulfonyl)-piperazine; 1-[3-(3-Chloro-benzyl)-[1,2,4]oxadiazol-5-yl]-4-(2-methyl-benzyl)-piperazine; 1-[3-(3-Chloro-benzyl)-[1,2,4]oxadiazol-5-yl]-4-[2-(3-methoxy-phenyl)-ethyl]-piperazine; 5-{4-[3-(3-Chloro-benzyl)-[1,2,4]oxadiazol-5-yl]-piperazine-1-sulfonyl}-3H-benzooxazol-2-one; 4-(3-(3-Chlorobenzyl)-1,2,4-oxadiazol-5-yl)-N,N-dimethylpiperazine-1-sulfonamide; 4-(3-(3-Chlorobenzyl)-1,2,4-oxadiazol-5-yl)-N,N-diethylpiperazine-1-sulfonamide; 4-((4-(3-(3-Chlorobenzyl)-1,2,4-oxadiazol-5-yl)piperazin-1-yl)sulfonyl)morpholine; 3-(3-Chlorobenzyl)-5-(4-(pyrrolidin-1-ylsulfonyl)piperazin-1-yl)-1,2,4-oxadiazole; 5-(4-(Azepan-1-ylsulfonyl)piperazin-1-yl)-3-(3-chlorobenzyl)-1,2,4-oxadiazole; 3-(3-Chlorobenzyl)-5-(4-((4-methoxypiperidin-1-yl)sulfonyl)piperazin-1-yl)-1,2,4-oxadiazole; 1-[3-(3-Fluoro-benzyl)-[1,2,4]oxadiazol-5-yl]-4-(4-methoxy-benzenesulfonyl)-piperazine; 1-(4-Fluoro-benzenesulfonyl)-4-[3-(3-fluoro-benzyl)-[1,2,4]oxadiazol-5-yl]-piperazine; N-(4-{4-[3-(3-Fluoro-benzyl)-[1,2,4]oxadiazol-5-yl]-piperazine-1-sulfonyl}-phenyl)-acetamide; 1-[3-(3-Fluoro-benzyl)-[1,2,4]oxadiazol-5-yl]-4-(4-trifluoromethoxy-benzenesulfonyl)-piperazine; 1-[3-(3-Fluoro-benzyl)-[1,2,4]oxadiazol-5-yl]-4-(3-trifluoromethyl-benzenesulfonyl)-piperazine; 1-[3-(3-Fluoro-benzyl)-[1,2,4]oxadiazol-5-yl]-4-(3-methyl-benzyl)-piperazine; 1-[3-(3-Fluoro-benzyl)-[1,2,4]oxadiazol-5-yl]-4-[2-(3-methoxy-phenyl)-ethyl]-piperazine; 1-(4-Ethoxy-benzenesulfonyl)-4-[3-(3-fluoro-benzyl)-[1,2,4]oxadiazol-5-yl]-piperazine; 1-(4-Difluoromethoxy-benzenesulfonyl)-4-[3-(3-fluoro-benzyl)-[1,2,4]oxadiazol-5-yl]-piperazine; 1-[3-(3-Fluoro-benzyl)-[1,2,4]oxadiazol-5-yl]-4-(4-isopropoxy-benzenesulfonyl)-piperazine; 3-((4-(3-(3-Fluorobenzyl)-1,2,4-oxadiazol-5-yl)piperazin-1-yl)sulfonyl)phenoxy)propanenitrile; 1-(2,3-Dihydro-benzofuran-5-sulfonyl)-4-[3-(3-fluoro-benzyl)-[1,2,4]oxadiazol-5-yl]-piperazine; 3-(3-Fluorobenzyl)-5-(4-((4-isopropoxyphenyl)sulfonyl)piperazin-1-yl)-1,2,4-oxadiazole; 1-(4-Chloro-benzyl)-4-[3-(3,4-difluoro-benzyl)-[1,2,4]oxadiazol-5-yl]-piperazine; 1-[3-(3,4-Difluoro-benzyl)-[1,2,4]oxadiazol-5-yl]-4-[2-(3-methoxy-phenyl)-ethyl]-piperazine; 1-[3-(3,4-Difluoro-benzyl)-[1,2,4]oxadiazol-5-yl]-4-(4-methoxy-benzenesulfonyl)-piperazine; 1-[3-(3,4-Difluoro-benzyl)-[1,2,4]oxadiazol-5-yl]-4-(4-ethoxy-benzenesulfonyl)-piperazine; 1-[3-(3,4-Difluoro-benzyl)-[1,2,4]oxadiazol-5-yl]-4-(4-difluoromethoxy-benzenesulfonyl)-piperazine; 1-[2-(4-Chloro-phenyl)-ethyl]-4-[3-(3,4-difluoro-benzyl)-[1,2,4]oxadiazol-5-yl]-piperazine; 1-[3-(3,4-Difluoro-benzyl)-[1,2,4]oxadiazol-5-yl]-4-[2-(6-methoxy-pyridin-3-yl)-ethyl]-piperazine; 1-[3-(3,4-Difluoro-benzyl)-[1,2,4]oxadiazol-5-yl]-4-(2-methyl-benzyl)-piperazine; 1-{3-[1-(4-Fluoro-phenyl)-cyclopropyl]-[1,2,4]oxadiazol-5-yl}-4-(4-methoxy-benzenesulfonyl)-piperazine; 1-(4-Ethoxy-benzenesulfonyl)-4-{3-[1-(4-fluoro-phenyl)-cyclopropyl]-[1,2,4]oxadiazol-5-yl}-piperazine; 3-(1-(4-Fluorophenyl)cyclopropyl)-5-(4-((4-(trifluoromethoxy)phenyl)sulfonyl)piperazin-1-yl)-1,2,4-oxadiazole; 3-(1-(4-Fluorophenyl)cyclopropyl)-5-(4-(2-methylbenzyl)piperazin-1-yl)-1,2,4-oxadiazole; 3-(1-(4-Fluorophenyl)cyclopropyl)-5-(4-(3-methoxyphenethyl)piperazin-1-yl)-1,2,4-oxadiazole; 1-{3-[1-(4-Fluoro-phenyl)-cyclopropyl]-[1,2,4]oxadiazol-5-yl}-4-(4-methylsulfanyl-benzenesulfonyl)-piperazine; 5-(4-(4-Chlorophenethyl)piperazin-1-yl)-3-(1-(4-fluorophenyl)cyclopropyl)-1,2,4-oxadiazole; 5-(4-((2,2-Difluorobenzo[d][1,3]dioxol-5-yl)methyl)piperazin-1-yl)-3-(1-(4-fluorophenyl)cyclopropyl)-1,2,4-oxadiazole; 1-{3-[1-(4-Fluoro-phenyl)-1-methyl-ethyl]-[1,2,4]oxadiazol-5-yl}-4-(4-methoxy-benzenesulfonyl)-piperazine; 1-(4-Difluoromethoxy-benzenesulfonyl)-4-{3-[1-(4-fluoro-phenyl)-1-methyl-ethyl]-[1,2,4]oxadiazol-5-yl}-piperazine; 1-(4-Ethoxy-benzenesulfonyl)-4-{3-[1-(4-fluoro-phenyl)-1-methyl-ethyl]-[1,2,4]oxadiazol-5-yl}-piperazine; 1-{3-[1-(4-Fluoro-phenyl)-1-methyl-ethyl]-[1,2,4]oxadiazol-5-yl}-4-(4-methylsulfanyl-benzenesulfonyl)-piperazine; 3-(2-(4-Fluorophenyl)propan-2-yl)-5-(4-(2-methylbenzyl)piperazin-1-yl)-1,2,4-oxadiazole; 3-(2-(4-Fluorophenyl)propan-2-yl)-5-(4-(3-methoxyphenethyl)piperazin-1-yl)-1,2,4-oxadiazole; 5-(4-(Benzo[d][1,3]dioxol-5-ylmethyl)piperazin-1-yl)-3-(2-(4-fluorophenyl)propan-2-yl)-1,2,4-oxadiazole; 1-(4-Methoxy-benzenesulfonyl)-4-[3-(1-phenyl-cyclopropyl)-[1,2,4]oxadiazol-5-yl]-piperazine; 1-(4-Ethoxy-benzenesulfonyl)-4-[3-(1-phenyl-cyclopropyl)-[1,2,4]oxadiazol-5-yl]-piperazine; 1-(4-Difluoromethoxy-benzenesulfonyl)-4-[3-(1-phenyl-cyclopropyl)-[1,2,4]oxadiazol-5-yl]-piperazine; 5-(4-(2-Methylbenzyl)piperazin-1-yl)-3-(1-phenylcyclopropyl)-1,2,4-oxadiazole; 5-(4-(Benzo[d][1,3]dioxol-5-ylmethyl)piperazin-1-yl)-3-(1-phenylcyclopropyl)-1,2,4-oxadiazole; 5-(4-(3-Methoxyphenethyl)piperazin-1-yl)-3-(1-phenylcyclopropyl)-1,2,4-oxadiazole; 1-(4-Methylsulfanyl-benzenesulfonyl)-4-[3-(1-phenyl-cyclopropyl)-[1,2,4]oxadiazol-5-yl]-piperazine; 5-(4-(4-Chlorophenethyl)piperazin-1-yl)-3-(1-phenylcyclopropyl)-1,2,4-oxadiazole; 5-(4-((2,2-Difluorobenzo[d][1,3]dioxol-5-yl)methyl)piperazin-1-yl)-3-(1-phenylcyclopropyl)-1,2,4-oxadiazole; 5-(4-(2-Chlorobenzyl)piperazin-1-yl)-3-(1-phenylcyclopropyl)-1,2,4-oxadiazole; 5-(4-(4-Methylbenzyl)piperazin-1-yl)-3-(1-phenylcyclopropyl)-1,2,4-oxadiazole; 5-(4-(2-(2-

Methoxypyridin-4-yl)ethyl)piperazin-1-yl)-3-(1-phenylcyclopropyl)-1,2,4-oxadiazole; 4-(2-(4-(3-(1-Phenylcyclopropyl)-1,2,4-oxadiazol-5-yl)piperazin-1-yl)ethyl)morpholine; 5-(4-Isopentylpiperazin-1-yl)-3-(1-phenylcyclopropyl)-1,2,4-oxadiazole; 1-{3-[1-(3-Chloro-phenyl)-cyclopropyl]-[1,2,4]oxadiazol-5-yl}-4-(4-methoxy-benzenesulfonyl)-piperazine; 1-{3-[1-(3-Chloro-phenyl)-cyclopropyl]-[1,2,4]oxadiazol-5-yl}-4-(4-ethoxy-benzenesulfonyl)-piperazine; 1-{3-[1-(3-Chloro-phenyl)-cyclopropyl]-[1,2,4]oxadiazol-5-yl}-4-(4-difluoromethoxy-benzenesulfonyl)-piperazine; 1-{3-[1-(3-Chloro-phenyl)-cyclopropyl]-[1,2,4]oxadiazol-5-yl}-4-(4-methylsulfanyl-benzenesulfonyl)-piperazine; 1-{3-[1-(4-Chloro-phenyl)-cyclopropyl]-[1,2,4]oxadiazol-5-yl}-4-(4-methoxy-benzenesulfonyl)-piperazine; 1-{3-[1-(4-Chloro-phenyl)-cyclopropyl]-[1,2,4]oxadiazol-5-yl}-4-(4-ethoxy-benzenesulfonyl)-piperazine; 1-{3-[1-(4-Chloro-phenyl)-cyclopropyl]-[1,2,4]oxadiazol-5-yl}-4-(4-difluoromethoxy-benzenesulfonyl)-piperazine; 1-{3-[1-(4-Chloro-phenyl)-cyclopropyl]-[1,2,4]oxadiazol-5-yl}-4-(4-methylsulfanyl-benzenesulfonyl)-piperazine; 1-{3-[(4-Chloro-phenyl)-difluoro-methyl]-[1,2,4]oxadiazol-5-yl}-4-(4-methoxy-benzenesulfonyl)-piperazine; 1-{3-[(4-Chloro-phenyl)-difluoro-methyl]-[1,2,4]oxadiazol-5-yl}-4-(4-ethoxy-benzenesulfonyl)-piperazine; 1-{3-[(4-Chloro-phenyl)-difluoro-methyl]-[1,2,4]oxadiazol-5-yl}-4-(4-difluoromethoxy-benzenesulfonyl)-piperazine; 1-{3-[(4-Chloro-phenyl)-difluoro-methyl]-[1,2,4]oxadiazol-5-yl}-4-(4-methylsulfanyl-benzenesulfonyl)-piperazine; 1-{3-[Difluoro-(4-fluoro-phenyl)-methyl]-[1,2,4]oxadiazol-5-yl}-4-(4-methoxy-benzenesulfonyl)-piperazine; 1-{3-[Difluoro-(4-fluoro-phenyl)-methyl]-[1,2,4]oxadiazol-5-yl}-4-(4-ethoxy-benzenesulfonyl)-piperazine; 1-{3-[Difluoro-(4-fluoro-phenyl)-methyl]-[1,2,4]oxadiazol-5-yl}-4-(4-difluoromethoxy-benzenesulfonyl)-piperazine; 5-(4-(Benzo[d][1,3]dioxol-5-ylmethyl)piperazin-1-yl)-3-(difluoro(4-fluorophenyl)methyl)-1,2,4-oxadiazole; 3-(Difluoro(4-fluorophenyl)methyl)-5-(4-(3-methoxyphenethyl)piperazin-1-yl)-1,2,4-oxadiazole; 1-{3-[Difluoro-(4-fluoro-phenyl)-methyl]-[1,2,4]oxadiazol-5-yl}-4-(4-methylsulfanyl-benzenesulfonyl)-piperazine; 1-{3-[1-(3-Chloro-phenyl)-1-methyl-ethyl]-[1,2,4]oxadiazol-5-yl}-4-(4-methoxy-benzenesulfonyl)-piperazine; 1-{3-[1-(3-Chloro-phenyl)-1-methyl-ethyl]-[1,2,4]oxadiazol-5-yl}-4-(4-ethoxy-benzenesulfonyl)-piperazine; 1-{3-[1-(3-Chloro-phenyl)-1-methyl-ethyl]-[1,2,4]oxadiazol-5-yl}-4-(4-difluoromethoxy-benzenesulfonyl)-piperazine; 1-{3-[1-(3-Chloro-phenyl)-1-methyl-ethyl]-[1,2,4]oxadiazol-5-yl}-4-(4-methylsulfanyl-benzenesulfonyl)-piperazine; 1-[3-(Difluoro-phenyl-methyl)-[1,2,4]oxadiazol-5-yl]-4-(4-methoxy-benzenesulfonyl)-piperazine; 1-[3-(Difluoro-phenyl-methyl)-[1,2,4]oxadiazol-5-yl]-4-(4-methylsulfanyl-benzenesulfonyl)-piperazine; 1-(4-Difluoromethoxy-benzenesulfonyl)-4-[3-(difluoro-phenyl-methyl)-[1,2,4]oxadiazol-5-yl]-piperazine; 3-(Cyclopropylmethyl)-5-(4-((4-methoxyphenyl)sulfonyl)piperazin-1-yl)-1,2,4-oxadiazole; 3-(Cyclopropylmethyl)-5-(4-((4-(difluoromethoxy)phenyl)sulfonyl)piperazin-1-yl)-1,2,4-oxadiazole; 3-(Cyclopropylmethyl)-5-(4-((4-(methylthio)phenyl)sulfonyl)piperazin-1-yl)-1,2,4-oxadiazole; 3-(Cyclopropylmethyl)-5-(4-((4-ethoxyphenyl)sulfonyl)piperazin-1-yl)-1,2,4-oxadiazole; 5-(4-(3-Methoxyphenethyl)piperazin-1-yl)-3-(2,2,2-trifluoroethyl)-1,2,4-oxadiazole; 5-(4-(4-Chlorophenethyl)piperazin-1-yl)-3-(2,2,2-trifluoroethyl)-1,2,4-oxadiazole; 5-(4-((Methoxyphenyl)sulfonyl)piperazin-1-yl)-3-(2,2,2-trifluoroethyl)-1,2,4-oxadiazole; 5-(4-((4-Ethoxyphenyl)sulfonyl)piperazin-1-yl)-3-(2,2,2-trifluoroethyl)-1,2,4-oxadiazole; 5-(4-((4-(Difluoromethoxy)phenyl)sulfonyl)piperazin-1-yl)-3-(2,2,2-trifluoroethyl)-1,2,4-oxadiazole; 5-(4-((4-(Methylthio)phenyl)sulfonyl)piperazin-1-yl)-3-(2,2,2-trifluoroethyl)-1,2,4-oxadiazole; 1-(4-Methoxy-benzenesulfonyl)-4-[3-(2-methyl-pyridin-4-ylmethyl)-[1,2,4]oxadiazol-5-yl]-piperazine; 5-(4-(4-Chlorophenethyl)piperazin-1-yl)-3-((2-methylpyridin-4-yl)methyl)-1,2,4-oxadiazole; 5-(4-((4-Methoxyphenyl)sulfonyl)piperazin-1-yl)-3-(3,3,3-trifluoropropyl)-1,2,4-oxadiazole; 5-(4-((4-(Methylthio)phenyl)sulfonyl)piperazin-1-yl)-3-(3,3,3-trifluoropropyl)-1,2,4-oxadiazole; 5-(4-((4-(Difluoromethoxy)phenyl)sulfonyl)piperazin-1-yl)-3-(3,3,3-trifluoropropyl)-1,2,4-oxadiazole; 5-(4-(4-Chlorophenethyl)piperazin-1-yl)-3-(3,3,3-trifluoropropyl)-1,2,4-oxadiazole; 5-(4-(2-(2-Methoxypyridin-4-yl)ethyl)piperazin-1-yl)-3-(3,3,3-trifluoropropyl)-1,2,4-oxadiazole; 5-(4-(2-Methylbenzyl)piperazin-1-yl)-3-(3,3,3-trifluoropropyl)-1,2,4-oxadiazole; 5-(4-(2-Chlorobenzyl)piperazin-1-yl)-3-(3,3,3-trifluoropropyl)-1,2,4-oxadiazole; 2-((4-(3-(3,3,3-Trifluoropropyl)-1,2,4-oxadiazol-5-yl)piperazin-1-yl)methyl)benzonitrile; 5-(4-Isopentylpiperazin-1-yl)-3-(3,3,3-trifluoropropyl)-1,2,4-oxadiazole; 4-(2-(4-(3-(3,3,3-Trifluoropropyl)-1,2,4-oxadiazol-5-yl)piperazin-1-yl)ethyl)morpholine; 4-(4-(3-(3,3,3-Trifluoropropyl)-1,2,4-oxadiazol-5-yl)piperazin-1-yl)butanenitrile; 5-(4-((6-Methylpyridin-2-yl)methyl)piperazin-1-yl)-3-(3,3,3-trifluoropropyl)-1,2,4-oxadiazole; 1-[2-(4-Chloro-phenyl)-ethyl]-4-[3-(4-trifluoromethyl-phenyl)-[1,2,4]oxadiazol-5-yl]-piperazine; 3-((1S,4R)-bicyclo[2.2.1]heptan-2-yl)-5-(4-(2-chlorobenzyl)piperazin-1-yl)-1,2,4-oxadiazole; 3-((1S,4R)-bicyclo[2.2.1]heptan-2-yl)-5-(4-(4-methylbenzyl)piperazin-1-yl)-1,2,4-oxadiazole; 3-((1S,4R)-bicyclo[2.2.1]heptan-2-yl)-5-(4-(4-chlorophenethyl)piperazin-1-yl)-1,2,4-oxadiazole; 3-((1S,4R)-bicyclo[2.2.1]heptan-2-yl)-5-(4-(2-(2-methoxypyridin-4-yl)ethyl)piperazin-1-yl)-1,2,4-oxadiazole; 4-(2-(4-(3-((1S,4R)-bicyclo[2.2.1]heptan-2-yl)-1,2,4-oxadiazol-5-yl)piperazin-1-yl)ethyl)morpholine; 3-((1S,4R)-bicyclo[2.2.1]heptan-2-yl)-5-(4-isopentylpiperazin-1-yl)-1,2,4-oxadiazole; 3-(Bicyclo[2.2.1]heptan-2-yl)-5-(4-((4-methoxyphenyl)sulfonyl)piperazin-1-yl)-1,2,4-oxadiazole; 3-(Bicyclo[2.2.1]heptan-2-yl)-5-(4-((4-(methylthio)phenyl)sulfonyl)piperazin-1-yl)-1,2,4-oxadiazole; 3-(Bicyclo[2.2.1]heptan-2-yl)-5-(4-((4-(difluoromethoxy)phenyl)sulfonyl)piperazin-1-yl)-1,2,4-oxadiazole; 3-Cyclopropyl-5-(4-((4-ethoxyphenyl)sulfonyl)piperazin-1-yl)-1,2,4-oxadiazole; 3-Cyclopropyl-5-(4-((4-methoxyphenyl)sulfonyl)piperazin-1-yl)-1,2,4-oxadiazole; 5-(4-((4-Methoxyphenyl)sulfonyl)piperazin-1-yl)-3-(2-(2-methylpyridin-4-yl)propan-2-yl)-1,2,4-oxadiazole; 1-(4-Difluoromethoxy-benzenesulfonyl)-4-[3-(1-methyl-1-phenyl-ethyl)-[1,2,4]oxadiazol-5-yl]-piperazine; 1-(4-Methoxy-benzenesulfonyl)-4-[3-(1-methyl-1-phenyl-ethyl)-[1,2,4]oxadiazol-5-yl]-piperazine; (5-(4-((4-Methoxyphenyl)sulfonyl)piperazin-1-yl)-1,2,4-oxadiazol-3-yl)methanol; 3-(Methoxymethyl)-5-(4-((4-methoxyphenyl)sulfonyl)piperazin-1-yl)-1,2,4-oxadiazole; 3-((4-Chlorophenoxy)methyl)-5-(4-((4-methoxyphenyl)sulfonyl)piperazin-1-yl)-1,2,4-oxadiazole; 3-((3-Chlorophenoxy)methyl)-5-(4-((4-methoxyphenyl)sulfonyl)piperazin-1-yl)-1,2,4-oxadiazole; 5-(4-((4-Methoxyphenyl)sulfonyl)piperazin-1-yl)-3-(phenoxymethyl)-1,2,4-oxadiazole; 3-((Cyclopropylmethoxy)methyl)-5-(4-((4-methoxyphenyl)sulfonyl)piperazin-1-yl)-1,2,4-oxadiazole; 5-(4-((4-Methoxyphenyl)sulfonyl)piperazin-1-yl)-3-((pyridin-3-yloxy)methyl)-1,2,4-oxadiazole; 4-((5-(4-((4-Methoxyphenyl)sulfonyl)piperazin-1-yl)-1,2,4-oxadiazol-3-yl)methoxy)benzonitrile; 3-((4-Fluorophenoxy)methyl)-5-(4-((4-methoxyphenyl)sulfonyl)piperazin-1-yl)-1,2,4-oxadiazole; 5-(4-((4-Methoxyphenyl)sulfonyl)piperazin-1-yl)-3-propyl-1,2,4-oxadiazole; 3-Butyl-5-(4-((4-methoxyphenyl)sulfonyl)piperazin-1-yl)-1,2,4-oxadiazole; 3-(Tert-butyl)-5-(4-((4-methoxyphenyl)sulfonyl)piperazin-1-yl)-1,2,4-oxadiazole; 3-Cyclohexyl-5-(4-((4-methoxyphenyl)sulfonyl)piperazin-1-yl)-1,2,4-oxadiazole; 3-Isopropyl-5-(4-((4-methoxyphenyl)sulfonyl)piperazin-1-yl)-1,2,4-oxadiazole; 3-(2-Methoxyethyl)-5-(4-((4-methoxyphenyl)sulfonyl)piperazin-1-yl)-1,2,4-oxadiazole; 3-(1-(4-Fluorophenyl)cyclopropyl)-5-(7-((4-methoxyphenyl)sulfonyl)-2,7-diazaspiro[3.5]nonan-2-yl)-1,2,4-oxadiazole; 5-(7-((4-Methoxyphenyl)sulfonyl)-2,7-diazaspiro[3.5]nonan-2-yl)-3-(2,2,2-trifluoroethyl)-1,2,4-oxadiazole; 5-(7-((4-(Methylthio)phenyl)sulfonyl)-2,7-diazaspiro[3.5]nonan-2-yl)-3-(2,2,2-trifluoroethyl)-1,2,4-oxadiazole; 5-(7-((4-Ethoxyphenyl)sulfonyl)-2,7-diazaspiro[3.5]nonan-2-yl)-3-(2,2,2-trifluoroethyl)-1,2,4-oxadiazole; 5-(7-((4-(Difluoromethoxy)phenyl)sulfonyl)-2,7-diazaspiro[3.5]nonan-2-yl)-3-(2,2,2-trifluoroethyl)-1,2,4-oxadiazole; (3-(4-Fluorobenzyl)-1,2,4-oxadiazol-5-yl)(7-((4-methoxyphenyl)sulfonyl)-2,7-diazaspiro[3.5]nonan-2-yl)methanone; 3-(4-Fluorobenzyl)-5-(7-((4-methoxyphenyl)sulfonyl)-2,7-diazaspiro[3.5]nonan-2-yl)-1,2,4-oxadiazole; 3-(2-Methoxyethyl)-5-(7-((4-methoxyphenyl)sulfonyl)-2,7-diazaspiro[3.5]nonan-2-yl)-1,2,4-oxadiazole; and a solvate, hydrate, pharmaceutically acceptable salt thereof.

170. A pharmaceutical composition comprising one or more pharmaceutically excipients and a therapeutically effective amount of a compound according to any one of statements 1 to 169; or a therapeutically effective amount of a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof.

171. A compound according to any one of statements 1 to 169 or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4- oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to statement 170, for use as a medicament.

172. A compound according to any one of statements 1 to 169, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to statement 170, for use as a medicine for the prevention and/or treatment of metabolic disorders and/or neurodegenerative diseases and/or protein misfolding disorders.

173. A compound according to any one of statements 1 to 169, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to statement 170, for use as a medicine for the prevention and/or treatment of diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension.

174. A compound according to any one of statements 1 to 169, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; or a pharmaceutical composition according to statement 170, for use as a medicine for the prevention and/or treatment of diabetes mellitus, Parkinson's disease and/or Alzheimer's disease.

175. A compound according to any one of statements 1 to 169, having one of formula (IA), (IIA), (IB), (IIB), (IC), (IIC), (ID), (IID), (IF), (IIF), (IH), (IIH), (IIJ), (IIK), for use as a medicine for the prevention and/or treatment of diabetes mellitus, and/or Parkinson's disease.

176. A compound according to any one of statements 1 to 169, having one of formula (I), (II), (IE), (IIE), (IG), (IIG), wherein $L^2$ is a single bond or is —$(CR^9R^{10})_q$—; (IJ) or (IIL); for use as a medicine for the prevention and/or treatment of Alzheimer's disease.

177. A compound according to any one of statements 1 to 169, or a pharmaceutical composition according to statement 170, for use as a medicine for the prevention and/or treatment of—diabetes mellitus type 1, diabetes mellitus type 2, Parkinson's disease and/or Alzheimer's disease.

178. A compound according to any one of statements 1 to 169, or a pharmaceutical composition according to statement 170, or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-i-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-

((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; for use as a medicine for the prevention and/or treatment of diabetes mellitus type 2, Parkinson's disease and/or Alzheimer's disease.

179. A method of prevention and/or treatment of metabolic disorders, and/or neurodegenerative diseases, and/or protein misfolding disorders, comprising administering an effective amount of a compound according to any one of statements 1 to 169, or a pharmaceutical composition according to statement 170; or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof to a subject in need thereof.

180. A method of prevention and/or treatment of diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension, comprising administering an effective amount of a compound according to any one of statements 1 to 169, or a pharmaceutical composition according to statement 170; or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin- 1-yl)-1,2,4-oxadiazole; 3-(3,4-dimethoxyphenyl)-5-(4-(2, 3,4-trimethoxybenzyl)piperazin-1-yl)-1,2,4-oxadiazole; 3-(2,3-dimethoxyphenyl)-5-(4-(2,3,4-trimethoxybenzyl) piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2, 4-oxadiazole; 3-phenyl-5-(4-(2,3,4-trimethoxybenzyl) piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3] dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl) sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof; to a subject in need thereof.

181. A method of prevention and/or treatment of diabetes mellitus, Parkinson's disease and/or Alzheimer's disease, comprising administering an effective amount of a compound according to any one of statements 1 to 169, or a pharmaceutical composition according to statement 170; or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl) ethanone; 5-(4-((2-methoxypyrimidin-5-yl)methyl) piperazin-1-yl)-3-phenyl-1,2,4-oxadiazole; 2-((4-(3-phenyl-1,2,4-oxadiazol-5-yl)piperazin-1-yl)methyl) benzoic acid; 5-(4-((2-ethyl-4-methyl-1H-imidazol-5-yl) methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl) piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo [d][1,3]dioxol-5-ylmethyl)piperazin-1-yl)-3-(3-methoxyphenyl)-1,2,4-oxadiazole; 5-(4-(benzo[d][1,3] dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2, 3,4-trimethoxybenzyl)piperazin-1-yl)-1,2,4-oxadiazole; 3-(2,3-dimethoxyphenyl)-5-(4-(2,3,4-trimethoxybenzyl) piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2, 4-oxadiazole; 3-phenyl-5-(4-(2,3,4-trimethoxybenzyl) piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3] dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl) sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof to a subject in need thereof.

182. A method of prevention and/or treatment of diabetes mellitus type 1, diabetes mellitus type 2, Parkinson's disease and/or Alzheimer's disease, comprising administering an effective amount of a compound according to any one of statements 1 to 169, or a pharmaceutical composition according to statement 170; or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl) piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo [d][1,3]dioxol-5-ylmethyl)piperazin-1-yl)-3-(3-methoxyphenyl)-1,2,4-oxadiazole; 5-(4-(benzo[d][1,3] dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2, 3,4-trimethoxybenzyl)piperazin-1-yl)-1,2,4-oxadiazole; 3-(2,3-dimethoxyphenyl)-5-(4-(2,3,4-trimethoxybenzyl) piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof to a subject in need thereof.

183. A method of prevention and/or treatment of diabetes mellitus type 2, Parkinson's disease and/or Alzheimer's disease, comprising administering an effective amount of a compound according to any one of statements 1 to 169, or a pharmaceutical composition according to statement 170; or a compound selected from the group consisting of 5-(4-((3-methylpyridin-2-yl)methyl)piperazin-1-yl)-3-phenyl-1,2,4-oxadiazole; 5-(4-(3-fluorobenzyl)piperazin-1-yl)-3-phenyl-1,2,4-oxadiazole; 3-(4-bromophenyl)-5-(4-(4-fluorophenethyl)piperazin-1-yl)-1,2,4-oxadiazole; 2-(4-(3-(3,5-dichlorophenyl)-1,2,4-oxadiazol-5-yl)piperazin-1-yl)-1-morpholinoethanone; 3-(3,5-dichlorophenyl)-5-(4-(pyridin-2-ylmethyl)piperazin-1-yl)-1,2,4-oxadiazole; 1-(7-methyl-1-(3-(4-(3-(pyridin-3-yl)-1,2,4-oxadiazol-5-yl)piperazin-1-yl)propyl)-1H-indol-3-yl)ethanone; 5-(4-((2-methoxypyrimidin-5-yl)methyl)piperazin-1-yl)-3-phenyl-1,2,4-oxadiazole; 2-((4-(3-phenyl-1,2,4-oxadiazol-5-yl)piperazin-1-yl)methyl)benzoic acid; 5-(4-((2-ethyl-4-methyl-1H-imidazol-5-yl)methyl)piperazin-1-yl)-3-phenyl-1,2,4-oxadiazole; 3-phenyl-5-(4-((2-phenylthiazol-4-yl)methyl)piperazin-1-yl)-1,2,4-oxadiazole; 5-(4-benzylpiperazin-1-yl)-3-(3-methoxyphenyl)-1,2,4-oxadiazole; 5-(4-benzylpiperazin-1-yl)-3-(2,3-dimethoxyphenyl)-1,2,4-oxadiazole; 5-(4-(benzo[d][1,3]dioxol-5-ylmethyl)piperazin-1-yl)-3-phenyl-1,2,4-oxadiazole; 5-(4-(benzo[d][1,3]dioxol-5-ylmethyl)piperazin-1-yl)-3-(3,4-dimethoxyphenyl)-1,2,4-oxadiazole; 5-(4-(benzo[d][1,3]dioxol-5-ylmethyl)piperazin-1-yl)-3-(4-methoxyphenyl)-1,2,4-oxadiazole; 5-(4-(benzo[d][1,3]dioxol-5-ylmethyl)piperazin-1-yl)-3-(2-fluorophenyl)-1,2,4-oxadiazole; 5-(4-benzylpiperazin-1-yl)-3-phenyl-1,2,4-oxadiazole; 5-(4-benzylpiperazin-1-yl)-3-(4-methoxyphenyl)-1,2,4-oxadiazole; 5-(4-(benzo[d][1,3]dioxol-5-ylmethyl)piperazin-1-yl)-3-(3-methoxyphenyl)-1,2,4-oxadiazole; 5-(4-(benzo[d][1,3]dioxol-5-ylmethyl)piperazin-1-yl)-3-(2,3-dimethoxyphenyl)-1,2,4-oxadiazole; 3-(4-methoxyphenyl)-5-(4-(2,3,4-trimethoxybenzyl)piperazin-1-yl)-1,2,4-oxadiazole; 3-(3,4-dimethoxyphenyl)-5-(4-(2,3,4-trimethoxybenzyl)piperazin-1-yl)-1,2,4-oxadiazole; 3-(2,3-dimethoxyphenyl)-5-(4-(2,3,4-trimethoxybenzyl)piperazin-1-yl)-1,2,4-oxadiazole; 3-(2-fluorophenyl)-5-(4-(2,3,4-trimethoxybenzyl)piperazin-1-yl)-1,2,4-oxadiazole; 5-(4-benzylpiperazin-1-yl)-3-(2-fluorophenyl)-1,2,4-oxadiazole; 3-phenyl-5-(4-(2,3,4-trimethoxybenzyl)piperazin-1-yl)-1,2,4-oxadiazole; 5-(4-benzylpiperazin-1-yl)-3-(3,4-dimethoxyphenyl)-1,2,4-oxadiazole; 5-(4-((2,3-dihydrobenzo[b][1,4]dioxin-6-yl)methyl)piperazin-1-yl)-3-methyl-1,2,4-oxadiazole; 5-(4-(benzo[d][1,3]dioxol-5-ylmethyl)piperazin-1-yl)-3-methyl-1,2,4-oxadiazole; 3-(4-bromophenyl)-5-(4-(4-isopropoxyphenethyl)piperazin-1-yl)-1,2,4-oxadiazole; 3-(4-bromophenyl)-5-(4-phenethylpiperazin-1-yl)-1,2,4-oxadiazole; 5-(4-(benzo[b][1,4]dioxin-6-ylmethyl)piperazin-1-yl)-1,2,4-oxadiazole; 5-(4-isobutylpiperazin-1-yl)-3-isopropyl-1,2,4-oxadiazole; N,N,2,2-tetramethyl-3-[4-(3-phenyl-1,2,4-oxadiazol-5-yl)piperazin-1-yl]propan-1-amine; 3-(4-bromophenyl)-5-[4-(2-nitrophenyl)sulfonylpiperazin-1-yl]-1,2,4-oxadiazole; 5-(4-benzylsulfonylpiperazin-1-yl)-3-cyclopropyl-1,2,4-oxadiazole; 5-[4-(4-methoxyphenyl)sulfonylpiperazin-1-yl]-3-phenyl-1,2,4-oxadiazole, and a solvate, hydrate, or pharmaceutically acceptable salt thereof to a subject in need thereof.

184. A method of prevention and/or treatment of diabetes mellitus, and/or Parkinson's disease, comprising administering an effective amount of a compound according to any one of statements 1 to 169, having one of formula (IA), (IIA), (IB), (IIB), (IC), (IIC), (ID), (IID), (IF), (IIF), (IH), (IIH), or a solvate, hydrate, pharmaceutically acceptable salt, or prodrug thereof to a subject in need thereof.

185. The compound according to any one of statements 1 to 168, wherein the group heteroaryl is selected from a group comprising 5 to 12 carbon-atom aromatic rings or ring systems containing 1 or 2 rings which can be fused together or linked covalently, typically containing 5 to 6 atoms; at least one of which is aromatic in which one or more carbon atoms in one or more of these rings can be replaced by N, O and/or S atoms where the N and S heteroatoms may optionally be oxidized and the N heteroatoms may optionally be quaternized, wherein said rings may be fused to an aryl, cycloalkyl, heteroaryl or heterocyclyl ring; and wherein at least one carbon atom of said heteroaryl can be oxidized to form at least one C=O.

186. The compound according to any one of statements 1 to 168, and 185, wherein the group heteroaryl is selected from the group comprising pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, thienopyridinyl, purinyl, imidazo[1,2-a]pyridinyl, 6-oxopyridazin-1 (6H)-yl, 2-oxopyridin-1 (2H)-yl, 6-oxopyridazin-1(6H)-yl, 2-oxopyridin-1(2H)-yl, 1,3-benzodioxolyl, quinolinyl, isoquinolinyl, cinnolinyl, quinazolinyl, quinoxalinyl; and wherein at least one carbon atom of said heteroaryl can be oxidized to form at least one C=O.

187. The compound according to any one of statements 1 to 168, 185-186, wherein the group heteroaryl is selected from the group comprising pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, purinyl, 1,3-benzodioxolyl; and wherein at least one carbon atom of said heteroaryl can be oxidized to form at least one C=O.

188. The compound according to any one of statements 1 to 168, 185 to 187, wherein said heteroaryl group is selected from the group consisting of pyridyl, 1,3-benzodioxolyl, benzo[d]oxazol-2(3H)-one, 2,3-dihydro-benzofuranyl, pyrazinyl, pyrazolyl, pyrrolyl, isoxazolyl, thiophenyl imidazolyl, benzimidazolyl, pyrimidinyl, triazolyl and thiazolyl; and wherein at least one carbon atom of said heteroaryl can be oxidized to form at least one C=O.

189. The compound according to any one of statements 1 to 168, and 185 to 188, wherein the group heterocyclyl is selected from the group comprising non-aromatic, fully saturated or partially unsaturated cyclic groups which have at least one heteroatom in at least one carbon atom-containing ring; preferably the group heterocyclyl is selected comprising non-aromatic, fully saturated or partially unsaturated cyclic groups which have at least one heteroatom in at least one carbon atom-containing ring, wherein each ring of the heterocyclyl group containing a heteroatom may have 1, 2, 3 or 4 heteroatoms selected from N, O and/or S, where the N and S heteroatoms may optionally be oxidized and the N heteroatoms may optionally be quaternized; and wherein at least one carbon atom of heterocyclyl can be oxidized to form at least one C=O.

190. The compound according to any one of statements 1 to 168, and 185 to 189, wherein the group heterocyclyl is selected from the group comprising aziridinyl, oxiranyl, thiiranyl, piperidinyl, azetidinyl, oxetanyl, pyrrolidinyl, thietanyl, 2-imidazolinyl, pyrazolidinyl imidazolidinyl, chromanyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl; and wherein at least one carbon atom of heterocyclyl can be oxidized to form at least one C=O.

According to an embodiment, the present invention provides compounds of formula (I), or (II), and any subgroup thereof such as (IA), (IIA), (IB), (IIB), (IC), (IIC), (ID), (IID), (IE), (IIE), (IF), (IIF), (IG), (IIG), (H), (IH), (J), (IIJ), (IIK), (IL) wherein, n is an integer selected from 0, 1, 2 or 3; preferably n is 0, 1 or 2; more preferably n is 0 or 1; more preferably n is 0;

$R^1$ is selected from the group consisting of $C_{1-6}$alkyl, halo, halo$C_{1-6}$alkyl, and halo$C_{1-6}$alkyloxy; preferably $R^1$ is selected from the group consisting of $C_{1-6}$alkyl, halo, and halo$C_{1-6}$alkyl; preferably $R^1$ is $C_{1-6}$alkyl, preferably n is 0 and there is no $R^1$;

$R^2$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{15}$, —$SR^{16}$, halo$C_{1-6}$alkyl, halo$C_{1-6}$alkyloxy, amino, —$NR^{17}R^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$; preferably $R^2$ is selected from the group consisting of $C_{6-12}$aryl, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{15}$ (preferably wherein $R^{15}$ is $C_{1-6}$alkyl, $C_{6-12}$aryl, heteroaryl, or $C_{3-12}$cycloalkyl), halo$C_{1-6}$alkyl, halo$C_{1-6}$alkyloxy, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^1$; preferably $R^2$ is selected from the group consisting of $C_{6-12}$aryl, $C_{1-6}$alkyl, $C_{3-12}$cycloalkyl, heterocyclyl, heteroaryl, halo, hydroxyl, —$OR^{15}$ (preferably wherein $R^{15}$ is $C_{1-6}$alkyl, $C_{6-12}$aryl, heteroaryl, or $C_{3-12}$cycloalkyl), halo$C_{1-6}$alkyl, halo$C_{1-6}$alkyloxy, and cyano; and wherein said $C_{6-12}$aryl, $C_{1-6}$alkyl, $C_{3-12}$cycloalkyl, heterocyclyl, heteroaryl, can be unsubstituted or substituted with one or more $Z^1$; preferably $R^2$ is selected from the group consisting of $C_{6-12}$aryl, $C_{1-6}$alkyl, $C_{3-12}$cycloalkyl, heterocyclyl, heteroaryl, halo, hydroxyl, $C_{6-12}$aryloxy, $C_{1-6}$alkyloxy, $C_{3-12}$cycloalkyloxy, heterocyclyloxy, heteroaryloxy, halo$C_{1-6}$alkyloxy, and cyano; and wherein said group can be unsubstituted or substituted with one or more $Z^1$;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, $C_{6-12}$aryl$C_{1-6}$alkyl$C_{6-12}$aryl, halo, hydroxyl, —$OR^{15}$, —$SR^{16}$, halo$C_{1-6}$alkyl, halo$C_{1-6}$alkyloxy, —$NR^{17}R^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$; preferably $R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, halo, hydroxyl, —$OR^{15}$, $C_{1-6}$alkyloxy, halo$C_{1-6}$alkyl, halo$C_{1-6}$alkyloxy, —$NR^{17}R^{18}$ and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$; preferably $R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, halo, hydroxyl, $C_{1-6}$alkyloxy, halo$C_{1-6}$alkyl, halo$C_{1-6}$alkyloxy, mono or di $C_{1-6}$alkylamino, and cyano; and wherein said group can be unsubstituted or substituted with one or more $Z^2$;

$L^1$ is a single bond, or is a group of formula (i); preferably $L$ is a single bond or is selected from the group comprising $C_{1-6}$alkylene, $C_{3-6}$cycloalkylene, or $C_{1-6}$alkyleneoxy, wherein each group can be unsubstituted or substituted with one or more substituents each independently selected from halo, or $C_{1-6}$alkyl;

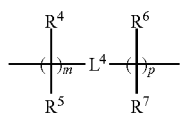

wherein the left side of the group of formula (i) is attached to $R^2$ and the right side thereof is attached to the oxadiazole ring; and wherein, m is an integer selected from 0, 1, 2, 3 or 4; preferably m is 0, 1, 2 or 3, preferably m is 0, 1 or 2, preferably m is 0 or 1, preferably m is 1;

p is an integer selected from 0, 1, 2, 3 or 4; preferably p is 0, 1, 2 or 3, preferably p is 0, 1 or 2, preferably p is 0 or 1, preferably p is 0;

$L^4$ is a single bond, or is selected from the group consisting of —O—, and —$NR^8$—; preferably $L^4$ is a single bond, or is —O—;

$R^4$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy; preferably $R^4$ is selected from the group consisting of hydrogen, $C_{1-6}$alkyl, halo, hydroxyl, halo$C_{1-6}$alkyl, and halo$C_{1-6}$ alkyloxy; preferably $R^4$ is selected from the group consisting of hydrogen, $C_{1-6}$alkyl, halo, and hydroxyl; preferably $R^4$ is selected from the group consisting of hydrogen, $C_{1-6}$alkyl, and halo;

$R^5$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy; preferably $R^5$ is selected from the group consisting of hydrogen, $C_{1-6}$alkyl, halo, hydroxyl, halo$C_{1-6}$alkyl, and halo$C_{1-6}$ alkyloxy; preferably $R^5$ is selected from the group consisting of hydrogen, $C_{1-6}$alkyl, halo, and hydroxyl; preferably $R^5$ is selected from the group consisting of hydrogen, $C_{1-6}$alkyl, and halo;

or $R^4$ and $R^5$ together with the carbon atom to which they are attached form a saturated or unsaturated 3-, 4-, 5-, 6- or 7-membered ring; preferably $R^4$ and $R^5$ together with the carbon atom to which they are attached form a saturated 3-, 4-, 5-, 6- or 7-carbon membered ring; preferably $R^4$ and $R^5$ together with the carbon atom to which they are attached form a saturated 3-, 4-, or 5-carbon membered ring; preferably $R^4$ and $R^5$ together with the carbon atom to which they are attached form a saturated or 3-, or 4-carbon membered ring; preferably $R^4$ and $R^5$ together with the carbon atom to which they are attached form a saturated 3-carbon membered ring;

$R^6$ is selected from the group consisting of hydrogen, $C_{1-6}$alkyl, halo, hydroxyl, —$OR^{15}$, —$SR^{16}$ halo$C_{1-6}$alkyl, and halo$C_{1-6}$alkyloxy; preferably $R^6$ is selected from the group consisting of hydrogen, $C_{1-6}$alkyl, halo, hydroxyl, halo$C_{1-6}$alkyl, and halo$C_{1-6}$ alkyloxy; preferably $R^6$ is selected from the group consisting of hydrogen, $C_{1-6}$alkyl, halo, and hydroxyl; preferably $R^6$ is selected from the group consisting of hydrogen, $C_{1-6}$alkyl, and halo;

$R^7$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy; preferably $R^7$ is selected from the group consisting of hydrogen, $C_{1-6}$alkyl, halo, hydroxyl, halo$C_{1-6}$alkyl, and halo$C_{1-6}$ alkyloxy; preferably $R^7$ is selected from the group consisting of hydrogen, $C_{1-6}$alkyl, halo, and hydroxyl; preferably $R^7$ is selected from the group consisting of hydrogen, $C_{1-6}$alkyl, and halo;

or $R^6$ and $R^7$ together with the carbon atom to which they are attached form a saturated or unsaturated 3-, 4-, 5-, 6- or 7-membered ring; preferably $R^6$ and $R^7$ together with the carbon atom to which they are attached form a saturated 3-, 4-, 5-, 6- or 7-carbon membered ring; preferably $R^6$ and $R^7$ together with the carbon atom to which they are attached form a saturated 3-, 4-, or 5-carbon membered ring; preferably $R^6$ and $R^7$ together with the carbon atom to which they are attached form a saturated or 3-, or 4-carbon membered ring; preferably $R^6$ and $R^7$ together with the carbon atom to which they are attached form a saturated 3-carbon membered ring;

$R^8$ is selected from the group consisting of hydrogen, and $C_{1-6}$alkyl; preferably $R^8$ is selected from the group consisting of hydrogen, and $C_{1-4}$alkyl; preferably $R^8$ is hydrogen;

$L^2$ is a single bond or is selected from the group consisting of —$SO_2$—, —$PO_4$—, —$PO_3$—, and —$(CR^9R^{10})_q$—; wherein, q is an integer selected from 1, 2 or 3; preferably $L^2$ is a single bond or is selected from the group consisting of —$SO_2$—, and —$(CR^9R^{10})_q$—; wherein, q is an integer selected from 1, 2 or 3; preferably $L^2$ is a single bond or is selected from the group consisting of —$SO_2$—, and —$(CR^9R^{10})_q$—; wherein, q is an integer selected from 1 or 2; preferably $L^2$ is a single bond or is selected from the group consisting of —$SO_2$—, —$CH_2$—, and —$CH_2$—$CH_2$—;

$R^9$ is selected from the group consisting of hydrogen, $C_{1-6}$alkyl, halo, hydroxyl, —$OR^{15}$, —$SR^{16}$ halo$C_{1-6}$alkyl, and halo$C_{1-6}$alkyloxy; preferably $R^9$ is selected from the group consisting of hydrogen, $C_{1-6}$alkyl, halo, and hydroxyl; preferably $R^9$ is selected from the group consisting of hydrogen, and $C_{1-6}$alkyl; preferably $R^9$ is hydrogen;

$R^{10}$ is selected from the group consisting of hydrogen, $C_{1-6}$alkyl, halo, hydroxyl, —$OR^{15}$, —$SR^{16}$ halo$C_{1-6}$alkyl, and halo$C_{1-6}$alkyloxy; preferably $R^{10}$ is selected from the group consisting of hydrogen, $C_{1-6}$alkyl, halo, hydroxyl; preferably $R^{10}$ is selected from the group consisting of hydrogen, and $C_{1-6}$alkyl; preferably $R^{10}$ is hydrogen;

or $R^9$ and $R^{10}$ together with the carbon atom to which they are attached form a saturated or unsaturated 3-, 4-, 5-, 6- or 7-membered ring; preferably $R^9$ and $R^{10}$ together with the carbon atom to which they are attached form a saturated 3-, 4-, 5-, 6- or 7-carbon membered ring; preferably $R^9$ and $R^{10}$ together with the carbon atom to which they are attached form a saturated 3-, 4-, or 5-carbon membered ring; preferably $R^9$ and $R^{10}$ together with the carbon atom to which they are attached form a saturated or 3-, or 4-carbon membered ring; preferably $R^9$ and $R^{10}$ together with the carbon atom to which they are attached form a saturated 3-carbon membered ring;

$L^3$ is a single bond or is selected from the group consisting of —$(CR^{11}R^{12})_r$—, —O—, and —$NR^{13}$—; wherein, r is an integer selected from 1, 2 or 3; preferably, $L^3$ is a single bond or is selected from the group consisting of —O—, and —$(CR^{11}R^{12})_r$—; wherein r is an integer selected from 1, or 2; preferably $L^3$ is a single bond or is —$(CR^{11}R^{12})_r$—; wherein, r is an integer selected from 1 or 2; preferably $L^3$ is a single bond or is selected from —$CH_2$—, or —$CH_2$—$CH_2$—;

$R^{11}$ is selected from the group consisting of hydrogen, $C_{1-6}$alkyl, halo, hydroxyl, —$OR^{15}$, —$SR^{16}$ halo$C_{1-6}$alkyl, and halo$C_{1-6}$alkyloxy; preferably $R^{11}$ is selected from the group consisting of hydrogen, $C_{1-6}$alkyl, halo, and hydroxyl; preferably $R^{11}$ is selected from the group consisting of hydrogen, and $C_{1-6}$alkyl; preferably $R^{11}$ is hydrogen;

$R^{12}$ is selected from the group consisting of hydrogen, $C_{1-6}$alkyl, halo, hydroxyl, —$OR^{15}$, —$SR^{16}$, halo$C_{1-6}$alkyl, and halo$C_{1-6}$alkyloxy; preferably $R^{12}$ is selected from the group consisting of hydrogen, $C_{1-6}$alkyl, halo, and hydroxyl; preferably $R^{12}$ is selected from the group consisting of hydrogen, and $C_{1-6}$alkyl; preferably $R^{12}$ is hydrogen;

or $R^{11}$ and $R^{12}$ together with the carbon atom to which they are attached form a saturated or unsaturated 3-, 4-, 5-, 6- or 7-membered ring; preferably $R^{11}$ and $R^{12}$ together with the carbon atom to which they are attached form a saturated 3-, 4-, 5-, 6- or 7-carbon membered ring; preferably $R^{11}$ and $R^{12}$ together with the carbon atom to which they are attached form a saturated 3-, 4-, or 5-carbon membered ring; preferably $R^{11}$ and $R^{12}$ together with the carbon atom to which they are attached form a saturated or 3-, or 4-carbon membered ring; preferably $R^{11}$ and $R^{12}$ together with the carbon atom to which they are attached form a saturated 3-carbon membered ring;

$R^{13}$ is selected from the group consisting of hydrogen, and $C_{1-6}$alkyl; preferably $R^{13}$ is selected from the group consisting of hydrogen, and $C_{1-4}$alkyl; preferably $R^{23}$ is hydrogen;

wherein at least one of $L^2$, $L^3$ is not a single bond;

$L^5$ is a single bond or —CO—;

each $R^{15}$ is independently selected from the group consisting of $C_{1-6}$alkyl, $C_{2-6}$alkenyl, $C_{2-6}$alkynyl, $C_{6-12}$aryl, $C_{3-8}$cycloalkyl$C_{1-6}$alkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl; and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^1$; preferably each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$alkyl, $C_{6-12}$aryl$C_{1-6}$alkyl, heterocyclyl, heteroaryl, and cyano$C_{1-6}$alkyl; and wherein said $C_{1-6}$alkyl, $C_{3-8}$cycloalkyl$C_{1-6}$alkyl, $C_{6-12}$aryl, $C_{3-8}$cycloalkyl, heterocyclyl, heteroaryl, and cyano$C_{1-6}$alkyl, can be unsubstituted or substituted with one or more $Z^1$; preferably each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$alkyl, and heteroaryl; and wherein said $C_{1-6}$alkyl, $C_{3-8}$cycloalkyl$C_{1-6}$alkyl, $C_{6-12}$aryl, $C_{3-8}$cycloalkyl, and heteroaryl, can be unsubstituted or substituted with one or more $Z^1$;

and wherein at least one carbon atom or heteroatom of $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{16}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, and wherein said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, and cyano$C_{1-6}$alkyl, can be unsubstituted or substituted with one or more $Z^2$; preferably wherein each $R^{16}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl; and wherein said $C_{1-6}$alkyl, $C_{6-12}$aryl, $C_{3-8}$cycloalkyl, $C_{6-12}$aryl$C_{1-6}$alkyl, heterocyclyl, heteroaryl, can be unsubstituted or substituted with one or more $Z^2$; preferably wherein each $R^{16}$ is independently selected from the group consisting of hydrogen, $C_{1-6}$alkyl, $C_{6-12}$aryl, $C_{3-8}$cycloalkyl, heterocyclyl, heteroaryl; and wherein said $C_{1-6}$alkyl, $C_{6-12}$aryl, $C_{3-8}$cycloalkyl, heterocyclyl, heteroaryl, can be unsubstituted or substituted with one or more $Z^2$;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O, C=S, N=O, N=S, S=O or $S(O)_2$;

each $R^{17}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{17}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{17}$ is independently selected from the group consisting of hydrogen, $C_{1-6}$alkyl, $C_{6-12}$aryl, $C_{3-8}$cycloalkyl, heterocyclyl, and heteroaryl; preferably each $R^{17}$ is independently selected from the group consisting of hydrogen, $C_{1-6}$alkyl, $C_{6-12}$aryl, $C_{3-8}$cycloalkyl, and heteroaryl; preferably each $R^{17}$ is independently selected from the group consisting of hydrogen, and $C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

each $R^{18}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{18}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{18}$ is independently selected from the group consisting of hydrogen, $C_{1-6}$alkyl, $C_{6-12}$aryl, $C_{3-8}$cycloalkyl, heterocyclyl, and heteroaryl; preferably each $R^{18}$ is independently selected from the group consisting of hydrogen, $C_{1-6}$alkyl, $C_{6-12}$aryl, $C_{3-8}$cycloalkyl, and heteroaryl; preferably each $R^{18}$ is independently selected from the group consisting of hydrogen, and $C_{1-6}$alkyl;

and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or $S(O)_2$;

or wherein $R^{17}$ and $R^{18}$ together with the nitrogen atom to which they are attached form a 5-, 6-, or 7-membered heterocyclyl; and wherein at least one carbon atom or heteroatom of said heterocyclyl can be oxidized to form at least one C=O, C=S, N=O, N=S, S=O or S(O)$_2$; or preferably wherein $R^{17}$ and $R^{18}$ together with the nitrogen atom to which they are attached form a 5-, or 6-membered heterocyclyl; and wherein at least one carbon atom or heteroatom of said heterocyclyl can be oxidized to form at least one C=O; or preferably wherein $R^{17}$ and $R^{18}$ together with the nitrogen atom to which they are attached form a 5-membered heterocyclyl; and wherein at least one carbon atom or heteroatom of said heterocyclyl can be oxidized to form at least one C=O;

each $R^{19}$ is independently selected from the group consisting of hydrogen, hydroxyl, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{19}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{19}$ is independently selected from the group consisting of hydrogen, $C_{1-6}$alkyl, $C_{6-12}$aryl, $C_{3-8}$cycloalkyl, heterocyclyl, and heteroaryl; preferably each $R^{19}$ is independently selected from the group consisting of hydrogen, $C_{1-6}$alkyl, $C_{6-12}$aryl, $C_{3-8}$cycloalkyl, and heteroaryl; preferably each $R^{19}$ is independently selected from the group consisting of hydrogen, $C_{1-6}$alkyl;
wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O, C=S, N=O, N=S, S=O or S(O)$_2$;

each $R^{20}$ is independently selected from the group consisting of hydrogen, $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{20}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{20}$ is independently selected from the group consisting of hydrogen, $C_{1-6}$alkyl, $C_{6-12}$aryl, $C_{3-8}$cycloalkyl, heterocyclyl, and heteroaryl; preferably each $R^{20}$ is independently selected from the group consisting of hydrogen, $C_{1-6}$alkyl, $C_{6-12}$aryl, $C_{3-8}$cycloalkyl, and heteroaryl; preferably each $R^{20}$ is independently selected from the group consisting of hydrogen, and $C_{1-6}$alkyl;
and wherein at least one carbon atom or heteroatom of said $C_{1-6}$alkyl, $C_{2-6}$alkenyl, $C_{2-6}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl can be oxidized to form at least one C=O, C=S, N=O, N=S, S=O or S(O)$_2$;

each $R^{21}$ is independently selected from $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene$C_{1-6}$alkylene*; wherein * represents where $R^{21}$ is bound to —CO—;
and wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O, C=S, N=O, N=S, S=O or S(O)$_2$;

each $Z^1$ is independently selected from the group consisting of halo, hydrogen, $C_{1-6}$alkyl, halo$C_{1-6}$alkyl, halo$C_{1-6}$ alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —OR$^{15}$, —SR$^{16}$, cyano, amino, —NR$^{17}$R$^{18}$, —CO$_2$R$^{19}$, —C(O)NR$^{17}$R$^{18}$, —C(O)R$^{19}$, —S(O)R$^{19}$, —S(O)$_2$R$^{19}$, —SO$_2$NR$^{17}$R$^{18}$, nitro, —NR$^{20}$C(O)R$^{19}$, —R$^{21}$—C(O)NR$^{17}$R$^{18}$, —NR$^{20}$S(O)$_2$R$^{19}$, and NR$^{20}$C(O)NR$^{17}$R$^{18}$; and wherein two $Z^1$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O, C=S, N=O, N=S, S=O or S(O)$_2$; preferably each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$ alkyl, hydroxyl, —OR$^{15}$, —SR$^{16}$, cyano, amino, —NR$^{17}$R$^{18}$; and wherein two $Z^1$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$ alkyl can be oxidized to form at least one C=O; preferably each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heteroaryl, hydroxyl, —OR$^{15}$, —SR$^{16}$, cyano, amino, and —NR$^{17}$R$^{18}$; and wherein two $Z^1$ together with the atom to which they are attached can form a 5-, or 6-membered ring; preferably each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$ aryl, $C_{1-6}$alkyl$C_{6-12}$aryl, heterocyclyl, heteroaryl, hydroxyl, and cyano;

each $Z^2$ is independently selected from the group consisting of halo, hydrogen, $C_{1-6}$alkyl, halo$C_{1-6}$alkyl, halo$C_{1-6}$ alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —OR$^{15}$, —SR$^{16}$, cyano, amino, —NR$^{17}$R$^{18}$, —CO$_2$R$^{19}$, —C(O)NR$^{17}$R$^{18}$, —C(O)R$^{19}$, —S(O)R$^{19}$, —S(O)$_2$R$^{19}$, —SO$_2$NR$^{17}$R$^{18}$, nitro, —NR$^{20}$C(O)R$^{19}$, —R$^{21}$—C(O)NR$^{17}$R$^{18}$, —NR$^{20}$S(O)$_2$R$^{19}$, and —NR$^{20}$C(O)NR$^{17}$R$^{18}$; and wherein two $Z^2$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$ alkyl can be oxidized to form at least one C=O, C=S, N=O, N=S, S=O or S(O)$_2$; preferably each $Z^2$ is independently selected from the group consisting of halo, hydrogen, $C_{1-6}$alkyl, halo$C_{1-6}$alkyl, $C_{1-6}$alkyloxy, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —OR$^{15}$, —SR$^{16}$, $C_{1-6}$alkylthio, cyano, cyanoC$_{1-6}$alkyloxy, amino, —NR$^{17}$R$^{18}$, —CO$_2$R$^{19}$, —C(O)NR$^{17}$R$^{18}$, —C(O)R$^{19}$, and C$_{1-6}$alkylcarbonyl; and wherein two Z$^2$ together with the atom to which they are attached can form a 5-, or 6-membered ring; and wherein at least one carbon atom or heteroatom of said ring, C$_{1-6}$alkyl, C$_{3-8}$cycloalkyl, C$_{6-12}$aryl, C$_{1-6}$alkylC$_{6-12}$aryl, heterocyclyl, heterocyclylC$_{1-6}$alkyl, heteroaryl, or heteroarylC$_{1-6}$alkyl can be oxidized to form at least one C=O; preferably each Z$^2$ is independently selected from the group consisting of halo, hydrogen, C$_{1-6}$alkyl, haloC$_{1-6}$alkyl, C$_{1-6}$alkyloxy, haloC$_{1-6}$alkyloxy, C$_{3-12}$cycloalkyl, C$_{6-12}$aryl, C$_{1-6}$alkylC$_{6-12}$aryl, heterocyclyl, heteroaryl, hydroxyl, —OR$^{15}$, —SR$^{16}$, C$_{1-6}$alkylthio, cyano, cyanoC$_{1-6}$alkyloxy, amino, —NR$^{17}$R$^{18}$, —CO$_2$R$^{19}$, —C(O)R$^{19}$, and C$_{1-6}$alkylcarbonyl; and wherein two Z$^2$ together with the atom to which they are attached can form a 5-, or 6-membered ring; and wherein at least one carbon atom or heteroatom of said ring, C$_{1-6}$alkyl, C$_{3-8}$cycloalkyl, C$_{6-12}$aryl, C$_{1-6}$alkylC$_{6-12}$aryl, heterocyclyl, heteroaryl, or heteroarylC$_{1-6}$alkyl can be oxidized to form at least one C=O; preferably each Z$^2$ is independently selected from the group consisting of halo, hydrogen, C$_{1-6}$alkyl, haloC$_{1-6}$alkyl, C$_{1-6}$alkyloxy, haloC$_{1-6}$alkyloxy, C$_{3-12}$cycloalkyl, C$_{6-12}$aryl, heterocyclyl, heteroaryl, hydroxyl, —OR$^{15}$, —SR$^{16}$, C$_{1-6}$alkylthio, cyano, cyanoC$_{1-6}$alkyloxy, amino, and C$_{1-6}$alkylcarbonyl.

In an embodiment, for a compound of formula (I) when R$^2$ is C$_{6-12}$aryl; L$^3$ is a single bond, —(CR$^{11}$R$^{12}$)$_r$—, —O—, or —NR$^{13}$—; then R$^3$ is not hydrogen, C$_{1-6}$alkyl, hydroxyl, or —OR$^{15}$.

In an embodiment, for a compound of formula (I) when L is a single bond, R$^2$ is not hydrogen.

In an embodiment, said compound is not
5-(4-((3-methylpyridin-2-yl)methyl)piperazin-1-yl)-3-phenyl-1,2,4-oxadiazole;
5-(4-(3-fluorobenzyl)piperazin-1-yl)-3-phenyl-1,2,4-oxadiazole;
3-(4-bromophenyl)-5-(4-(4-fluorophenethyl)piperazin-1-yl)-1,2,4-oxadiazole;
3-(3,5-dichlorophenyl)-5-(4-(pyridin-2-ylmethyl)piperazin-1-yl)-1,2,4-oxadiazole;
1-(7-methyl-1-(3-(4-(3-(pyridin-3-yl)-1,2,4-oxadiazol-5-yl)piperazin-1-yl)propyl)-1H-indol-3-yl)ethanone;
5-(4-((2-methoxypyrimidin-5-yl)methyl)piperazin-1-yl)-3-phenyl-1,2,4-oxadiazole;
2-((4-(3-phenyl-1,2,4-oxadiazol-5-yl)piperazin-1-yl)methyl)benzoic acid;
5-(4-((2-ethyl-4-methyl-1H-imidazol-5-yl)methyl)piperazin-1-yl)-3-phenyl-1,2,4-oxadiazole;
3-phenyl-5-(4-((2-phenylthiazol-4-yl)methyl)piperazin-1-yl)-1,2,4-oxadiazole;
5-(4-benzylpiperazin-1-yl)-3-(3-methoxyphenyl)-1,2,4-oxadiazole;
5-(4-benzylpiperazin-1-yl)-3-(2,3-dimethoxyphenyl)-1,2,4-oxadiazole;
5-(4-(benzo[d][1,3]dioxol-5-ylmethyl)piperazin-1-yl)-3-phenyl-1,2,4-oxadiazole;
5-(4-(benzo[d][1,3]dioxol-5-ylmethyl)piperazin-1-yl)-3-(3,4-dimethoxyphenyl)-1,2,4-oxadiazole;
5-(4-(benzo[d][1,3]dioxol-5-ylmethyl)piperazin-1-yl)-3-(4-methoxyphenyl)-1,2,4-oxadiazole;
5-(4-(benzo[d][1,3]dioxol-5-ylmethyl)piperazin-1-yl)-3-(2-fluorophenyl)-1,2,4-oxadiazole;
5-benzylpiperazin-1-yl)-3-phenyl-1,2,4-oxadiazole;
5-(4-benzylpiperazin-1-yl)-3-(4-methoxyphenyl)-1,2,4-oxadiazole;
5-(4-(benzo[d][1,3]dioxol-5-ylmethyl)piperazin-1-yl)-3-(3-methoxyphenyl)-1,2,4-oxadiazole;
5-(4-(benzo[d][1,3]dioxol-5-ylmethyl)piperazin-1-yl)-3-(2,3-dimethoxyphenyl)-1,2,4-oxadiazole;
3-(4-methoxyphenyl)-5-(4-(2,3,4-trimethoxybenzyl)piperazin-1-yl)-1,2,4-oxadiazole;
3-(3,4-dimethoxyphenyl)-5-(4-(2,3,4-trimethoxybenzyl)piperazin-1-yl)-1,2,4-oxadiazole;
3-(2,3-dimethoxyphenyl)-5-(4-(2,3,4-trimethoxybenzyl)piperazin-1-yl)-1,2,4-oxadiazole;
3-(2-fluorophenyl)-5-(4-(2,3,4-trimethoxybenzyl)piperazin-1-yl)-1,2,4-oxadiazole;
5-(4-benzylpiperazin-1-yl)-3-(2-fluorophenyl)-1,2,4-oxadiazole;
3-phenyl-5-(4-(2,3,4-trimethoxybenzyl)piperazin-1-yl)-1,2,4-oxadiazole;
5-(4-benzylpiperazin-1-yl)-3-(3,4-dimethoxyphenyl)-1,2,4-oxadiazole;
5-(4-((2,3-dihydrobenzo[b][1,4]dioxin-6-yl)methyl)piperazin-1-yl)-3-methyl-1,2,4-oxadiazole;
5-(4-(benzo[d][1,3]dioxol-5-ylmethyl)piperazin-1-yl)-3-methyl-1,2,4-oxadiazole;
3-(4-bromophenyl)-5-(4-(4-isopropoxyphenethyl)piperazin-1-yl)-1,2,4-oxadiazole;
3-(4-bromophenyl)-5-(4-phenethylpiperazin-1-yl)-1,2,4-oxadiazole;
5-(4-(benzo[b][1,4]dioxin-6-ylmethyl)piperazin-1-yl)-1,2,4-oxadiazole;
5-(4-isobutylpiperazin-1-yl)-3-isopropyl-1,2,4-oxadiazole;
N,N,2,2-tetramethyl-3-[4-(3-phenyl-1,2,4-oxadiazol-5-yl)piperazin-1-yl]propan-1-amine;
3-(4-bromophenyl)-5-[4-(2-nitrophenyl)sulfonylpiperazin-1-yl]-1,2,4-oxadiazole;
5-(4-benzylsulfonylpiperazin-1-yl)-3-cyclopropyl-1,2,4-oxadiazole;
5-[4-(4-methoxyphenyl)sulfonylpiperazin-1-yl]-3-phenyl-1,2,4-oxadiazole
or a solvate, hydrate, pharmaceutically acceptable salt, or prodrug thereof.

According to an embodiment, the present invention provides compounds of formula (I), or (II), and any subgroup thereof such as (IA), (IIA), (IB), (IIB), (IC), (IIC), (ID), (IID), (IE), (IIE), (IF), (IIF), (IG), (IIG), (IH), (IIH), (IJ), (IIJ), (IIK), (IIL) wherein, n is 0, 1 or 2, more preferably n is 0 or 1, more preferably n is 0;
R$^1$ is selected from the group consisting of C$_{1-6}$alkyl, halo, and haloC$_{1-6}$alkyl; preferably R$^1$ is C$_{1-6}$alkyl; preferably n is 0 and there is no R$^1$;
R$^2$ is selected from the group consisting of C$_{6-12}$aryl, C$_{1-6}$alkyl, C$_{3-12}$cycloalkyl, heterocyclyl, heteroaryl, C$_{6-12}$arylC$_{1-6}$alkyl, C$_{6-12}$arylC$_{1-6}$alkylC$_{6-12}$aryl, halo, hydroxyl, —OR$^{15}$, (preferably wherein R$^{15}$ is C$_{1-6}$alkyl, C$_{6-12}$aryl, heteroaryl, or C$_{3-12}$cycloalkyl), haloC$_{1-6}$alkyl, haloC$_{1-6}$alkyloxy, and cyano; and wherein said C$_{6-12}$aryl, C$_{1-6}$alkyl, C$_{3-12}$cycloalkyl, heterocyclyl, heteroaryl, C$_{6-12}$arylC$_{1-6}$alkyl, or C$_{6-12}$arylC$_{1-6}$alkylC$_{6-12}$aryl can be unsubstituted or substituted with one or more Z$^1$; preferably R$^2$ is selected from the group consisting of C$_{6-12}$aryl, C$_{1-6}$alkyl, C$_{3-12}$cycloalkyl, heterocyclyl, heteroaryl, halo, hydroxyl, —OR$^{15}$, (preferably wherein R$^{15}$ is C$_{1-6}$alkyl, C$_{6-12}$aryl, heteroaryl, or C$_{3-12}$cycloalkyl), haloC$_{1-6}$alkyl, haloC$_{1-6}$alkyloxy, and cyano; and wherein said C$_{6-12}$aryl, C$_{1-6}$alkyl, C$_{3-12}$cycloalkyl, heterocyclyl, heteroaryl, can be unsubstituted or substituted with one or more Z$^1$; preferably R$^2$ is selected from the group consisting of C$_{6-12}$aryl, C$_{1-6}$alkyl, C$_{3-12}$cycloalkyl, heterocyclyl, heteroaryl, halo, hydroxyl, $C_{6-12}$aryloxy, $C_{1-6}$alkyloxy, $C_{3-12}$cycloalkyloxy, heterocyclyloxy, heteroaryloxy, halo$C_{1-6}$alkyloxy, and cyano; and wherein said group can be unsubstituted or substituted with one or more $Z^1$;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, halo, hydroxyl, —$OR^{15}$, $C_{1-6}$alkyloxy, halo$C_{1-6}$alkyl, halo$C_{1-6}$alkyloxy, —$NR^{17}R^{18}$, and cyano; and wherein said $C_{6-12}$aryl, $C_{1-6}$alkyl, $C_{3-12}$cycloalkyl, heterocyclyl, heteroaryl, $C_{6-12}$aryl$C_{1-6}$alkyl, or $C_{6-12}$aryl$C_{1-6}$alkyl$C_{6-12}$aryl can be unsubstituted or substituted with one or more $Z^2$; preferably $R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, halo, hydroxyl, $C_{1-6}$alkyloxy, halo$C_{1-6}$ alkyl, halo$C_{1-6}$alkyloxy, mono or di $C_{1-6}$alkylamino, and cyano; and wherein said group can be unsubstituted or substituted with one or more $Z^2$;

$L^1$ is a single bond, or is a group of formula (i); preferably L is a single bond or is a group of formula (i) or is selected from the group comprising $C_{1-6}$alkylene, $C_{3-6}$cycloalkylene, or $C_{1-6}$alkyleneoxy, wherein each group can be unsubstituted or substituted with one or more substituents each independently selected from halo, or $C_{1-6}$alkyl;

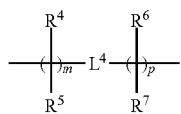

(i)

wherein the left side of the group of formula (i) is attached to $R^2$ and the right side thereof is attached to the oxadiazole ring; and wherein, m is 0, 1, 2 or 3; preferably m is 0, 1 or 2; preferably m is 0 or 1; preferably m is 1;

p is 0, 1, 2 or 3; preferably p is 0, 1 or 2; preferably p is 0 or 1; preferably p is 0;

$L^4$ is a single bond, or is —O—;

$R^4$ is selected from the group consisting of hydrogen, $C_{1-6}$alkyl, halo, hydroxyl, halo$C_{1-6}$alkyl, and halo$C_{1-6}$alkyloxy; preferably $R^4$ is selected from the group consisting of hydrogen, $C_{1-6}$alkyl, halo, hydroxyl; preferably $R^4$ is selected from the group consisting of hydrogen, $C_{1-6}$alkyl, and halo;

$R^5$ is selected from the group consisting of hydrogen, $C_{1-6}$alkyl, halo, hydroxyl, halo$C_{1-6}$alkyl, and halo$C_{1-6}$alkyloxy; preferably $R^5$ is selected from the group consisting of hydrogen, $C_{1-6}$alkyl, halo, and hydroxyl; preferably $R^5$ is selected from the group consisting of hydrogen, $C_{1-6}$alkyl, and halo;

or $R^4$ and $R^5$ together with the carbon atom to which they are attached form a saturated 3-, 4-, 5-, 6- or 7-carbon membered ring; preferably $R^4$ and $R^5$ together with the carbon atom to which they are attached form a saturated 3-, 4-, or 5-carbon membered ring; preferably $R^4$ and $R^5$ together with the carbon atom to which they are attached form a saturated or 3-, or 4-carbon membered ring; preferably $R^4$ and $R^5$ together with the carbon atom to which they are attached form a saturated 3-carbon membered ring;

$R^6$ is selected from the group consisting of hydrogen, $C_{1-6}$alkyl, halo, hydroxyl, halo$C_{1-6}$alkyl, and halo$C_{1-6}$alkyloxy; preferably $R^6$ is selected from the group consisting of hydrogen, $C_{1-6}$alkyl, halo, and hydroxyl; preferably $R^6$ is selected from the group consisting of hydrogen, $C_{1-6}$alkyl, and halo;

$R^7$ is selected from the group consisting of hydrogen, $C_{1-6}$alkyl, halo, hydroxyl, halo$C_{1-6}$alkyl, and halo$C_{1-6}$alkyloxy; preferably $R^7$ is selected from the group consisting of hydrogen, $C_{1-6}$alkyl, halo, and hydroxyl; preferably $R^7$ is selected from the group consisting of hydrogen, $C_{1-6}$alkyl, and halo;

or $R^6$ and $R^7$ together with the carbon atom to which they are attached form a saturated 3-, 4-, 5-, 6- or 7-carbon membered ring; preferably $R^6$ and $R^7$ together with the carbon atom to which they are attached form a saturated 3-, 4-, or 5-carbon membered ring; preferably $R^6$ and $R^7$ together with the carbon atom to which they are attached form a saturated or 3-, or 4-carbon membered ring; preferably $R^6$ and $R^7$ together with the carbon atom to which they are attached form a saturated 3-carbon membered ring;

$R^8$ is selected from the group consisting of hydrogen, and $C_{1-4}$alkyl; preferably $R^8$ is hydrogen;

$L^2$ is a single bond or is selected from the group consisting of —$SO_2$—, and —$(CR^9R^{10})_q$—; wherein, q is an integer selected from 1, 2 or 3; preferably $L^2$ is a single bond or is selected from the group consisting of —$SO_2$—, and —$(CR^9R^{10})_q$—; wherein, q is an integer selected from 1 or 2; preferably $L^2$ is a single bond or is selected from the group consisting of —$SO_2$—, —$CH_2$—, and —$CH_2$—$CH_2$—;

$R^9$ is selected from the group consisting of hydrogen, $C_{1-6}$alkyl, halo, and hydroxyl; preferably $R^9$ is selected from the group consisting of hydrogen, and $C_{1-6}$alkyl; preferably $R^9$ is hydrogen;

$R^{10}$ is selected from the group consisting of hydrogen, $C_{1-6}$alkyl, halo, and hydroxyl; preferably $R^{10}$ is selected from the group consisting of hydrogen, and $C_{1-6}$alkyl; preferably $R^{10}$ is hydrogen;

or $R^9$ and $R^{10}$ together with the carbon atom to which they are attached form a saturated 3-, 4-, 5-, 6- or 7-carbon membered ring; preferably $R^9$ and $R^{10}$ together with the carbon atom to which they are attached form a saturated 3-, 4-, or 5-carbon membered ring; preferably $R^9$ and $R^{10}$ together with the carbon atom to which they are attached form a saturated or 3-, or 4-carbon membered ring; preferably $R^9$ and $R^{10}$ together with the carbon atom to which they are attached form a saturated 3-carbon membered ring;

$L^3$ is a single bond or is selected from the group consisting of —O—, and —$(CR^{11}R^{12})_r$—; wherein, r is an integer selected from 1, or 2; preferably $L^3$ is a single bond or is —$(CR^{11}R^{12})_r$—; wherein, r is an integer selected from 1 or 2; preferably $L^3$ is a single bond; or is selected from —$CH_2$—, or —$CH_2$—$CH_2$—;

$R^{11}$ is selected from the group consisting of hydrogen, $C_{1-6}$alkyl, halo, and hydroxyl; preferably $R^{11}$ is selected from the group consisting of hydrogen, and $C_{1-6}$alkyl; preferably $R^{11}$ is hydrogen;

$R^{12}$ is selected from the group consisting of hydrogen, $C_{1-6}$alkyl, halo, and hydroxyl; preferably $R^{12}$ is selected from the group consisting of hydrogen, and $C_{1-6}$alkyl; preferably $R^{12}$ is hydrogen;

or $R^{11}$ and $R^{12}$ together with the carbon atom to which they are attached form a saturated 3-, 4-, 5-, 6- or 7-carbon membered ring; preferably $R^{11}$ and $R^{12}$ together with the carbon atom to which they are attached form a saturated 3-, 4-, or 5-carbon membered ring; preferably $R^{11}$ and $R^{12}$ together with the carbon atom to which they are attached form a saturated or 3-, or 4-carbon membered ring; preferably $R^{11}$ and $R^{12}$ together with the carbon atom to which they are attached form a saturated 3-carbon membered ring;

$R^{13}$ is selected from the group consisting of hydrogen, and $C_1$-4alkyl; preferably $R^{23}$ is hydrogen; wherein at least one of $L^2$, $L^3$ is not a single bond;

$L^5$ is a single bond or —CO—;

each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$ alkyl, $C_{6-12}$aryl$C_{1-6}$alkyl, heterocyclyl, heteroaryl, and cyano$C_{1-6}$alkyl, and wherein said $C_{1-6}$alkyl, $C_{3-8}$cycloalkyl$C_{1-6}$alkyl, $C_{6-12}$aryl, $C_{3-8}$cycloalkyl, heterocyclyl, heteroaryl, and cyano$C_{1-6}$alkyl, can be unsubstituted or substituted with one or more $Z^1$; preferably each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$alkyl, and heteroaryl; and wherein said $C_{1-6}$alkyl, $C_{3-8}$cycloalkyl$C_{1-6}$alkyl, $C_{6-12}$aryl, $C_{3-8}$cycloalkyl, and heteroaryl, can be unsubstituted or substituted with one or more $Z^1$;

and wherein at least one carbon atom or heteroatom of $C_{1-6}$alkyl, $C_{2-6}$alkenyl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O;

each $R^{16}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, and heteroaryl; and wherein said $C_{1-6}$alkyl, $C_{6-12}$aryl, $C_{3-8}$cycloalkyl, $C_{6-12}$aryl$C_{1-6}$alkyl, heterocyclyl, and heteroaryl, can be unsubstituted or substituted with one or more $Z^2$; preferably wherein each $R^{16}$ is independently selected from the group consisting of hydrogen, $C_{1-6}$alkyl, $C_{6-12}$aryl, $C_{3-8}$cycloalkyl, heterocyclyl, and heteroaryl; and wherein said $C_{1-6}$alkyl, $C_{6-12}$aryl, $C_{3-8}$cycloalkyl, heterocyclyl, and heteroaryl, can be unsubstituted or substituted with one or more $Z^2$;

and wherein at least one carbon atom or heteroatom of said $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, or cyano$C_{1-6}$alkyl can be oxidized to form at least one C=O;

each $R^{17}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{17}$ is independently selected from the group consisting of hydrogen, $C_{1-6}$alkyl, $C_{6-12}$aryl, $C_{3-8}$cycloalkyl, heterocyclyl, and heteroaryl; preferably each $R^{17}$ is independently selected from the group consisting of hydrogen, $C_{1-6}$alkyl, $C_{6-12}$aryl, $C_{3-8}$cycloalkyl, and heteroaryl; preferably each $R^{17}$ is independently selected from the group consisting of hydrogen, and $C_{1-6}$alkyl;

and wherein at least one carbon atom or heteroatom of said $C_{1-6}$alkyl, $C_{6-12}$aryl, $C_{3-8}$cycloalkyl, $C_{6-12}$aryl$C_6$alkyl, heterocyclyl, heteroaryl, heterocyclyl$C_{1-6}$alkyl, or heteroaryl$C_{1-6}$alkyl can be oxidized to form at least one C=O;

each $R^{18}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{18}$ is independently selected from the group consisting of hydrogen, $C_{1-6}$alkyl, $C_{6-12}$aryl, $C_{3-8}$cycloalkyl, heterocyclyl, and heteroaryl; preferably each $R^{18}$ is independently selected from the group consisting of hydrogen, $C_{1-6}$alkyl, $C_{6-12}$aryl, $C_{3-8}$cycloalkyl, and heteroaryl; preferably each $R^{18}$ is independently selected from the group consisting of hydrogen, and $C_{1-6}$alkyl;

and wherein at least one carbon atom or heteroatom of said $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O;

or wherein $R^{17}$ and $R^{18}$ together with the nitrogen atom to which they are attached form a 5-, or 6-membered heterocyclyl; and wherein at least one carbon atom or heteroatom of said heterocyclyl can be oxidized to form at least one C=O; or preferably wherein $R^{17}$ and $R^{18}$ together with the nitrogen atom to which they are attached form a 5-membered heterocyclyl; and wherein at least one carbon atom or heteroatom of said heterocyclyl can be oxidized to form at least one C=O;

each $R^{19}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{19}$ is independently selected from the group consisting of hydrogen, $C_{1-6}$alkyl, $C_{6-12}$aryl, $C_{3-8}$cycloalkyl, heterocyclyl, and heteroaryl; preferably each $R^{19}$ is independently selected from the group consisting of hydrogen, $C_{1-6}$alkyl, $C_{6-12}$aryl, $C_{3-8}$cycloalkyl, heteroaryl; preferably each $R^{19}$ is independently selected from the group consisting of hydrogen, and $C_{1-6}$alkyl;

wherein at least one carbon atom or heteroatom of said $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, or heteroaryl$C_{1-6}$alkyl can be oxidized to form at least one C=O;

each $R^{20}$ is independently selected from the group consisting of hydrogen, $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl; preferably each $R^{20}$ is independently selected from the group consisting of hydrogen, $C_{1-6}$alkyl, $C_{6-12}$aryl, $C_{3-8}$cycloalkyl, heterocyclyl, and heteroaryl; preferably each $R^{20}$ is independently selected from the group consisting of hydrogen, $C_{1-6}$alkyl, $C_{6-12}$aryl, $C_{3-8}$cycloalkyl, and heteroaryl; preferably each $R^{20}$ is independently selected from the group consisting of hydrogen, and $C_{1-6}$alkyl;

and wherein at least one carbon atom or heteroatom of said $C_{1-6}$alkyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, and heteroaryl$C_{1-6}$alkyl can be oxidized to form at least one C=O;

each $R^{21}$ is independently selected from $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene*, heterocyclylene, heteroarylene, heterocyclylene$C_{1-6}$alkylene*, and heteroarylene$C_{1-6}$alkylene*; wherein * represents where $R^{21}$ is bound to —CO—;

and wherein at least one carbon atom or heteroatom of said $C_{1-6}$alkylene, $C_{2-6}$alkenylene, $C_{2-6}$alkynylene, $C_{6-12}$arylene, $C_{3-8}$cycloalkylene, $C_{6-12}$arylene$C_{1-6}$alkylene, heterocyclylene, heteroarylene, heterocyclylene$C_{1-6}$alkylene, or heteroarylene$C_{1-6}$alkylene can be oxidized to form at least one C=O;

each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —$OR^{15}$, —$SR^{16}$, cyano, amino, —$NR^{17}R^{18}$, and wherein two $Z^1$ together with the atom to which they are attached can form a 5-, 6-, or 7-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O; preferably each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heteroaryl, hydroxyl, —OR$^{15}$, —SR$^{16}$, cyano, amino, and —NR$^{17}$R$^{18}$; and wherein two $Z^1$ together with the atom to which they are attached can form a 5-, or 6-membered ring; preferably each $Z^1$ is independently selected from the group consisting of halo, hydrogen, $C_{1-6}$alkyl, halo$C_{1-6}$alkyl, halo$C_{1-6}$alkyloxy, $C_{3-12}$cycloalkyl, $C_{6-12}$aryl, $C_{1-6}$alkyl$C_{6-12}$aryl, heterocyclyl, heteroaryl, hydroxyl, and cyano;

each $Z^2$ is independently selected from the group consisting of halo, hydrogen, $C_{1-6}$alkyl, halo$C_{1-6}$alkyl, $C_{1-6}$alkyloxy, halo$C_{1-6}$alkyloxy, $C_{3-12}$cycloalkyl, $C_{6-12}$aryl, $C_{1-6}$alkyl$C_{6-12}$aryl, heterocyclyl, heterocyclyl$C_{1-6}$alkyl, heteroaryl, heteroaryl$C_{1-6}$alkyl, hydroxyl, —OR$^{15}$, —SR$^{16}$, $C_{1-6}$alkylthio, cyano, cyano$C_{1-6}$alkyloxy, amino, —NR$^{17}$R$^{18}$, —CO$_2$R$^{19}$, —C(O)NR$^{17}$R$^{18}$, —C(O)R$^{19}$, and $C_{1-6}$alkylcarbonyl; and wherein two $Z^2$ together with the atom to which they are attached can form a 5-, or 6-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heterocyclyl$C_{1-6}$alkyl, heteroaryl, or heteroaryl$C_{1-6}$alkyl can be oxidized to form at least one C=O; preferably each $Z^2$ is independently selected from the group consisting of halo, hydrogen, $C_{1-6}$alkyl, halo$C_{1-6}$alkyl, $C_{1-6}$alkyloxy, halo$C_{1-6}$ alkyloxy, $C_{3-12}$cycloalkyl, $C_{6-12}$aryl, $C_{1-6}$alkyl$C_{6-12}$aryl, heterocyclyl, heteroaryl, hydroxyl, —OR$^{15}$, —SR$^{16}$, $C_{1-6}$alkylthio, cyano, cyano$C_{1-6}$alkyloxy, amino, —NR$^{17}$R$^{18}$, —CO$_2$R$^{19}$, —C(O)R$^{19}$, and $C_{1-6}$alkylcarbonyl; and wherein two $Z^2$ together with the atom to which they are attached can form a 5-, or 6-membered ring; and wherein at least one carbon atom or heteroatom of said ring, $C_{1-6}$alkyl, $C_{3-8}$cycloalkyl, $C_{6-12}$aryl, $C_{1-6}$alkyl$C_{6-12}$aryl, heterocyclyl, heteroaryl, or heteroaryl$C_{1-6}$alkyl can be oxidized to form at least one C=O; preferably each $Z^2$ is independently selected from the group consisting of halo, hydrogen, $C_{1-6}$alkyl, halo$C_{1-6}$ alkyl, $C_{1-6}$alkyloxy, halo$C_{1-6}$alkyloxy, $C_{3-12}$cycloalkyl, $C_{6-12}$aryl, heterocyclyl, heteroaryl, hydroxyl, —OR$^5$, —SR$^{16}$, $C_{1-6}$alkylthio, cyano, cyano$C_{1-6}$alkyloxy, amino, and $C_{1-6}$alkylcarbonyl.

According to an embodiment, the present invention provides compounds of formula (I), or (II), and any subgroup thereof such as (IA), (IIA), (IB), (IIB), (IC), (IIC), (ID), (IID), (IE), (IIE), (IF), (IIF), (IG), (IIG), (IH), (IIH), (IJ), (IIJ), (IIK), (IIL) wherein, n is 0 or 1, more preferably n is 0;

$R^1$ is $C_{1-6}$alkyl; preferably n is 0 and there is no $R^1$;

$R^2$ is selected from the group consisting of $C_{6-12}$aryl, $C_{1-6}$alkyl, $C_{3-12}$cycloalkyl, heterocyclyl, heteroaryl, halo, hydroxyl, —OR$^{15}$, (preferably wherein $R^{15}$ is $C_{1-6}$alkyl, $C_{6-12}$aryl, heteroaryl, or $C_{3-12}$cycloalkyl), halo$C_{1-6}$alkyl, halo$C_{1-6}$alkyloxy, and cyano; and wherein said $C_{6-12}$aryl, $C_{1-6}$alkyl, $C_{3-12}$cycloalkyl, heterocyclyl, heteroaryl, can be unsubstituted or substituted with one or more $Z^1$; preferably $R^2$ is selected from the group consisting of $C_{6-12}$aryl, $C_{1-6}$alkyl, $C_{3-12}$cycloalkyl, heterocyclyl, heteroaryl, halo, hydroxyl, $C_{6-12}$aryloxy, $C_{1-6}$alkyloxy, $C_{3-12}$cycloalkyloxy, heterocyclyloxy, heteroaryloxy, halo$C_{1-6}$alkyloxy, and cyano; and wherein said group can be unsubstituted or substituted with one or more $Z^1$;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$aryl$C_{1-6}$alkyl, halo, hydroxyl, $C_{1-6}$alkyloxy, halo$C_{1-6}$ alkyl, halo$C_{1-6}$alkyloxy, mono or di $C_{1-6}$alkylamino, and cyano; and wherein said group can be unsubstituted or substituted with one or more $Z^2$;

$L^1$ is a single bond or is a group of formula (i) or is selected from the group comprising $C_{1-6}$alkylene, $C_{3-6}$cycloalkylene, or $C_{1-6}$alkyleneoxy, wherein each group can be unsubstituted or substituted with one or more substituents each independently selected from halo, or $C_{1-6}$alkyl;

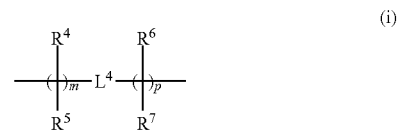

(i)

wherein the left side of the group of formula (i) is attached to $R^2$ and the right side thereof is attached to the oxadiazole ring; and wherein, m is 0, 1 or 2, preferably m is 0 or 1, preferably m is 1;

p is 0, 1 or 2, preferably p is 0 or 1, preferably p is 0;

$L^4$ is a single bond, or is —O—;

$R^4$ is selected from the group consisting of hydrogen, $C_{1-6}$alkyl, halo, and hydroxyl; preferably $R^4$ is selected from the group consisting of hydrogen, $C_{1-6}$alkyl, and halo;

$R^5$ is selected from the group consisting of hydrogen, $C_{1-6}$alkyl, halo, and hydroxyl; preferably $R^5$ is selected from the group consisting of hydrogen, $C_{1-6}$alkyl, and halo;

or $R^4$ and $R^5$ together with the carbon atom to which they are attached form a saturated 3-, 4-, or 5-carbon membered ring; preferably $R^4$ and $R^5$ together with the carbon atom to which they are attached form a saturated or 3-, or 4-carbon membered ring; preferably $R^4$ and $R^5$ together with the carbon atom to which they are attached form a saturated 3-carbon membered ring;

$R^6$ is selected from the group consisting of hydrogen, $C_{1-6}$alkyl, halo, and hydroxyl; preferably $R^6$ is selected from the group consisting of hydrogen, $C_{1-6}$alkyl, and halo;

$R^7$ is selected from the group consisting of hydrogen, $C_{1-6}$alkyl, halo, and hydroxyl; preferably $R^7$ is selected from the group consisting of hydrogen, $C_{1-6}$alkyl, and halo;

or $R^6$ and $R^7$ together with the carbon atom to which they are attached form a saturated 3-, 4-, or 5-carbon membered ring; preferably $R^6$ and $R^7$ together with the carbon atom to which they are attached form a saturated or 3-, or 4-carbon membered ring; preferably $R^6$ and $R^7$ together with the carbon atom to which they are attached form a saturated 3-carbon membered ring;

$R^8$ is hydrogen;

$L^2$ is a single bond or is selected from the group consisting of —SO$_2$—, and —(CR$^9$R$^{10}$)$_q$—; wherein q is an integer selected from 1 or 2; preferably $L^2$ is a single bond or is selected from the group consisting of —SO$_2$—, —CH$_2$—, and —CH$_2$—CH$_2$—;

$R^9$ is selected from the group consisting of hydrogen, and $C_{1-6}$alkyl; preferably $R^9$ is hydrogen;

$R^{10}$ is selected from the group consisting of hydrogen, and $C_{1-6}$alkyl; preferably $R^{10}$ is hydrogen;

or $R^9$ and $R^{10}$ together with the carbon atom to which they are attached form a saturated 3-, 4-, or 5-carbon membered ring; preferably $R^9$ and $R^{10}$ together with the carbon atom to which they are attached form a saturated or 3-, or 4-carbon membered ring; preferably $R^9$ and $R^{10}$ together with the carbon atom to which they are attached form a saturated 3-carbon membered ring;

$L^3$ is a single bond or is $-(CR^{11}R^{12})_r-$; wherein r is an integer selected from 1 or 2; preferably $L^3$ is a single bond, or is selected from $-CH_2-$, or $-CH_2-CH_2-$;

$R^{11}$ is selected from the group consisting of hydrogen, and $C_{1-6}$alkyl; preferably $R^{11}$ is hydrogen;

$R^{12}$ is selected from the group consisting of hydrogen, and $C_{1-6}$alkyl; preferably $R^{12}$ is hydrogen;

or $R^{11}$ and $R^{12}$ together with the carbon atom to which they are attached form a saturated 3-, 4-, or 5-carbon membered ring; preferably $R^{11}$ and $R^{12}$ together with the carbon atom to which they are attached form a saturated or 3-, or 4-carbon membered ring; preferably $R^{11}$ and $R^{12}$ together with the carbon atom to which they are attached form a saturated 3-carbon membered ring;

$R^{13}$ is hydrogen;

wherein at least one of $L^2$, $L^3$ is not a single bond;

$L^5$ is a single bond or $-CO-$;

each $R^{15}$ is independently selected from the group consisting of $C_{1-6}$alkyl, $C_{6-12}$aryl, $C_{3-8}$cycloalkyl, $C_{3-8}$cycloalkyl$C_{1-6}$alkyl, and heteroaryl; and wherein said $C_{1-6}$alkyl, $C_{3-8}$cycloalkyl$C_{1-6}$alkyl, $C_{6-12}$aryl, $C_{3-8}$cycloalkyl, and heteroaryl, can be unsubstituted or substituted with one or more $Z^1$;

each $R^{16}$ is independently selected from the group consisting of hydrogen, $C_{1-6}$alkyl, $C_{6-12}$aryl, $C_{3-8}$cycloalkyl, heterocyclyl, and heteroaryl; and wherein said $C_{1-6}$alkyl, $C_{6-12}$aryl, $C_{3-8}$cycloalkyl, heterocyclyl, and heteroaryl, can be unsubstituted or substituted with one or more $Z^2$;

each $R^{17}$ is independently selected from the group consisting of hydrogen, $C_{1-6}$alkyl, $C_{6-12}$aryl, $C_{3-8}$cycloalkyl, heterocyclyl, and heteroaryl; preferably each $R^{17}$ is independently selected from the group consisting of hydrogen, $C_{1-6}$alkyl, $C_{6-12}$aryl, $C_{3-8}$cycloalkyl, and heteroaryl; preferably each $R^{17}$ is independently selected from the group consisting of hydrogen, and $C_{1-6}$alkyl;

each $R^{18}$ is independently selected from the group consisting of hydrogen, $C_{1-6}$alkyl, $C_{6-12}$aryl, $C_{3-8}$cycloalkyl, heterocyclyl, and heteroaryl; preferably each $R^{18}$ is independently selected from the group consisting of hydrogen, $C_{1-6}$alkyl, $C_{6-12}$aryl, $C_{3-8}$cycloalkyl, and heteroaryl; preferably each $R^{18}$ is independently selected from the group consisting of hydrogen, and $C_{1-6}$alkyl;

or $R^{17}$ and $R^{18}$ together with the nitrogen atom to which they are attached form a 5-membered heterocyclyl; and wherein at least one carbon atom or heteroatom of said heterocyclyl can be oxidized to form at least one $C=O$;

each $R^{19}$ is independently selected from the group consisting of hydrogen, $C_{1-6}$alkyl, $C_{6-12}$aryl, $C_{3-8}$cycloalkyl, heterocyclyl, and heteroaryl; preferably each $R^{19}$ is independently selected from the group consisting of hydrogen, $C_{1-6}$alkyl, $C_{6-12}$aryl, $C_{3-8}$cycloalkyl, and heteroaryl; preferably each $R^{19}$ is independently selected from the group consisting of hydrogen, and $C_{1-6}$alkyl;

each $R^{20}$ is independently selected from the group consisting of hydrogen, $C_{1-6}$alkyl, $C_{6-12}$aryl, $C_{3-8}$cycloalkyl, heterocyclyl, and heteroaryl; preferably each $R^{20}$ is independently selected from the group consisting of hydrogen, $C_{1-6}$alkyl, $C_{6-12}$aryl, $C_{3-8}$cycloalkyl, and heteroaryl; preferably each $R^{20}$ is independently selected from the group consisting of hydrogen, and $C_{1-6}$alkyl;

each $R^{21}$ is independently selected from the group consisting of $C_{1-6}$alkylene, $C_{2-6}$alkenylene, $C_{2-6}$alkynylene, $C_{6-12}$arylene, $C_{3-8}$cycloalkylene, $C_{6-12}$aryleneC$_{1-6}$alkylene*, heterocyclylene, heteroarylene, heterocyclyleneC$_{1-6}$alkylene*, and heteroaryleneC$_{1-6}$alkylene*; wherein * represents where $R^{21}$ is bound to $-CO-$;

each $Z^1$ is independently selected from the group consisting of halo, hydrogen, $C_{1-6}$alkyl, haloC$_{1-6}$alkyl, haloC$_{1-6}$alkyloxy, $C_{3-12}$cycloalkyl, $C_{6-12}$aryl, $C_{1-6}$alkylC$_{6-12}$aryl, heterocyclyl, heteroaryl, hydroxyl, $-OR^{15}$, $-SR^{16}$, cyano, amino, and $-NR^{17}R^{18}$; and wherein two $Z^1$ together with the atom to which they are attached can form a 5-, or 6-membered ring; preferably each $Z^1$ is independently selected from the group consisting of halo, hydrogen, $C_{1-6}$alkyl, haloC$_{1-6}$alkyl, haloC$_{1-6}$alkyloxy, $C_{3-12}$cycloalkyl, $C_{6-12}$aryl, $C_{1-6}$alkylC$_{6-12}$aryl, heterocyclyl, heteroaryl, hydroxyl, and cyano;

each $Z^2$ is independently selected from the group consisting of halo, hydrogen, $C_{1-6}$alkyl, haloC$_{1-6}$alkyl, $C_{1-6}$alkyloxy, haloC$_{1-6}$alkyloxy, $C_{3-12}$cycloalkyl, $C_{6-12}$aryl, $C_{1-6}$alkylC$_{6-12}$aryl, heterocyclyl, heteroaryl, hydroxyl, $-OR^{15}$, $-SR^{16}$, $C_{1-6}$alkylthio, cyano, cyanoC$_{1-6}$alkyloxy, amino, $-NR^{17}R^{18}$, $-CO_2R^{19}$, $-C(O)R^{19}$ and $C_{1-6}$alkylcarbonyl; and wherein two $Z^2$ together with the atom to which they are attached can form a 5-, or 6-membered ring; and wherein at least one carbon atom or heteroatom of said ring, $C_{1-6}$alkyl, $C_{3-8}$cycloalkyl, $C_{6-12}$aryl, $C_{1-6}$alkylC$_{6-12}$aryl, heterocyclyl, heteroaryl, or heteroarylC$_{1-6}$alkyl can be oxidized to form at least one $C=O$; preferably each $Z^2$ is independently selected from the group consisting of halo, hydrogen, $C_{1-6}$alkyl, haloC$_{1-6}$alkyl, $C_{1-6}$alkyloxy, haloC$_{1-6}$alkyloxy, $C_{3-12}$cycloalkyl, $C_{6-12}$aryl, heterocyclyl, heteroaryl, hydroxyl, $-OR^{15}$, $-SR^{16}$, $C_{1-6}$alkylthio, cyano, cyanoC$_{1-6}$alkyloxy, amino, and $C_{1-6}$alkylcarbonyl.

According to an embodiment, the present invention provides compounds of formula (I) or (II), and any subgroup thereof such as (IA), (IIA), (IB), (IIB), (IC), (IIC), (ID), (IID), (IE), (IIE), (IF), (IIF), (IG), (IIG), (IH), (IIH), (IJ), (IIJ), (IIK), (IIL) wherein, n is 0;

$R^2$ is selected from the group consisting of $C_{6-12}$aryl, $C_{1-6}$alkyl, $C_{3-12}$cycloalkyl, heterocyclyl, heteroaryl, halo, hydroxyl, $C_{6-12}$aryloxy, $C_{1-6}$alkyloxy, $C_{3-12}$cycloalkyloxy, heterocyclyloxy, heteroaryloxy, haloC$_{1-6}$alkyloxy, and cyano; and wherein said group can be unsubstituted or substituted with one or more $Z^1$;

$R^3$ is selected from the group consisting of $C_{6-12}$aryl, hydrogen, $C_{1-6}$alkyl, $C_{3-12}$cycloalkyl, heterocyclyl, heteroaryl, $C_{6-12}$arylC$_{1-6}$alkyl, halo, hydroxyl, $C_{1-6}$alkyloxy, haloC$_{1-6}$alkyl, haloC$_{1-6}$alkyloxy, mono or di $C_{1-6}$alkylamino, and cyano; and wherein said group can be unsubstituted or substituted with one or more $Z^2$;

$L^1$ is a single bond or is selected from the group comprising $C_{1-6}$alkylene, $C_{3-6}$cycloalkylene, or $C_{1-6}$alkyleneoxy, wherein each group can be unsubstituted or substituted with one or more substituents each independently selected from halo, or $C_{1-6}$alkyl;

$L^2$ is a single bond or is selected from the group consisting of —SO$_2$—, and —(CR$^9$R$^{10}$)$_q$—; wherein q is an integer selected from 1 or 2; preferably $L^2$ is a single bond or is selected from the group consisting of —SO$_2$—, —CH$_2$—, and —CH$_2$—CH$_2$—;

$L^3$ is a single bond or is —(CR$^{11}$R$^{12}$)$_r$—; wherein r is an integer selected from 1 or 2; preferably $L^3$ is a single bond, or is selected from —CH$_2$—, or —CH$_2$—CH$_2$—;

$R^{11}$ is selected from the group consisting of hydrogen, and C$_{1-6}$alkyl; preferably $R^{11}$ is hydrogen;

$R^{12}$ is selected from the group consisting of hydrogen, and C$_{1-6}$alkyl; preferably $R^{12}$ is hydrogen;

or $R^{11}$ and $R^{12}$ together with the carbon atom to which they are attached form a saturated or 3-, or 4-carbon membered ring; preferably $R^{11}$ and $R^{12}$ together with the carbon atom to which they are attached form a saturated 3-carbon membered ring;

wherein at least one of $L^2$, $L^3$ is not a single bond;

$L^5$ is a single bond or —CO—;

each $R^{15}$ is independently selected from the group consisting of C$_{1-6}$alkyl, C$_{6-12}$aryl, C$_{3-8}$cycloalkyl, C$_{3-8}$cycloalkylC$_{1-6}$alkyl, and heteroaryl; and wherein said C$_{1-6}$alkyl, C$_{3-8}$cycloalkylC$_{1-6}$alkyl, C$_{6-12}$aryl, C$_{3-8}$cycloalkyl, and heteroaryl, can be unsubstituted or substituted with one or more $Z^1$;

each $R^{16}$ is independently selected from the group consisting of hydrogen, C$_{1-6}$alkyl, C$_{6-12}$aryl, C$_{3-8}$cycloalkyl, heterocyclyl, and heteroaryl; and wherein said C$_{1-6}$alkyl, C$_{6-12}$aryl, C$_{3-8}$cycloalkyl, heterocyclyl, and heteroaryl, can be unsubstituted or substituted with one or more $Z^2$;

each $R^{17}$ is independently selected from the group consisting of hydrogen, C$_{1-6}$alkyl, C$_{6-12}$aryl, C$_{3-8}$cycloalkyl, and heteroaryl; preferably each $R^{17}$ is independently selected from the group consisting of hydrogen, and C$_{1-6}$alkyl;

each $R^{18}$ is independently selected from the group consisting of hydrogen, C$_{1-6}$alkyl, C$_{6-12}$aryl, C$_{3-8}$cycloalkyl, and heteroaryl; preferably each $R^{18}$ is independently selected from the group consisting of hydrogen, and C$_{1-6}$alkyl;

or $R^{17}$ and $R^{18}$ together with the nitrogen atom to which they are attached form a 5-membered heterocyclyl; and wherein at least one carbon atom or heteroatom of said heterocyclyl can be oxidized to form at least one C=O;

$R^{19}$ is independently selected from the group consisting of hydrogen, C$_{1-6}$alkyl, C$_{6-12}$aryl, C$_{3-8}$cycloalkyl, and heteroaryl; preferably each $R^{19}$ is independently selected from the group consisting of hydrogen, and C$_{1-6}$alkyl;

$R^{20}$ is independently selected from the group consisting of hydrogen, C$_{1-6}$alkyl, C$_{6-12}$aryl, C$_{3-8}$cycloalkyl, and heteroaryl; preferably each $R^{20}$ is independently selected from the group consisting of hydrogen, and C$_{1-6}$alkyl;

each $R^{21}$ is independently selected from the group consisting of C$_{1-6}$alkylene, C$_{2-6}$alkenylene, C$_{2-6}$alkynylene, C$_{6-12}$arylene, C$_{3-8}$cycloalkylene, C$_{6-12}$aryleneC$_{1-6}$alkylene*, heterocyclylene, heteroarylene, heterocyclyleneC$_{1-6}$alkylene*, and heteroaryleneC$_{1-6}$alkylene*; wherein * represents where $R^{21}$ is bound to —CO—;

each $Z^1$ is independently selected from the group consisting of halo, hydrogen, C$_{1-6}$alkyl, haloC$_{1-6}$alkyl, haloC$_{1-6}$alkyloxy, C$_{3-12}$cycloalkyl, C$_{6-12}$aryl, C$_{1-6}$alkylC$_{6-12}$aryl, heterocyclyl, heteroaryl, hydroxyl, and cyano;

each $Z^2$ is independently selected from the group consisting of halo, hydrogen, C$_{1-6}$alkyl, haloC$_{1-6}$alkyl, C$_{1-6}$alkyloxy, haloC$_{1-6}$alkyloxy, C$_{3-12}$cycloalkyl, C$_{6-12}$aryl, heterocyclyl, heteroaryl, hydroxyl, —OR$^5$, —SR$^{16}$, C$_{1-6}$alkylthio, cyano, cyanoC$_{1-6}$alkyloxy, amino, and C$_{1-6}$alkylcarbonyl.

In some embodiments, said compound is not
2[[(2R)-4-(3-cyclopropyl-1,2,4-oxadiazol-5-yl)-2-methyl-piperazin-1-yl]methyl]-7-methoxy-[1,2,4]triazolo[1,5-c]quinazolin-5-amine;
2[[(2R)-4-(3-rwer-butyl-1,2,4-oxadiazol-5-yl)-2-methyl-piperazin-1-yl]methyl]-7-methoxy-[1,2,4]triazolo[1,5-c]quinazolin-5-amine.

The present invention also encompasses a pharmaceutical composition comprising one or more pharmaceutically excipients and a therapeutically effective amount of a compound formula (I) or (II), and any subgroup thereof such as (IA), (IIA), (IB), (IIB), (IC), (IIC), (ID), (IID), (IE), (IIE), (IF), (IIF), (IG), (IIG), (IH), (IIH), (IJ), (IIJ), (IIK), (IIL).

The present invention includes all possible stereoisomers compounds of formula (I) or (II) and any subgroup thereof and includes not only racemic compounds but the individual enantiomers as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

The compounds of the invention may be in the form of pharmaceutically acceptable salts, as generally described below. Some preferred, but non-limiting examples of suitable pharmaceutically acceptable organic and/or inorganic acids are as hydrochloric acid, hydrobromic acid, sulfuric acid, nitric acid, acetic acid and citric acid, as well as other pharmaceutically acceptable acids known per se (for which reference is made to the prior art referred to below).

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of the compounds of formula (I) or (II) and any subgroup thereof include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Pharmaceutically acceptable salts of compounds of formula (I) or (II) may be prepared by one or more of these methods:

(i) by reacting the compound of formula (I) or (II) with the desired acid;
(ii) by reacting the compound of formula (I) or (II) with the desired base;
(iii) by removing an acid- or base-labile protecting group from a suitable precursor of the compound of formula (I) or (II) or by ring-opening a suitable cyclic precursor, for example, a lactone or lactam, using the desired acid; or
(iv) by converting one salt of the compound of formula (I) or (II) to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Britain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3{}^-$Na$^+$) or non-ionic (such as —N$^-$N$^+$(CH$_3$)$_3$) polar head group. For more information, see Crystals and the Polarizing Microscope by N. H. Hartshorne and A. Stuart, 4$^{th}$ Edition (Edward Arnold, 1970), incorporated herein by reference.

All references to compounds of formula (I) or (II) or any subgroups thereof include references to salts, solvates, multi-component complexes and liquid crystals thereof and to solvates, multi-component complexes and liquid crystals of salts thereof.

The compounds of the invention include compounds of formula (I) or (II) or any subgroups thereof as hereinbefore defined, including all polymorphs and crystal habits thereof, prodrugs and isomers thereof (including optical, geometric and tautomeric isomers) as hereinafter defined and isotopically-labeled compounds of formula (I) or (II).

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of formula (I) or (II) above.

The invention also generally covers all pharmaceutically acceptable prodrugs or "pre-drugs" of the compounds of formula (I) or (II) or any subgroups thereof for which general reference is made to the prior art cited hereinbelow.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active inhibitors in vivo. The term "pre-drug", as used herein, means any compound that will be modified to form a drug species, wherein the modification may take place either inside or outside of the body, and either before or after the pre-drug reaches the area of the body where administration of the drug is indicated.

Where a compound of formula (I) or (II) or any subgroup thereof contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, diastereomers, geometric isomers and tautomeric forms of the compounds of formula (I) or (II) or any subgroups thereof, including compounds exhibiting more than one type of isomerism, and mixtures of one or more thereof. Also included are acid addition or base salts wherein the counterion is optically active, for example, d-lactate or /-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC).

The compounds of formula (I) or (II) or any subgroups thereof may be prepared as described in the experimental section below using methods and chemistries with which those skilled in the art shall be familiar.

Generally, the compounds of the invention are prepared from the intermediates described hereinafter which may be reacted with complementary reactive molecules so as to form the desired compound.

The present invention also encompasses a compound selected from the group comprising:
5-(4-(2-Chlorobenzyl)piperazin-1-yl)-3-phenyl-1,2,4-oxadiazole;
5-(4-(4-Methylbenzyl)piperazin-1-yl)-3-phenyl-1,2,4-oxadiazole;
5-(4-(4-Chlorophenethyl)piperazin-1-yl)-3-phenyl-1,2,4-oxadiazole;
5-(4-(2-(2-Methoxypyridin-4-yl)ethyl)piperazin-1-yl)-3-phenyl-1,2,4-oxadiazole;
4-(2-(4-(3-Phenyl-1,2,4-oxadiazol-5-yl)piperazin-1-yl)ethyl)morpholine;
5-(4-Isopentylpiperazin-1-yl)-3-phenyl-1,2,4-oxadiazole;
5-(4-(Benzo[d][1,3]dioxol-5-ylmethyl)piperazin-1-yl)-3-(p-tolyl)-1,2,4-oxadiazole;
5-(4-(4-Chlorobenzyl)piperazin-1-yl)-3-(p-tolyl)-1,2,4-oxadiazole;
5-(4-(3-Methoxyphenethyl)piperazin-1-yl)-3-(p-tolyl)-1,2,4-oxadiazole;
5-(4-(2-Methylbenzyl)piperazin-1-yl)-3-(p-tolyl)-1,2,4-oxadiazole;
5-(4-((4-(Oxazol-5-yl)phenyl)sulfonyl)piperazin-1-yl)-3-(p-tolyl)-1,2,4-oxadiazole;
5-(4-((4-(Difluoromethoxy)phenyl)sulfonyl)piperazin-1-yl)-3-(p-tolyl)-1,2,4-oxadiazole;
3-(p-Tolyl)-5-(4-((4-(trifluoromethoxy)phenyl)sulfonyl)piperazin-1-yl)-1,2,4-oxadiazole;
5-(4-((4-Fluorophenyl)sulfonyl)piperazin-1-yl)-3-(p-tolyl)-1,2,4-oxadiazole;
5-(4-((4-Isopropylphenyl)sulfonyl)piperazin-1-yl)-3-(p-tolyl)-1,2,4-oxadiazole;
3-(p-Tolyl)-5-(4-((4-(trifluoromethyl)phenyl)sulfonyl)piperazin-1-yl)-1,2,4-oxadiazole;
1-(4-((4-(3-(p-Tolyl)-1,2,4-oxadiazol-5-yl)piperazin-1-yl)sulfonyl)phenyl)pyrrolidin-2-one;
5-(4-((4-Methoxyphenyl)sulfonyl)piperazin-1-yl)-3-(p-tolyl)-1,2,4-oxadiazole;
5-(4-(4-Chlorophenethyl)piperazin-1-yl)-3-(4-chlorophenyl)-1,2,4-oxadiazole;
3-(4-Chlorophenyl)-5-(4-phenethylpiperazin-1-yl)-1,2,4-oxadiazole;
3-(4-Chlorophenyl)-5-(4-(3-methoxyphenethyl)piperazin-1-yl)-1,2,4-oxadiazole;
3-(4-Chlorophenyl)-5-(4-(2-methylbenzyl)piperazin-1-yl)-1,2,4-oxadiazole;
3-(4-Chlorophenyl)-5-(4-(2-(2-methoxypyridin-4-yl)ethyl)piperazin-1-yl)-1,2,4-oxadiazole;
5-(4-(4-Chlorophenethyl)piperazin-1-yl)-3-(3-chlorophenyl)-1,2,4-oxadiazole;
3-(3-Chlorophenyl)-5-(4-(2-(2-methoxypyridin-4-yl)ethyl)piperazin-1-yl)-1,2,4-oxadiazole;
3-(3-Chlorophenyl)-5-(4-(2-methylbenzyl)piperazin-1-yl)-1,2,4-oxadiazole;
5-(4-(2-Chlorobenzyl)piperazin-1-yl)-3-(3-chlorophenyl)-1,2,4-oxadiazole;
2-((4-(3-(3-Chlorophenyl)-1,2,4-oxadiazol-5-yl)piperazin-1-yl)methyl)benzonitrile;
5-(4-(2-Chlorobenzyl)piperazin-1-yl)-3-(3-fluorophenyl)-1,2,4-oxadiazole;
3-(3-Fluorophenyl)-5-(4-(4-methylbenzyl)piperazin-1-yl)-1,2,4-oxadiazole;
5-(4-(4-Chlorophenethyl)piperazin-1-yl)-3-(3-fluorophenyl)-1,2,4-oxadiazole;
3-(3-Fluorophenyl)-5-(4-(2-(2-methoxypyridin-4-yl)ethyl)piperazin-1-yl)-1,2,4-oxadiazole;
4-(2-(4-(3-(3-Fluorophenyl)-1,2,4-oxadiazol-5-yl)piperazin-1-yl)ethyl)morpholine;
3-(3-Fluorophenyl)-5-(4-isopentylpiperazin-1-yl)-1,2,4-oxadiazole;
5-(4-(2-Chlorobenzyl)piperazin-1-yl)-3-(3,4-difluorophenyl)-1,2,4-oxadiazole;
1-[2-(4-Chloro-phenyl)-ethyl]-4-[3-(3,4-difluoro-phenyl)-[1,2,4]oxadiazol-5-yl]-piperazine;
1-(3-Benzyl-[1,2,4]oxadiazol-5-yl)-4-(4-methoxy-benzenesulfonyl)-piperazine;
1-(3-Benzyl-[1,2,4]oxadiazol-5-yl)-4-(4-ethoxy-benzenesulfonyl)-piperazine;
1-(3-Benzyl-[1,2,4]oxadiazol-5-yl)-4-(4-difluoromethoxy-benzenesulfonyl)-piperazine;
1-Benzo[1,3]dioxol-5-ylmethyl-4-(3-benzyl-[1,2,4]oxadiazol-5-yl)-piperazine;
1-(3-Benzyl-[1,2,4]oxadiazol-5-yl)-4-(2-methyl-benzyl)-piperazine;
1-(3-Benzyl-[1,2,4]oxadiazol-5-yl)-4-[2-(3-methoxy-phenyl)-ethyl]-piperazine;
5-((4-(3-Benzyl-1,2,4-oxadiazol-5-yl)piperazin-1-yl)sulfonyl)benzo[d]oxazol-2(3H)-one;
5-(4-((4-Methoxyphenyl)sulfonyl)piperazin-1-yl)-3-(1-phenylpropyl)-1,2,4-oxadiazole;

1-(4-Ethoxy-benzenesulfonyl)-4-[3-(1-phenyl-propyl)-[1,2,4]oxadiazol-5-yl]-piperazine;
1-(4-Difluoromethoxy-benzenesulfonyl)-4-[3-(1-phenyl-propyl)-[1,2,4]oxadiazol-5-yl]-piperazine;
5-(4-(Benzo[d][1,3]dioxol-5-ylmethyl)piperazin-1-yl)-3-(1-phenylpropyl)-1,2,4-oxadiazole;
5-(4-(2-Methylbenzyl)piperazin-1-yl)-3-(1-phenylpropyl)-1,2,4-oxadiazole;
5-(4-(3-Methoxyphenethyl)piperazin-1-yl)-3-(1-phenylpropyl)-1,2,4-oxadiazole;
1-(4-Methoxy-benzenesulfonyl)-4-[3-((S)-1-phenyl-propyl)-[1,2,4]oxadiazol-5-yl]-piperazine;
1-(4-Methoxy-benzenesulfonyl)-4-[3-((R)-1-phenyl-propyl)-[1,2,4]oxadiazol-5-yl]-piperazine;
1-[3-(4-Chloro-benzyl)-[1,2,4]oxadiazol-5-yl]-4-(4-methoxy-benzenesulfonyl)-piperazine;
1-[3-(4-Chloro-benzyl)-[1,2,4]oxadiazol-5-yl]-4-(4-ethoxy-benzenesulfonyl)-piperazine;
1-[3-(4-Chloro-benzyl)-[1,2,4]oxadiazol-5-yl]-4-(4-difluoromethoxy-benzenesulfonyl)-piperazine;
1-Benzo[1,3]dioxol-5-ylmethyl-4-[3-(4-chloro-benzyl)-[1,2,4]oxadiazol-5-yl]-piperazine;
1-[3-(4-Chloro-benzyl)-[1,2,4]oxadiazol-5-yl]-4-[2-(3-methoxy-phenyl)-ethyl]-piperazine;
5-((4-(3-(4-Chlorobenzyl)-1,2,4-oxadiazol-5-yl)piperazin-1-yl)sulfonyl)benzo[d]oxazol-2(3H)-one;
1-[3-(4-Chloro-benzyl)-[1,2,4]oxadiazol-5-yl]-4-(2-methyl-benzyl)-piperazine;
1-[3-(4-Chloro-benzyl)-[1,2,4]oxadiazol-5-yl]-4-[2-(4-chloro-phenyl)-ethyl]-piperazine;
1-[3-(4-Chloro-benzyl)-[1,2,4]oxadiazol-5-yl]-4-[2-(6-methoxy-pyridin-3-yl)-ethyl]-piperazine;
3-(4-Chlorobenzyl)-5-(4-(2-fluorobenzyl)piperazin-1-yl)-1,2,4-oxadiazole;
1-(2-Chloro-benzyl)-4-[3-(4-chloro-benzyl)-[1,2,4]oxadiazol-5-yl]-piperazine;
1-[3-(4-Chloro-benzyl)-[1,2,4]oxadiazol-5-yl]-4-(4-methyl-benzyl)-piperazine;
4-{4-[3-(4-Chloro-benzyl)-[1,2,4]oxadiazol-5-yl]-piperazin-1-yl}-butyronitrile;
1-[3-(4-Chloro-benzyl)-[1,2,4]oxadiazol-5-yl]-4-(2-ethoxy-ethyl)-piperazine;
1-[3-(4-Chloro-benzyl)-[1,2,4]oxadiazol-5-yl]-4-propyl-piperazine;
3-(4-Chlorobenzyl)-5-(4-isopentylpiperazin-1-yl)-1,2,4-oxadiazole;
1-[3-(4-Chloro-benzyl)-[1,2,4]oxadiazol-5-yl]-4-(4,4,4-trifluoro-butyl)-piperazine;
3-(4-Chlorobenzyl)-5-(4-((tetrahydro-2H-pyran-4-yl)methyl)piperazin-1-yl)-1,2,4-oxadiazole;
4-(2-(4-(3-(4-Chlorobenzyl)-1,2,4-oxadiazol-5-yl)piperazin-1-yl)ethyl)morpholine;
3-(4-Chlorobenzyl)-5-(4-isopropylpiperazin-1-yl)-1,2,4-oxadiazole;
1-[3-(3-Chloro-benzyl)-[1,2,4]oxadiazol-5-yl]-4-(4-methoxy-benzenesulfonyl)-piperazine;
1-[3-(3-Chloro-benzyl)-[1,2,4]oxadiazol-5-yl]-4-(4-ethoxy-benzenesulfonyl)-piperazine;
1-[3-(3-Chloro-benzyl)-[1,2,4]oxadiazol-5-yl]-4-(4-difluoromethoxy-benzenesulfonyl)-piperazine;
1-[3-(3-Chloro-benzyl)-[1,2,4]oxadiazol-5-yl]-4-(2-methyl-benzyl)-piperazine;
1-[3-(3-Chloro-benzyl)-[1,2,4]oxadiazol-5-yl]-4-[2-(3-methoxy-phenyl)-ethyl]-piperazine;
5-{4-[3-(3-Chloro-benzyl)-[1,2,4]oxadiazol-5-yl]-piperazine-1-sulfonyl}-3H-benzooxazol-2-one;
4-(3-(3-Chlorobenzyl)-1,2,4-oxadiazol-5-yl)-N,N-dimethylpiperazine-1-sulfonamide;
4-(3-(3-Chlorobenzyl)-1,2,4-oxadiazol-5-yl)-N,N-diethylpiperazine-1-sulfonamide;
4-((4-(3-(3-Chlorobenzyl)-1,2,4-oxadiazol-5-yl)piperazin-1-yl)sulfonyl)morpholine;
3-(3-Chlorobenzyl)-5-(4-(pyrrolidin-1-ylsulfonyl)piperazin-1-yl)-1,2,4-oxadiazole;
5-(4-(Azepan-1-ylsulfonyl)piperazin-1-yl)-3-(3-chlorobenzyl)-1,2,4-oxadiazole;
3-(3-Chlorobenzyl)-5-(4-((4-methoxypiperidin-1-yl)sulfonyl)piperazin-1-yl)-1,2,4-oxadiazole;
1-[3-(3-Fluoro-benzyl)-[1,2,4]oxadiazol-5-yl]-4-(4-methoxy-benzenesulfonyl)-piperazine;
1-(4-Fluoro-benzenesulfonyl)-4-[3-(3-fluoro-benzyl)-[1,2,4]oxadiazol-5-yl]-piperazine;
N-(4-{4-[3-(3-Fluoro-benzyl)-[1,2,4]oxadiazol-5-yl]-piperazine-1-sulfonyl}-phenyl)-acetamide;
1-[3-(3-Fluoro-benzyl)-[1,2,4]oxadiazol-5-yl]-4-(4-trifluoromethoxy-benzenesulfonyl)-piperazine;
1-[3-(3-Fluoro-benzyl)-[1,2,4]oxadiazol-5-yl]-4-(3-trifluoromethyl-benzenesulfonyl)-piperazine;
1-[3-(3-Fluoro-benzyl)-[1,2,4]oxadiazol-5-yl]-4-(3-methyl-benzyl)-piperazine;
1-[3-(3-Fluoro-benzyl)-[1,2,4]oxadiazol-5-yl]-4-[2-(3-methoxy-phenyl)-ethyl]-piperazine;
1-(4-Ethoxy-benzenesulfonyl)-4-[3-(3-fluoro-benzyl)-[1,2,4]oxadiazol-5-yl]-piperazine;
1-(4-Difluoromethoxy-benzenesulfonyl)-4-[3-(3-fluoro-benzyl)-[1,2,4]oxadiazol-5-yl]-piperazine;
1-[3-(3-Fluoro-benzyl)-[1,2,4]oxadiazol-5-yl]-4-(4-isopropoxy-benzenesulfonyl)-piperazine;
3-(4-((4-(3-(3-Fluorobenzyl)-1,2,4-oxadiazol-5-yl)piperazin-1-yl)sulfonyl)phenoxy)propanenitrile;
1-(2,3-Dihydro-benzofuran-5-sulfonyl)-4-[3-(3-fluoro-benzyl)-[1,2,4]oxadiazol-5-yl]-piperazine;
3-(3-Fluorobenzyl)-5-(4-((4-isopropoxyphenyl)sulfonyl)piperazin-1-yl)-1,2,4-oxadiazole;
1-(4-Chloro-benzyl)-4-[3-(3,4-difluoro-benzyl)-[1,2,4]oxadiazol-5-yl]-piperazine;
1-[3-(3,4-Difluoro-benzyl)-[1,2,4]oxadiazol-5-yl]-4-[2-(3-methoxy-phenyl)-ethyl]-piperazine;
1-[3-(3,4-Difluoro-benzyl)-[1,2,4]oxadiazol-5-yl]-4-(4-methoxy-benzenesulfonyl)-piperazine;
1-[3-(3,4-Difluoro-benzyl)-[1,2,4]oxadiazol-5-yl]-4-(4-ethoxy-benzenesulfonyl)-piperazine;
1-[3-(3,4-Difluoro-benzyl)-[1,2,4]oxadiazol-5-yl]-4-(4-difluoromethoxy-benzenesulfonyl)-piperazine;
1-[2-(4-Chloro-phenyl)-ethyl]-4-[3-(3,4-difluoro-benzyl)-[1,2,4]oxadiazol-5-yl]-piperazine;
1-[3-(3,4-Difluoro-benzyl)-[1,2,4]oxadiazol-5-yl]-4-[2-(6-methoxy-pyridin-3-yl)-ethyl]-piperazine;
1-[3-(3,4-Difluoro-benzyl)-[1,2,4]oxadiazol-5-yl]-4-(2-methyl-benzyl)-piperazine;
1-{3-[1-(4-Fluoro-phenyl)-cyclopropyl]-[1,2,4]oxadiazol-5-yl}-4-(4-methoxy-benzenesulfonyl)-piperazine;
1-(4-Ethoxy-benzenesulfonyl)-4-{3-[1-(4-fluoro-phenyl)-cyclopropyl]-[1,2,4]oxadiazol-5-yl}-piperazine;
3-(1-(4-Fluorophenyl)cyclopropyl)-5-(4-((4-(trifluoromethoxy)phenyl)sulfonyl)piperazin-1-yl)-1,2,4-oxadiazole;
3-(1-(4-Fluorophenyl)cyclopropyl)-5-(4-(2-methylbenzyl)piperazin-1-yl)-1,2,4-oxadiazole;
3-(1-(4-Fluorophenyl)cyclopropyl)-5-(4-(3-methoxyphenethyl)piperazin-1-yl)-1,2,4-oxadiazole;
1-{3-[1-(4-Fluoro-phenyl)-cyclopropyl]-[1,2,4]oxadiazol-5-yl}-4-(4-methylsulfanyl-benzenesulfonyl)-piperazine;

5-(4-(4-Chlorophenethyl)piperazin-1-yl)-3-(1-(4-fluorophenyl)cyclopropyl)-1,2,4-oxadiazole;
5-(4-((2,2-Difluorobenzo[d][1,3]dioxol-5-yl)methyl)piperazin-1-yl)-3-(1-(4-fluorophenyl)cyclopropyl)-1,2,4-oxadiazole;
1-{3-[1-(4-Fluoro-phenyl)-1-methyl-ethyl]-[1,2,4]oxadiazol-5-yl}-4-(4-methoxy-benzenesulfonyl)-piperazine;
1-(4-Difluoromethoxy-benzenesulfonyl)-4-{3-[1-(4-fluoro-phenyl)-1-methyl-ethyl]-[1,2,4]oxadiazol-5-yl}-piperazine;
1-(4-Ethoxy-benzenesulfonyl)-4-{3-[1-(4-fluoro-phenyl)-1-methyl-ethyl]-[1,2,4]oxadiazol-5-yl}-piperazine;
1-{3-[1-(4-Fluoro-phenyl)-1-methyl-ethyl]-[1,2,4]oxadiazol-5-yl}-4-(4-methylsulfanyl-benzenesulfonyl)-piperazine;
3-(2-(4-Fluorophenyl)propan-2-yl)-5-(4-(2-methylbenzyl)piperazin-1-yl)-1,2,4-oxadiazole;
3-(2-(4-Fluorophenyl)propan-2-yl)-5-(4-(3-methoxyphenethyl)piperazin-1-yl)-1,2,4-oxadiazole;
5-(4-(Benzo[d][1,3]dioxol-5-ylmethyl)piperazin-1-yl)-3-(2-(4-fluorophenyl)propan-2-yl)-1,2,4-oxadiazole;
1-(4-Methoxy-benzenesulfonyl)-4-[3-(1-phenyl-cyclopropyl)-[1,2,4]oxadiazol-5-yl]-piperazine;
1-(4-Ethoxy-benzenesulfonyl)-4-[3-(1-phenyl-cyclopropyl)-[1,2,4]oxadiazol-5-yl]-piperazine;
1-(4-Difluoromethoxy-benzenesulfonyl)-4-[3-(1-phenyl-cyclopropyl)-[1,2,4]oxadiazol-5-yl]-piperazine;
5-(4-(2-Methylbenzyl)piperazin-1-yl)-3-(1-phenylcyclopropyl)-1,2,4-oxadiazole;
5-(4-(Benzo[d][1,3]dioxol-5-ylmethyl)piperazin-1-yl)-3-(1-phenylcyclopropyl)-1,2,4-oxadiazole;
5-(4-(3-Methoxyphenethyl)piperazin-1-yl)-3-(1-phenylcyclopropyl)-1,2,4-oxadiazole;
1-(4-Methylsulfanyl-benzenesulfonyl)-4-[3-(1-phenyl-cyclopropyl)-[1,2,4]oxadiazol-5-yl]-piperazine;
5-(4-(4-Chlorophenethyl)piperazin-1-yl)-3-(1-phenylcyclopropyl)-1,2,4-oxadiazole;
5-(4-((2,2-Difluorobenzo[d][1,3]dioxol-5-yl)methyl)piperazin-1-yl)-3-(1-phenylcyclopropyl)-1,2,4-oxadiazole;
5-(4-(2-Chlorobenzyl)piperazin-1-yl)-3-(1-phenylcyclopropyl)-1,2,4-oxadiazole;
5-(4-(4-Methylbenzyl)piperazin-1-yl)-3-(1-phenylcyclopropyl)-1,2,4-oxadiazole;
5-(4-(2-(2-Methoxypyridin-4-yl)ethyl)piperazin-1-yl)-3-(1-phenylcyclopropyl)-1,2,4-oxadiazole;
4-(2-(4-(3-(1-Phenylcyclopropyl)-1,2,4-oxadiazol-5-yl)piperazin-1-yl)ethyl)morpholine;
5-(4-Isopentylpiperazin-1-yl)-3-(1-phenylcyclopropyl)-1,2,4-oxadiazole;
1-{3-[1-(3-Chloro-phenyl)-cyclopropyl]-[1,2,4]oxadiazol-5-yl}-4-(4-methoxy-benzenesulfonyl)-piperazine;
1-{3-[1-(3-Chloro-phenyl)-cyclopropyl]-[1,2,4]oxadiazol-5-yl}-4-(4-ethoxy-benzenesulfonyl)-piperazine;
1-{3-[1-(3-Chloro-phenyl)-cyclopropyl]-[1,2,4]oxadiazol-5-yl}-4-(4-difluoromethoxy-benzenesulfonyl)-piperazine;
1-{3-[1-(3-Chloro-phenyl)-cyclopropyl]-[1,2,4]oxadiazol-5-yl}-4-(4-methylsulfanyl-benzenesulfonyl)-piperazine;
1-{3-[1-(4-Chloro-phenyl)-cyclopropyl]-[1,2,4]oxadiazol-5-yl}-4-(4-methoxy-benzenesulfonyl)-piperazine;
1-{3-[1-(4-Chloro-phenyl)-cyclopropyl]-[1,2,4]oxadiazol-5-yl}-4-(4-ethoxy-benzenesulfonyl)-piperazine;
1-{3-[1-(4-Chloro-phenyl)-cyclopropyl]-[1,2,4]oxadiazol-5-yl}-4-(4-difluoromethoxy-benzenesulfonyl)-piperazine;
1-{3-[1-(4-Chloro-phenyl)-cyclopropyl]-[1,2,4]oxadiazol-5-yl}-4-(4-methylsulfanyl-benzenesulfonyl)-piperazine;
1-{3-[(4-Chloro-phenyl)-difluoro-methyl]-[1,2,4]oxadiazol-5-yl}-4-(4-methoxy-benzenesulfonyl)-piperazine;
1-{3-[(4-Chloro-phenyl)-difluoro-methyl]-[1,2,4]oxadiazol-5-yl}-4-(4-ethoxy-benzenesulfonyl)-piperazine;
1-{3-[(4-Chloro-phenyl)-difluoro-methyl]-[1,2,4]oxadiazol-5-yl}-4-(4-difluoromethoxy-benzenesulfonyl)-piperazine;
1-{3-[(4-Chloro-phenyl)-difluoro-methyl]-[1,2,4]oxadiazol-5-yl}-4-(4-methylsulfanyl-benzenesulfonyl)-piperazine;
1-{3-[Difluoro-(4-fluoro-phenyl)-methyl]-[1,2,4]oxadiazol-5-yl}-4-(4-methoxy-benzenesulfonyl)-piperazine;
1-{3-[Difluoro-(4-fluoro-phenyl)-methyl]-[1,2,4]oxadiazol-5-yl}-4-(4-ethoxy-benzenesulfonyl)-piperazine;
1-{3-[Difluoro-(4-fluoro-phenyl)-methyl]-[1,2,4]oxadiazol-5-yl}-4-(4-difluoromethoxy-benzenesulfonyl)-piperazine;
5-(4-(Benzo[d][1,3]dioxol-5-ylmethyl)piperazin-1-yl)-3-(difluoro(4-fluorophenyl)methyl)-1,2,4-oxadiazole;
3-(Difluoro(4-fluorophenyl)methyl)-5-(4-(3-methoxyphenethyl)piperazin-1-yl)-1,2,4-oxadiazole;
1-{3-[Difluoro-(4-fluoro-phenyl)-methyl]-[1,2,4]oxadiazol-5-yl}-4-(4-methylsulfanyl-benzenesulfonyl)-piperazine;
1-{3-[1-(3-Chloro-phenyl)-1-methyl-ethyl]-[1,2,4]oxadiazol-5-yl}-4-(4-methoxy-benzenesulfonyl)-piperazine;
1-{3-[1-(3-Chloro-phenyl)-1-methyl-ethyl]-[1,2,4]oxadiazol-5-yl}-4-(4-ethoxy-benzenesulfonyl)-piperazine;
1-{3-[1-(3-Chloro-phenyl)-1-methyl-ethyl]-[1,2,4]oxadiazol-5-yl}-4-(4-difluoromethoxy-benzenesulfonyl)-piperazine;
1-{3-[1-(3-Chloro-phenyl)-1-methyl-ethyl]-[1,2,4]oxadiazol-5-yl}-4-(4-methylsulfanyl-benzenesulfonyl)-piperazine;
1-[3-(Difluoro-phenyl-methyl)-[1,2,4]oxadiazol-5-yl]-4-(4-methoxy-benzenesulfonyl)-piperazine;
1-[3-(Difluoro-phenyl-methyl)-[1,2,4]oxadiazol-5-yl]-4-(4-methylsulfanyl-benzenesulfonyl)-piperazine;
1-(4-Difluoromethoxy-benzenesulfonyl)-4-[3-(difluoro-phenyl-methyl)-[1,2,4]oxadiazol-5-yl]-piperazine;
3-(Cyclopropylmethyl)-5-(4-((4-methoxyphenyl)sulfonyl)piperazin-1-yl)-1,2,4-oxadiazole;
3-(Cyclopropylmethyl)-5-(4-((4-(difluoromethoxy)phenyl)sulfonyl)piperazin-1-yl)-1,2,4-oxadiazole;
3-(Cyclopropylmethyl)-5-(4-((4-(methylthio)phenyl)sulfonyl)piperazin-1-yl)-1,2,4-oxadiazole;
3-(Cyclopropylmethyl)-5-(4-((4-ethoxyphenyl)sulfonyl)piperazin-1-yl)-1,2,4-oxadiazole;
5-(4-(3-Methoxyphenethyl)piperazin-1-yl)-3-(2,2,2-trifluoroethyl)-1,2,4-oxadiazole;
5-(4-(4-Chlorophenethyl)piperazin-1-yl)-3-(2,2,2-trifluoroethyl)-1,2,4-oxadiazole;
5-(4-((4-Methoxyphenyl)sulfonyl)piperazin-1-yl)-3-(2,2,2-trifluoroethyl)-1,2,4-oxadiazole;
5-(4-((4-Ethoxyphenyl)sulfonyl)piperazin-1-yl)-3-(2,2,2-trifluoroethyl)-1,2,4-oxadiazole;
5-(4-((4-(Difluoromethoxy)phenyl)sulfonyl)piperazin-1-yl)-3-(2,2,2-trifluoroethyl)-1,2,4-oxadiazole;
5-(4-((4-(Methylthio)phenyl)sulfonyl)piperazin-1-yl)-3-(2,2,2-trifluoroethyl)-1,2,4-oxadiazole;
1-(4-Methoxy-benzenesulfonyl)-4-[3-(2-methyl-pyridin-4-ylmethyl)-[1,2,4]oxadiazol-5-yl]-piperazine;
5-(4-(4-Chlorophenethyl)piperazin-1-yl)-3-((2-methylpyridin-4-yl)methyl)-1,2,4-oxadiazole;
5-(4-((4-Methoxyphenyl)sulfonyl)piperazin-1-yl)-3-(3,3,3-trifluoropropyl)-1,2,4-oxadiazole;
5-(4-((4-(Methylthio)phenyl)sulfonyl)piperazin-1-yl)-3-(3,3,3-trifluoropropyl)-1,2,4-oxadiazole;

5-(4-((4-(Difluoromethoxy)phenyl)sulfonyl)piperazin-1-yl)-3-(3,3,3-trifluoropropyl)-1,2,4-oxadiazole;
5-(4-(4-Chlorophenethyl)piperazin-1-yl)-3-(3,3,3-trifluoropropyl)-1,2,4-oxadiazole;
5-(4-(2-(2-Methoxypyridin-4-yl)ethyl)piperazin-1-yl)-3-(3,3,3-trifluoropropyl)-1,2,4-oxadiazole;
5-(4-(2-Methylbenzyl)piperazin-1-yl)-3-(3,3,3-trifluoropropyl)-1,2,4-oxadiazole;
5-(4-(2-Chlorobenzyl)piperazin-1-yl)-3-(3,3,3-trifluoropropyl)-1,2,4-oxadiazole;
2-((4-(3-(3,3,3-Trifluoropropyl)-1,2,4-oxadiazol-5-yl)piperazin-1-yl)methyl)benzonitrile
5-(4-Isopentylpiperazin-1-yl)-3-(3,3,3-trifluoropropyl)-1,2,4-oxadiazole;
4-(2-(4-(3-(3,3,3-Trifluoropropyl)-1,2,4-oxadiazol-5-yl)piperazin-1-yl)ethyl)morpholine;
4-(4-(3-(3,3,3-Trifluoropropyl)-1,2,4-oxadiazol-5-yl)piperazin-1-yl)butanenitrile;
5-(4-((6-Methylpyridin-2-yl)methyl)piperazin-1-yl)-3-(3,3,3-trifluoropropyl)-1,2,4-oxadiazole;
1-[2-(4-Chloro-phenyl)-ethyl]-4-[3-(4-trifluoromethyl-phenyl)-[1,2,4]oxadiazol-5-yl]-piperazine;
3-((1S,4R)-bicyclo[2.2.1]heptan-2-yl)-5-(4-(2-chlorobenzyl)piperazin-1-yl)-1,2,4-oxadiazole;
3-((1 S,4R)-bicyclo[2.2.1]heptan-2-yl)-5-(4-(4-methylbenzyl)piperazin-1-yl)-1,2,4-oxadiazole;
3-((1S,4R)-bicyclo[2.2.1]heptan-2-yl)-5-(4-(4-chlorophenethyl)piperazin-1-yl)-1,2,4-oxadiazole;
3-((1S,4R)-bicyclo[2.2.1]heptan-2-yl)-5-(4-(2-(2-methoxypyridin-4-yl)ethyl)piperazin-1-yl)-1,2,4-oxadiazole;
4-(2-(4-(3-((1 S,4R)-bicyclo[2.2.1]heptan-2-yl)-1,2,4-oxadiazol-5-yl)piperazin-1-yl)ethyl)morpholine;
3-((1S,4R)-bicyclo[2.2.1]heptan-2-yl)-5-(4-isopentylpiperazin-1-yl)-1,2,4-oxadiazole;
3-(Bicyclo[2.2.1]heptan-2-yl)-5-(4-((4-methoxyphenyl)sulfonyl)piperazin-1-yl)-1,2,4-oxadiazole;
3-(Bicyclo[2.2.1]heptan-2-yl)-5-(4-((4-(methylthio)phenyl)sulfonyl)piperazin-1-yl)-1,2,4-oxadiazole;
3-(Bicyclo[2.2.1]heptan-2-yl)-5-(4-((4-(difluoromethoxy)phenyl)sulfonyl)piperazin-1-yl)-1,2,4-oxadiazole;
3-Cyclopropyl-5-(4-((4-ethoxyphenyl)sulfonyl)piperazin-1-yl)-1,2,4-oxadiazole;
3-Cyclopropyl-5-(4-((4-methoxyphenyl)sulfonyl)piperazin-1-yl)-1,2,4-oxadiazole;
5-(4-((4-Methoxyphenyl)sulfonyl)piperazin-1-yl)-3-(2-(2-methylpyridin-4-yl)propan-2-yl)-1,2,4-oxadiazole;
1-(4-Difluoromethoxy-benzenesulfonyl)-4-[3-(1-methyl-1-phenyl-ethyl)-[1,2,4]oxadiazol-5-yl]-piperazine;
1-(4-Methoxy-benzenesulfonyl)-4-[3-(1-methyl-1-phenyl-ethyl)-[1,2,4]oxadiazol-5-yl]-piperazine;
(5-(4-((4-Methoxyphenyl)sulfonyl)piperazin-1-yl)-1,2,4-oxadiazol-3-yl)methanol;
3-(Methoxymethyl)-5-(4-((4-methoxyphenyl)sulfonyl)piperazin-1-yl)-1,2,4-oxadiazole;
3-((4-Chlorophenoxy)methyl)-5-(4-((4-methoxyphenyl)sulfonyl)piperazin-1-yl)-1,2,4-oxadiazole;
3-((3-Chlorophenoxy)methyl)-5-(4-((4-methoxyphenyl)sulfonyl)piperazin-1-yl)-1,2,4-oxadiazole;
5-(4-((4-Methoxyphenyl)sulfonyl)piperazin-1-yl)-3-(phenoxymethyl)-1,2,4-oxadiazole;
3-((Cyclopropylmethoxy)methyl)-5-(4-((4-methoxyphenyl)sulfonyl)piperazin-1-yl)-1,2,4-oxadiazole;
5-(4-((4-Methoxyphenyl)sulfonyl)piperazin-1-yl)-3-((pyridin-3-yloxy)methyl)-1,2,4-oxadiazole;
4-((5-(4-((4-Methoxyphenyl)sulfonyl)piperazin-1-yl)-1,2,4-oxadiazol-3-yl)methoxy)benzonitrile;
3-((4-Fluorophenoxy)methyl)-5-(4-((4-methoxyphenyl)sulfonyl)piperazin-1-yl)-1,2,4-oxadiazole;
5-(4-((4-Methoxyphenyl)sulfonyl)piperazin-1-yl)-3-propyl-1,2,4-oxadiazole;
3-Butyl-5-(4-((4-methoxyphenyl)sulfonyl)piperazin-1-yl)-1,2,4-oxadiazole;
3-(Tert-butyl)-5-(4-((4-methoxyphenyl)sulfonyl)piperazin-1-yl)-1,2,4-oxadiazole;
3-Cyclohexyl-5-(4-((4-methoxyphenyl)sulfonyl)piperazin-1-yl)-1,2,4-oxadiazole;
3-Isopropyl-5-(4-((4-methoxyphenyl)sulfonyl)piperazin-1-yl)-1,2,4-oxadiazole;
3-(2-Methoxyethyl)-5-(4-((4-methoxyphenyl)sulfonyl)piperazin-1-yl)-1,2,4-oxadiazole;
3-(1-(4-Fluorophenyl)cyclopropyl)-5-(7-((4-methoxyphenyl)sulfonyl)-2,7-diazaspiro[3.5]nonan-2-yl)-1,2,4-oxadiazole;
5-(7-((4-Methoxyphenyl)sulfonyl)-2,7-diazaspiro[3.5]nonan-2-yl)-3-(2,2,2-trifluoroethyl)-1,2,4-oxadiazole;
5-(7-((4-(Methylthio)phenyl)sulfonyl)-2,7-diazaspiro[3.5]nonan-2-yl)-3-(2,2,2-trifluoroethyl)-1,2,4-oxadiazole;
5-(7-((4-Ethoxyphenyl)sulfonyl)-2,7-diazaspiro[3.5]nonan-2-yl)-3-(2,2,2-trifluoroethyl)-1,2,4-oxadiazole;
5-(7-((4-(Difluoromethoxy)phenyl)sulfonyl)-2,7-diazaspiro[3.5]nonan-2-yl)-3-(2,2,2-trifluoroethyl)-1,2,4-oxadiazole;
(3-(4-Fluorobenzyl)-1,2,4-oxadiazol-5-yl)(7-((4-methoxyphenyl)sulfonyl)-2,7-diazaspiro[3.5]nonan-2-yl)methanone;
3-(4-Fluorobenzyl)-5-(7-((4-methoxyphenyl)sulfonyl)-2,7-diazaspiro[3.5]nonan-2-yl)-1,2,4-oxadiazole;
3-(2-Methoxyethyl)-5-(7-((4-methoxyphenyl)sulfonyl)-2,7-diazaspiro[3.5]nonan-2-yl)-1,2,4-oxadiazole;

and a solvate, hydrate, pharmaceutically acceptable salt thereof.

The present invention also encompasses processes for the preparation of compounds formula (I) or (II) and any subgroup thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999. Protected forms of the inventive compounds are included within the scope of the present invention. It will also be clear to the skilled person that compounds of the invention in which one or more functional groups have been protected with suitable functional groups can find use as intermediates in the production and/or synthesis of the compounds of the invention, and as such form a further aspect of the invention.

The compounds formula (I) or (II), the subgroups thereof and their pharmaceutically acceptable salts can be prepared as described hereunder.

In the general schemes described below, all substituents are defined as in the general formula (I), (II), (IA), (IIA), (IB), (IIB), (IC), (IIC), (ID), (IID), (IE), (IIE), (IF), (IIF), (IG), (IIG), (IH), (IIH), (IJ), (IIJ), (IIK), (IIL) or any subgroups thereof, unless otherwise mentioned or indicated.

The present compounds of formula (I) or (II) and their pharmaceutically acceptable salts can be prepared by methods known in the art, for example, by processes described below, which process comprises coupling a compound of formula XII or XIII:

XII

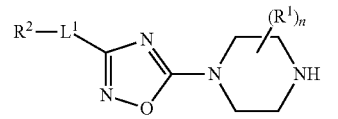

XIII

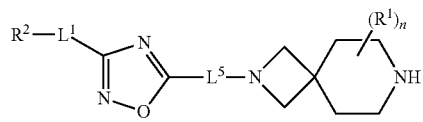

with a derivative of formula III:

III

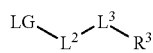

wherein LG is a leaving group; or by coupling a compound of formula XIV or XVI:

XIV

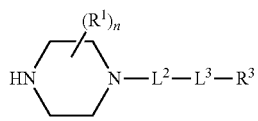

XVI

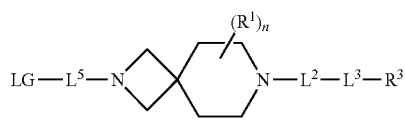

wherein LG is a leaving group, with a derivative of formula VI:

VI

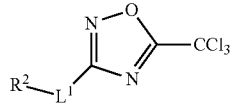

to give a compound of formula (I) or (II) or if desired, converting the compounds obtained into pharmaceutically acceptable acid addition salts.

The preparation of compounds of formula (I) or (II) of the present invention may be carried out in sequential or convergent synthetic routes. In some embodiments, syntheses of the compounds of the invention are shown in the following General Schemes 1 and 2. The skills required for carrying out the reaction and purification of the resulting products are known to those skilled in the art. The substituents and indices used in the following description of the processes have the significance given herein before unless indicated to the contrary.

In more detail, the compounds of formula (I) or (II) can be manufactured by the methods given below, by the methods given in the examples or by analogous methods. Appropriate reaction conditions for the individual reaction steps are known to a person skilled in the art. The reaction sequence is not limited to the one displayed in General Schemes 1 and 2, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The invention includes all stereoisomeric forms, including individual diastereoisomers and enantiomers of the compound of formula (I) or (II) as well as racemic and non-racemic mixtures thereof.

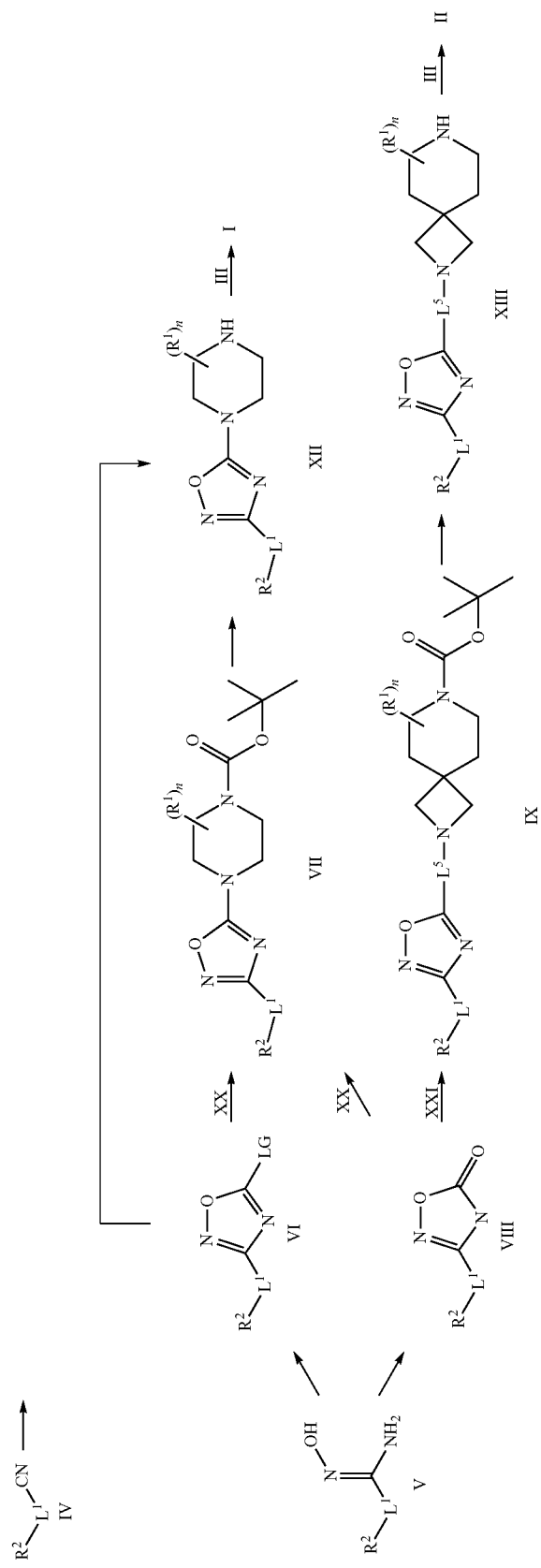

wherein LG is a leaving group such as CCl₃ or halogen.

Compounds of formula XII and XIII can be prepared as described in General Scheme 1. The nitrile moiety of intermediate IV is converted into the N-hydroxy amidine intermediate V upon addition of hydroxyl amine. The oxadiazole derivative VI may be formed by reaction with for instance trichloroacetic anhydride in the presence of trichloroacetic acid, whereupon LG is CCl₃. A nucleophilic aromatic substitution of VI with an excess of piperazine at high temperature affords intermediate XII. Alternatively, coupling of VI with commercially available protected piperazine XX (for instance, tert-butyl-piperazine-1-carboxylate), affords VII which after cleavage of the protecting group gives intermediate XII.

Alternatively, the hydroxy-amidine V can be converted into an oxadiazolone intermediate VIII in a one-step sequence (e.g. with carbonyldiimidazole (CDI)) or in a two steps sequence by reacting it first with ethyl chloroformate followed by thermal cyclisation. Coupling of VIII with commercially available protected piperazine XX (for instance, tert-butyl-piperazine-1-carboxylate) affords VII which after cleavage of the protecting group (e.g. with trifluoroacetic acid (TFA)) gives intermediate XII.

Coupling of VIII with a commercially available protected 2,7-diazaspiro[3.5]nonane XXI (for instance tert-butyl 2,7-diazaspiro[3.5]nonane-7-carboxylate) affords IX which after cleavage of the protecting group (e.g. with TFA) gives intermediate XIII.

Compounds of formula XII or XIII can then undergo nucleophilic substitution with compounds of formula III, where the leaving group is typically a halogen to yield compound of formula (I) and (II) respectively.

General scheme 2

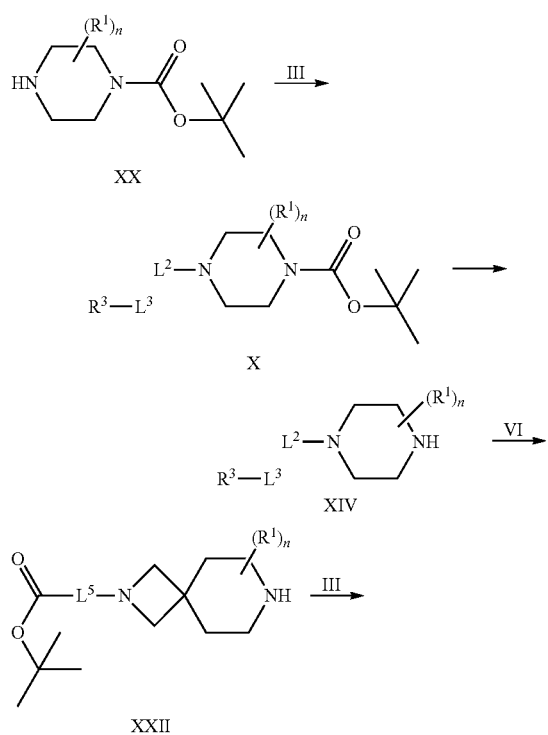

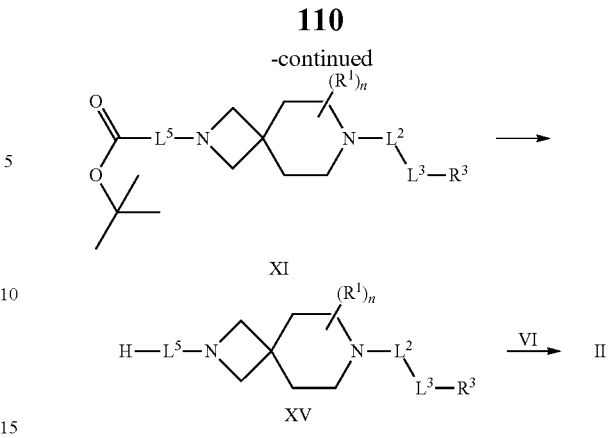

Another possibility to prepare compounds of formula (I) or (II) is described in General Scheme 2. Commercially available protected piperazine XX and 2,7-diazaspiro[3.5]nonane XXII, can be reacted with intermediates of formula III to give protected intermediates of formula X and XI respectively. Deprotection, under standard conditions known to the skilled in the art, leads to derivatives of formula XIV and XV. Nucleophilic aromatic substitution with derivative VI leads to the formation of desired compounds (I) and (II).

The present invention encompasses compounds according to the invention, as well as the compounds obtained by the methods of the invention. The present invention also encompasses pharmaceutical composition comprising at least one compound of the present invention. The present invention also encompasses pharmaceutical composition comprising at least one compound of the invention and at least one carrier, excipient or diluent acceptable for pharmaceutical purposes.

In some embodiments, the present invention relates to the use of at least one compound of formula (I) or (II), or any subgroups thereof, in (the preparation of a composition for) the prevention and/or treatment of metabolic disorders and/or neurodegenerative diseases, and/or protein misfolding disorders.

In some embodiments, the present invention relates to a method of prevention and/or of treatment of metabolic disorders and/or neurodegenerative diseases, and/or protein misfolding disorders, comprising administering to a subject in need thereof an effective amount of at least one compound of formula (I) or (II), or any subgroups thereof, or a pharmaceutical composition comprising said at least one compound of formula (I) or (II) or any subgroups thereof.

In some embodiments, the present invention relates to the use of at least one compound of formula (I) or (II), or any subgroups thereof, in (the preparation of a composition for) the prevention and/or treatment of neurodegenerative disorders and/or protein misfolding disorders, preferably neurodegenerative disorders and/or protein misfolding disorders related to amyloidosis; more preferably neurodegenerative disorders and/or protein misfolding disorders related to synucleinopathies comprising Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease; yet more preferably for the prevention and/or treatment of Parkinson's disease and/or Alzheimer's disease.

In some embodiments, the present invention relates to the use of at least one compound of formula (I) or (II), or any subgroups thereof, in (the preparation of a composition for) the prevention and/or treatment of metabolic disorders, preferably metabolic disorders related to amyloidosis, yet more preferably Metabolic disorders such as diabetes mellitus, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases, hypertension; yet more preferably diabetes mellitus such as diabetes mellitus type 1 or type 2, more preferably diabetes mellitus type 2.

The term "subject" as used herein refers to a mammal. The subject will preferably be a human, but may also be a domestic livestock, laboratory or pet animals.

In some embodiments, at least one compound of formula (I) or (II) is used (for the preparation of a medicament) for preventing and/or treating a disease selected from the group comprising diabetes mellitus, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease, impaired glucose tolerance, hyperglycemia, hypoglycemia, glyceraldehyde-3-phosphate dehydrogenase deficiency, hyperinsulinism, impaired insulin production, impaired insulin sensitivity, metabolic syndrome, insulin resistance syndrome, obesity, lipidoses, cardiac lipidoses, dyslipidemia, fatty liver, lipodistrophy, cardiovascular diseases and hypertension and/or for preventing, treating and/or alleviating complications and/or symptoms associated therewith.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I) or (II), as well as stereoisomers, tautomers, racemics, salts, hydrates or solvates thereof, may be administered as the raw chemical. Additionally, the active ingredient may be presented as a pharmaceutical composition.

Accordingly, the invention further provides pharmaceutical compositions that include effective amounts of compounds of formula (I) or (II), or stereoisomers, tautomers, racemics, salts, hydrates or solvates thereof, and one or more pharmaceutically acceptable carriers, diluents, or excipients. The compounds of formula (I) or (II) or stereoisomers, tautomers, racemics, salts, hydrates or solvates thereof, are as herein described.

The compounds according to the invention may be administered as the sole active ingredient or together, i.e. in a fixed or free combination, with other therapeutic agents used in clinical practice for the treatment of those diseases listed above.

The compounds according to the invention and the other pharmaceutical active agent(s) may be administered together or separately and, when administered separately, administration may occur simultaneously or sequentially, in any order. The amounts of the compounds according to the invention and the other pharmaceutically active agent (s) and the relative timings of administration will be selected in order to achieve the desired combined therapeutic effect. The administration in combination of a compound of formula (I) or (II) or a stereoisomer, tautomer, racemic, salt, hydrate or solvate thereof, with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention can be more suitable due to their increased water solubility.

Appropriate cyclodextrins are α-, β- or γ-cyclodextrins (CDs) or ethers and mixed ethers thereof wherein one or more of the hydroxyl groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkoxycarbonylalkyl or carboxyalkoxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxyl groups are etherified with different groups such as, for example, hydroxypropyl and hydroxyethyl. An interesting way of formulating the compounds in combination with a cyclodextrin or a derivative thereof has been described in EP-A-721,331. Although the formulations described therein are with antifungal active ingredients, they are equally interesting for formulating the compounds. Said formulations may also be rendered more palatable by adding pharmaceutically acceptable sweeteners and/or flavors. In particular, the present invention encompasses a pharmaceutical composition comprising an effective amount of a compound according to the invention with a pharmaceutically acceptable cyclodextrin. The present invention also encompasses cyclodextrin complexes consisting of a compound according to the invention and a cyclodextrin.

Particular reference is made to the compositions, formulations (and carriers, excipients, diluents, etc. for use therein), routes of administration etc., which are known per se such as those described in U.S. Pat. No. 4,997,834 and EP-A-0 370 498.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa·s when dissolved in a 2% aqueous solution at 20° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products, and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded, or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides, and derivatives thereof.

The preparations may be prepared in a manner known per se, which usually involves mixing the at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the formula (I) or (II) above that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a (pharmaceutical) composition for veterinary use that contains at least one compound of the invention and at least one suitable carrier (i.e. a carrier suitable for veterinary use). The invention also relates to the use of a compound of the invention in the preparation of such a composition.

The following examples are provided for the purpose of illustrating the present invention and by no means should be interpreted to limit the scope of the present invention.

EXAMPLES

The synthesis of the compounds of table 1 is described in this experimental part.

TABLE 1

| Compound | Structure | Name | Example No |
|---|---|---|---|
| Cmpd001 | 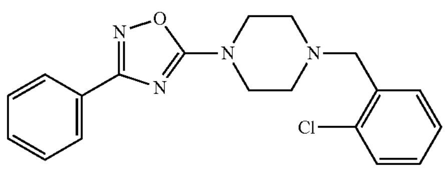 [SMILES: Clc1ccccc1CN1CCN(c2nc(-c3ccccc3)no2)CC1] | 5-(4-(2-Chlorobenzyl)piperazin-1-yl)-3-phenyl-1,2,4-oxadiazole | 1 |
| Cmpd002 | 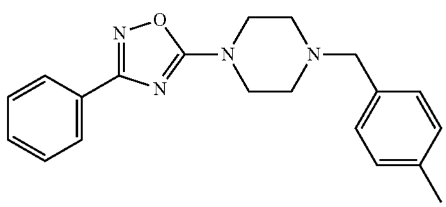 [SMILES: Cc1ccc(CN2CCN(c3nc(-c4ccccc4)no3)CC2)cc1] | 5-(4-(4-Methylbenzyl)piperazin-1-yl)-3-phenyl-1,2,4-oxadiazole | 2 |
| Cmpd003 | 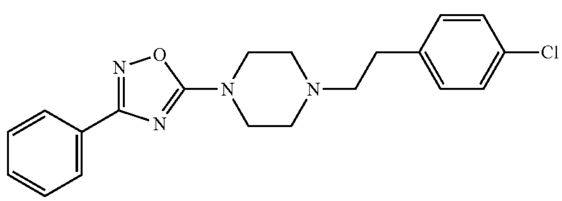 [SMILES: Clc1ccc(CCN2CCN(c3nc(-c4ccccc4)no3)CC2)cc1] | 5-(4-(4-Chlorophenethyl)piperazin-1-yl)-3-phenyl-1,2,4-oxadiazole | 3 |
| Cmpd004 | 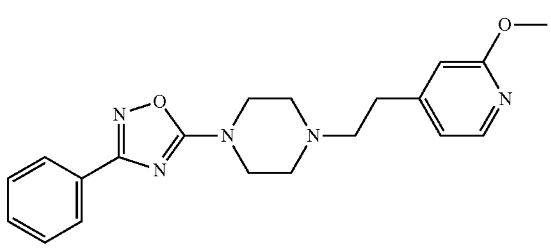 [SMILES: COc1cc(CCN2CCN(c3nc(-c4ccccc4)no3)CC2)ccn1] | 5-(4-(2-(2-Methoxypyridin-4-yl)ethyl)piperazin-1-yl)-3-phenyl-1,2,4-oxadiazole | 4 |
| Cmpd005 | 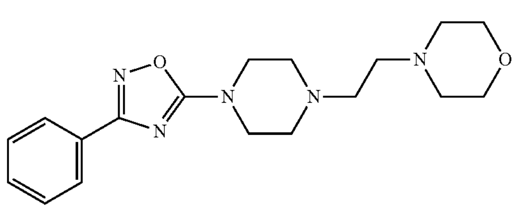 [SMILES: c1ccc(-c2noc(N3CCN(CCN4CCOCC4)CC3)n2)cc1] | 4-(2-(4-(3-Pphenyl-1,2,4-oxadiazol-5-yl)piperazin-1-yl)ethyl)morpholine | 5 |
| Cmpd006 | 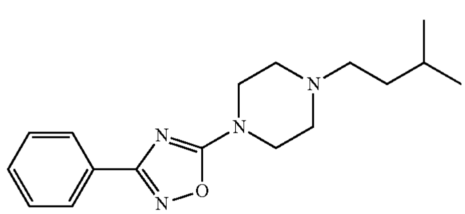 [SMILES: CC(C)CCN1CCN(c2nc(-c3ccccc3)no2)CC1] | 5-(4-Isopentylpiperazin-1-yl)-3-phenyl-1,2,4-oxadiazole | 6 |

TABLE 1-continued

| COMPOUND | STRUCTURE | NAME | Example No |
|---|---|---|---|
| Cmpd007 | 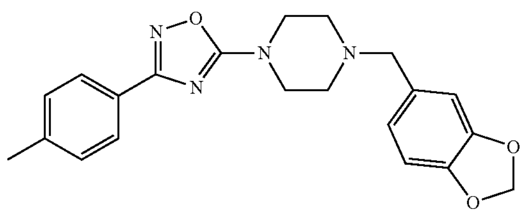 [SMILES: Cc1ccc(-c2noc(N3CCN(Cc4ccc5c(c4)OCO5)CC3)n2)cc1] | 5-(4-(Benzo[d][1,3]dioxol-5-ylmethyl)piperazin-1-yl)-3-(p-tolyl)-1,2,4-oxadiazole | 7 |
| Cmpd008 | 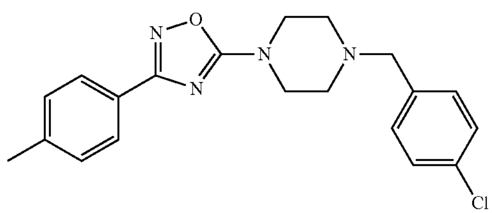 [SMILES: Cc1ccc(-c2noc(N3CCN(Cc4ccc(Cl)cc4)CC3)n2)cc1] | 5-(4-(4-Chlorobenzyl)piperazin-1-yl)-3-(p-tolyl)-1,2,4-oxadiazole | 8 |
| Cmpd009 | 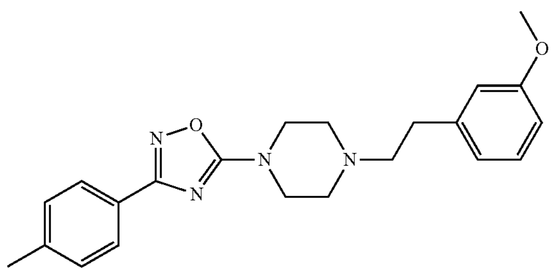 [SMILES: COc1cccc(CCN2CCN(c3nc(-c4ccc(C)cc4)no3)CC2)c1] | 5-(4-(3-Methoxyphenethyl)piperazin-1-yl)-3-(p-tolyl)-1,2,4-oxadiazole | 9 |
| Cmpd010 | 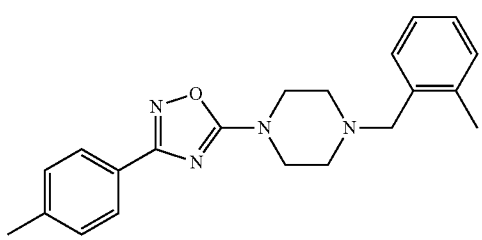 | 5-(4-(2-Methylbenzyl)piperazin-1-yl)-3-(p-tolyl)-1,2,4-oxadiazole | 10 |
| Cmpd011 | 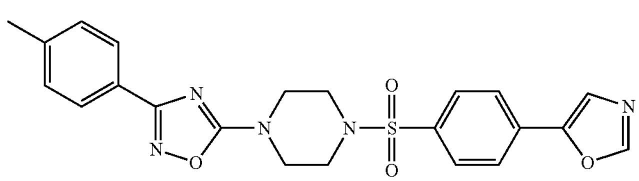 [SMILES: Cc1ccc(-c2noc(N3CCN(S(=O)(=O)c4ccc(-c5cnco5)cc4)CC3)n2)cc1] | 5-(4-((4-(Oxazol-5-yl)phenyl)sulfonyl)piperazin-1-yl)-3-(p-tolyl)-1,2,4-oxadiazole | 11 |
| Cmpd012 | 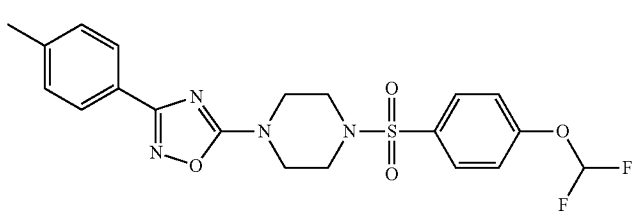 [SMILES: Cc1ccc(-c2noc(N3CCN(S(=O)(=O)c4ccc(OC(F)F)cc4)CC3)n2)cc1] | 5-(4-((4-(Difluoromethoxy)phenyl)sulfonyl)piperazin-1-yl)-3-(p-tolyl)-1,2,4-oxadiazole | 12 |
| Cmpd013 | 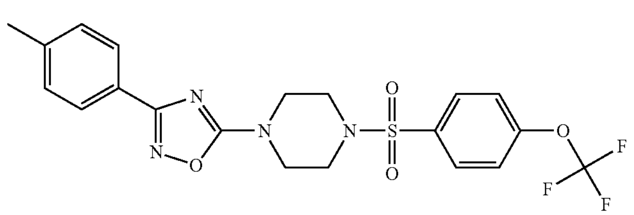 [SMILES: Cc1ccc(-c2noc(N3CCN(S(=O)(=O)c4ccc(OC(F)(F)F)cc4)CC3)n2)cc1] | 3-(p-Tolyl)-5-(4-((4-(trifluoromethoxy)phenyl)sulfonyl)piperazin-1-yl)-1,2,4-oxadiazole | 13 |

TABLE 1-continued

| COMPOUND | STRUCTURE | NAME | Example No |
|---|---|---|---|
| Cmpd014 | 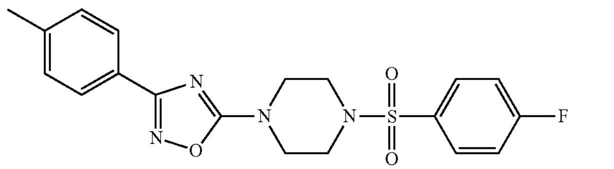 [SMILES: Cc1ccc(-c2noc(N3CCN(S(=O)(=O)c4ccc(F)cc4)CC3)n2)cc1] | 5-(4-((4-Fluorophenyl)sulfonyl)piperazin-1-yl)-3-(p-tolyl)-1,2,4-oxadiazole | 14 |
| Cmpd015 | 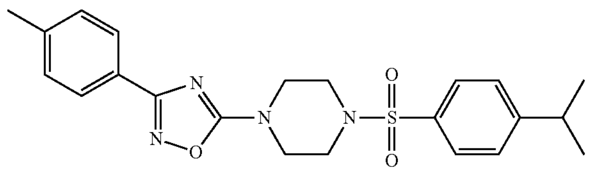 [SMILES: Cc1ccc(-c2noc(N3CCN(S(=O)(=O)c4ccc(C(C)C)cc4)CC3)n2)cc1] | 5-(4-((4-Isopropylphenyl)sulfonyl)piperazin-1-yl)-3-(p-tolyl)-1,2,4-oxadiazole | 15 |
| Cmpd016 | 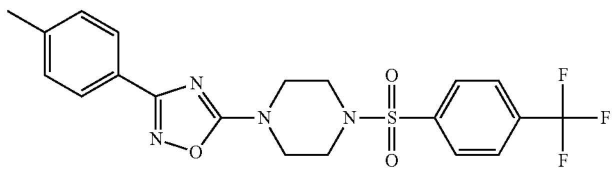 [SMILES: Cc1ccc(-c2noc(N3CCN(S(=O)(=O)c4ccc(C(F)(F)F)cc4)CC3)n2)cc1] | 3-(p-Tolyl)-5-(4-((4-(trifluoromethyl)phenyl)sulfonyl)piperazin-1-yl)-1,2,4-oxadiazole | 16 |
| Cmpd017 | 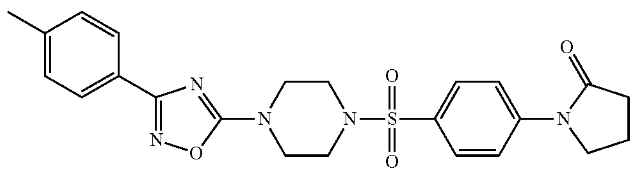 [SMILES: Cc1ccc(-c2noc(N3CCN(S(=O)(=O)c4ccc(N5CCCC5=O)cc4)CC3)n2)cc1] | 1-(4-((4-(3-(p-Tolyl)-1,2,4-oxadiazol-5-yl)piperazin-1-yl)sulfonyl)phenyl)pyrrolidin-2-one | 17 |
| Cmpd018 | 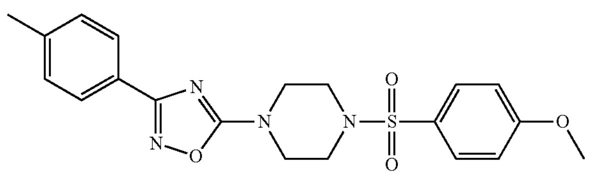 | 5-(4-((4-Methoxyphenyl)sulfonyl)piperazin-1-yl)-3-(p-tolyl)-1,2,4-oxadiazole | 18 |
| Cmpd019 | 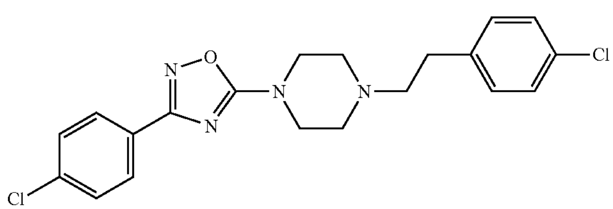 [SMILES: Clc1ccc(CCN2CCN(c3nc(-c4ccc(Cl)cc4)no3)CC2)cc1] | 5-(4-(4-Chlorophenethyl)piperazin-1-yl)-3-(4-chlorophenyl)-1,2,4-oxadiazole | 19 |
| Cmpd020 | 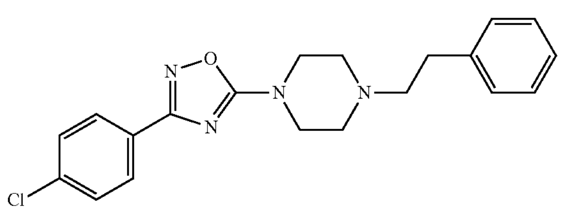 [SMILES: Clc1ccc(-c2noc(N3CCN(CCc4ccccc4)CC3)n2)cc1] | 3-(4-Chlorophenyl)-5-(4-phenethylpiperazin-1-yl)-1,2,4-oxadiazole | 20 |
| Cmpd021 | 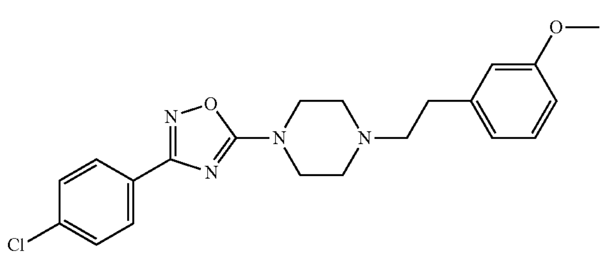 [SMILES: COc1cccc(CCN2CCN(c3nc(-c4ccc(Cl)cc4)no3)CC2)c1] | 3-(4-Chlorophenyl)-5-(4-(3-methoxyphenethyl)piperazin-1-yl)-1,2,4-oxadiazole | 21 |

TABLE 1-continued

| COMPOUND | STRUCTURE | NAME | Example No |
|---|---|---|---|
| Cmpd022 | 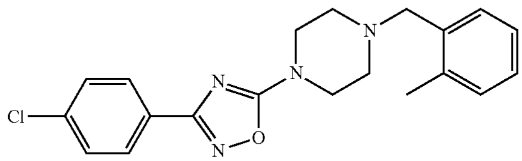 [SMILES: Cc1ccccc1CN1CCN(c2nc(-c3ccc(Cl)cc3)no2)CC1] | 3-(4-Chlorophenyl)-5-(4-(2-methylbenzyl)piperazin-1-yl)-1,2,4-oxadiazole | 22 |
| Cmpd023 | 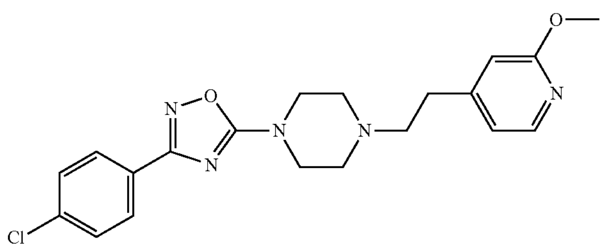 [SMILES: COc1cc(CCN2CCN(c3nc(-c4ccc(Cl)cc4)no3)CC2)ccn1] | 3-(4-Chlorophenyl)-5-(4-(2-(2-methoxypyridin-4-yl)ethyl)piperazin-1-yl)-1,2,4-oxadiazole | 23 |
| Cmpd024 | 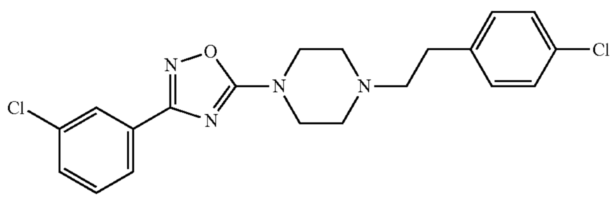 [SMILES: Clc1ccc(CCN2CCN(c3nc(-c4cccc(Cl)c4)no3)CC2)cc1] | 5-(4-(4-Chlorophenethyl)piperazin-1-yl)-3-(3-chlorophenyl)-1,2,4-oxadiazole | 24 |
| Cmpd025 | 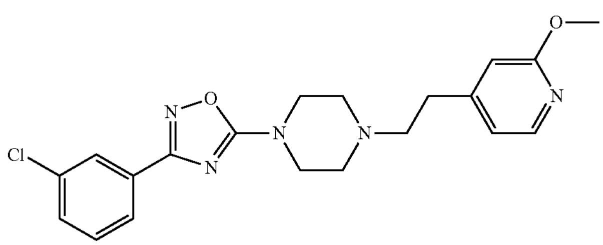 [SMILES: COc1cc(CCN2CCN(c3nc(-c4cccc(Cl)c4)no3)CC2)ccn1] | 3-(3-Chlorophenyl)-5-(4-(2-(2-methoxypyridin-4-yl)ethyl)piperazin-1-yl)-1,2,4-oxadiazole | 25 |
| Cmpd026 | 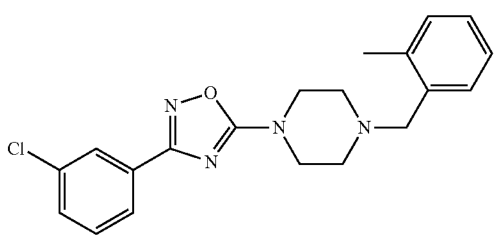 [SMILES: Cc1ccccc1CN1CCN(c2nc(-c3cccc(Cl)c3)no2)CC1] | 3-(3-Chlorophenyl)-5-(4-(2-methylbenzyl)piperazin-1-yl)-1,2,4-oxadiazole | 26 |
| Cmpd027 | 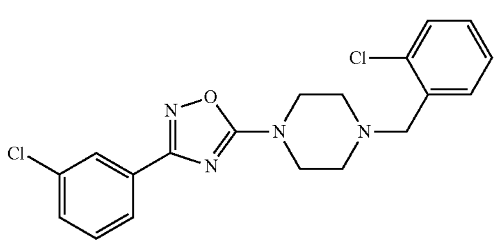 [SMILES: Clc1cccc(-c2noc(N3CCN(Cc4ccccc4Cl)CC3)n2)c1] | 5-(4-(2-Chlorobenzyl)piperazin-1-yl)-3-(3-chlorophenyl)-1,2,4-oxadiazole | 27 |
| Cmpd028 | 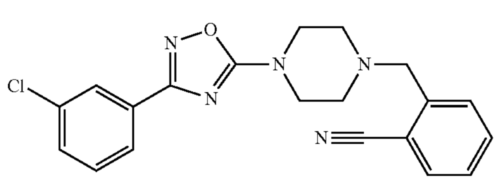 [SMILES: N#Cc1ccccc1CN1CCN(c2nc(-c3cccc(Cl)c3)no2)CC1] | 2-((4-(3-(3-Chlorophenyl)-1,2,4-oxadiazol-5-yl)piperazin-1-yl)methyl)benzonitrile | 28 |

TABLE 1-continued

| COMPOUND | STRUCTURE | NAME | Example No |
|---|---|---|---|
| Cmpd029 | 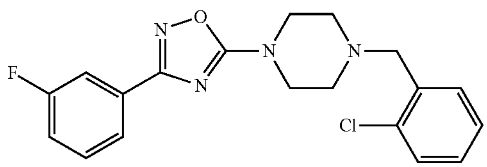 [SMILES: Fc1cccc(-c2noc(N3CCN(Cc4ccccc4Cl)CC3)n2)c1] | 5-(4-(2-Chlorobenzyl)piperazin-1-yl)-3-(3-fluorophenyl)-1,2,4-oxadiazole | 29 |
| Cmpd030 | 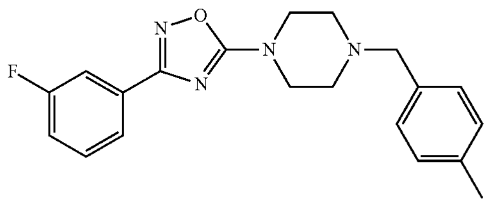 [SMILES: Cc1ccc(CN2CCN(c3nc(-c4cccc(F)c4)no3)CC2)cc1] | 3-(3-Fluorophenyl)-5-(4-(4-methylbenzyl)piperazin-1-yl)-1,2,4-oxadiazole | 30 |
| Cmpd031 | 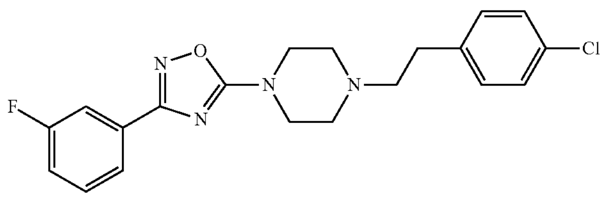 [SMILES: Fc1cccc(-c2noc(N3CCN(CCc4ccc(Cl)cc4)CC3)n2)c1] | 5-(4-(4-Chlorophenethyl)piperazin-1-yl)-3-(3-fluorophenyl)-1,2,4-oxadiazole | 31 |
| Cmpd032 | 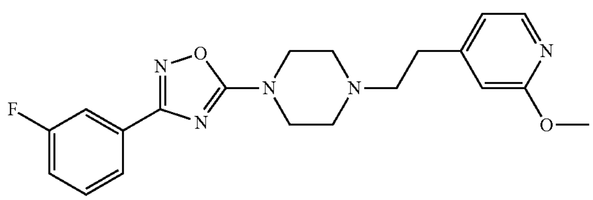 [SMILES: COc1cc(CCN2CCN(c3nc(-c4cccc(F)c4)no3)CC2)ccn1] | 3-(3-Fluorophenyl)-5-(4-(2-(2-methoxypyridin-4-yl)ethyl)piperazin-1-yl)-1,2,4-oxadiazole | 32 |
| Cmpd033 | 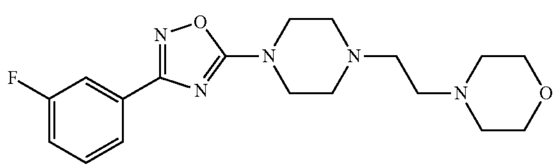 [SMILES: Fc1cccc(-c2noc(N3CCN(CCN4CCOCC4)CC3)n2)c1] | 4-(2-(4-(3-(3-Fluorophenyl)-1,2,4-oxadiazol-5-yl)piperazin-1-yl)ethyl)morpholine | 33 |
| Cmpd034 | 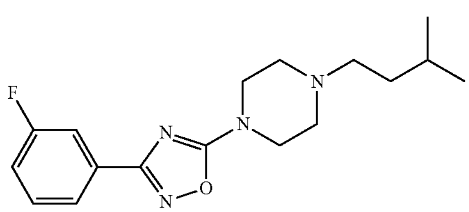 [SMILES: CC(C)CCN1CCN(c2nc(-c3cccc(F)c3)no2)CC1] | 3-(3-Fluorophenyl)-5-(4-isopentylpiperazin-1-yl)-1,2,4-oxadiazole | 34 |
| Cmpd035 | 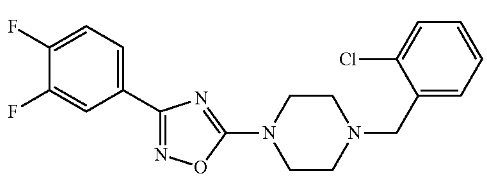 [SMILES: Fc1ccc(-c2noc(N3CCN(Cc4ccccc4Cl)CC3)n2)cc1F] | 5-(4-(2-Chlorobenzyl)piperazin-1-yl)-3-(3,4-difluorophenyl)-1,2,4-oxadiazole | 35 |
| Cmpd036 | 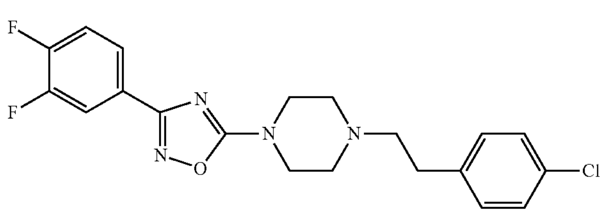 [SMILES: Fc1ccc(-c2noc(N3CCN(CCc4ccc(Cl)cc4)CC3)n2)cc1F] | 1-[2-(4-Chloro-phenyl)-ethyl]-4-[3-(3,4-difluoro-phenyl)-[1,2,4]oxadiazol-5-yl]-piperazine | 36 |

TABLE 1-continued

| COMPOUND | STRUCTURE | NAME | Example No |
|---|---|---|---|
| Cmpd037 | 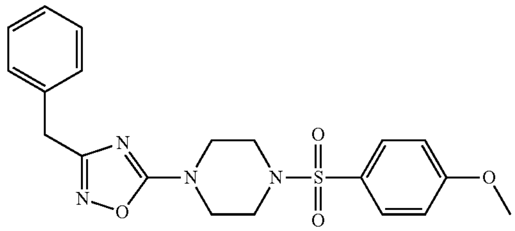 [SMILES: COc1ccc(S(=O)(=O)N2CCN(c3nc(Cc4ccccc4)no3)CC2)cc1] | 1-(3-Benzyl-[1,2,4]oxadiazol-5-yl)-4-(4-methoxy-benzenesulfonyl)-piperazine | 37 |
| Cmpd038 | 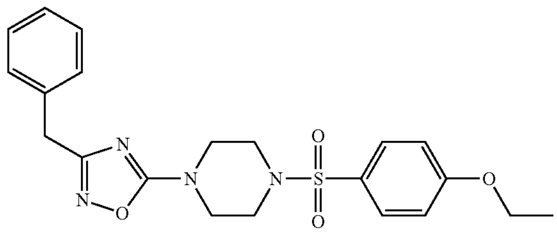 [SMILES: CCOc1ccc(S(=O)(=O)N2CCN(c3nc(Cc4ccccc4)no3)CC2)cc1] | 1-(3-Benzyl-[1,2,4]oxadiazol-5-yl)-4-(4-ethoxy-benzenesulfonyl)-piperazine | 38 |
| Cmpd039 | 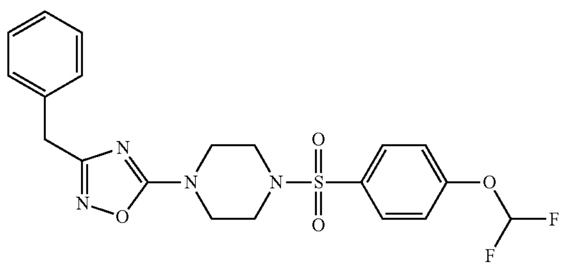 [SMILES: O=S(=O)(c1ccc(OC(F)F)cc1)N1CCN(c2nc(Cc3ccccc3)no2)CC1] | 1-(3-Benzyl-[1,2,4]oxadiazol-5-yl)-4-(4-difluoromethoxy-benzenesulfonyl)-piperazine | 39 |
| Cmpd040 | 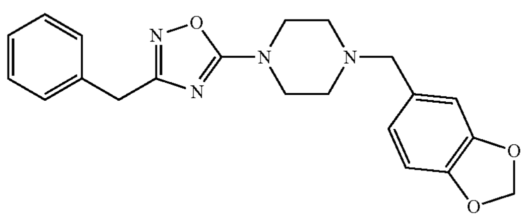 [SMILES: c1ccc(Cc2noc(N3CCN(Cc4ccc5c(c4)OCO5)CC3)n2)cc1] | 1-Benzo[1,3]dioxol-5-ylmethyl-4-(3-benzyl-[1,2,4]oxadiazol-5-yl)-piperazine | 40 |
| Cmpd041 | 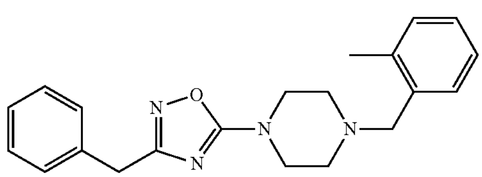 [SMILES: Cc1ccccc1CN1CCN(c2nc(Cc3ccccc3)no2)CC1] | 1-(3-Benzyl-[1,2,4]oxadiazol-5-yl)-4-(2-methylbenzyl)-piperazine | 41 |
| Cmpd042 | 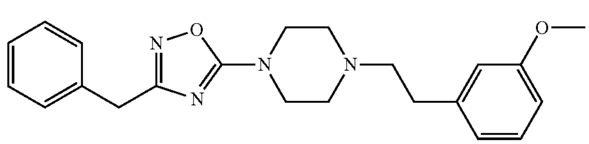 [SMILES: COc1cccc(CCN2CCN(c3nc(Cc4ccccc4)no3)CC2)c1] | 1-(3-Benzyl-[1,2,4]oxadiazol-5-yl)-4-[2-(3-methoxy-phenyl)-ethyl]-piperazine | 42 |
| Cmpd043 | 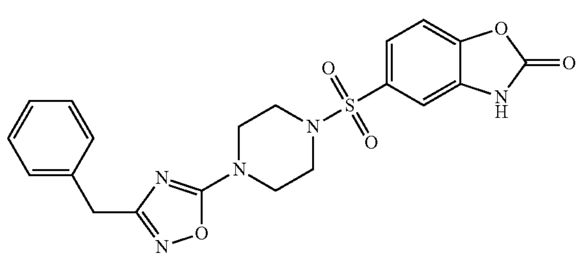 [SMILES: O=c1[nH]c2cc(S(=O)(=O)N3CCN(c4nc(Cc5ccccc5)no4)CC3)ccc2o1] | 5-((4-(3-Benzyl-1,2,4-oxadiazol-5-yl)piperazin-1-yl)sulfonyl)benzo[d]oxazol-2(3H)-one | 43 |

TABLE 1-continued

| COMPOUND | STRUCTURE | NAME | Example No |
|---|---|---|---|
| Cmpd044 | 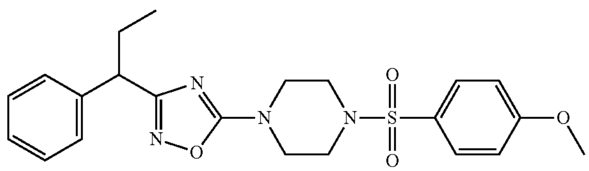 [SMILES: CCC(c1ccccc1)c1noc(N2CCN(S(=O)(=O)c3ccc(OC)cc3)CC2)n1] | 5-(4-((4-Methoxyphenyl)sulfonyl)piperazin-1-yl)-3-(1-phenylpropyl)-1,2,4-oxadiazole | 44 |
| Cmpd045 | 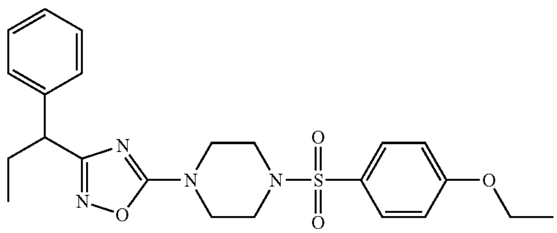 [SMILES: CCOc1ccc(S(=O)(=O)N2CCN(c3nc(C(CC)c4ccccc4)no3)CC2)cc1] | 1-(4-Ethoxy-benzenesulfonyl)-4-[3-(1-phenyl-propyl)-[1,2,4]oxadiazol-5-yl]-piperazine | 45 |
| Cmpd046 | 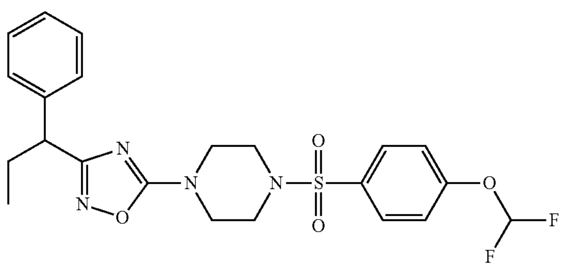 [SMILES: CCC(c1ccccc1)c1noc(N2CCN(S(=O)(=O)c3ccc(OC(F)F)cc3)CC2)n1] | 1-(4-Difluoromethoxy-benzenesulfonyl)-4-[3-(1-phenyl-propyl)-[1,2,4]oxadiazol-5-yl]-piperazine | 46 |
| Cmpd047 | 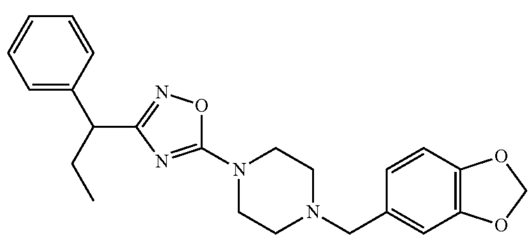 [SMILES: CCC(c1ccccc1)c1noc(N2CCN(Cc3ccc4c(c3)OCO4)CC2)n1] | 5-(4-(Benzo[d][1,3]dioxol-5-ylmethyl)piperazin-1-yl)-3-(1-phenylpropyl)-1,2,4-oxadiazole | 47 |
| Cmpd048 | 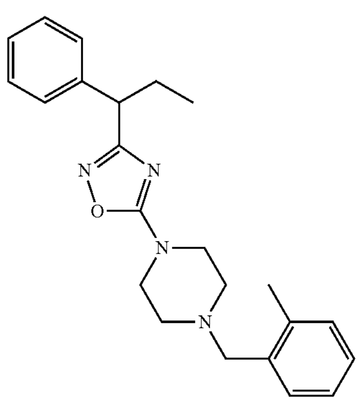 [SMILES: CCC(c1ccccc1)c1noc(N2CCN(Cc3ccccc3C)CC2)n1] | 5-(4-(2-Methylbenzyl)piperazin-1-yl)-3-(1-phenylpropyl)-1,2,4-oxadiazole | 48 |

TABLE 1-continued

| COMPOUND | STRUCTURE | NAME | Example No |
|---|---|---|---|
| Cmpd049 | 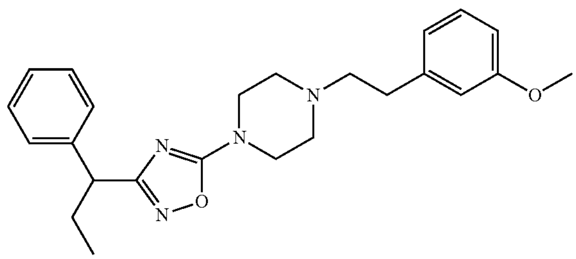 [SMILES: CCC(c1ccccc1)c1noc(N2CCN(CCc3cccc(OC)c3)CC2)n1] | 5-(4-(3-Methoxyphenethyl)piperazin-1-yl)-3-(1-phenylpropyl)-1,2,4-oxadiazole | 49 |
| Cmpd050 | 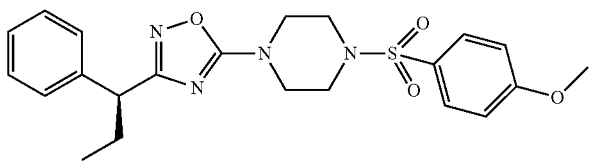 [SMILES: CC[C@@H](c1ccccc1)c1noc(N2CCN(S(=O)(=O)c3ccc(OC)cc3)CC2)n1] | 1-(4-Methoxy-benzenesulfonyl)-4-[3-((S)-1-phenyl-propyl)-[1,2,4]oxadiazol-5-yl]-piperazine | 50 |
| Cmpd051 | 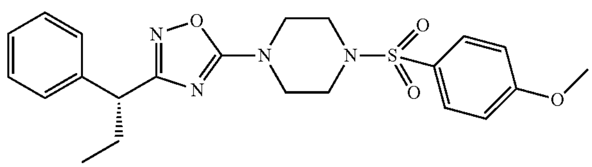 [SMILES: CC[C@H](c1ccccc1)c1noc(N2CCN(S(=O)(=O)c3ccc(OC)cc3)CC2)n1] | 1-(4-Methoxy-benzenesulfonyl)-4-[3-((R)-1-phenyl-propyl)-[1,2,4]oxadiazol-5-yl]-piperazine | 51 |
| Cmpd052 | 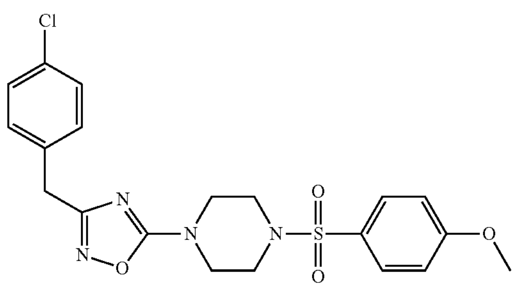 [SMILES: COc1ccc(S(=O)(=O)N2CCN(c3nc(Cc4ccc(Cl)cc4)no3)CC2)cc1] | 1-[3-(4-Chloro-benzyl)-[1,2,4]oxadiazol-5-yl]-4-(4-methoxy-benzenesulfonyl)-piperazine | 52 |
| Cmpd053 | 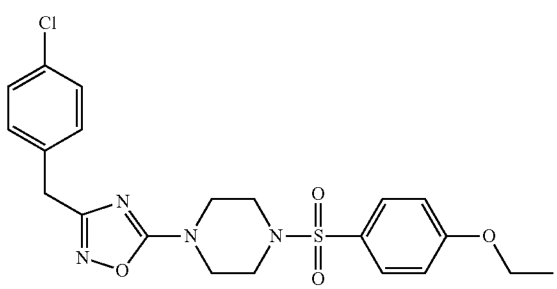 [SMILES: CCOc1ccc(S(=O)(=O)N2CCN(c3nc(Cc4ccc(Cl)cc4)no3)CC2)cc1] | 1-[3-(4-Chloro-benzyl)-[1,2,4]oxadiazol-5-yl]-4-(4-ethoxy-benzenesulfonyl)-piperazine | 53 |
| Cmpd054 | 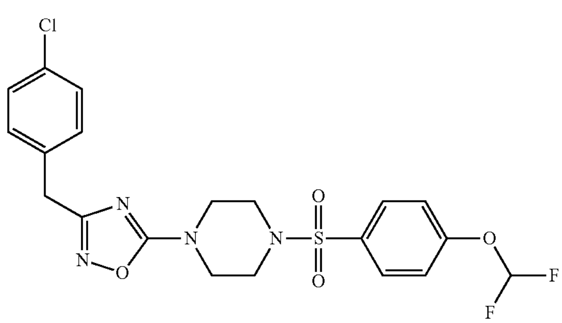 [SMILES: O=S(=O)(c1ccc(OC(F)F)cc1)N1CCN(c2nc(Cc3ccc(Cl)cc3)no2)CC1] | 1-[3-(4-Chloro-benzyl)-[1,2,4]oxadiazol-5-yl]-4-(4-difluoromethoxy-benzenesulfonyl)-piperazine | 54 |

TABLE 1-continued

| COMPOUND | STRUCTURE | NAME | Example No |
|---|---|---|---|
| Cmpd055 | 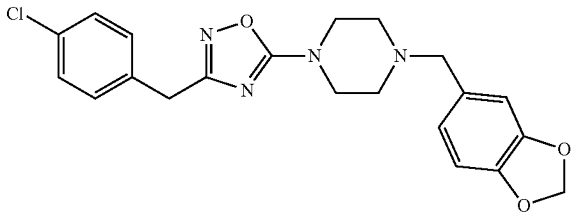 [SMILES: Clc1ccc(Cc2noc(N3CCN(Cc4ccc5c(c4)OCO5)CC3)n2)cc1] | 1-Benzo[1,3]dioxol-5-ylmethyl-4-[3-(4-chloro-benzyl)-[1,2,4]oxadiazol-5-yl]-piperazine | 55 |
| Cmpd056 | 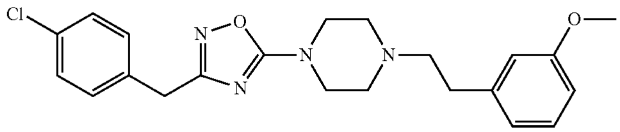 [SMILES: COc1cccc(CCN2CCN(c3nc(Cc4ccc(Cl)cc4)no3)CC2)c1] | 1-[3-(4-Chloro-benzyl)-[1,2,4]oxadiazol-5-yl]-4-[2-(3-methoxy-phenyl)-ethyl]-piperazine | 56 |
| Cmpd057 | 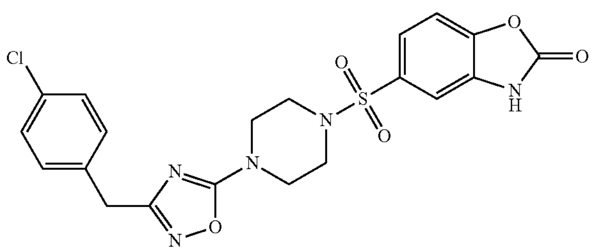 [SMILES: O=c1[nH]c2cc(S(=O)(=O)N3CCN(c4nc(Cc5ccc(Cl)cc5)no4)CC3)ccc2o1] | 5-((4-(3-(4-Chlorobenzyl)-1,2,4-oxadiazol-5-yl)piperazin-1-yl)sulfonyl)benzo[d]oxazol-2(3H)-one | 57 |
| Cmpd058 | 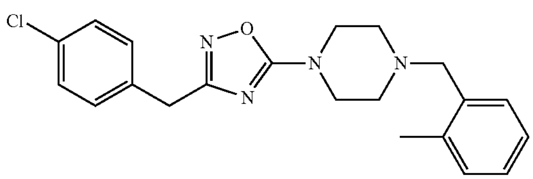 [SMILES: Cc1ccccc1CN1CCN(c2nc(Cc3ccc(Cl)cc3)no2)CC1] | 1-[3-(4-Chloro-benzyl)-[1,2,4]oxadiazol-5-yl]-4-(2-methyl-benzyl)-piperazine | 58 |
| Cmpd059 | 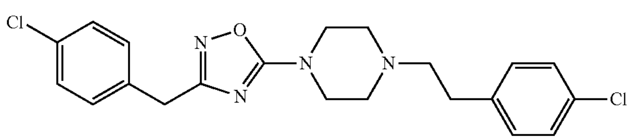 [SMILES: Clc1ccc(CCN2CCN(c3nc(Cc4ccc(Cl)cc4)no3)CC2)cc1] | 1-[3-(4-Chloro-benzyl)-[1,2,4]oxadiazol-5-yl]-4-[2-(4-chloro-phenyl)-ethyl]-piperazine | 59 |
| Cmpd060 | 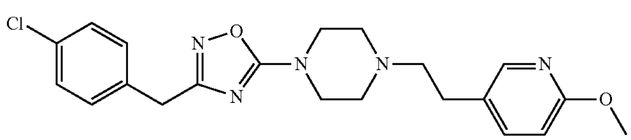 [SMILES: COc1ccc(CCN2CCN(c3nc(Cc4ccc(Cl)cc4)no3)CC2)cn1] | 1-[3-(4-Chloro-benzyl)-[1,2,4]oxadiazol-5-yl]-4-[2-(6-methoxy-pyridin-3-yl)-ethyl]-piperazine | 60 |
| Cmpd061 | 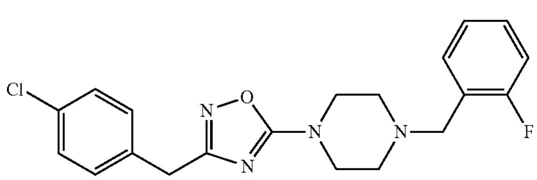 [SMILES: Fc1ccccc1CN1CCN(c2nc(Cc3ccc(Cl)cc3)no2)CC1] | 3-(4-Chlorobenzyl)-5-(4-(2-fluorobenzyl)piperazin-1-yl)-1,2,4-oxadiazole | 61 |
| Cmpd062 | 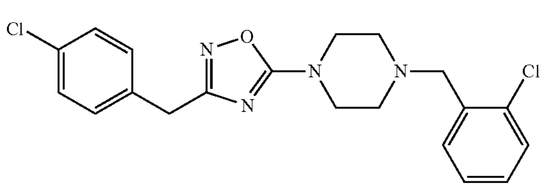 [SMILES: Clc1ccc(Cc2noc(N3CCN(Cc4ccccc4Cl)CC3)n2)cc1] | 1-(2-Chloro-benzyl)-4-[3-(4-chloro-benzyl)-[1,2,4]oxadiazol-5-yl]-piperazine | 62 |

TABLE 1-continued

| COMPOUND | STRUCTURE | NAME | Example No |
|---|---|---|---|
| Cmpd063 | 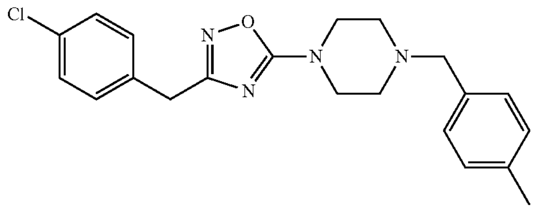 [SMILES: Cc1ccc(CN2CCN(c3nc(Cc4ccc(Cl)cc4)no3)CC2)cc1] | 1-[3-(4-Chloro-benzyl)-[1,2,4]oxadiazol-5-yl]-4-(4-methyl-benzyl)-piperazine | 63 |
| Cmpd064 | 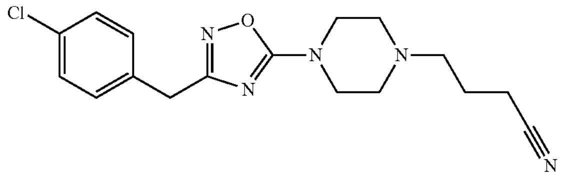 [SMILES: N#CCCCN1CCN(c2nc(Cc3ccc(Cl)cc3)no2)CC1] | 4-{4-[3-(4-Chloro-benzyl)-[1,2,4]oxadiazol-5-yl]-piperazin-1-yl}-butyronitrile | 64 |
| Cmpd065 | 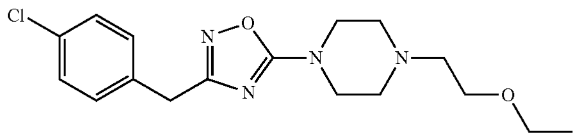 [SMILES: CCOCCN1CCN(c2nc(Cc3ccc(Cl)cc3)no2)CC1] | 1-[3-(4-Chloro-benzyl)-[1,2,4]oxadiazol-5-yl]-4-(2-ethoxy-ethyl)-piperazine | 65 |
| Cmpd066 | 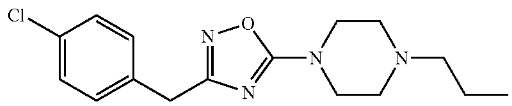 [SMILES: CCCN1CCN(c2nc(Cc3ccc(Cl)cc3)no2)CC1] | 1-[3-(4-Chloro-benzyl)-[1,2,4]oxadiazol-5-yl]-4-propyl-piperazine | 66 |
| Cmpd067 | 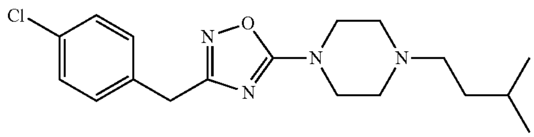 [SMILES: CC(C)CCN1CCN(c2nc(Cc3ccc(Cl)cc3)no2)CC1] | 3-(4-Chlorobenzyl)-5-(4-isopentylpiperazin-1-yl)-1,2,4-oxadiazole | 67 |
| Cmpd068 | 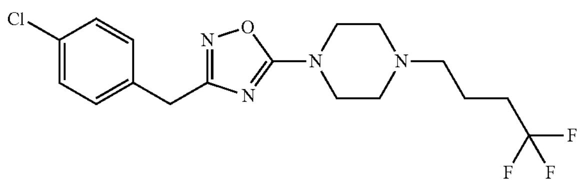 [SMILES: FC(F)(F)CCCN1CCN(c2nc(Cc3ccc(Cl)cc3)no2)CC1] | 1-[3-(4-Chloro-benzyl)-[1,2,4]oxadiazol-5-yl]-4-(4,4,4-trifluoro-butyl)-piperazine | 68 |
| Cmpd069 | 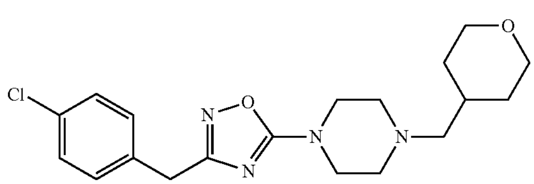 [SMILES: Clc1ccc(Cc2noc(N3CCN(CC4CCOCC4)CC3)n2)cc1] | 3-(4-Chlorobenzyl)-5-(4-((tetrahydro-2H-pyran-4-yl)methyl)piperazin-1-yl)-1,2,4-oxadiazole | 69 |
| Cmpd070 | 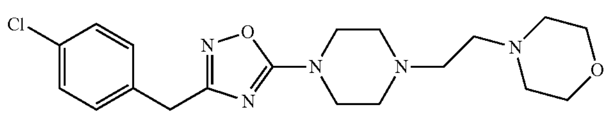 [SMILES: Clc1ccc(Cc2noc(N3CCN(CCN4CCOCC4)CC3)n2)cc1] | 4-(2-(4-(3-(4-Chlorobenzyl)-1,2,4-oxadiazol-5-yl)piperazin-1-yl)ethyl)morpholine | 70 |
| Cmpd071 | 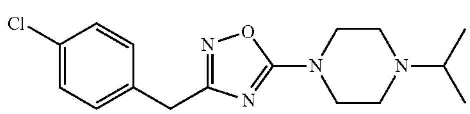 [SMILES: CC(C)N1CCN(c2nc(Cc3ccc(Cl)cc3)no2)CC1] | 3-(4-Chlorobenzyl)-5-(4-isopropylpiperazin-1-yl)-1,2,4-oxadiazole | 71 |

TABLE 1-continued

| COMPOUND | STRUCTURE | NAME | Example No |
|---|---|---|---|
| Cmpd072 | 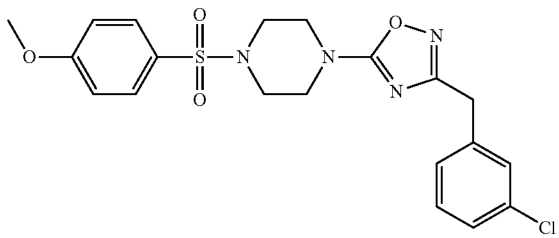 [SMILES: COc1ccc(S(=O)(=O)N2CCN(c3nc(Cc4cccc(Cl)c4)no3)CC2)cc1] | 1-[3-(3-Chloro-benzyl)-[1,2,4]oxadiazol-5-yl]-4-(4-methoxy-benzenesulfonyl)-piperazine | 72 |
| Cmpd073 | 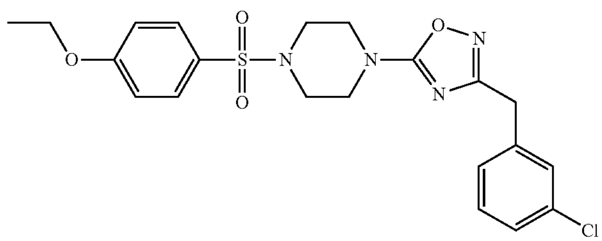 [SMILES: CCOc1ccc(S(=O)(=O)N2CCN(c3nc(Cc4cccc(Cl)c4)no3)CC2)cc1] | 1-[3-(3-Chloro-benzyl)-[1,2,4]oxadiazol-5-yl]-4-(4-ethoxy-benzenesulfonyl)-piperazine | 73 |
| Cmpd074 | 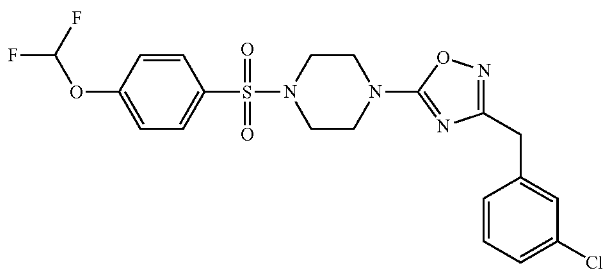 [SMILES: O=S(=O)(c1ccc(OC(F)F)cc1)N1CCN(c2nc(Cc3cccc(Cl)c3)no2)CC1] | 1-[3-(3-Chloro-benzyl)-[1,2,4]oxadiazol-5-yl]-4-(4-difluoromethoxy-benzenesulfonyl)-piperazine | 74 |
| Cmpd075 | 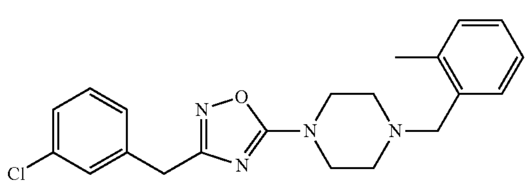 [SMILES: Cc1ccccc1CN1CCN(c2nc(Cc3cccc(Cl)c3)no2)CC1] | 1-[3-(3-Chloro-benzyl)-[1,2,4]oxadiazol-5-yl]-4-(2-methyl-benzyl)-piperazine | 75 |
| Cmpd076 | 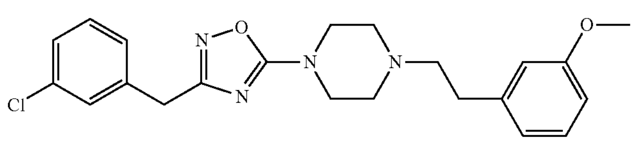 [SMILES: COc1cccc(CCN2CCN(c3nc(Cc4cccc(Cl)c4)no3)CC2)c1] | 1-[3-(3-Chloro-benzyl)-[1,2,4]oxadiazol-5-yl]-4-[2-(3-methoxy-phenyl)-ethyl]-piperazine | 76 |
| Cmpd077 | 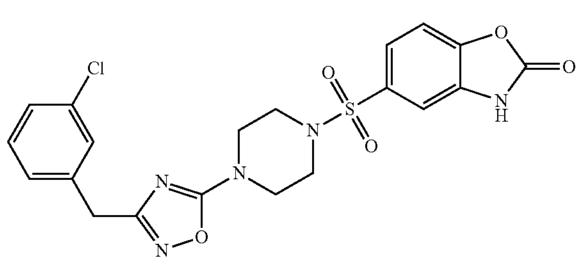 [SMILES: O=c1[nH]c2cc(S(=O)(=O)N3CCN(c4nc(Cc5cccc(Cl)c5)no4)CC3)ccc2o1] | 5-{4-[3-(3-Chloro-benzyl)-[1,2,4]oxadiazol-5-yl]-piperazine-1-sulfonyl}-3H-benzooxazol-2-one | 77 |

TABLE 1-continued

| COMPOUND | STRUCTURE | NAME | Example No |
|---|---|---|---|
| Cmpd078 | 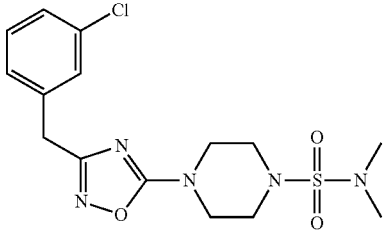 [SMILES: CN(C)S(=O)(=O)N1CCN(c2nc(Cc3cccc(Cl)c3)no2)CC1] | 4-(3-(3-Chlorobenzyl)-1,2,4-oxadiazol-5-yl)-N,N-dimethylpiperazine-1-sulfonamide | 78 |
| Cmpd079 | 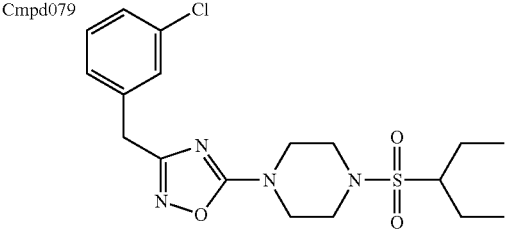 | 4-(3-(3-Chlorobenzyl)-1,2,4-oxadiazol-5-yl)-N,N-diethylpiperazine-1-sulfonamide | 79 |
| Cmpd080 | 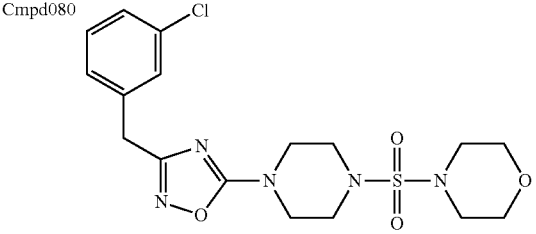 | 4-((4-(3-(3-Chlorobenzyl)-1,2,4-oxadiazol-5-yl)piperazin-1-yl)sulfonyl)morpholine | 80 |
| Cmpd081 | 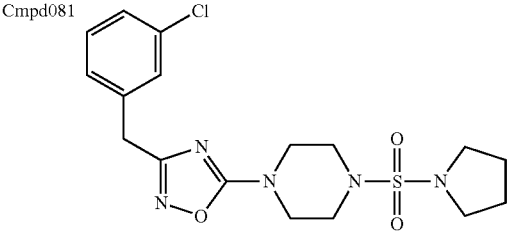 | 3-(3-Chlorobenzyl)-5-(4-(pyrrolidin-1-ylsulfonyl)piperazin-1-yl)-1,2,4-oxadiazole | 81 |
| Cmpd082 | 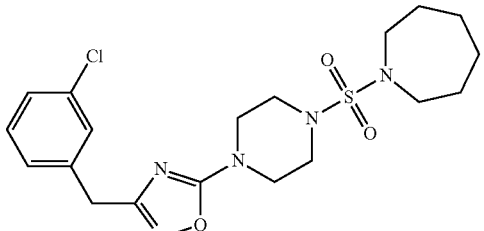 | 5-(4-(Azepan-1-ylsulfonyl)piperazin-1-yl)-3-(3-chlorobenzyl)-1,2,4-oxadiazole | 82 |
| Cmpd083 | 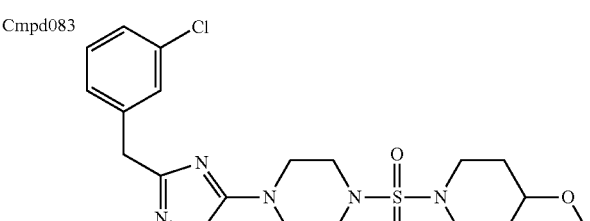 | 3-(3-Chlorobenzyl)-5-(4-((4-methoxypiperidin-1-yl)sulfonyl)piperazin-1-yl)-1,2,4-oxadiazole | 83 |

TABLE 1-continued

| COMPOUND | STRUCTURE | NAME | Example No |
|---|---|---|---|
| Cmpd084 | 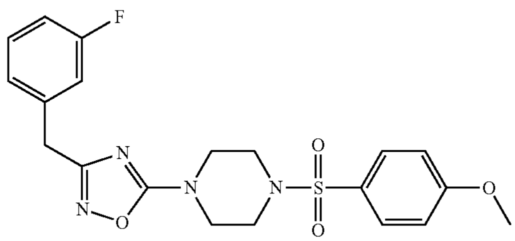 [SMILES: COc1ccc(S(=O)(=O)N2CCN(c3nc(Cc4cccc(F)c4)no3)CC2)cc1] | 1-[3-(3-Fluoro-benzyl)-[1,2,4]oxadiazol-5-yl]-4-(4-methoxy-benzenesulfonyl)-piperazine | 84 |
| Cmpd085 | 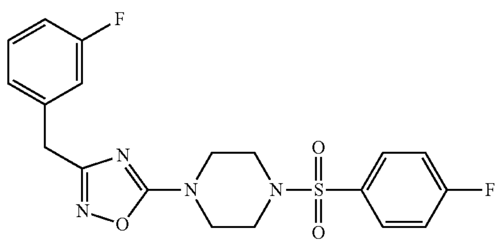 [SMILES: O=S(=O)(c1ccc(F)cc1)N1CCN(c2nc(Cc3cccc(F)c3)no2)CC1] | 1-(4-Fluoro-benzenesulfonyl)-4-[3-(3-fluoro-benzyl)-[1,2,4]oxadiazol-5-yl]-piperazine | 85 |
| Cmpd086 | 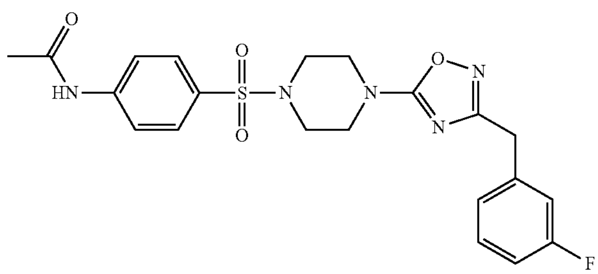 [SMILES: CC(=O)Nc1ccc(S(=O)(=O)N2CCN(c3nc(Cc4cccc(F)c4)no3)CC2)cc1] | N-(4-{4-[3-(3-Fluoro-benzyl)-[1,2,4]oxadiazol-5-yl]-piperazine-1-sulfonyl}-phenyl)-acetamide | 86 |
| Cmpd087 | 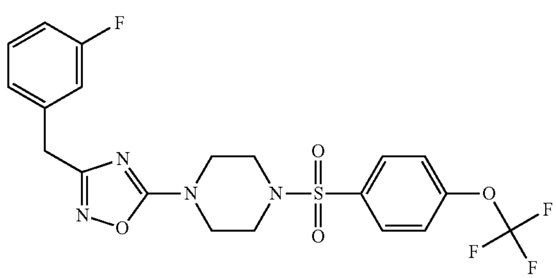 [SMILES: O=S(=O)(c1ccc(OC(F)(F)F)cc1)N1CCN(c2nc(Cc3cccc(F)c3)no2)CC1] | 1-[3-(3-Fluoro-benzyl)-[1,2,4]oxadiazol-5-yl]-4-(4-trifluoromethoxy-benzenesulfonyl)-piperazine | 87 |
| Cmpd088 | 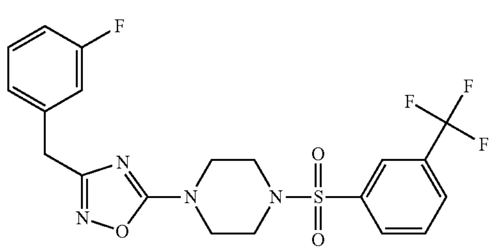 [SMILES: O=S(=O)(c1cccc(C(F)(F)F)c1)N1CCN(c2nc(Cc3cccc(F)c3)no2)CC1] | 1-[3-(3-Fluoro-benzyl)-[1,2,4]oxadiazol-5-yl]-4-(3-trifluoromethyl-benzenesulfonyl)-piperazine | 88 |
| Cmpd089 | 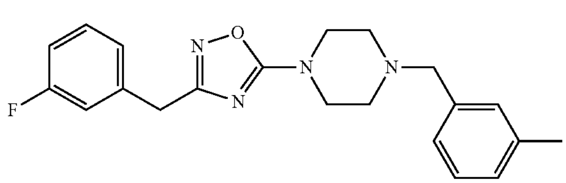 [SMILES: Cc1cccc(CN2CCN(c3nc(Cc4cccc(F)c4)no3)CC2)c1] | 1-[3-(3-Fluoro-benzyl)-[1,2,4]oxadiazol-5-yl]-4-(3-methyl-benzyl)-piperazine | 89 |

TABLE 1-continued

| COMPOUND | STRUCTURE | NAME | Example No |
|---|---|---|---|
| Cmpd090 | 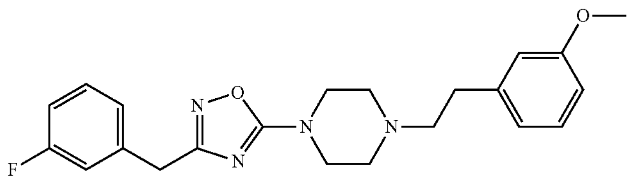 [SMILES: COc1cccc(CCN2CCN(c3nc(Cc4cccc(F)c4)no3)CC2)c1] | 1-[3-(3-Fluoro-benzyl)-[1,2,4]oxadiazol-5-yl]-4-[2-(3-methoxy-phenyl)-ethyl]-piperazine | 90 |
| Cmpd091 | 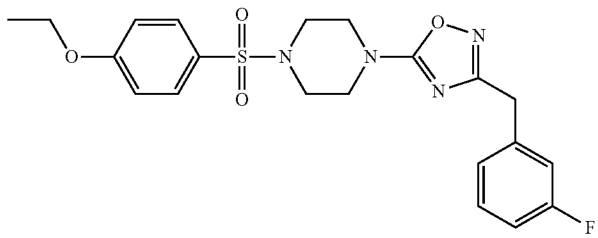 [SMILES: CCOc1ccc(S(=O)(=O)N2CCN(c3nc(Cc4cccc(F)c4)no3)CC2)cc1] | 1-(4-Ethoxy-benzenesulfonyl)-4-[3-(3-fluoro-benzyl)-[1,2,4]oxadiazol-5-yl]-piperazine | 91 |
| Cmpd092 | 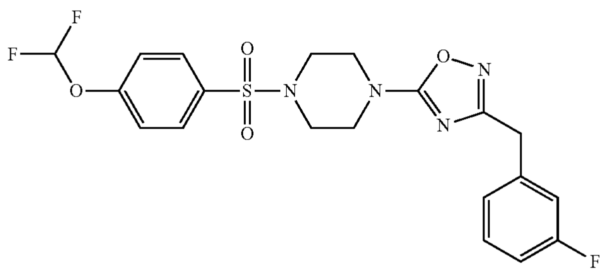 [SMILES: O=S(=O)(c1ccc(OC(F)F)cc1)N1CCN(c2nc(Cc3cccc(F)c3)no2)CC1] | 1-(4-Difluoromethoxy-benzenesulfonyl)-4-[3-(3-fluoro-benzyl)-[1,2,4]oxadiazol-5-yl]-piperazine | 92 |
| Cmpd093 | 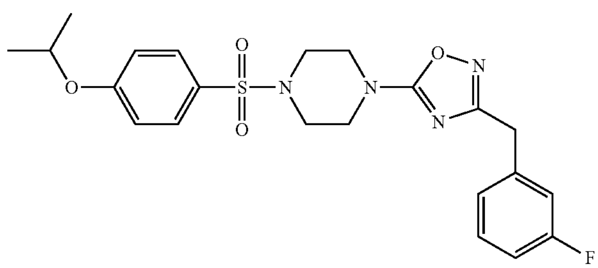 [SMILES: CC(C)Oc1ccc(S(=O)(=O)N2CCN(c3nc(Cc4cccc(F)c4)no3)CC2)cc1] | 1-[3-(3-Fluoro-benzyl)-[1,2,4]oxadiazol-5-yl]-4-(4-isopropoxy-benzenesulfonyl)-piperazine | 93 |
| Cmpd094 | 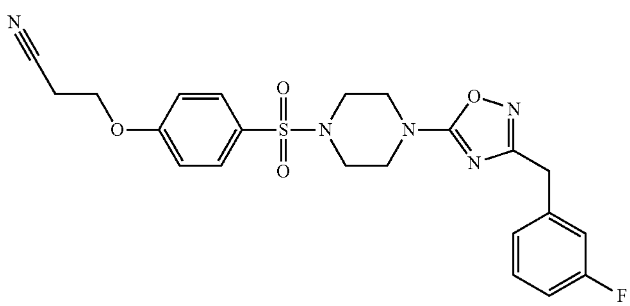 [SMILES: N#CCCOc1ccc(S(=O)(=O)N2CCN(c3nc(Cc4cccc(F)c4)no3)CC2)cc1] | 3-(4-((4-(3-(3-Fluorobenzyl)-1,2,4-oxadiazol-5-yl)piperazin-1-yl)sulfonyl)phenoxy)propanenitrile | 94 |
| Cmpd095 | 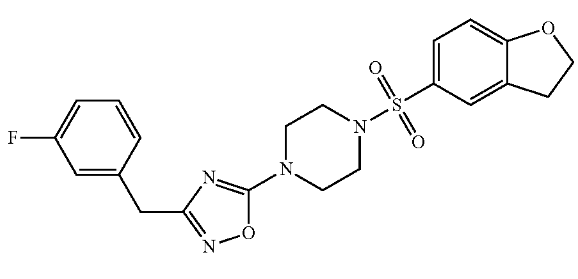 [SMILES: O=S(=O)(c1ccc2c(c1)CCO2)N1CCN(c2nc(Cc3cccc(F)c3)no2)CC1] | 1-(2,3-Dihydro-benzofuran-5-sulfonyl)-4-[3-(3-fluoro-benzyl)-[1,2,4]oxadiazol-5-yl]-piperazine | 95 |

TABLE 1-continued

| COMPOUND | STRUCTURE | NAME | Example No |
|---|---|---|---|
| Cmpd096 | 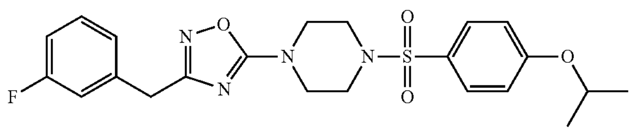 [SMILES: CC(C)Oc1ccc(S(=O)(=O)N2CCN(c3nc(Cc4cccc(F)c4)no3)CC2)cc1] | 3-(3-Fluorobenzyl)-5-(4-((4-isopropoxyphenyl)sulfonyl)piperazin-1-yl)-1,2,4-oxadiazole | 96 |
| Cmpd097 | 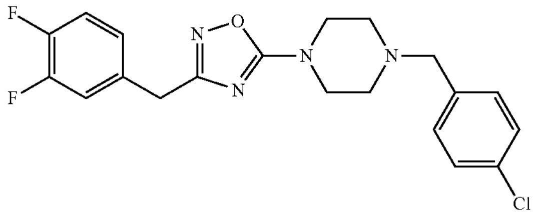 [SMILES: Fc1ccc(Cc2noc(N3CCN(Cc4ccc(Cl)cc4)CC3)n2)cc1F] | 1-(4-Chloro-benzyl)-4-[3-(3,4-difluoro-benzyl)-[1,2,4]oxadiazol-5-yl]-piperazine | 97 |
| Cmpd098 | 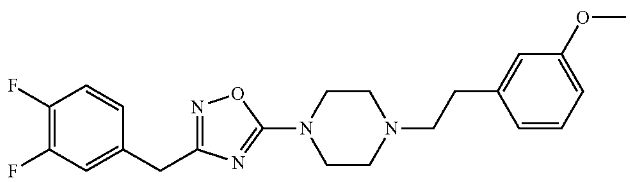 [SMILES: COc1cccc(CCN2CCN(c3nc(Cc4ccc(F)c(F)c4)no3)CC2)c1] | 1-[3-(3,4-Difluoro-benzyl)-[1,2,4]oxadiazol-5-yl]-4-[2-(3-methoxy-phenyl)-ethyl]-piperazine | 98 |
| Cmpd099 | 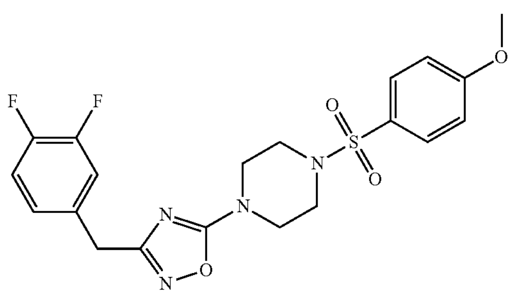 [SMILES: COc1ccc(S(=O)(=O)N2CCN(c3nc(Cc4ccc(F)c(F)c4)no3)CC2)cc1] | 1-[3-(3,4-Difluoro-benzyl)-[1,2,4]oxadiazol-5-yl]-4-(4-methoxy-benzenesulfonyl)-piperazine | 99 |
| Cmpd100 | 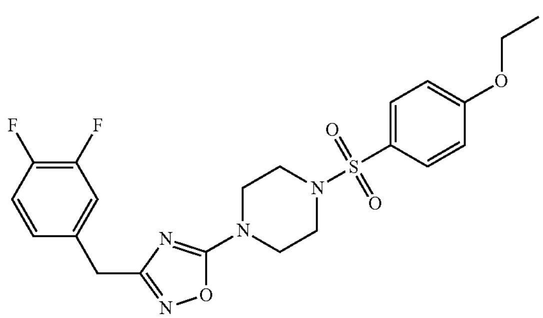 [SMILES: CCOc1ccc(S(=O)(=O)N2CCN(c3nc(Cc4ccc(F)c(F)c4)no3)CC2)cc1] | 1-[3-(3,4-Difluoro-benzyl)-[1,2,4]oxadiazol-5-yl]-4-(4-ethoxy-benzenesulfonyl)-piperazine | 100 |
| Cmpd101 | 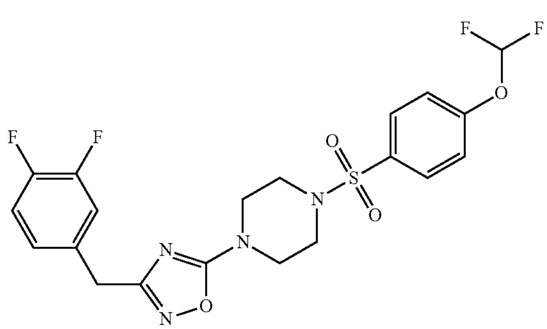 [SMILES: O=S(=O)(c1ccc(OC(F)F)cc1)N1CCN(c2nc(Cc3ccc(F)c(F)c3)no2)CC1] | 1-[3-(3,4-Difluoro-benzyl)-[1,2,4]oxadiazol-5-yl]-4-(4-difluoromethoxy-benzenesulfonyl)-piperazine | 101 |

TABLE 1-continued

| COMPOUND | STRUCTURE | NAME | Example No |
|---|---|---|---|
| Cmpd102 | 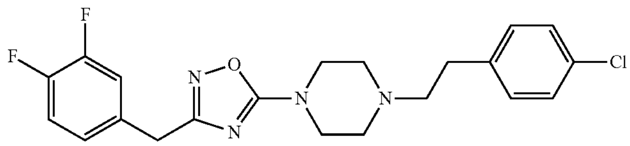 [SMILES: Fc1ccc(Cc2noc(N3CCN(CCc4ccc(Cl)cc4)CC3)n2)cc1F] | 1-[2-(4-Chloro-phenyl)-ethyl]-4-[3-(3,4-difluoro-benzyl)-[1,2,4]oxadiazol-5-yl]-piperazine | 102 |
| Cmpd103 | 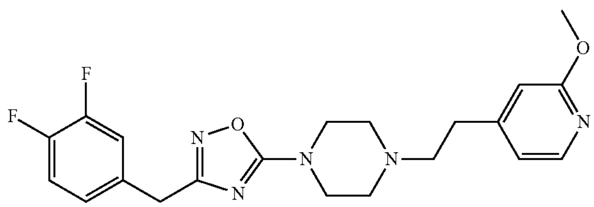 [SMILES: COc1cc(CCN2CCN(c3nc(Cc4ccc(F)c(F)c4)no3)CC2)ccn1] | 1-[3-(3,4-Difluoro-benzyl)-[1,2,4]oxadiazol-5-yl]-4-[2-(6-methoxy-pyridin-3-yl)-ethyl]-piperazine | 103 |
| Cmpd104 | 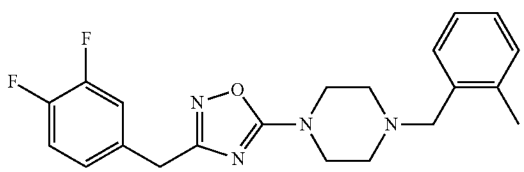 [SMILES: Cc1ccccc1CN1CCN(c2nc(Cc3ccc(F)c(F)c3)no2)CC1] | 1-[3-(3,4-Difluoro-benzyl)-[1,2,4]oxadiazol-5-yl]-4-(2-methyl-benzyl)-piperazine | 104 |
| Cmpd105 | 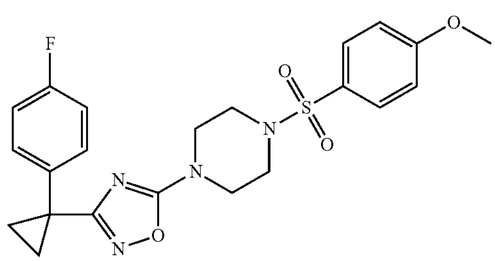 [SMILES: COc1ccc(S(=O)(=O)N2CCN(c3nc(C4(c5ccc(F)cc5)CC4)no3)CC2)cc1] | 1-{3-[1-(4-Fluoro-phenyl)-cyclopropyl]-[1,2,4]oxadiazol-5-yl}-4-(4-methoxy-benzenesulfonyl)-piperazine | 105 |
| Cmpd106 | 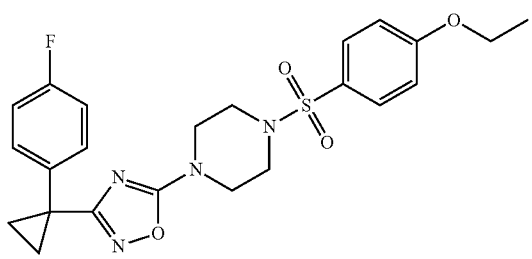 [SMILES: CCOc1ccc(S(=O)(=O)N2CCN(c3nc(C4(c5ccc(F)cc5)CC4)no3)CC2)cc1] | 1-(4-Ethoxy-benzenesulfonyl)-4-{3-[1-(4-fluoro-phenyl)-cyclopropyl]-[1,2,4]oxadiazol-5-yl}-piperazine | 106 |
| Cmpd107 | 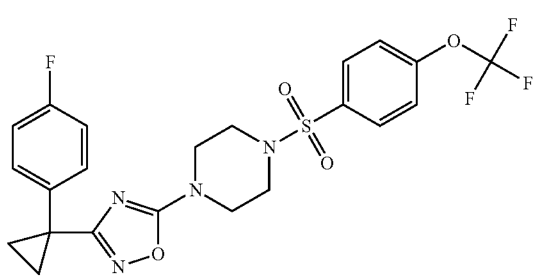 [SMILES: O=S(=O)(c1ccc(OC(F)(F)F)cc1)N1CCN(c2nc(C3(c4ccc(F)cc4)CC3)no2)CC1] | 3-(1-(4-Fluorophenyl)cyclopropyl)-5-(4-((4-(trifluoromethoxy)phenyl)sulfonyl)piperazin-1-yl)-1,2,4-oxadiazole | 107 |
| Cmpd108 | 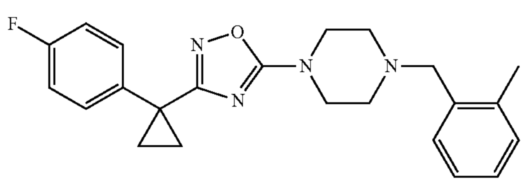 [SMILES: Cc1ccccc1CN1CCN(c2nc(C3(c4ccc(F)cc4)CC3)no2)CC1] | 3-(1-(4-Fluorophenyl)cyclopropyl)-5-(4-(2-methylbenzyl)piperazin-1-yl)-1,2,4-oxadiazole | 108 |

TABLE 1-continued

| COMPOUND | STRUCTURE | NAME | Example No |
|---|---|---|---|
| Cmpd109 | 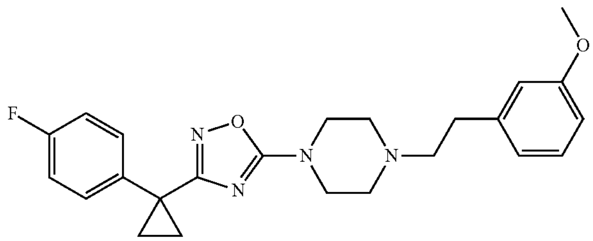 [SMILES: COc1cccc(CCN2CCN(c3nc(C4(c5ccc(F)cc5)CC4)no3)CC2)c1] | 3-(1-(4-Fluorophenyl)cyclopropyl)-5-(4-(3-methoxyphenethyl)piperazin-1-yl)-1,2,4-oxadiazole | 109 |
| Cmpd110 | 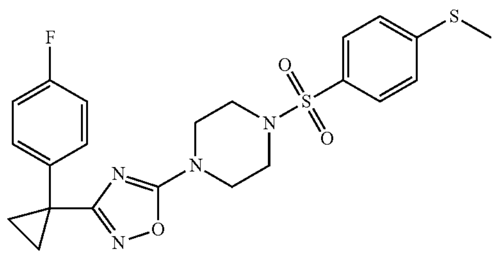 [SMILES: CSc1ccc(S(=O)(=O)N2CCN(c3nc(C4(c5ccc(F)cc5)CC4)no3)CC2)cc1] | 1-{3-[1-(4-Fluoro-phenyl)-cyclopropyl]-[1,2,4]oxadiazol-5-yl}-4-(4-methylsulfanyl-benzenesulfonyl)-piperazine | 110 |
| Cmpd111 | 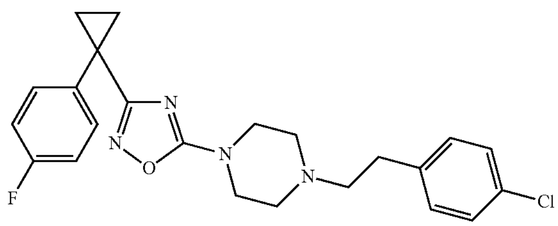 [SMILES: Fc1ccc(C2(c3noc(N4CCN(CCc5ccc(Cl)cc5)CC4)n3)CC2)cc1] | 5-(4-(4-Chlorophenethyl)piperazin-1-yl)-3-(1-(4-fluorophenyl)cyclopropyl)-1,2,4-oxadiazole | 111 |
| Cmpd112 | 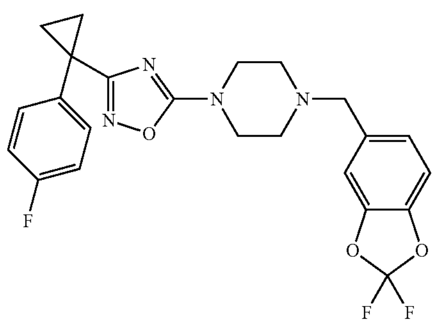 [SMILES: Fc1ccc(C2(c3noc(N4CCN(Cc5ccc6c(c5)OC(F)(F)O6)CC4)n3)CC2)cc1] | 5-(4-((2,2-Difluorobenzo[d][1,3]dioxol-5-yl)methyl)piperazin-1-yl)-3-(1-(4-fluorophenyl)cyclopropyl)-1,2,4-oxadiazole | 112 |
| Cmpd113 | 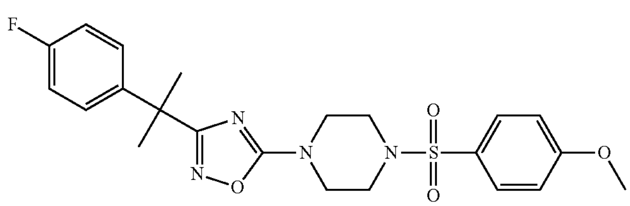 [SMILES: COc1ccc(S(=O)(=O)N2CCN(c3nc(C(C)(C)c4ccc(F)cc4)no3)CC2)cc1] | 1-{3-[1-(4-Fluoro-phenyl)-1-methyl-ethyl]-[1,2,4]oxadiazol-5-yl}-4-(4-methoxy-benzenesulfonyl)-piperazine | 113 |
| Cmpd114 | 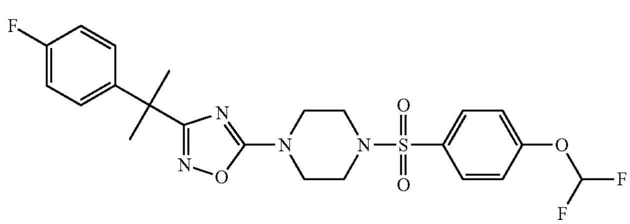 [SMILES: CC(C)(c1ccc(F)cc1)c1noc(N2CCN(S(=O)(=O)c3ccc(OC(F)F)cc3)CC2)n1] | 1-(4-Difluoromethoxy-benzenesulfonyl)-4-{3-[1-(4-fluoro-phenyl)-1-methyl-ethyl]-[1,2,4]oxadiazol-5-yl}-piperazine | 114 |

TABLE 1-continued

| COMPOUND | STRUCTURE | NAME | Example No |
|---|---|---|---|
| Cmpd115 | 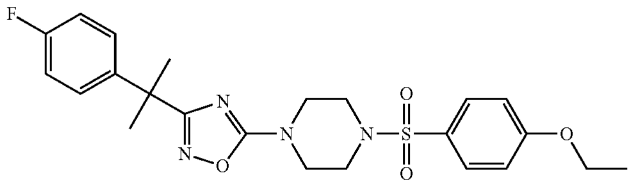 [SMILES: CCOc1ccc(S(=O)(=O)N2CCN(c3nc(C(C)(C)c4ccc(F)cc4)no3)CC2)cc1] | 1-(4-Ethoxy-benzenesulfonyl)-4-{3-[1-(4-fluoro-phenyl)-1-methyl-ethyl]-[1,2,4]oxadiazol-5-yl}-piperazine | 115 |
| Cmpd116 | 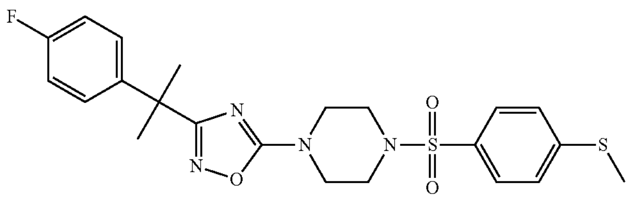 [SMILES: CSc1ccc(S(=O)(=O)N2CCN(c3nc(C(C)(C)c4ccc(F)cc4)no3)CC2)cc1] | 1-{3-[1-(4-Fluoro-phenyl)-1-methyl-ethyl]-[1,2,4]oxadiazol-5-yl}-4-(4-methylsulfanyl-benzenesulfonyl)-piperazine | 116 |
| Cmpd117 | 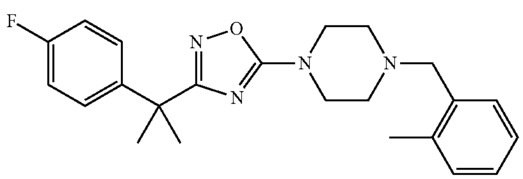 [SMILES: Cc1ccccc1CN1CCN(c2nc(C(C)(C)c3ccc(F)cc3)no2)CC1] | 3-(2-(4-Fluorophenyl)propan-2-yl)-5-(4-(2-methylbenzyl)piperazin-1-yl)-1,2,4-oxadiazole | 117 |
| Cmpd118 | 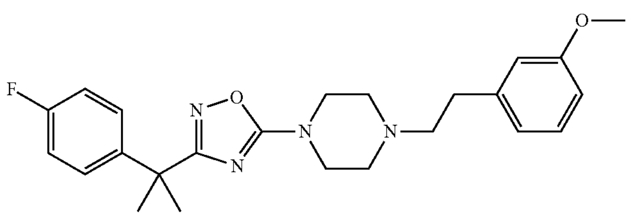 [SMILES: COc1cccc(CCN2CCN(c3nc(C(C)(C)c4ccc(F)cc4)no3)CC2)c1] | 3-(2-(4-Fluorophenyl)propan-2-yl)-5-(4-(3-methoxyphenethyl)piperazin-1-yl)-1,2,4-oxadiazole | 118 |
| Cmpd119 | 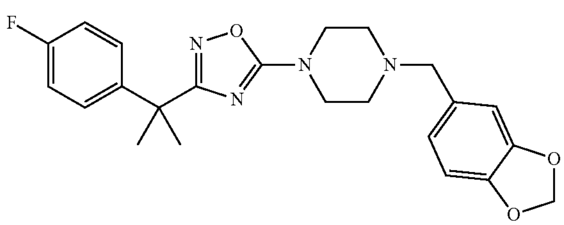 [SMILES: CC(C)(c1ccc(F)cc1)c1noc(N2CCN(Cc3ccc4c(c3)OCO4)CC2)n1] | 5-(4-(Benzo[d][1,3]dioxol-5-ylmethyl)piperazin-1-yl)-3-(2-(4-fluorophenyl)propan-2-yl)-1,2,4-oxadiazole | 119 |
| Cmpd120 | 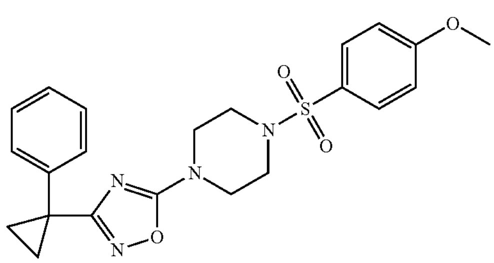 | 1-(4-Methoxy-benzenesulfonyl)-4-[3-(1-phenyl-cyclopropyl)-[1,2,4]oxadiazol-5-yl]-piperazine | 120 |
| Cmpd121 | 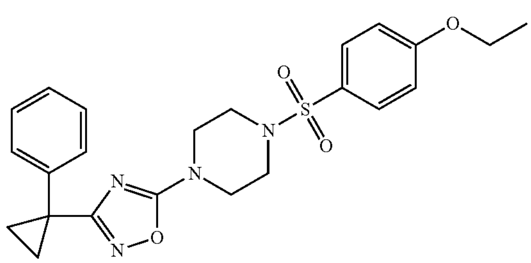 [SMILES: CCOc1ccc(S(=O)(=O)N2CCN(c3nc(C4(c5ccccc5)CC4)no3)CC2)cc1] | 1-(4-Ethoxy-benzenesulfonyl)-4-[3-(1-phenyl-cyclopropyl)-[1,2,4]oxadiazol-5-yl]-piperazine | 121 |

TABLE 1-continued

| COMPOUND | STRUCTURE | NAME | Example No |
|---|---|---|---|
| Cmpd122 | 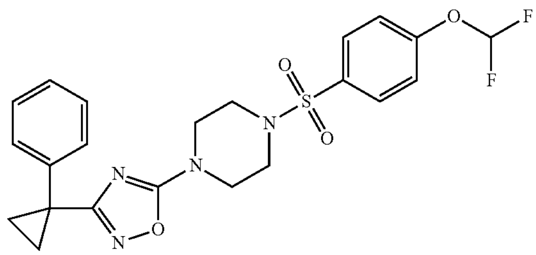 [SMILES: O=S(=O)(c1ccc(OC(F)F)cc1)N1CCN(c2nc(C3(c4ccccc4)CC3)no2)CC1] | 1-(4-Difluoromethoxy-benzenesulfonyl)-4-[3-(1-phenyl-cyclopropyl)-[1,2,4]oxadiazol-5-yl]-piperazine | 122 |
| Cmpd123 | 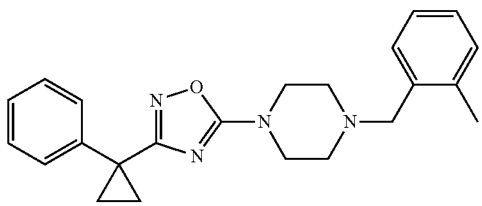 [SMILES: Cc1ccccc1CN1CCN(c2nc(C3(c4ccccc4)CC3)no2)CC1] | 5-(4-(2-Methylbenzyl)piperazin-1-yl)-3-(1-phenylcyclopropyl)-1,2,4-oxadiazole | 123 |
| Cmpd124 | 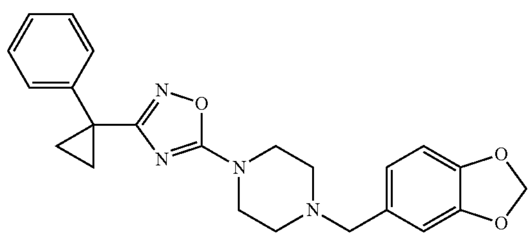 [SMILES: c1ccc(C2(c3noc(N4CCN(Cc5ccc6c(c5)OCO6)CC4)n3)CC2)cc1] | 5-(4-(Benzo[d][1,3]dioxol-5-ylmethyl)piperazin-1-yl)-3-(1-phenylcyclopropyl)-1,2,4-oxadiazole | 124 |
| Cmpd125 | 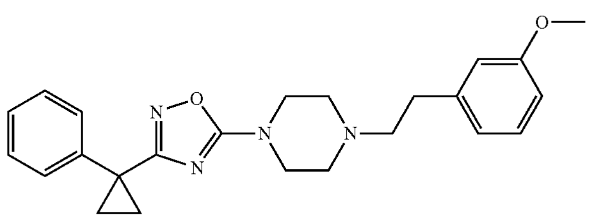 [SMILES: COc1cccc(CCN2CCN(c3nc(C4(c5ccccc5)CC4)no3)CC2)c1] | 5-(4-(3-Methoxyphenethyl)piperazin-1-yl)-3-(1-phenylcyclopropyl)-1,2,4-oxadiazole | 125 |
| Cmpd126 | 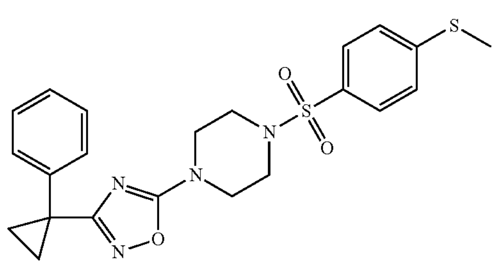 [SMILES: CSc1ccc(S(=O)(=O)N2CCN(c3nc(C4(c5ccccc5)CC4)no3)CC2)cc1] | 1-(4-Methylsulfanyl-benzenesulfonyl)-4-[3-(1-phenyl-cyclopropyl)-[1,2,4]oxadiazol-5-yl)-piperazine | 126 |
| Cmpd127 | 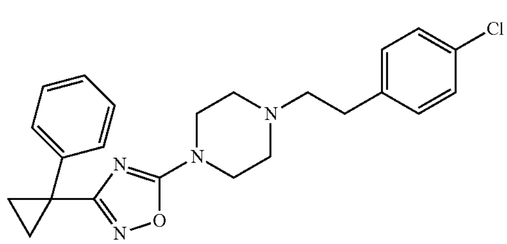 [SMILES: Clc1ccc(CCN2CCN(c3nc(C4(c5ccccc5)CC4)no3)CC2)cc1] | 5-(4-(4-Chlorophenethyl)piperazin-1-yl)-3-(1-phenylcyclopropyl)-1,2,4-oxadiazole | 127 |

TABLE 1-continued

| COMPOUND | STRUCTURE | NAME | Example No |
|---|---|---|---|
| Cmpd128 | 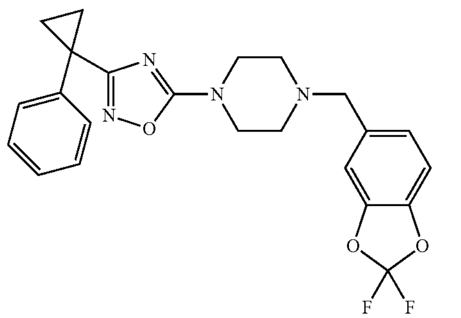 [SMILES: FC1(F)Oc2ccc(CN3CCN(c4nc(C5(c6ccccc6)CC5)no4)CC3)cc2O1] | 5-(4-((2,2-Difluorobenzo[d][1,3]dioxol-5-yl)methyl)piperazin-1-yl)-3-(1-phenylcyclopropyl)-1,2,4-oxadiazole | 128 |
| Cmpd129 | 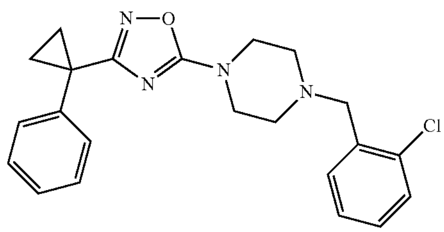 [SMILES: Clc1ccccc1CN1CCN(c2nc(C3(c4ccccc4)CC3)no2)CC1] | 5-(4-(2-Chlorobenzyl)piperazin-1-yl)-3-(1-phenylcyclopropyl)-1,2,4-oxadiazole | 129 |
| Cmpd130 | 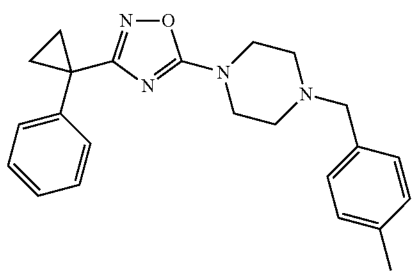 [SMILES: Cc1ccc(CN2CCN(c3nc(C4(c5ccccc5)CC4)no3)CC2)cc1] | 5-(4-(4-Methylbenzyl)piperazin-1-yl)-3-(1-phenylcyclopropyl)-1,2,4-oxadiazole | 130 |
| Cmpd131 | 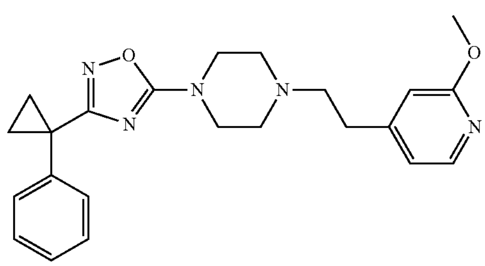 [SMILES: COc1cc(CCN2CCN(c3nc(C4(c5ccccc5)CC4)no3)CC2)ccn1] | 5-(4-(2-(2-Methoxypyridin-4-yl)ethyl)piperazin-1-yl)-3-(1-phenylcyclopropyl)-1,2,4-oxadiazole | 131 |
| Cmpd132 | 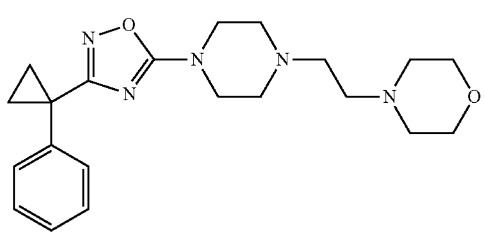 [SMILES: c1ccc(C2(c3noc(N4CCN(CCN5CCOCC5)CC4)n3)CC2)cc1] | 4-(2-(4-(3-(1-Phenylcyclopropyl)-1,2,4-oxadiazol-5-yl)piperazin-1-yl)ethyl)morpholine | 132 |
| Cmpd133 | 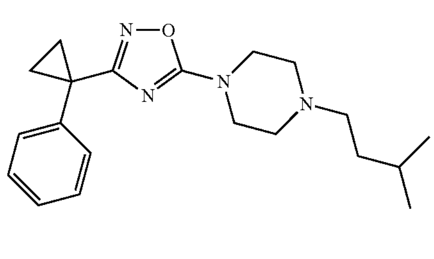 [SMILES: CC(C)CCN1CCN(c2nc(C3(c4ccccc4)CC3)no2)CC1] | 5-(4-Isopentylpiperazin-1-yl)-3-(1-phenylcyclopropyl)-1,2,4-oxadiazole | 133 |

TABLE 1-continued

| COMPOUND | STRUCTURE | NAME | Example No |
|---|---|---|---|
| Cmpd134 | 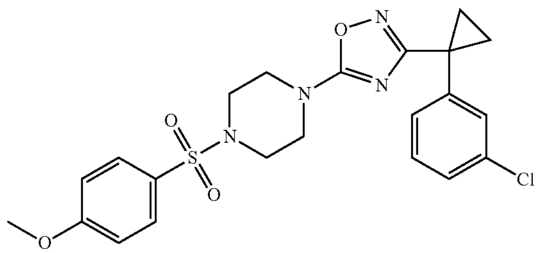 [SMILES: COc1ccc(S(=O)(=O)N2CCN(c3nc(C4(c5cccc(Cl)c5)CC4)no3)CC2)cc1] | 1-{3-[1-(3-Chloro-phenyl)-cyclopropyl]-[1,2,4]oxadiazol-5-yl}-4-(4-methoxy-benzenesulfonyl)-piperazine | 134 |
| Cmpd135 | 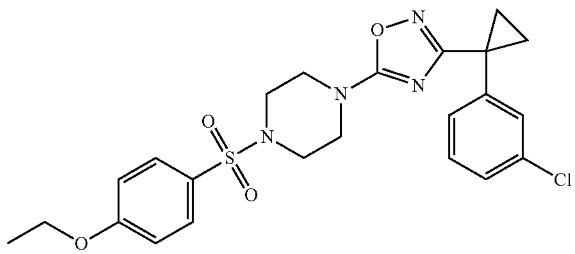 [SMILES: CCOc1ccc(S(=O)(=O)N2CCN(c3nc(C4(c5cccc(Cl)c5)CC4)no3)CC2)cc1] | 1-{3-[1-(3-Chloro-phenyl)-cyclopropyl]-[1,2,4]oxadiazol-5-yl}-4-(4-ethoxy-benzenesulfonyl)-piperazine | 135 |
| Cmpd136 | 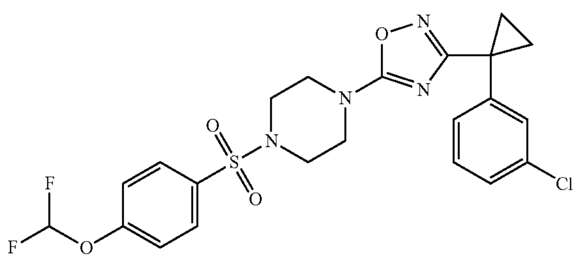 [SMILES: O=S(=O)(c1ccc(OC(F)F)cc1)N1CCN(c2nc(C3(c4cccc(Cl)c4)CC3)no2)CC1] | 1-{3-[1-(3-Chloro-phenyl)-cyclopropyl]-[1,2,4]oxadiazol-5-yl}-4-(4-difluoromethoxy-benzenesulfonyl)-piperazine | 136 |
| Cmpd137 | 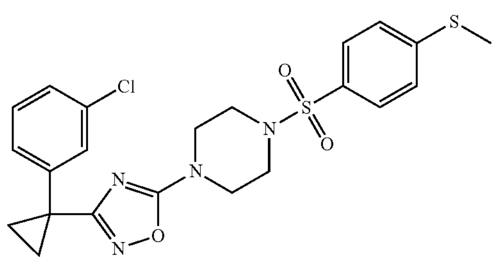 [SMILES: CSc1ccc(S(=O)(=O)N2CCN(c3nc(C4(c5cccc(Cl)c5)CC4)no3)CC2)cc1] | 1-{3-[1-(3-Chloro-phenyl)-cyclopropyl]-[1,2,4]oxadiazol-5-yl}-4-(4-methylsulfanyl-benzenesulfonyl)-piperazine | 137 |
| Cmpd138 | 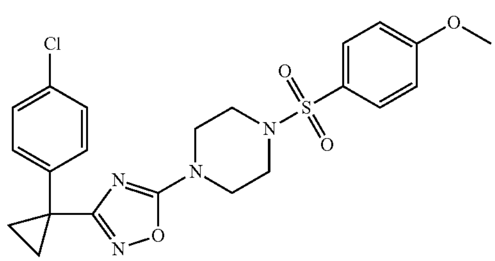 [SMILES: COc1ccc(S(=O)(=O)N2CCN(c3nc(C4(c5ccc(Cl)cc5)CC4)no3)CC2)cc1] | 1-{3-[1-(4-Chloro-phenyl)-cyclopropyl]-[1,2,4]oxadiazol-5-yl}-4-(4-methoxy-benzenesulfonyl)-piperazine | 138 |
| Cmpd139 | 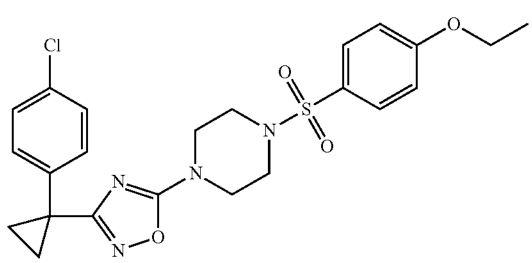 | 1-{3-[1-(4-Chloro-phenyl)-cyclopropyl]-[1,2,4]oxadiazol-5-yl}-4-(4-ethoxy-benzenesulfonyl)-piperazine | 139 |

TABLE 1-continued

| COMPOUND | STRUCTURE | NAME | Example No |
|---|---|---|---|
| Cmpd140 | 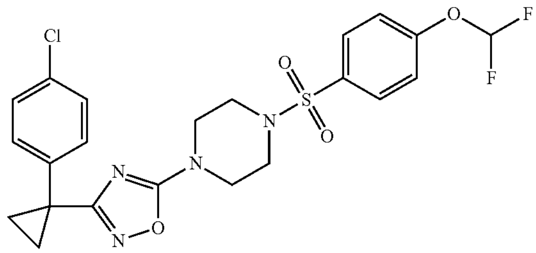 [SMILES: O=S(=O)(c1ccc(OC(F)F)cc1)N1CCN(c2nc(C3(c4ccc(Cl)cc4)CC3)no2)CC1] | 1-{3-[1-(4-Chloro-phenyl)-cyclopropyl]-[1,2,4]oxadiazol-5-yl}-4-(4-difluoromethoxy-benzenesulfonyl)-piperazine | 140 |
| Cmpd141 | 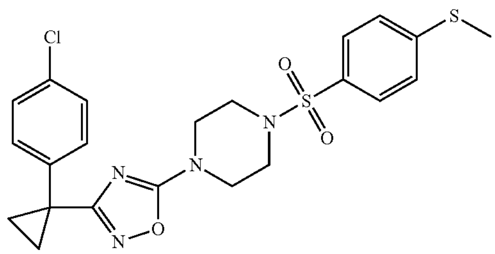 | 1-{3-[1-(4-Chloro-phenyl)-cyclopropyl]-[1,2,4]oxadiazol-5-yl}-4-(4-methylsulfanyl-benzenesulfonyl)-piperazine | 141 |
| Cmpd142 | 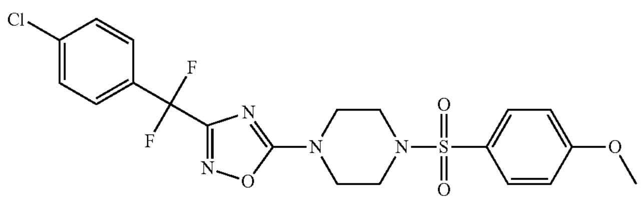 [SMILES: COc1ccc(S(=O)(=O)N2CCN(c3nc(C(F)(F)c4ccc(Cl)cc4)no3)CC2)cc1] | 1-{3-[(4-Chloro-phenyl)-difluoro-methyl]-[1,2,4]oxadiazol-5-yl}-4-(4-methoxy-benzenesulfonyl)-piperazine | 142 |
| Cmpd143 | 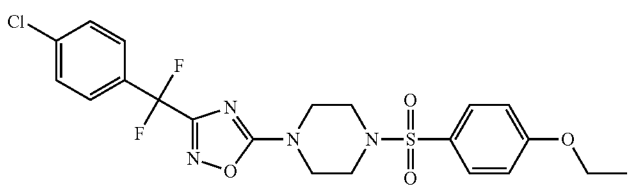 [SMILES: CCOc1ccc(S(=O)(=O)N2CCN(c3nc(C(F)(F)c4ccc(Cl)cc4)no3)CC2)cc1] | 1-{3-[(4-Chloro-phenyl)-difluoro-methyl]-[1,2,4]oxadiazol-5-yl}-4-(4-ethoxy-benzenesulfonyl)-piperazine | 143 |
| Cmpd144 | 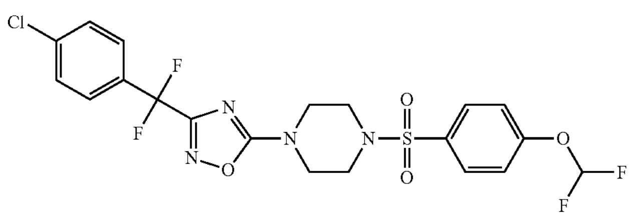 [SMILES: O=S(=O)(c1ccc(OC(F)F)cc1)N1CCN(c2nc(C(F)(F)c3ccc(Cl)cc3)no2)CC1] | 1-{3-[(4-Chloro-phenyl)-difluoro-methyl]-[1,2,4]oxadiazol-5-yl}-4-(4-difluoromethoxy-benzenesulfonyl)-piperazine | 144 |
| Cmpd145 | 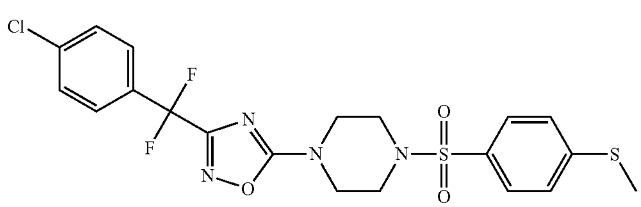 [SMILES: CSc1ccc(S(=O)(=O)N2CCN(c3nc(C(F)(F)c4ccc(Cl)cc4)no3)CC2)cc1] | 1-{3-[(4-Chloro-phenyl)-difluoro-methyl]-[1,2,4]oxadiazol-5-yl}-4-(4-methylsulfanyl-benzenesulfonyl)-piperazine | 145 |
| Cmpd146 | 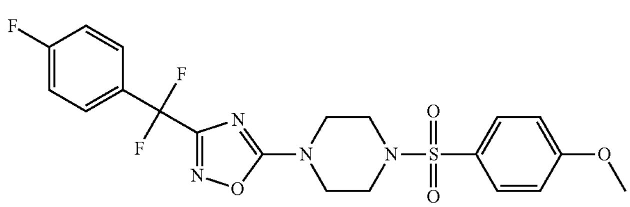 | 1-{3-[Difluoro-(4-fluoro-phenyl)-methyl]-[1,2,4]oxadiazol-5-yl}-4-(4-methoxy-benzenesulfonyl)-piperazine | 146 |

TABLE 1-continued

| COMPOUND | STRUCTURE | NAME | Example No |
|---|---|---|---|
| Cmpd147 | 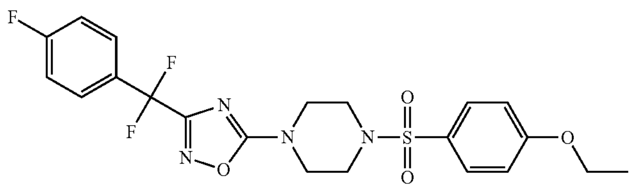 | 1-{3-[Difluoro-(4-fluoro-phenyl)-methyl]-[1,2,4]oxadiazol-5-yl}-4-(4-ethoxy-benzenesulfonyl)-piperazine | 147 |
| Cmpd148 | 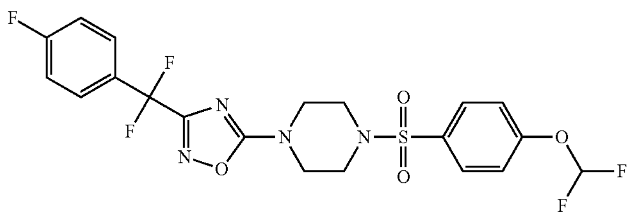 [SMILES: O=S(=O)(c1ccc(OC(F)F)cc1)N1CCN(c2nc(C(F)(F)c3ccc(F)cc3)no2)CC1] | 1-{3-[Difluoro-(4-fluoro-phenyl)-methyl]-[1,2,4]oxadiazol-5-yl}-4-(4-difluoromethoxy-benzenesulfonyl)-piperazine | 148 |
| Cmpd149 | 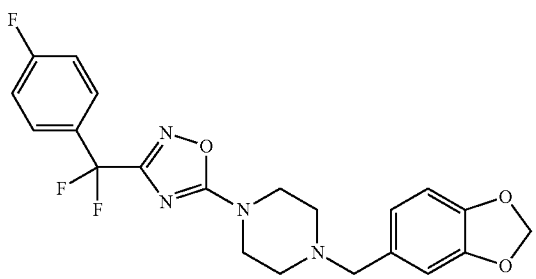 [SMILES: Fc1ccc(C(F)(F)c2noc(N3CCN(Cc4ccc5c(c4)OCO5)CC3)n2)cc1] | 5-(4-(Benzo[d][1,3]dioxol-5-ylmethyl)piperazin-1-yl)-3-(difluoro(4-fluorophenyl)methyl)-1,2,4-oxadiazole | 149 |
| Cmpd150 | 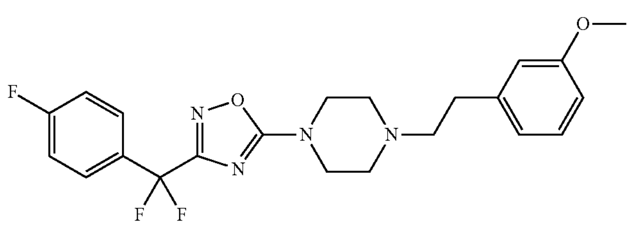 [SMILES: COc1cccc(CCN2CCN(c3nc(C(F)(F)c4ccc(F)cc4)no3)CC2)c1] | 3-(Difluoro(4-fluorophenyl)methyl)-5-(4-(3-methoxyphenethyl)piperazin-1-yl)-1,2,4-oxadiazole | 150 |
| Cmpd151 | 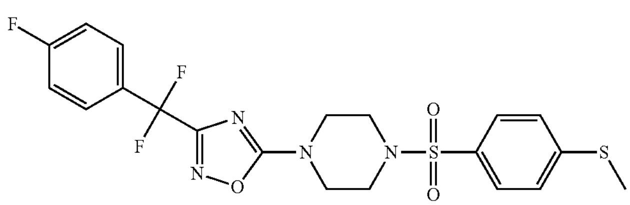 | 1-{3-[Difluoro-(4-fluoro-phenyl)-methyl]-[1,2,4]oxadiazol-5-yl}-4-(4-methylsulfanyl-benzenesulfonyl)-piperazine | 151 |
| Cmpd152 | 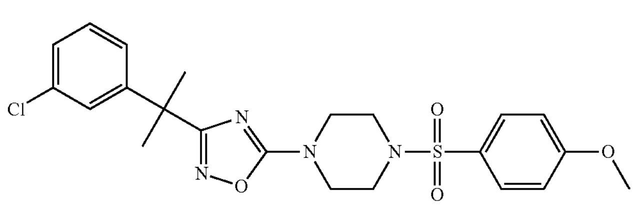 [SMILES: COc1ccc(S(=O)(=O)N2CCN(c3nc(C(C)(C)c4cccc(Cl)c4)no3)CC2)cc1] | 1-{3-[1-(3-Chloro-phenyl)-1-methyl-ethyl]-[1,2,4]oxadiazol-5-yl}-4-(4-methoxy-benzenesulfonyl)-piperazine | 152 |
| Cmpd153 | 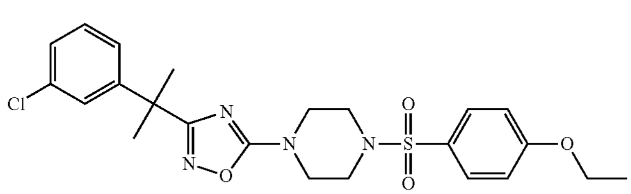 [SMILES: CCOc1ccc(S(=O)(=O)N2CCN(c3nc(C(C)(C)c4cccc(Cl)c4)no3)CC2)cc1] | 1-{3-[1-(3-Chloro-phenyl)-1-methyl-ethyl]-[1,2,4]oxadiazol-5-yl}-4-(4-ethoxy-benzenesulfonyl)-piperazine | 153 |

TABLE 1-continued

| COMPOUND | STRUCTURE | NAME | Example No |
|---|---|---|---|
| Cmpd154 | 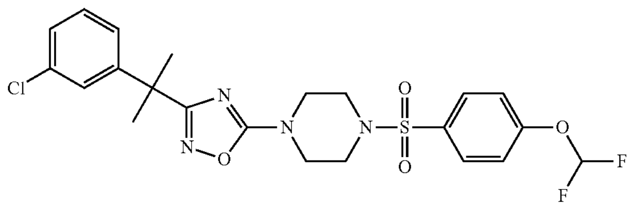 [SMILES: CC(C)(c1cccc(Cl)c1)c1noc(N2CCN(S(=O)(=O)c3ccc(OC(F)F)cc3)CC2)n1] | 1-{3-[1-(3-Chloro-phenyl)-1-methyl-ethyl]-[1,2,4]oxadiazol-5-yl}-4-(4-difluoromethoxy-benzenesulfonyl)-piperazine | 154 |
| Cmpd155 | 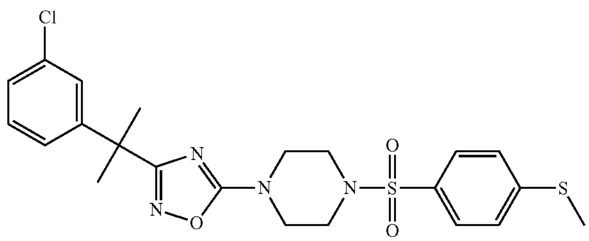 [SMILES: CSc1ccc(S(=O)(=O)N2CCN(c3nc(C(C)(C)c4cccc(Cl)c4)no3)CC2)cc1] | 1-{3-[1-(3-Chloro-phenyl)-1-methyl-ethyl]-[1,2,4]oxadiazol-5-yl}-4-(4-methylsulfanyl-benzenesulfonyl)-piperazine | 155 |
| Cmpd156 | 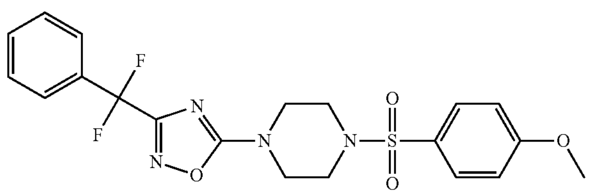 [SMILES: COc1ccc(S(=O)(=O)N2CCN(c3nc(C(F)(F)c4ccccc4)no3)CC2)cc1] | 1-[3-(Difluoro-phenyl-methyl)-[1,2,4]oxadiazol-5-yl]-4-(4-methoxy-benzenesulfonyl)-piperazine | 156 |
| Cmpd157 | 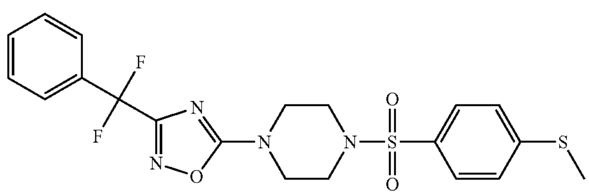 [SMILES: CSc1ccc(S(=O)(=O)N2CCN(c3nc(C(F)(F)c4ccccc4)no3)CC2)cc1] | 1-[3-(Difluoro-phenyl-methyl)-[1,2,4]oxadiazol-5-yl]-4-(4-methylsulfanyl-benzenesulfonyl)-piperazine | 157 |
| Cmpd158 | 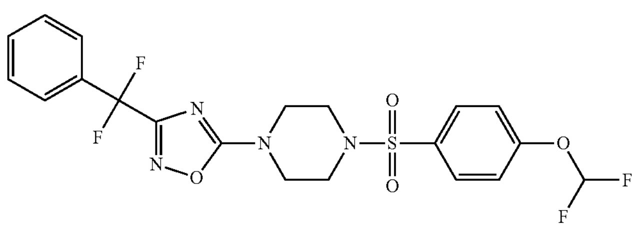 [SMILES: O=S(=O)(c1ccc(OC(F)F)cc1)N1CCN(c2nc(C(F)(F)c3ccccc3)no2)CC1] | 1-(4-Difluoromethoxy-benzenesulfonyl)-4-[3-(difluoro-phenyl-methyl)-[1,2,4]oxadiazol-5-yl]-piperazine | 158 |
| Cmpd159 | 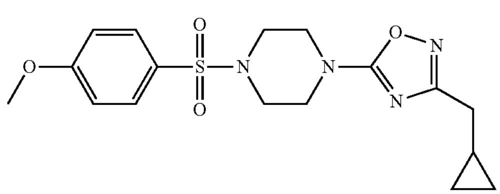 | 3-(Cyclopropylmethyl)-5-(4-((4-methoxyphenyl)sulfonyl)piperazin-1-yl)-1,2,4-oxadiazole | 159 |
| Cmpd160 | 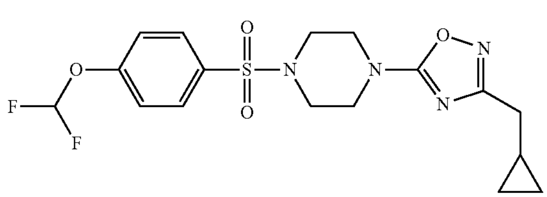 [SMILES: O=S(=O)(c1ccc(OC(F)F)cc1)N1CCN(c2nc(CC3CC3)no2)CC1] | 3-(Cyclopropylmethyl)-5-(4-((4-(difluoromethoxy)phenyl)sulfonyl)piperazin-1-yl)-1,2,4-oxadiazole | 160 |

TABLE 1-continued

| COMPOUND | STRUCTURE | NAME | Example No |
|---|---|---|---|
| Cmpd161 | 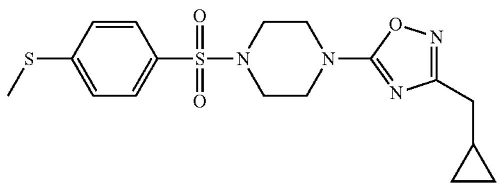 [SMILES: CSc1ccc(S(=O)(=O)N2CCN(c3nc(CC4CC4)no3)CC2)cc1] | 3-(Cyclopropylmethyl)-5-(4-((4-(methylthio)phenyl)sulfonyl)piperazin-1-yl)-1,2,4-oxadiazole | 161 |
| Cmpd162 | 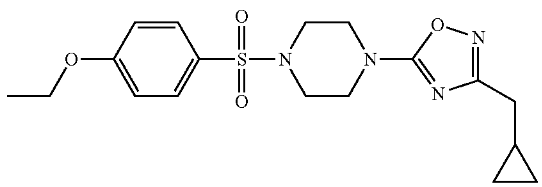 [SMILES: CCOc1ccc(S(=O)(=O)N2CCN(c3nc(CC4CC4)no3)CC2)cc1] | 3-(Cyclopropylmethyl)-5-(4-((4-ethoxyphenyl)sulfonyl)piperazin-1-yl)-1,2,4-oxadiazole | 162 |
| Cmpd163 | 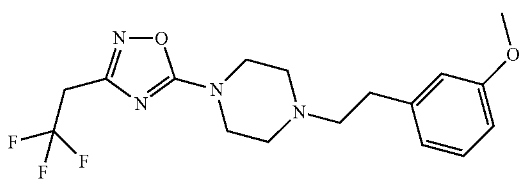 [SMILES: COc1cccc(CCN2CCN(c3nc(CC(F)(F)F)no3)CC2)c1] | 5-(4-(3-Methoxyphenethyl)piperazin-1-yl)-3-(2,2,2-trifluoroethyl)-1,2,4-oxadiazole | 163 |
| Cmpd164 | 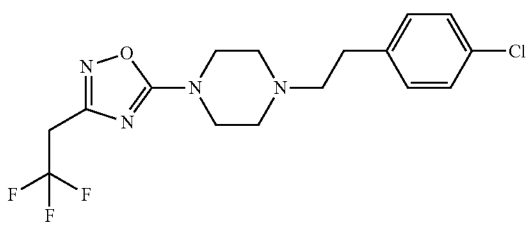 [SMILES: FC(F)(F)Cc1noc(N2CCN(CCc3ccc(Cl)cc3)CC2)n1] | 5-(4-(4-Chlorophenethyl)piperazin-1-yl)-3-(2,2,2-trifluoroethyl)-1,2,4-oxadiazole | 164 |
| Cmpd165 | 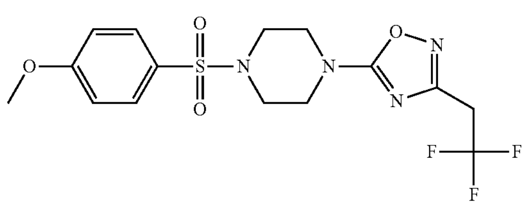 | 5-(4-((4-Methoxyphenyl)sulfony)piperazin-1-yl)-3-(2,2,2-trifluoroethyl)-1,2,4-oxadiazole | 165 |
| Cmpd166 | 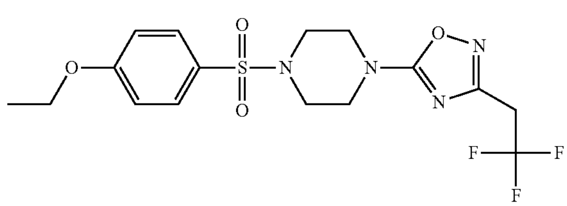 [SMILES: CCOc1ccc(S(=O)(=O)N2CCN(c3nc(CC(F)(F)F)no3)CC2)cc1] | 5-(4-((4-Ethoxyphenyl)sulfonyl)piperazin-1-yl)-3-(2,2,2-trifluoroethyl)-1,2,4-oxadiazole | 166 |
| Cmpd167 | 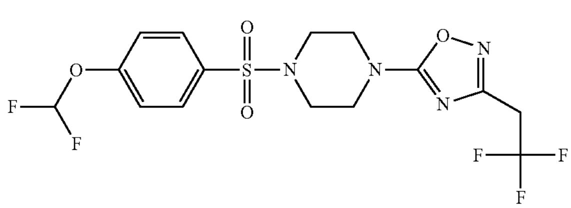 [SMILES: O=S(=O)(c1ccc(OC(F)F)cc1)N1CCN(c2nc(CC(F)(F)F)no2)CC1] | 5-(4-((4-(Difluoromethoxy)phenyl)sulfonyl)piperazin-1-yl)-3-(2,2,2-trifluoroethyl)-1,2,4-oxadiazole | 167 |

TABLE 1-continued

| Compound | Structure | Name | Example No |
|---|---|---|---|
| Cmpd168 | 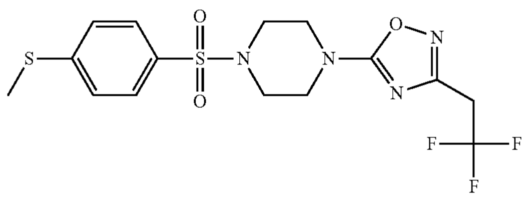 | 5-(4-((4-(Methylthio)phenyl)sulfonyl)piperazin-1-yl)-3-(2,2,2-trifluoroethyl)-1,2,4-oxadiazole | 168 |
| Cmpd169 | 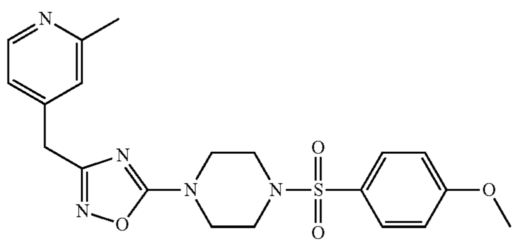 [SMILES: COc1ccc(S(=O)(=O)N2CCN(c3nc(Cc4ccnc(C)c4)no3)CC2)cc1] | 1-(4-Methoxy-benzenesulfonyl)-4-[3-(2-methyl-pyridin-4-ylmethyl)-[1,2,4]oxadiazol-5-yl]-piperazine | 169 |
| Cmpd170 | 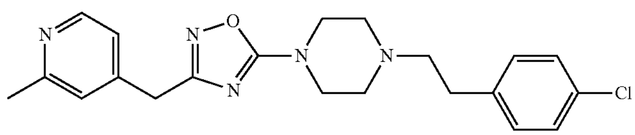 [SMILES: Cc1cc(Cc2noc(N3CCN(CCc4ccc(Cl)cc4)CC3)n2)ccn1] | 5-(4-(4-Chlorophenethyl)piperazin-1-yl)-3-((2-methylpyridin-4-yl)methyl)-1,2,4-oxadiazole | 170 |
| Cmpd171 | 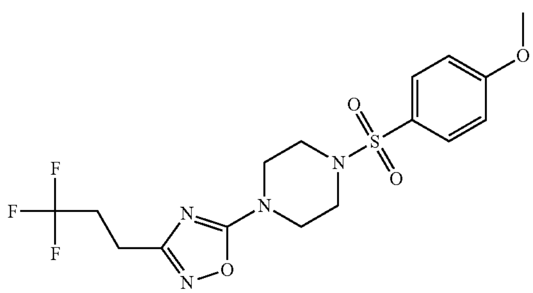 [SMILES: COc1ccc(S(=O)(=O)N2CCN(c3nc(CCC(F)(F)F)no3)CC2)cc1] | 5-(4-((4-Methoxyphenyl)sulfonyl)piperazin-1-yl)-3-(3,3,3-trifluoropropyl)-1,2,4-oxadiazole | 171 |
| Cmpd172 | 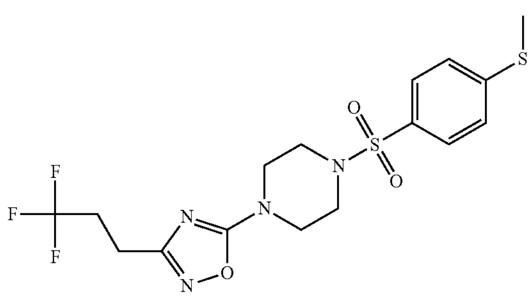 [SMILES: CSc1ccc(S(=O)(=O)N2CCN(c3nc(CCC(F)(F)F)no3)CC2)cc1] | 5-(4-((4-(Methylthio)phenyl)sulfonyl)piperazin-1-yl)-3-(3,3,3-trifluoropropyl)-1,2,4-oxadiazole | 172 |
| Cmpd173 | 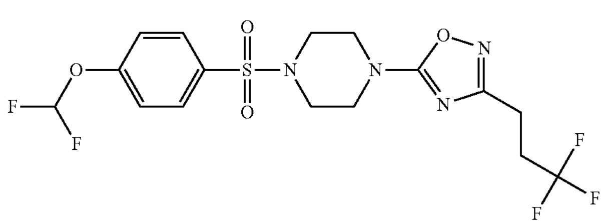 [SMILES: O=S(=O)(c1ccc(OC(F)F)cc1)N1CCN(c2nc(CCC(F)(F)F)no2)CC1] | 5-(4-((4-(Difluoromethoxy)phenyl)sulfonyl)piperazin-1-yl)-3-(3,3,3-trifluoropropyl)-1,2,4-oxadiazole | 173 |

TABLE 1-continued

| COMPOUND | STRUCTURE | NAME | Example No |
|---|---|---|---|
| Cmpd174 | 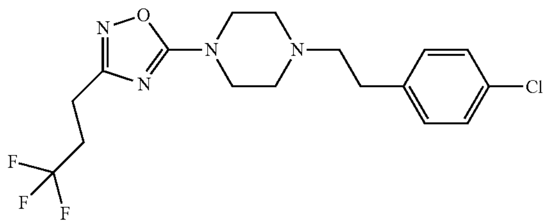 [SMILES: FC(F)(F)CCc1noc(N2CCN(CCc3ccc(Cl)cc3)CC2)n1] | 5-(4-(4-Chlorophenethyl)piperazin-1-yl)-3-(3,3,3-trifluoropropyl)-1,2,4-oxadiazole | 174 |
| Cmpd175 | 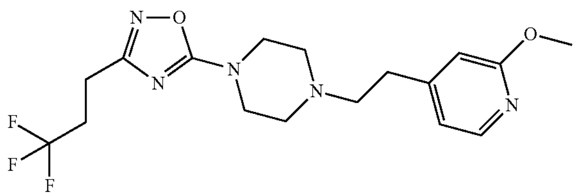 [SMILES: COc1cc(CCN2CCN(c3nc(CCC(F)(F)F)no3)CC2)ccn1] | 5-(4-(2-(2-Methoxypyridin-4-yl)ethyl)piperazin-1-yl)-3-(3,3,3-trifluoropropyl)-1,2,4-oxadiazole | 175 |
| Cmpd176 | 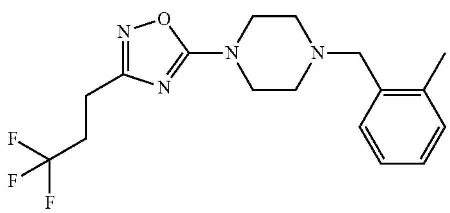 [SMILES: Cc1ccccc1CN1CCN(c2nc(CCC(F)(F)F)no2)CC1] | 5-(4-(2-Methylbenzyl)piperazin-1-yl)-3-(3,3,3-trifluoropropyl)-1,2,4-oxadiazole | 176 |
| Cmpd177 | 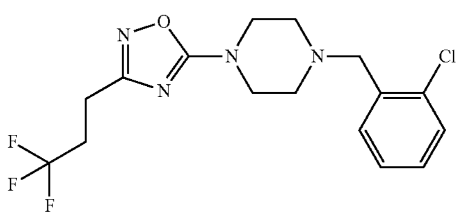 [SMILES: FC(F)(F)CCc1noc(N2CCN(Cc3ccccc3Cl)CC2)n1] | 5-(4-(2-Chlorobenzyl)piperazin-1-yl)-3-(3,3,3-trifluoropropyl)-1,2,4-oxadiazole | 177 |
| Cmpd178 | 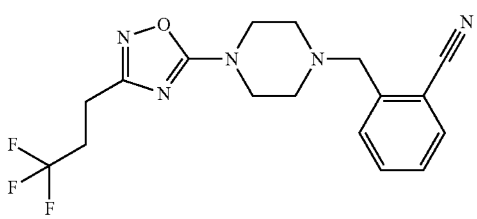 [SMILES: N#Cc1ccccc1CN1CCN(c2nc(CCC(F)(F)F)no2)CC1] | 2-((4-(3-(3,3,3-Trifluoropropyl)-1,2,4-oxadiazol-5-yl)piperazin-1-yl)methyl)benzonitrile | 178 |
| Cmpd179 | 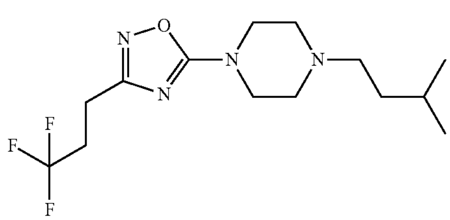 [SMILES: CC(C)CCN1CCN(c2nc(CCC(F)(F)F)no2)CC1] | 5-(4-Isopentylpiperazin-1-yl)-3-(3,3,3-trifluoropropyl)-1,2,4-oxadiazole | 179 |
| Cmpd180 | 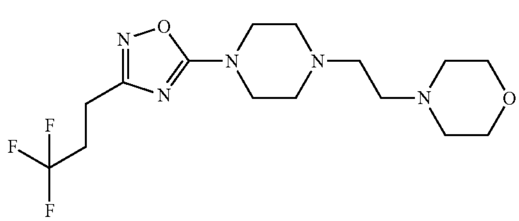 [SMILES: FC(F)(F)CCc1noc(N2CCN(CCN3CCOCC3)CC2)n1] | 4-(2-(4-(3-(3,3,3-Trifluoropropyl)-1,2,4-oxadiazol-5-yl)piperazin-1-yl)ethyl)morpholine | 180 |

TABLE 1-continued

| COMPOUND | STRUCTURE | NAME | Example No |
|---|---|---|---|
| Cmpd181 | 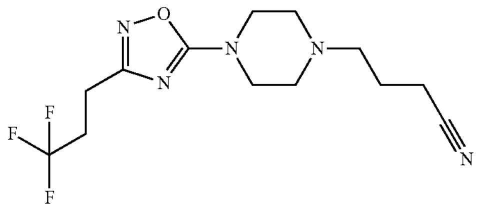 [SMILES: N#CCCCN1CCN(c2nc(CCC(F)(F)F)no2)CC1] | 4-(4-(3-(3,3,3-Trifluoropropyl)-1,2,4-oxadiazol-5-yl)piperazin-1-yl)butanenitrile | 181 |
| Cmpd182 | 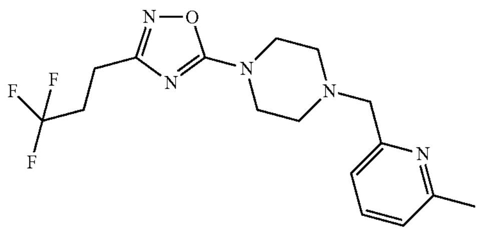 [SMILES: Cc1cccc(CN2CCN(c3nc(CCC(F)(F)F)no3)CC2)n1] | 5-(4-((6-Methylpyridin-2-yl)methyl)piperazin-1-yl)-3-(3,3,3-trifluoropropyl)-1,2,4-oxadiazole | 182 |
| Cmpd183 | 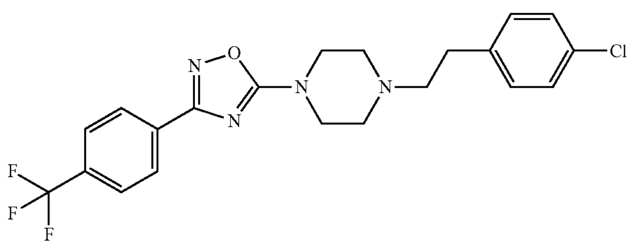 [SMILES: FC(F)(F)c1ccc(-c2noc(N3CCN(CCc4ccc(Cl)cc4)CC3)n2)cc1] | 1-[2-(4-Chloro-phenyl)-ethyl]-4-[3-(4-trifluoromethyl-phenyl)-[1,2,4]oxadiazol-5-yl]-piperazine | 183 |
| Cmpd184 | 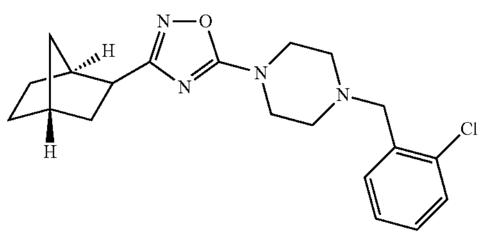 [SMILES: Clc1ccccc1CN1CCN(c2nc(C3C[C@@H]4CC[C@H]3C4)no2)CC1] | 3-((1S,4R)-bicyclo[2.2.1]heptan-2-yl)-5-(4-(2-chlorobenzyl)piperazin-1-yl)-1,2,4-oxadiazole | 184 |
| Cmpd185 | 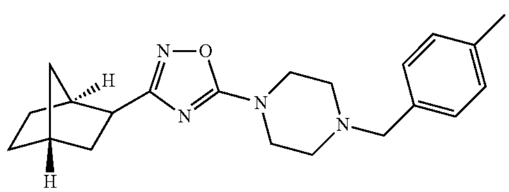 [SMILES: Cc1ccc(CN2CCN(c3nc(C4C[C@@H]5CC[C@H]4C5)no3)CC2)cc1] | 3-((1S,4R)-bicyclo[2.2.1]heptan-2-yl)-5-(4-(4-methylbenzyl)piperazin-1-yl)-1,2,4-oxadiazole | 185 |
| Cmpd186 | 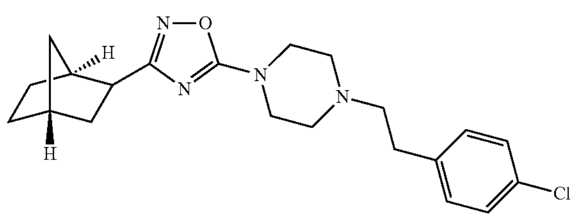 [SMILES: Clc1ccc(CCN2CCN(c3nc(C4C[C@@H]5CC[C@H]4C5)no3)CC2)cc1] | 3-((1S,4R)-bicyclo[2.2.1]heptan-2-yl)-5-(4-(4-chlorophenethyl)piperazin-1-yl)-1,2,4-oxadiazole | 186 |
| Cmpd187 | 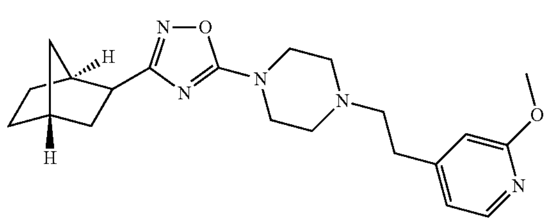 [SMILES: COc1cc(CCN2CCN(c3nc(C4C[C@@H]5CC[C@H]4C5)no3)CC2)ccn1] | 3-((1S,4R)-bicyclo[2.2.1]heptan-2-yl)-5-(4-(2-(2-methoxypyridin-4-yl)ethyl)piperazin-1-yl)-1,2,4-oxadiazole | 187 |

TABLE 1-continued

| COMPOUND | STRUCTURE | NAME | Example No |
|---|---|---|---|
| Cmpd188 | 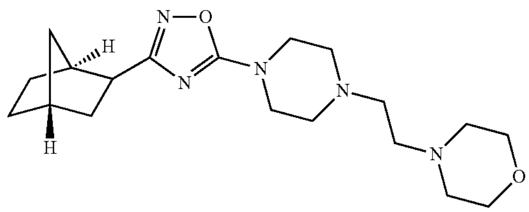 [SMILES: C1CN(CCN2CCN(c3nc(C4C[C@@H]5CC[C@H]4C5)no3)CC2)CCO1] | 4-(2-(4-(3-((1S,4R)-bicyclo[2.2.1]heptan-2-yl)-1,2,4-oxadiazol-5-yl)piperazin-1-yl)ethyl)morpholine | 188 |
| Cmpd189 | 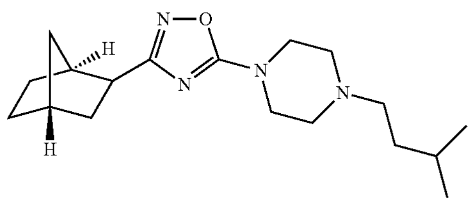 [SMILES: CC(C)CCN1CCN(c2nc(C3C[C@@H]4CC[C@H]3C4)no2)CC1] | 3-((1S,4R)-bicyclo[2.2.1]heptan-2-yl)-5-(4-isopentylpiperazin-1-yl)-1,2,4-oxadiazole | 189 |
| Cmpd190 | 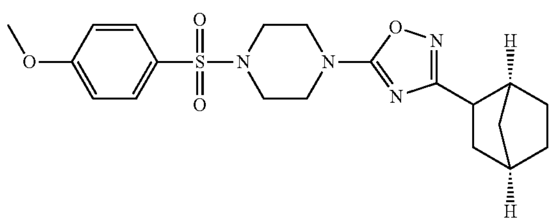 [SMILES: COc1ccc(S(=O)(=O)N2CCN(c3nc(C4C[C@@H]5CC[C@H]4C5)no3)CC2)cc1] | 3-(Bicyclo[2.2.1]heptan-2-yl)-5-(4-((4-methoxyphenyl)sulfonyl)piperazin-1-yl)-1,2,4-oxadiazole | 190 |
| Cmpd191 | 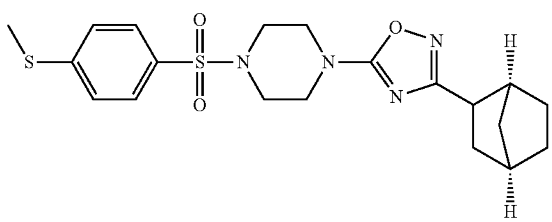 | 3-(Bicyclo[2.2.1]heptan-2-yl)-5-(4-((4-(methylthio)phenyl)sulfonyl)piperazin-1-yl)-1,2,4-oxadiazole | 191 |
| Cmpd192 | 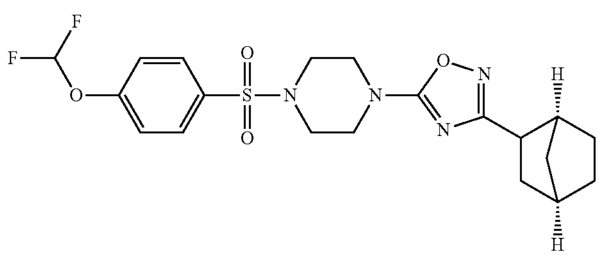 [SMILES: O=S(=O)(c1ccc(OC(F)F)cc1)N1CCN(c2nc(C3C[C@@H]4CC[C@H]3C4)no2)CC1] | 3-(Bicyclo[2.2.1]heptan-2-yl)-5-(4-((4-(difluoromethoxy)phenyl)sulfonyl)piperazin-1-yl)-1,2,4-oxadiazole | 192 |
| Cmpd193 | 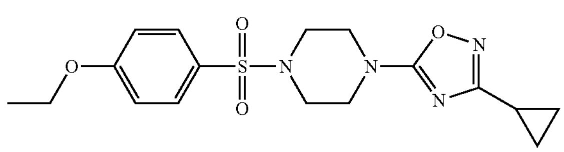 [SMILES: CCOc1ccc(S(=O)(=O)N2CCN(c3nc(C4CC4)no3)CC2)cc1] | 3-Cyclopropyl-5-(4-((4-ethoxyphenyl)sulfonyl)piperazin-1-yl)-1,2,4-oxadiazole | 193 |
| Cmpd194 | 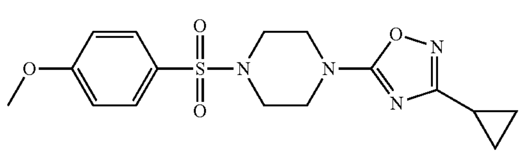 [SMILES: COc1ccc(S(=O)(=O)N2CCN(c3nc(C4CC4)no3)CC2)cc1] | 3-Cyclopropyl-5-(4-((4-methoxyphenyl)sulfonyl)piperazin-1-yl)-1,2,4-oxadiazole | 194 |

TABLE 1-continued

| COMPOUND | STRUCTURE | NAME | Example No |
|---|---|---|---|
| Cmpd195 | 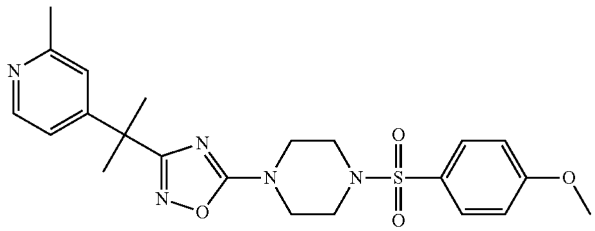 [SMILES: COc1ccc(S(=O)(=O)N2CCN(c3nc(C(C)(C)c4ccnc(C)c4)no3)CC2)cc1] | 5-(4-((4-Methoxyphenyl)sulfonyl)piperazin-1-yl)-3-(2-(2-methylpyridin-4-yl)propan-2-yl)-1,2,4-oxadiazole | 195 |
| Cmpd196 | 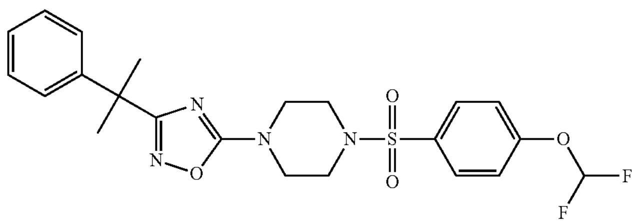 [SMILES: CC(C)(c1ccccc1)c1noc(N2CCN(S(=O)(=O)c3ccc(OC(F)F)cc3)CC2)n1] | 1-(4-Difluoromethoxy-benzenesulfonyl)-4-[3-(1-methyl-1-phenyl-ethyl)-[1,2,4]oxadiazol-5-yl]-piperazine | 196 |
| Cmpd197 | 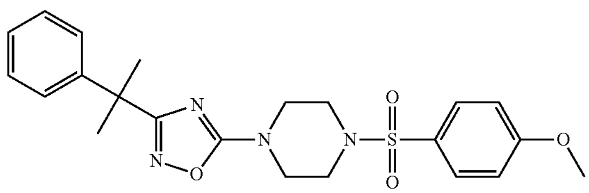 [SMILES: COc1ccc(S(=O)(=O)N2CCN(c3nc(C(C)(C)c4ccccc4)no3)CC2)cc1] | 1-(4-Methoxy-benzenesulfonyl)-4-[3-(1-methyl-1-phenyl-ethyl)-[1,2,4]oxadiazol-5-yl]-piperazine | 197 |
| Cmpd198 | 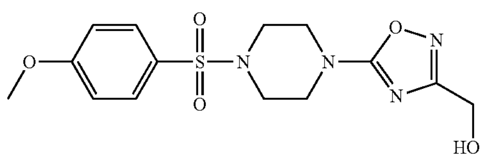 [SMILES: COc1ccc(S(=O)(=O)N2CCN(c3nc(CO)no3)CC2)cc1] | (5-(4-((4-Methoxyphenyl)sulfonyl)piperazin-1-yl)-1,2,4-oxadiazol-3-yl)methanol | 198 |
| Cmpd199 | 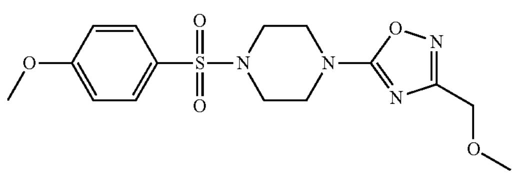 | 3-(Methoxymethyl)-5-(4-((4-methoxyphenyl)sulfonyl)piperazin-1-yl)-1,2,4-oxadiazole | 199 |
| Cmpd200 | 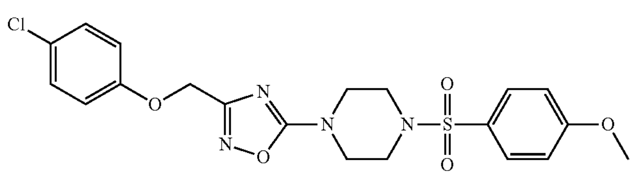 [SMILES: COc1ccc(S(=O)(=O)N2CCN(c3nc(COc4ccc(Cl)cc4)no3)CC2)cc1] | 3-((4-Chlorophenoxy)methyl)-5-(4-((4-methoxyphenyl)sulfonyl)piperazin-1-yl)-1,2,4-oxadiazole | 200 |
| Cmpd201 | 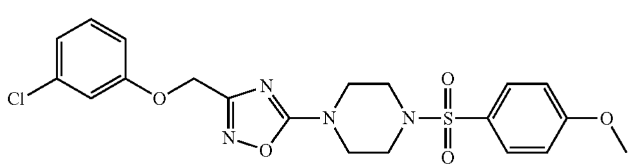 [SMILES: COc1ccc(S(=O)(=O)N2CCN(c3nc(COc4cccc(Cl)c4)no3)CC2)cc1] | 3-((3-Chlorophenoxy)methyl)-5-(4-((4-methoxyphenyl)sulfonyl)piperazin-1-yl)-1,2,4-oxadiazole | 201 |
| Cmpd202 | 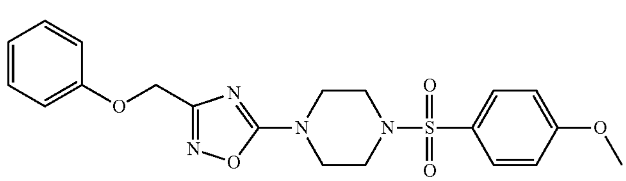 [SMILES: COc1ccc(S(=O)(=O)N2CCN(c3nc(COc4ccccc4)no3)CC2)cc1] | 5-(4-((4-Methoxyphenyl)sulfonyl)piperazin-1-yl)-3-(phenoxymethyl)-1,2,4-oxadiazole | 202 |

TABLE 1-continued

| COMPOUND | STRUCTURE | NAME | Example No |
|---|---|---|---|
| Cmpd203 | 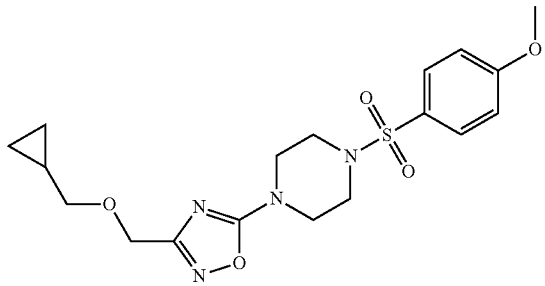 [SMILES: COc1ccc(S(=O)(=O)N2CCN(c3nc(COCC4CC4)no3)CC2)cc1] | 3-((Cyclopropylmethoxy)methyl)-5-(4-((4-methoxyphenyl)sulfonyl)piperazin-1-yl)-1,2,4-oxadiazole | 203 |
| Cmpd204 | 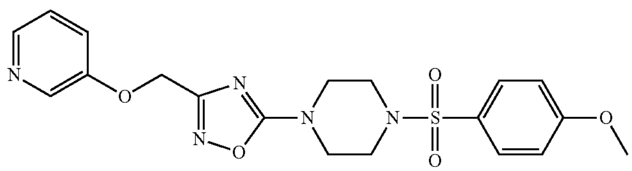 [SMILES: COc1ccc(S(=O)(=O)N2CCN(c3nc(COc4cccnc4)no3)CC2)cc1] | 5-(4-((4-Methoxyphenyl)sulfonyl)piperazin-1-yl)-3-((pyridin-3-yloxy)methyl)-1,2,4-oxadiazole | 204 |
| Cmpd205 | 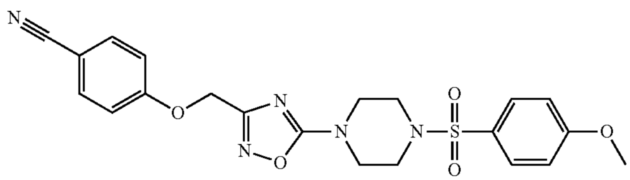 [SMILES: COc1ccc(S(=O)(=O)N2CCN(c3nc(COc4ccc(C#N)cc4)no3)CC2)cc1] | 4-((5-(4-((4-Methoxyphenyl)sulfonyl)piperazin-1-yl)-1,2,4-oxadiazol-3-yl)methoxy)benzonitrile | 205 |
| Cmpd206 | 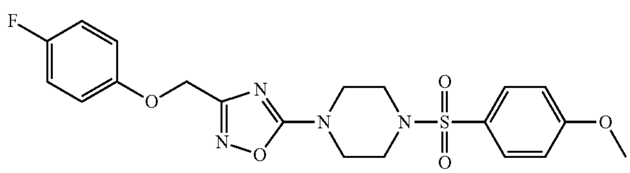 [SMILES: COc1ccc(S(=O)(=O)N2CCN(c3nc(COc4ccc(F)cc4)no3)CC2)cc1] | 3-((4-Fluorophenoxy)methyl)-5-(4-((4-methoxyphenyl)sulfonyl)piperazin-1-yl)-1,2,4-oxadiazole | 206 |
| Cmpd207 | 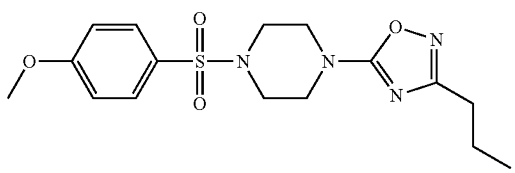 | 5-(4-((4-Methoxyphenyl)sulfonyl)piperazin-1-yl)-3-propyl-1,2,4-oxadiazole | 207 |
| Cmpd208 | 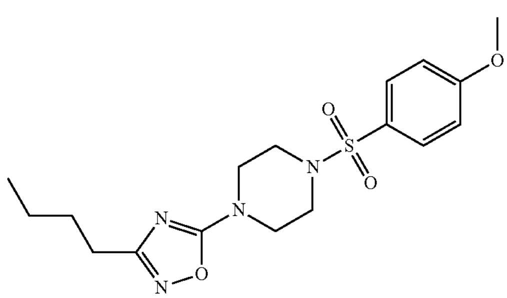 [SMILES: CCCCc1noc(N2CCN(S(=O)(=O)c3ccc(OC)cc3)CC2)n1] | 3-Butyl-5-(4-((4-methoxyphenyl)sulfonyl)piperazin-1-yl)-1,2,4-oxadiazole | 208 |
| Cmpd209 | 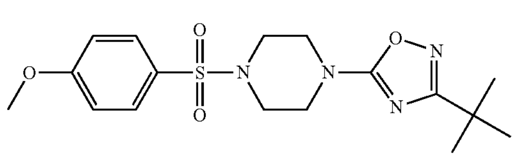 [SMILES: COc1ccc(S(=O)(=O)N2CCN(c3nc(C(C)(C)C)no3)CC2)cc1] | 3-(Tert-butyl)-5-(4-((4-methoxyphenyl)sulfonyl)piperazin-1-yl)-1,2,4-oxadiazole | 209 |

TABLE 1-continued

| COMPOUND | STRUCTURE | NAME | Example No |
|---|---|---|---|
| Cmpd210 | 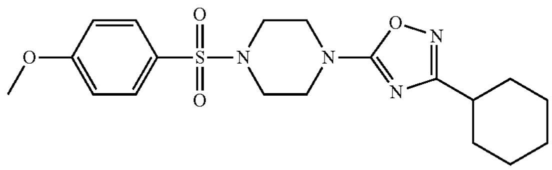 [SMILES: COc1ccc(S(=O)(=O)N2CCN(c3nc(C4CCCCC4)no3)CC2)cc1] | 3-Cyclohexyl-5-(4-((4-methoxyphenyl)sulfonyl)piperazin-1-yl)-1,2,4-oxadiazole | 210 |
| Cmpd211 | 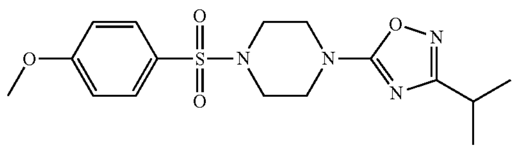 [SMILES: COc1ccc(S(=O)(=O)N2CCN(c3nc(C(C)C)no3)CC2)cc1] | 3-Isopropyl-5-(4-((4-methoxyphenyl)sulfonyl)piperazin-1-yl)-1,2,4-oxadiazole | 211 |
| Cmpd212 | 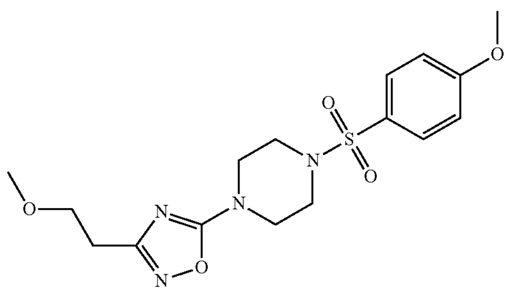 | 3-(2-Methoxyethyl)-5-(4-((4-methoxyphenyl)sulfonyl)piperazin-1-yl)-1,2,4-oxadiazole | 212 |
| Cmpd213 | 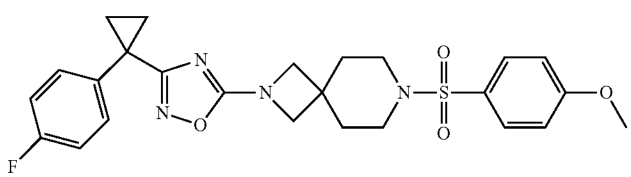 [SMILES: COc1ccc(S(=O)(=O)N2CCC3(CC2)CN(c2nc(C4(c5ccc(F)cc5)CC4)no2)C3)cc1] | 3-(1-(4-Fluorophenyl)cyclopropyl)-5-(7-((4-methoxyphenyl)sulfonyl)-2,7-diazaspiro[3.5]nonan-2-yl)-1,2,4-oxadiazole | 213 |
| Cmpd214 | 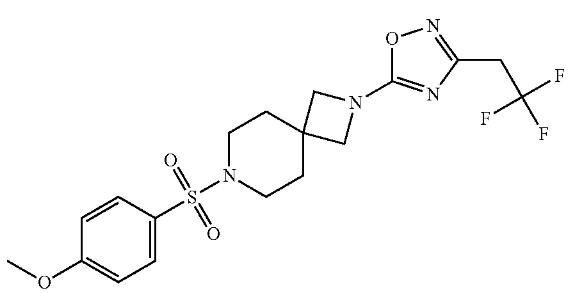 [SMILES: CSc1ccc(S(=O)(=O)N2CCC3(CC2)CN(c2nc(CC(F)(F)F)no2)C3)cc1] | 5-(7-((4-Methoxyphenyl)sulfonyl)-2,7-diazaspiro[3.5]nonan-2-yl)-3-(2,2,2-trifluoroethyl)-1,2,4-oxadiazole | 214 |

TABLE 1-continued

| COMPOUND | STRUCTURE | NAME | Example No |
|---|---|---|---|
| Cmpd215 | 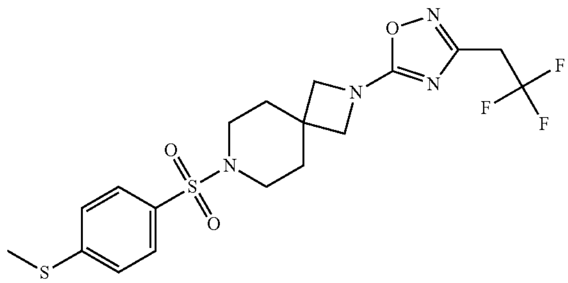 | 5-(7-((4-(Methylthio)phenyl)sulfonyl)-2,7-diazaspiro[3.5]nonan-2-yl)-3-(2,2,2-trifluoroethyl)-1,2,4-oxadiazole | 215 |
| Cmpd216 | 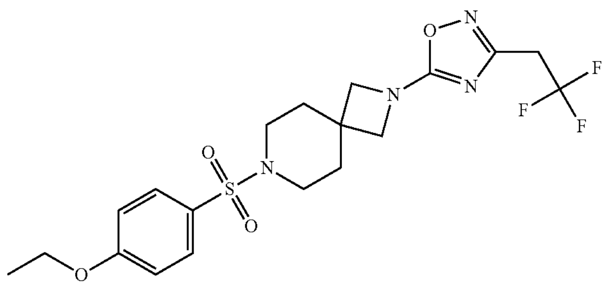 [SMILES: CCOc1ccc(S(=O)(=O)N2CCC3(CC2)CN(c2nc(CC(F)(F)F)no2)C3)cc1] | 5-(7-((4-Ethoxyphenyl)sulfonyl)-2,7-diazaspiro[3.5]nonan-2-yl)-3-(2,2,2-trifluoroethyl)-1,2,4-oxadiazole | 216 |
| Cmpd217 | 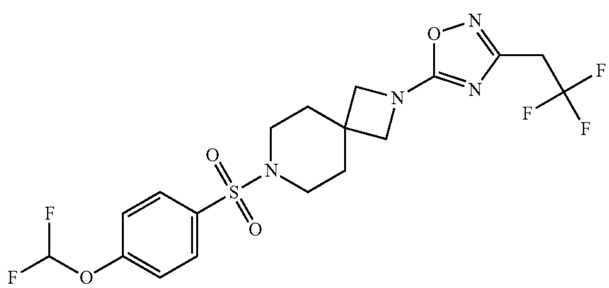 [SMILES: O=S(=O)(c1ccc(OC(F)F)cc1)N1CCC2(CC1)CN(c1nc(CC(F)(F)F)no1)C2] | 5-(7-((4-(Difluoromethoxy)phenyl)sulfonyl)-2,7-diazaspiro[3.5]nonan-2-yl)-3-(2,2,2-trifluoroethyl)-1,2,4-oxadiazole | 217 |
| Cmpd218 | 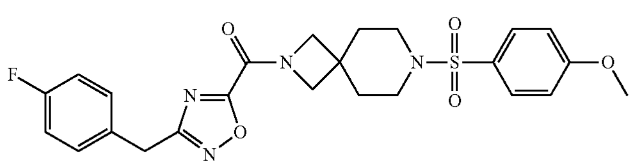 [SMILES: COc1ccc(S(=O)(=O)N2CCC3(CC2)CN(C(=O)c2nc(Cc4ccc(F)cc4)no2)C3)cc1] | (3-(4-Fluorobenzyl)-1,2,4-oxadiazol-5-yl)(7-((4-methoxyphenyl)sulfonyl)-2,7-diazaspiro[3.5]nonan-2-yl)methanone | 218 |
| Cmpd219 | 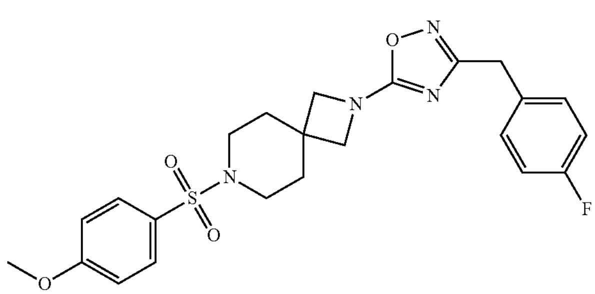 [SMILES: COc1ccc(S(=O)(=O)N2CCC3(CC2)CN(c2nc(Cc4ccc(F)cc4)no2)C3)cc1] | 3-(4-Fluorobenzyl)-5-(7-((4-methoxyphenyl)sulfonyl)-2,7-diazaspiro[3.5]nonan-2-yl)-1,2,4-oxadiazole | 219 |

TABLE 1-continued

| COMPOUND | STRUCTURE | NAME | Example No |
|---|---|---|---|
| Cmpd220 | 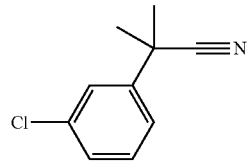 | 3-(2-Methoxyethyl)-5-(7-((4-methoxyphenyl)sulfonyl)-2,7-diazaspiro[3.5]nonan-2-yl)-1,2,4-oxadiazole | 220 |

Abbreviations:
BOP = (Benzotriazol-1-yloxy)tris(dimethylamino)phosphonium hexafluorophosphate;
CH$_2$Cl$_2$ = dichloromethane;
DMAP = dimethylaminopyridine;
DMF = dimethylformamide;
EDC = 1-(3-dimethylaminopropyl)-3-ethylcarbodiimide hydrochloride;
EE/H = Ethyl acetate/Heptane;
EtOH = ethanol;
EtOAc = ethyl acetate;
Et$_3$N = triethylamine;
h = hour;
HPLC = high performance liquid chromatography;
HOBt = 1-hydroxy-benzotriazol hydrate;
iPr$_2$NEt = Ethyl-diisopropyl-amine;
MeOH = methanol;
o/n = overnight;
RT = room temperature;
THF = tetrahydrofuran;
TFA = trifluoroacetic acid.

Process for Preparation of Intermediates of Formula IV

Intermediate IV-16;
2-(4-Fluoro-phenyl)-2-methyl-propionitrile

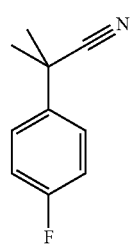

To a stirred solution of (4-fluoro-phenyl)-acetonitrile (8.0 g, 59.2 mmol) in DMF (80 mL) at 0° C. was added sodium hydride (5.68 g, 50% in oil, 118 mmol). After 40 minutes, methyl iodide (11.1 mL, 178 mmol) was added and the reaction mixture stirred at RT overnight. The reaction mixture was poured on an aqueous saturated solution of NH$_4$Cl and the product extracted with EtOAc. The combined organic phases were dried on Na$_2$SO$_4$, and a column chromatography (silica gel, EtOAc/Heptane=1/9) gave the title product 4.2 g (43%) as a light yellow oil.

Intermediate IV-22;
2-(3-Chloro-phenyl)-2-methyl-propionitrile

To a stirred solution of (3-chloro-phenyl)-acetonitrile (6.0 g, 39.6 mmol) in DMF (150 mL) at 0° C. was added sodium hydride (3.45 g, 50% in oil, 79.2 mmol). After 40 minutes, methyl iodide (11.1 mL, 178 mmol) was added and the reaction mixture stirred at RT overnight. The reaction mixture was poured on an aqueous saturated solution of NH$_4$Cl and the product extracted with EtOAc. The combined organic phases were dried on Na$_2$SO$_4$, and a column chromatography (silica gel, EtOAc/Heptane=1/9) gave the title product 6.42 g (90%) as a colorless oil.

Intermediate IV-31; 2-Methyl-2-(2-methylpyridin-4-yl)propanenitrile

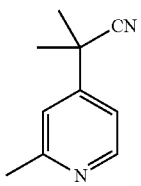

In a 100 mL three-necked flask, 2-(2-methylpyridin-4-yl)acetonitrile (950 mg, 7.19 mmol) was combined with DMF (30 ml) to give an orange solution. The solution was then cooled to 0° C. and sodium hydride (690 mg, 14.4 mmol) was added (in 3 portions). The reaction mixture was then stirred for 30 minutes and methyl iodide (3.06 g, 1.35 ml, 21.6 mmol) was added. The reaction mixture was left stirring for 1 h. The reaction mixture was then quenched with sat. ammonium chloride solution and the DMF was evaporated. The crude residue was then poured into sat. ammonium chloride solution and extracted with EtOAc. The organic layers were dried over $Na_2SO_4$ and concentrated in vacuo. The crude residue was then purified by column chromatography (silica, EE/H 1:1) to yield 846 mg (5.28 mmol, 73.5%) of 2-methyl-2-(2-methylpyridin-4-yl)propanenitrile. ES-MS m/e: 161.2 (M+H+).

Intermediate IV-32; 2-Methyl-2-phenyl-propionitrile

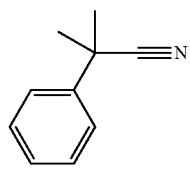

To a stirred solution of phenyl-acetonitrile (10 g, 85.4 mmol) in DMF (500 mL) at 0° C. was added sodium hydride (8.18 g, 50% in oil, 187.8 mmol). After 40 minutes, methyl iodide (18.7 mL, 299 mmol) was added and the reaction mixture stirred at RT overnight. The reaction mixture was poured on an aqueous saturated solution of $NH_4Cl$ and the product extracted with EtOAc. The combined organic phases were dried on $Na_2SO_4$, and a column chromatography (silica gel, EtOAc/Heptane=1/9) gave the title product 6.12 g (49%) as a colorless oil.

Process for Preparation of Intermediates of Formula V

Intermediate V-2; N'-hydroxy-4-methylbenzimidamide

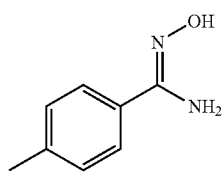

In a 500 ml round bottom flask, hydroxylamine hydrochloride (6.4 g, 92.1 mmol) and sodium bicarbonate (7.74 g, 92.1 mmol) were combined with ethanol (100 ml) and water (20 ml). The suspension was stirred for 15 min. 4-Methylbenzonitrile (9.81 g, 83.7 mmol) was added and the mixture was heated for 5 h at reflux. The reaction was cooled to room temperature. Ethanol was removed by evaporation. The solid residue was suspended in water (100 ml), filtered off and washed with water (3×30 ml) and heptane (3×40 ml). The filter cake was dried in vacuo to yield, N'-hydroxy-4-methylbenzimidamide (10.8 g, 71.9 mmol, 85.9% yield) as light blue solid. Melting point: 146.8-147.1° C. (Lit: 147° C.)

Intermediate V-7; N-Hydroxy-2-phenyl-acetamidine

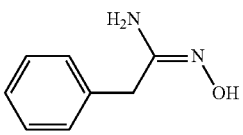

To a solution of the commercially available phenyl-acetonitrile (1.0 g, 8.54 mmol) in ethanol (15 mL) and water (5.0 mL) were added $Na_2CO_3$ (1.81 g, 17.1 mmol) and hydroxylamine hydrochloride (1.19 g, 17.1 mmol). The reaction mixture was heated to 80° C. for 4 hours, poured into 50 mL water and extracted with EtOAc (150 mL). The organic phase was dried over $Na_2SO_4$ and concentrated under vacuo. The crude material was purified by flash chromatography ($CH_2Cl_2$/MeOH 95/5) to afford 1.16 g (90%) of the title compound as a white solid. ES-MS m/e: 151.1 (M+H+).

The following acetamidines were prepared according to the same procedure from the commercially available or previously described phenyl-acetonitrile derivatives as shown in Table 2:

TABLE 2

| Phenyl-acetonitrile derivative | Scale | Reaction time | Yield | Analysis | Structure | Name | Intermediate |
|---|---|---|---|---|---|---|---|
| 2-phenyl-butyronitrile | 5 g | o/n | 93% | ES-MS m/e: 179.1 (M + H+) | (structure) | N-hydroxy-2-phenyl-butyramidine | V-8 |

TABLE 2-continued

| Phenyl-acetonitrile derivative | Scale | Reaction time | Yield | Analysis | Structure | Name | Intermediate |
|---|---|---|---|---|---|---|---|
| (4-chloro-phenyl)-acetonitrile | 4.5 g | 2 h | 66% | ES-MS m/e: 185.1 (M + H+) | 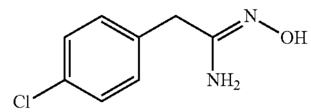 [SMILES: N/C(Cc1ccc(Cl)cc1)=N\O] | 2-(4-chloro-phenyl)-N-hydroxy-acetamidine | V-9 |
| (3-chloro-phenyl)-acetonitrile | 5 g | 2 h | 75% | ES-MS m/e: 185.1 (M + H+) | 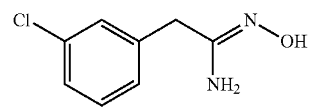 [SMILES: N/C(Cc1cccc(Cl)c1)=N\O] | 2-(3-chloro-phenyl)-N-hydroxy-acetamidine | V-10 |
| (4-fluoro-phenyl)-acetonitrile | 2 g | 2 h | 90% | ES-MS m/e: 169.1 (M + H+) | 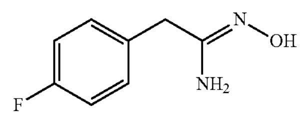 [SMILES: N/C(Cc1ccc(F)cc1)=N\O] | 2-(4-fluoro-phenyl)-N-hydroxy-acetamidine | V-11 |
| (3,4-difluoro-phenyl)-acetonitrile | 2 g | 3 h | 89% | ES-MS m/e: 187.1 (M + H+) | 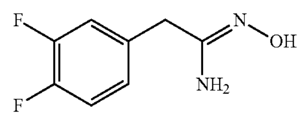 [SMILES: N/C(Cc1ccc(F)c(F)c1)=N\O] | 2-(3,4-Difluoro-phenyl)-N-hydroxy-acetamidine | V-13 |
| 1-(4-fluoro-phenyl)-cyclopropanecarbonitrile | 3 g | o/n | 98% | ES-MS m/e: 195.2 (M + H+) | 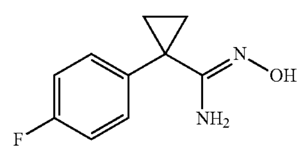 [SMILES: N/C(=N\O)C1(c2ccc(F)cc2)CC1] | 1-(4-Fluoro-phenyl)-N-hydroxy-cyclopropanecarboxamidine | V-15 |
| IV-16 | 4.1 g | o/n | 81% | ES-MS m/e: 197.7 (M + H+) | 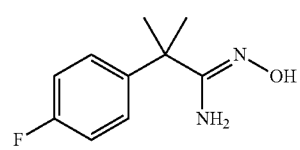 | 2-(4-Fluoro-phenyl)-N-hydroxy-isobutyramidine | V-16 |
| 1-phenyl-cyclopropanecarbonitrile | 10 g | o/n | 72% | ES-MS m/e: 177.1 (M + H+) | 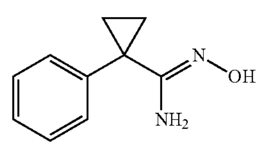 [SMILES: N/C(=N\O)C1(c2ccccc2)CC1] | N-Hydroxy-1-phenyl-cyclopropanecarboxamidine | V-17 |
| 1-(3-chloro-phenyl)-cyclopropanecarbonitrile | 2 g | 5 h | 99% | ES-MS m/e: 211.1 (M + H+) | 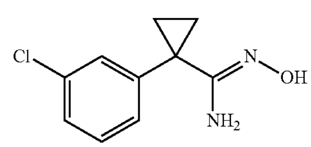 [SMILES: N/C(=N\O)C1(c2cccc(Cl)c2)CC1] | 1-(3-Chloro-phenyl)-N-hydroxy-cyclopropanecarboxamidine | V-18 |
| 1-(4-chloro-phenyl)-cyclopropanecarbonitrile | 3 g | 5 h | 79% | ES-MS m/e: 211.1 (M + H+) | 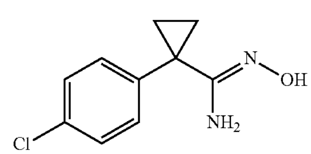 [SMILES: N/C(=N\O)C1(c2ccc(Cl)cc2)CC1] | 1-(4-Chloro-phenyl)-N-hydroxy-cyclopropanecarboxamidine | V-19 |
| (4-chloro-phenyl)-difluoro-acetonitrile | 1 g | 2 h | 80% | ES-MS m/e: 221.1 (M + H+ | 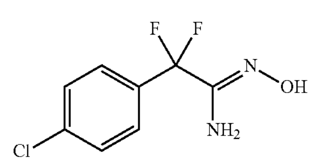 [SMILES: N/C(=N\O)C(F)(F)c1ccc(Cl)cc1] | 2-(4-Chloro-phenyl)-2,2-difluoro-N-hydroxy-acetamidine | V-20 |
| difluoro-(4-fluoro-phenyl)-acetonitrile | 1 g | 4 h | 43% | ES-MS m/e: 205.1 (M + H+) | 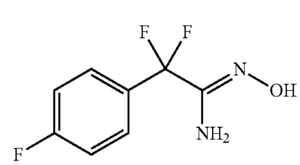 [SMILES: N/C(=N\O)C(F)(F)c1ccc(F)cc1] | 2,2-Difluoro-2-(4-fluoro-phenyl)-N-hydroxy-acetamidine | V-21 |

TABLE 2-continued

| Phenyl-acetonitrile derivative | Scale | Reaction time | Yield | Analysis | Structure | Name | Intermediate |
|---|---|---|---|---|---|---|---|
| IV-22 | 1.3 g | o/n | 47% | 213.1 (M + H+) | 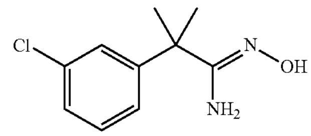 | 2-(3-Chloro-phenyl)-N-hydroxy-isobutyramidine | V-22 |
| difluoro-phenyl-acetonitrile | 2 g | 2 h | 82% | ES-MS m/e: 187.1 (M + H+). | 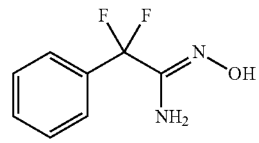 [SMILES: N/C(=N\O)C(F)(F)c1ccccc1] | 2,2-Difluoro-N-hydroxy-2-phenyl-acetamidine | V-23 |
| (2-methyl-pyridin-4-yl)-acetonitrile | 1.07 g | o/n | 86% | ES-MS m/e 166.2 (M + H+) | 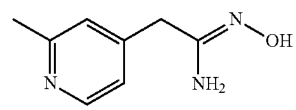 | N-Hydroxy-2-(2-methyl-pyridin-4-yl)-acetamidine | V-26 |
| 4,4,4-trifluorobutanenitrile | 2 g | o/n | 71% | ES-MS m/e 157.1 (M + H+) | 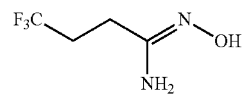 | 4,4,4-trifluoro-N'-hydroxybutanimidamide | V-27 |
| (1S,2S,4R)-bicyclo[2.2.1]heptane-2-carbonitrile | 3.5 g | 5 h | 34% | ES-MS m/e 155.2 (M + H+) | 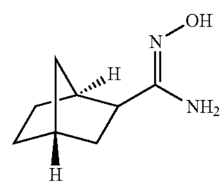 [SMILES: N/C(=N\O)C1C[C@@H]2CC[C@H]1C2] | (1S,4R)-N'-hydroxybicyclo[2.2.1]heptane-2-carboximidamide | V-29 |
| IV-31 | 836 mg | o/n | 60% | | 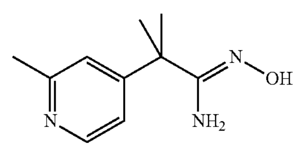 | N'-hydroxy-2-methyl-2-(2-methylpyridin-4-yl)propanimidamide | V-31 |
| IV-32 | 1.62 g | o/n | 41% | ES-MS m/e 179.1 (M + H+) | 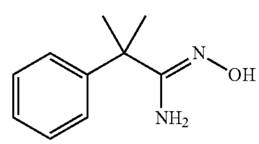 | N-Hydroxy-2-phenyl-isobutyramidine | V-32 |
| ethyl carbonocyanidate | 1.6 g | o/n | 89% | | 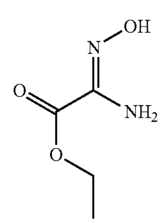 | ethyl 2-amino-2-(hydroxyimino)acetate | V-33 |
| 3-methoxypropanenitrile | 2 g | o/n | 10% | | 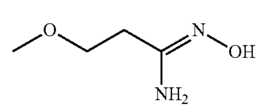 | N'-hydroxy-3-methoxypropanimidamide | V-39 |

Intermediate V-24;
2-cyclopropyl-N'-hydroxyacetimidamide

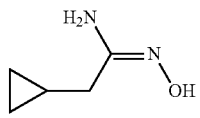

In a 250 mL round-bottomed flask, cyclopropylacetonitrile (5 g, 61.6 mmol), sodium carbonate (13.1 g, 123 mmol) and hydroxylamine hydrochloride (8.57 g, 123 mmol) were combined with ethanol (120 ml) and water (40.0 ml). The reaction mixture was heated to 80° C. and stirred overnight. The ethanol was evaporated. Then, the thick white mixture was poured into EtOAc and extracted with water. The organic phase dried over $Na_2SO_4$ and evaporated to give 7.04 g of crude 2-cyclopropyl-N'-hydroxyacetimidamide which was used in the next step without further purification.

The following acetamidines were prepared according to the same procedure from the commercially available phenylacetonitrile derivatives as shown in Table 3:

TABLE 3

| Phenyl-acetonitrile derivative | Scale | Reaction time | Yield | Structure | Name | Intermediate |
|---|---|---|---|---|---|---|
| 3,3,3-trifluoropropionitrile | 4.33 g | o/n | 13% | F₃C-C(=N-OH)-NH₂ | 3,3,3-trifluoro-N'-hydroxypropanimidamide | V-25 |
| butyronitrile | 2 g | o/n | 30% | CH₃CH₂CH₂-C(=N-OH)-NH₂ | N'-hydroxybutyrimidamide | V-34 |
| pentanenitrile | 2 g | o/n | 60% | CH₃(CH₂)₃-C(=N-OH)-NH₂ | N'-hydroxypentanimidamide | V-35 |

Process for Preparation Intermediates of Formula VI

Intermediate VI-7; 3-Benzyl-5-trichloromethyl-[1,2,4]oxadiazole

To N-hydroxy-2-phenyl-acetamidine (1.14 g, 7.59 mmol) were added trichloroacetic anhydride (2.91 mL, 15.9 mmol) and trichloroacetic acid (4.96 g). The reaction mixture was heated to 115° C. for 20 minutes, cooled down to RT, diluted with EtOAc (100 mL), washed several times with water, and then with an aqueous solution of $NaHCO_3$. The organic phase was dried over $Na_2SO_4$, concentrated under vacuo and the resulting crude material was purified by chromatography (silica gel, EtOAc/Heptane: 1/6) to give 1.66 g (79%) as a light yellow oil.

The following 5-trichloromethyl-[1,2,4]oxadiazole intermediates were prepared according to the same procedure from the commercially available or previously described amidine derivatives as shown in Table 4:

TABLE 4

| Phenyl-acetonitrile derivatives | Scale | Reaction time | Yield | Analysis | Structure | Name | Intermediate |
|---|---|---|---|---|---|---|---|
| V-8 | 5.40 g | 30 min | 95% | ES-MS m/e: 305.0/306.9 (M + H+) | 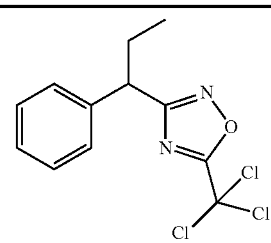 | 3-(1-phenylpropyl)-5-(trichloromethyl)-1,2,4-oxadiazole | VI-8 |

TABLE 4-continued

| Phenyl-acetonitrile derivatives | Scale | Reaction time | Yield | Analysis | Structure | Name | Intermediate |
|---|---|---|---|---|---|---|---|
| V-9 | 2.0 g | 20 min | 73% | | 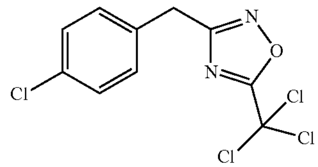 [SMILES: Clc1ccc(Cc2noc(C(Cl)(Cl)Cl)n2)cc1] | 3-(4-chlorobenzyl)-5-(trichloromethyl)-1,2,4-oxadiazole | VI-9 |
| V-10 | 4.56 g | 30 min | 77% | | 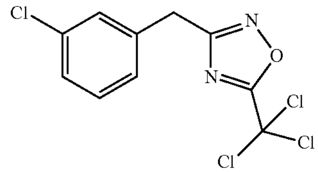 [SMILES: Clc1cccc(Cc2noc(C(Cl)(Cl)Cl)n2)c1] | 3-(3-chlorobenzyl)-5-(trichloromethyl)-1,2,4-oxadiazole | VI-10 |
| V-11 | 2.48 g | 30 min | 73% | ES-MS m/e: 294 (M + H+) | 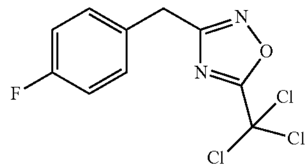 [SMILES: Fc1ccc(Cc2noc(C(Cl)(Cl)Cl)n2)cc1] | 3-(4-fluorobenzyl)-5-(trichloromethyl)-1,2,4-oxadiazole | VI-11 |
| V-13 | 492 mg | 30 min | 38% | Light yellow oil | 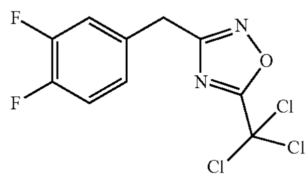 [SMILES: Fc1ccc(Cc2noc(C(Cl)(Cl)Cl)n2)cc1F] | 3-(3,4-Difluoro-benzyl)-5-trichloromethyl-[1,2,4]oxadiazole | VI-13 |
| V-16 | 2.0 g | 40 min | 88% | Light yellow oil | 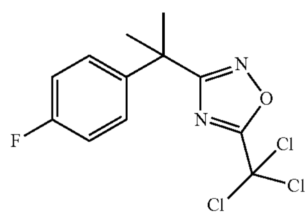 [SMILES: CC(C)(c1ccc(F)cc1)c1noc(C(Cl)(Cl)Cl)n1] | 3-[1-(4-Fluoro-phenyl)-1-methyl-ethyl]-5-trichloromethyl-[1,2,4]oxadiazole | VI-16 |
| V-17 | 3.50 g | 1 h | | Waxy oil | 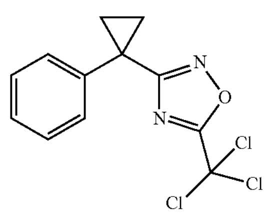 [SMILES: ClC(Cl)(Cl)c1nc(C2(c3ccccc3)CC2)no1] | 3-(1-Phenyl-cyclopropyl)-5-trichloromethyl-[1,2,4]oxadiazole | VI-17 |
| V-18 | 2.18 g | 1 h | 72% | Waxy oil | 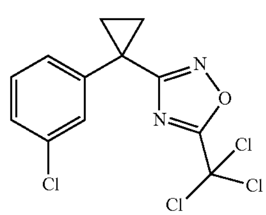 [SMILES: Clc1cccc(C2(c3noc(C(Cl)(Cl)Cl)n3)CC2)c1] | 3-[1-(3-Chloro-phenyl)-cyclopropyl]-5-trichloromethyl-[1,2,4]oxadiazole | VI-18 |
| V-19 | 1.4 g | 90 min | 77% | Waxy oil | 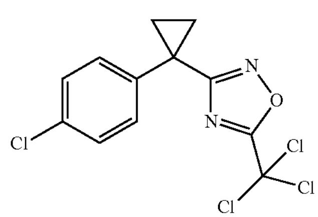 [SMILES: Clc1ccc(C2(c3noc(C(Cl)(Cl)Cl)n3)CC2)cc1] | 3-[1-(4-Chloro-phenyl)-cyclopropyl]-5-trichloromethyl-[1,2,4]oxadiazole | VI-19 |

TABLE 4-continued

| Phenyl-acetonitrile derivatives | Scale | Reaction time | Yield | Analysis | Structure | Name | Intermediate |
|---|---|---|---|---|---|---|---|
| V-20 | 940 mg | 20 min | 80% | White solid | 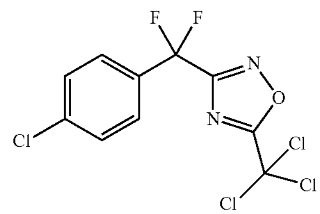 [SMILES: FC(F)(c1ccc(Cl)cc1)c1noc(C(Cl)(Cl)Cl)n1] | 3-[(4-Chloro-phenyl)-difluoro-methyl]-5-trichloromethyl-[1,2,4]oxadiazole | VI-20 |
| V-21 | 520 mg | 30 min | 69% | Colorless oil | 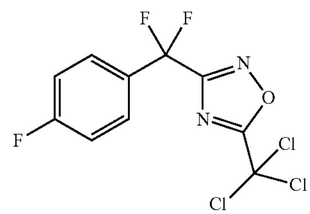 [SMILES: Fc1ccc(C(F)(F)c2noc(C(Cl)(Cl)Cl)n2)cc1] | 3-[Difluoro-(4-fluoro-phenyl)-methyl]-5-trichloromethyl-[1,2,4]oxadiazole | VI-21 |
| V-22 | 715 mg | 30 min | 82% | White solid | 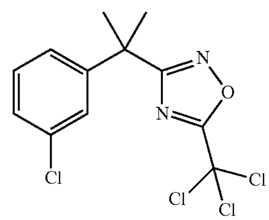 [SMILES: CC(C)(c1cccc(Cl)c1)c1noc(C(Cl)(Cl)Cl)n1] | 3-[1-(3-Chloro-phenyl)-1-methyl-ethyl]-5-trichloromethyl-[1,2,4]oxadiazole | VI-22 |
| V-23 | 1.90 g | 40 min | 92% | White solid | 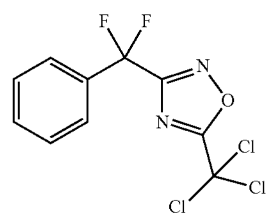 [SMILES: FC(F)(c1ccccc1)c1noc(C(Cl)(Cl)Cl)n1] | 3-(Difluoro-phenyl-methyl)-5-trichloromethyl-[1,2,4]oxadiazole | VI-23 |
| V-26 | 1.10 g | 70 min | 11% | Waxy oil | 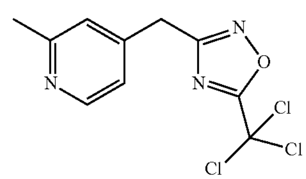 [SMILES: Cc1cc(Cc2noc(C(Cl)(Cl)Cl)n2)ccn1] | 2-Methyl-4-(5-trichloromethyl-[1,2,4]oxadiazol-3-ylmethyl)-pyridine | VI-26 |
| V-27 | 1.75 g | 60 min | 90% | ES-MS m/e: 157.1 (M + H+) | 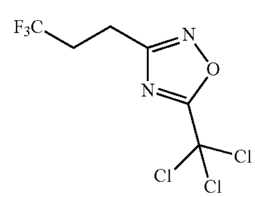 [SMILES: FC(F)(F)CCc1noc(C(Cl)(Cl)Cl)n1] | 5-(trichloromethyl)-3-(3,3,3-trifluoropropyl)-1,2,4-oxadiazole | VI-27 |
| V-29 | 1.4 g | 20 min | 74% | Colorless oil | 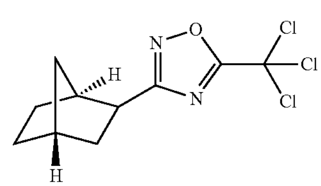 [SMILES: ClC(Cl)(Cl)c1nc(C2C[C@@H]3CC[C@H]2C3)no1] | 3-((1S,4R)-bicyclo[2.2.1]heptan-2-yl)-5-(trichloromethyl)-1,2,4-oxadiazole | VI-29 |

TABLE 4-continued

| Phenyl-acetonitrile derivatives | Scale | Reaction time | Yield | Analysis | Structure | Name | Intermediate |
|---|---|---|---|---|---|---|---|
| N'-hydroxy-cyclopropane carboximidamide | 900 mg | 30 min | 68% | | 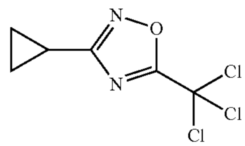 [SMILES: ClC(Cl)(Cl)c1nc(C2CC2)no1] | 3-cyclopropyl-5-(trichloromethyl)-1,2,4-oxadiazole | VI-30 |
| V-31 | 200 mg | 15 min | 87% | Colorless oil | 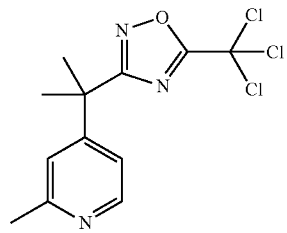 [SMILES: Cc1cc(C(C)(C)c2noc(C(Cl)(Cl)Cl)n2)ccn1] | 3-(2-(2-methylpyridin-4-yl)propan-2-yl)-5-(trichloromethyl)-1,2,4-oxadiazole | VI-31 |
| V-32 | 820 mg | 30 min | 82% | Colorless oil | 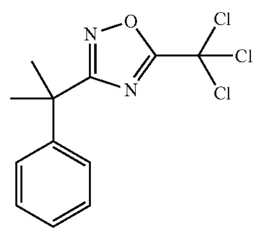 [SMILES: CC(C)(c1ccccc1)c1noc(C(Cl)(Cl)Cl)n1] | 3-(1-Methyl-1-phenyl-ethyl)-5-trichloromethyl-[1,2,4]oxadiazole | VI-32 |
| V-33 | 2.5 g | 15 min | 92% | Yellow oil | 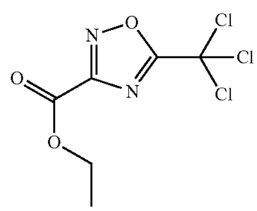 | ethyl 5-(trichloromethyl)-1,2,4-oxadiazole-3-carboxylate | VI-33 |
| V-34 | 800 mg | 45 min | 49% | | 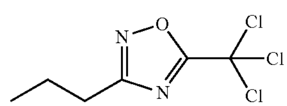 | 3-propyl-5-(trichloromethyl)-1,2,4-oxadiazole | VI-34 |
| V-35 | 2.3 g | 30 min | 89% | | 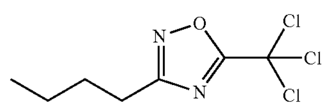 | 3-butyl-5-(trichloromethyl)-1,2,4-oxadiazole | VI-35 |
| N'-hydroxy-pivalimidamide | 500 mg | 60 min | 54% | | 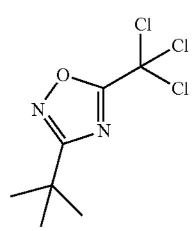 | 3-(tert-butyl)-5-(trichloromethyl)-1,2,4-oxadiazole | VI-36 |
| N'-hydroxy-cyclohexane carboximidamide | 500 mg | 60 min | 51% | | 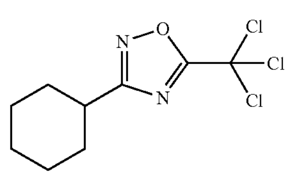 [SMILES: ClC(Cl)(Cl)c1nc(C2CCCCC2)no1] | 3-cyclohexyl-5-(trichloromethyl)-1,2,4-oxadiazole | VI-37 |

TABLE 4-continued

| Phenyl-acetonitrile derivatives | Scale | Reaction time | Yield Analysis | Structure | Name | Intermediate |
|---|---|---|---|---|---|---|
| N'-hydroxyiso-butyrimidamide | 300 mg | 30 min | 41% | 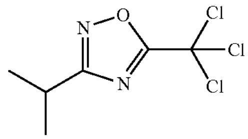 | 3-isopropyl-5-(trichloromethyl)-1,2,4-oxadiazole | VI-38 |
| V-39 | 250 mg | 30 min | 60% | 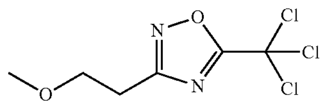 | 3-(2-methoxyethyl)-5-(trichloromethyl)-1,2,4-oxadiazole | VI-39 |

Intermediate VI-24; 3-(Cyclopropylmethyl)-5-(trichloromethyl)-1,2,4-oxadiazole

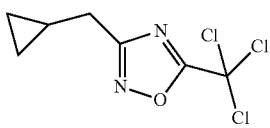 [SMILES: ClC(Cl)(Cl)c1nc(CC2CC2)no1]

A suspension of 2-cyclopropyl-N-hydroxy-acetamidine V-24 (625 mg, 5.48 mmol), trichloroacetic acid (3.58 g, 21.9 mmol) and trichloroacetic anhydride (3.55 g, 2.1 ml, 11.5 mmol) under argon atmosphere was heated to 110° C. for 40 minutes. The resulting brown solution was diluted with water (200 ml) and neutralized with a saturated solution of NaHCO$_3$ and extracted with ethyl acetate. The combined organic layers were washed with brine, dried over Na$_2$SO$_4$ and evaporated to give 1.36 g of a dark brown oil which was used in the next step without further purification.

The following 5-trichloromethyl-[1,2,4]oxadiazole intermediates were prepared according to the same procedure from the commercially available or previously described amidine derivatives as shown in Table 5:

Process for Preparation Intermediates of Formula VIII

Intermediate VIII-1; 3-Phenyl-4H-[1,2,4]oxadiazol-5-one

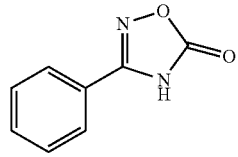 [SMILES: O=c1[nH]c(-c2ccccc2)no1]

To a solution of N-hydroxy-benzamidine (5.0 g, 36.7 mmol) in acetonitrile (150 mL) was added 1,1'-carbonyldiimidazole (6.55 g, 40.5 mmol). The reaction mixture was heated to reflux for five hours, cooled down to RT, concentrated under vacuo and purified by column chromatography (EtOAc/Heptane 4/1) to give 3.8 g (64%) of the title product as a white solid.

The following oxadiazol-5-one intermediates were prepared according to the same procedure from the commercially available or previously described amidine derivatives as shown in Table 6:

TABLE 5

| Phenyl-acetonitrile derivative | Scale | Reaction time | Yield | Structure | Name | Intermediate |
|---|---|---|---|---|---|---|
| V-25 | 718 mg | 60 min | 96% | 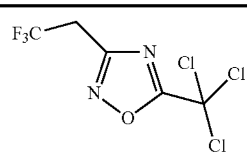 | 5-(trichloromethyl)-3-(2,2,2-trifluoroethyl)-1,2,4-oxadiazole | VI-25 |

TABLE 6

| Amidine derivative | Scale | Reaction time | Yield | Analysis | Structure | Name | Intermediate |
|---|---|---|---|---|---|---|---|
| V-2 | 5 g | 15 h | 56.6% | ES-MS m/e: 175.0 (M − H+) | 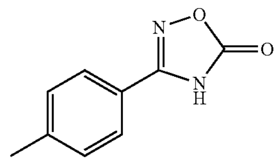 | 3-p-Tolyl-4H-[1,2,4]oxadiazol-5-one | VIII-2 |
| 4-chloro-N-hydroxy-benzamidine | 5 g | 5 h | 46% | ES-MS m/e: 195.0 (M − H+) | 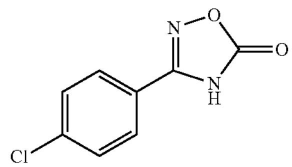 [SMILES: O=c1[nH]c(-c2ccc(Cl)cc2)no1] | 3-(4-Chloro-phenyl)-4H-[1,2,4]oxadiazol-5-one | VIII-3 |
| 3-chloro-N-hydroxy-benzamidine | 4 g | 6 h | 32% | ES-MS m/e: 195.1 (M − H+) | 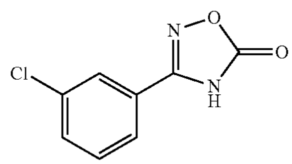 [SMILES: O=c1[nH]c(-c2cccc(Cl)c2)no1] | 3-(3-Chloro-phenyl)-4H-[1,2,4]oxadiazol-5-one | VIII-4 |
| 3-fluoro-N-hydroxy-benzamidine | 4 g | 5 h | 38% | ES-MS m/e: 179.0 (M − H+) | 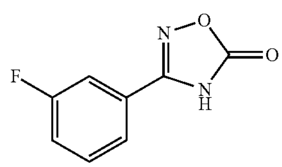 [SMILES: O=c1[nH]c(-c2cccc(F)c2)no1] | 3-(3-Fluoro-phenyl)-4H-[1,2,4]oxadiazol-5-one | VIII-5 |
| 3,4-difluoro-N-hydroxy-benzamidine | 5 g | 5 h | 25% | ES-MS m/e: 197.1 (M − H+) | 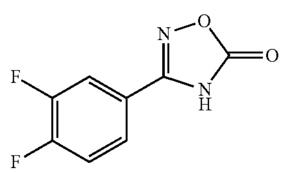 [SMILES: O=c1[nH]c(-c2ccc(F)c(F)c2)no1] | 3-(3,4-Difluoro-phenyl)-4H-[1,2,4]oxadiazol-5-one | VIII-6 |
| N-hydroxy-4-trifluoromethyl-benzamidine | 1 g | 5 h | 54% | ES-MS m/e: 229.2 (M − H+) | 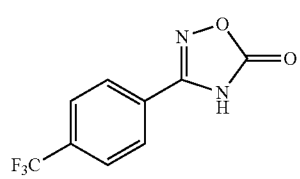 [SMILES: O=c1[nH]c(-c2ccc(C(F)(F)F)cc2)no1] | 3-(4-Trifluoromethyl-phenyl)-4H-[1,2,4]oxadiazol-5-one | VIII-28 |

Intermediate VIII-15; 3-[1-(4-Fluoro-phenyl)-cyclopropyl]-4H-[1,2,4]oxadiazol-5-one

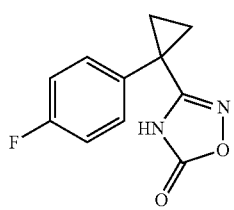 [SMILES: O=c1[nH]c(C2(c3ccc(F)cc3)CC2)no1]

1-(4-Fluoro-phenyl)-N-hydroxy-cyclopropanecarboxamidine (1.66 g, 8.55 mmol) and Et$_3$N (1.79 mL, 12.8 mmol) were combined with CH$_2$Cl$_2$ (16 mL) to give a colorless solution. Ethyl chloroformate (0.83 mL, 8.72 mmol) was added dropwise and stirred for one hour. The reaction was poured on CH$_2$Cl$_2$ (100 mL) and washed with water. The organic layer was dried over Na$_2$SO$_4$, concentrated under vacuo. The crude residue was dissolved in toluene (30 mL) and heated to 125° C. overnight. Concentration under vacuo and column flash chromatography afforded 1.4 g (74%) of the title product as a white solid.

Process for Preparation Intermediates of Formula VII

Intermediate VII-1; 4-(3-Phenyl-[1,2,4]oxadiazol-5-yl)-piperazine-1-carboxylic acid tert-butyl ester

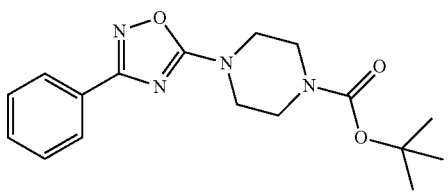 [SMILES: CC(C)(C)OC(=O)N1CCN(c2nc(-c3ccccc3)no2)CC1]

To a solution of 3-phenyl-4H-[1,2,4]oxadiazol-5-one VIII-1 (3.60 g, 22.2 mmol) in DMF (125 mL) was added iPr$_2$NEt (19.4 mL, 111 mmol), piperazine-1-carboxylic acid tert-butyl ester (8.27 g, 44.4 mmol) and BOP (10.8 g, 24.4 mmol). The reaction mixture was stirred at reflux for 24 hours. The volatiles were removed under vacuo, and the residue taken up in EtOAC and washed with a saturated aqueous solution of NaHCO$_3$. The organic phase was dried over Na$_2$SO$_4$, concentrated under vacuo, and a column chromatography (EtOAc/Heptane 1/4) gave 2.1 g (28%) of the title product as a white powder.

The following oxadiazol-5-one intermediates were prepared according to the same procedure from the commercially available or previously described oxazol-5-one derivatives as shown in Table 7:

TABLE 7

| Amidine derivative | Scale | Reaction time | Yield | Analysis | Structure | Name | Intermediate |
|---|---|---|---|---|---|---|---|
| VIII-3 | 1.7 g | 24 h | 27% | ES-MS m/e: 365.1 (M + H+). | 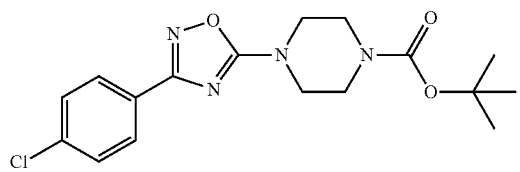 [SMILES: CC(C)(C)OC(=O)N1CCN(c2nc(-c3ccc(Cl)cc3)no2)CC1] | 4-[3-(4-Chlorophenyl)-[1,2,4]oxadiazol-5-yl]-piperazine-1-carboxylic acid tert-butyl ester | VII-3 |
| VIII-4 | 1.5 g | 24 h | 26% | White powder | 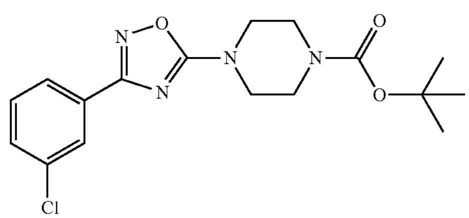 [SMILES: CC(C)(C)OC(=O)N1CCN(c2nc(-c3cccc(Cl)c3)no2)CC1] | 4-[3-(3-Chlorophenyl)-[1,2,4]oxadiazol-5-yl]-piperazine-1-carboxylic acid tert-butyl ester | VII-4 |
| VIII-5 | 1.6 g | 20 h | 23% | White powder | 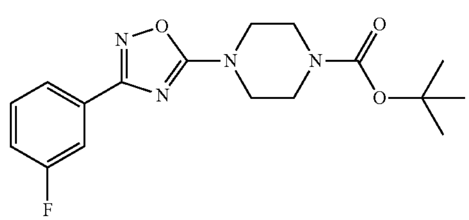 | tert-butyl 4-(3-(3-fluorophenyl)-1,2,4-oxadiazol-5-yl)piperazine-1-carboxylate | VII-5 |
| VIII-6 | 1.43 g | 24 h | 12% | White powder | 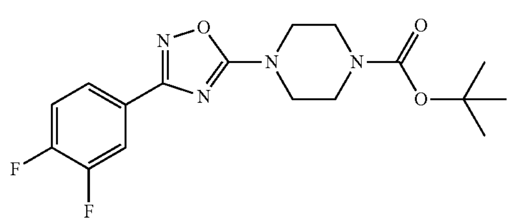 [SMILES: CC(C)(C)OC(=O)N1CCN(c2nc(-c3ccc(F)c(F)c3)no2)CC1] | 4-[3-(3,4-Difluorophenyl)-[1,2,4]oxadiazol-5-yl]-piperazine-1-carboxylic acid tert-butyl ester | VII-6 |

TABLE 7-continued

| Amidine derivative | Scale | Reaction time | Yield | Analysis | Structure | Name | Intermediate |
|---|---|---|---|---|---|---|---|
| 3-(3-fluoro-benzyl)-4H-[1,2,4]oxadiazol-5-one | 1.40 g | o/n | 28% | ES-MS m/e: 363.3 (M + H+) | | 4-[3-(3-Fluoro-benzyl)-[1,2,4]oxadiazol-5-yl]-piperazine-1-carboxylic acid tert-butyl ester | VII-12 |
| VIII-15 | 1.4 g | o/n | 36% | White powder | 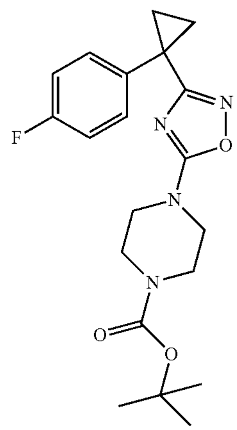 [SMILES: CC(C)(C)OC(=O)N1CCN(c2nc(C3(c4ccc(F)cc4)CC3)no2)CC1] | 4-{3-[1-(4-Fluoro-phenyl)-cyclopropyl]-[1,2,4]oxadiazol-5-yl}-piperazine-1-carboxylic acid tert-butyl ester | VII-15 |
| VIII-28 | 600 mg | 24 h | 9% | White powder | 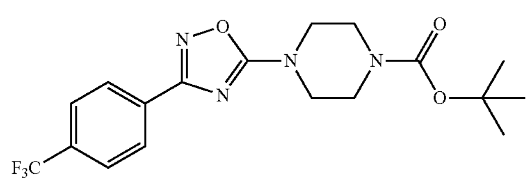 [SMILES: CC(C)(C)OC(=O)N1CCN(c2nc(-c3ccc(C(F)(F)F)cc3)no2)CC1] | 4-[3-(4-Trifluoromethyl-phenyl)-[1,2,4]oxadiazol-5-yl]-piperazine-1-carboxylic acid tert-butyl ester | VII-28 |

Process for Preparation Intermediates of Formula XII

Intermediate XII-2; 1-(3-p-Tolyl-[1,2,4]oxadiazol-5-yl)-piperazine

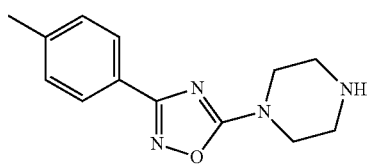 [SMILES: Cc1ccc(-c2noc(N3CCNCC3)n2)cc1]

3-p-Tolyl-4H-[1,2,4]oxadiazol-5-one VIII-2 (3.35 g, 19.0 mmol) was suspended in POCl₃ (6.2 mL, 66.6 mmol) and pyridine (0.769 mL, 9.51 mmol) was added dropwise. Upon heating to reflux, the reaction mixture turned into a brown solution. After 22 hours, it was cooled to RT and carefully poured onto ice, and the product extracted with EtOAc (2 times 50 mL). The organic phase was dried on Na₂SO₄, concentrated under vacuo, and a column chromatography (EtOAc/Heptane: 1:9 to 3:7) gave 2.77 g (75%) of 5-chloro-3-p-tolyl-[1,2,4]oxadiazole as a light yellow oil.

To a solution of 5-chloro-3-p-tolyl-[1,2,4]oxadiazole (0.95 g, 4.88 mmol) in EtOH (10 mL), was added iPr₂NEt (2.56 mL, 14.6 mmol) and piperazine (0.681 g, 7.91 mmol). The resulting mixture was heated to reflux for 30 minutes, cooled to RT, concentrated under vacuo. A column chromatography (EtOAc/heptane 3/7 to EtOAc/MeOH 9/1) gave 360 mg (30%) of the title product as a light yellow viscous oil. ES-MS m/e: 245.4 (M–H+).

Intermediate XII-3; 1-[3-(4-Chloro-phenyl)-[1,2,4]oxadiazol-5-yl]-piperazine

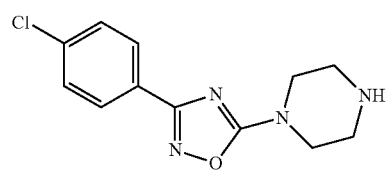 [SMILES: Clc1ccc(-c2noc(N3CCNCC3)n2)cc1]

To a solution of 4-[3-(4-chloro-phenyl)-[1,2,4]oxadiazol-5-yl]-piperazine-1-carboxylic acid tert-butyl ester VII-3 (0.85 g, 2.33 mmol) in CH$_2$Cl$_2$ (18 mL) was added TFA (4 mL). After stirring 2 hours at RT, the reaction mixture was diluted with CH$_2$Cl$_2$ (100 mL) and a saturated aqueous solution of NaHCO$_3$ was added until pH=8. The organic phase was dried over Na$_2$SO$_4$, concentrated under vacuo, and a column chromatography (CH$_2$Cl$_2$/MeOH 9/1) gave 0.56 g (90%) of the title product as a white solid. ES-MS m/e: 265.1 (M–H$^+$).

The following intermediates of formula XII were prepared according to the same procedure from intermediates VII previously described as shown in Table 8:

TABLE 8

| Intermediate | Scale | Reaction time | Yield | Analysis | Structure | Name | Intermediate |
|---|---|---|---|---|---|---|---|
| VII-1 | 2.1 g | 2 h | 52% | ES-MS m/e: 231.2 (M – H$^+$) | 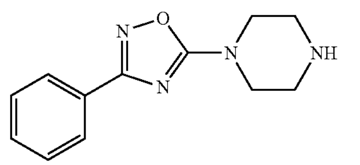 [SMILES: c1ccc(-c2noc(N3CCNCC3)n2)cc1] | 1-(3-Phenyl-[1,2,4]oxadiazol-5-yl)-piperazine | XII-1 |
| VII-4 | 724 mg | 2 h | 58% | ES-MS m/e: 265.1 (M – H$^+$) | 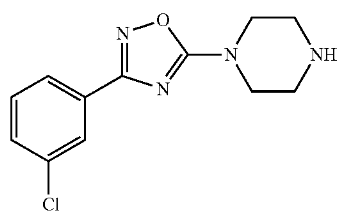 [SMILES: Clc1cccc(-c2noc(N3CCNCC3)n2)c1] | 1-[3-(3-Chloro-phenyl)-[1,2,4]oxadiazol-5-yl]-piperazine | XII-4 |
| VII-5 | 690 mg | 2 h | 37% | ES-MS m/e: 249.1 (M – H$^+$) | 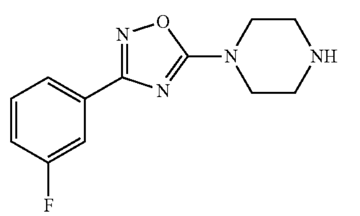 [SMILES: Fc1cccc(-c2noc(N3CCNCC3)n2)c1] | 1-[3-(3-Fluoro-phenyl)-[1,2,4]oxadiazol-5-yl]-piperazine | XII-5 |
| VII-6 | 323 mg | 2 h | 20% | ES-MS m/e: 267.1 (M – H$^+$) | 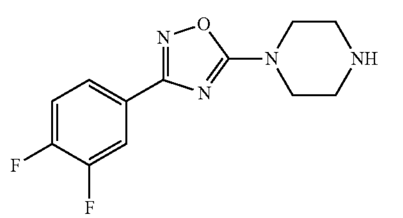 [SMILES: Fc1ccc(-c2noc(N3CCNCC3)n2)cc1F] | 1-[3-(3,4-Difluoro-phenyl)-[1,2,4]oxadiazol-5-yl]-piperazine | XII-6 |
| VII-12 | 750 mg | 1 h | 97% | ES-MS m/e: 263.5 (M + H$^+$) | 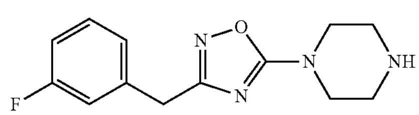 [SMILES: Fc1cccc(Cc2noc(N3CCNCC3)n2)c1] | 1-[3-(3-Fluoro-benzyl)-[1,2,4]oxadiazol-5-yl]-piperazine | XII-12 |
| VII-15 | 900 mg | 1 h | 98% | ES-MS m/e: 289.1 (M + H$^+$) | 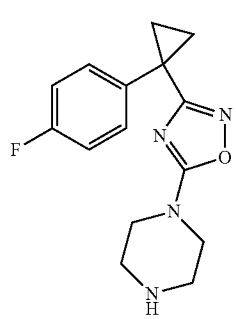 [SMILES: Fc1ccc(C2(c3noc(N4CCNCC4)n3)CC2)cc1] | 1-{3-[1-(4-Fluoro-phenyl)-cyclopropyl]-[1,2,4]oxadiazol-5-yl}-piperazine | XII-15 |

TABLE 8-continued

| Intermediate | Scale | Reaction time | Yield | Analysis | Structure | Name | Intermediate |
|---|---|---|---|---|---|---|---|
| VII-28 | 90 mg | 2 h | 96% | ES-MS m/e: 299.1 (M − H⁺) | 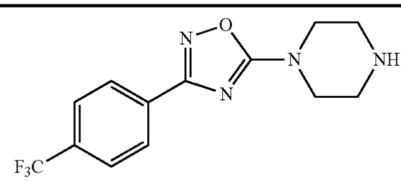 | 1-[3-(4-Trifluoromethyl-phenyl)-[1,2,4]oxadiazol-5-yl]-piperazine | XII-28 |

Intermediate XII-7; 1-(3-Benzyl-[1,2,4]oxadiazol-5-yl)-piperazine

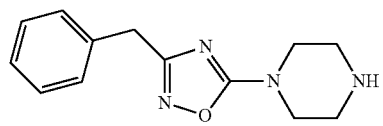 [SMILES: c1ccc(Cc2noc(N3CCNCC3)n2)cc1]

To a solution of 3-benzyl-5-trichloromethyl-[1,2,4]oxadiazole VI-7 (1.46 g, 5.26 mmol) in EtOH (20 mL) was added piperazine (2.72 g, 31.6 mmol). The reaction mixture was heated to 85° C. for 4 hours, cooled down to RT, and all volatiles evaporated. The crude residue was purified on column chromatography (CH$_2$Cl$_2$/MeOH: 9/1) to give 0.79 g (62%) of the title product as a light yellow oil. ES-MS m/e: 245.2 (M+H⁺).

The following intermediates of formula XII were prepared according to the same procedure from intermediates VI previously described as shown in Table 9:

TABLE 9

| Intermediate | Scale | Reaction time | Yield | Analysis | Structure | Name | Intermediate |
|---|---|---|---|---|---|---|---|
| VI-8 | 8.8 g | 6 h | 20% | ES-MS m/e: 273.2(M + H+) | 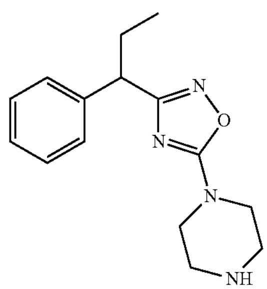 [SMILES: CCC(c1ccccc1)c1noc(N2CCNCC2)n1] | 3-(1-phenylpropyl)-5-(piperazin-1-yl)-1,2,4-oxadiazole | XII-8 |
| VI-9 | 2.448 g | 2.5 h | 51% | ES-MS m/e: 279.1(M + H+) | 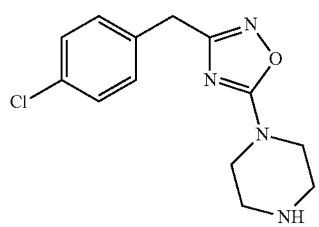 [SMILES: Clc1ccc(Cc2noc(N3CCNCC3)n2)cc1] | 1-[3-(4-Chloro-benzyl)-[1,2,4]oxadiazol-5-yl]-piperazine | XII-9 |
| VI-10 | 3.0 g | 2.5 h | 69% | ES-MS m/e: 279.2 (M + H+) | 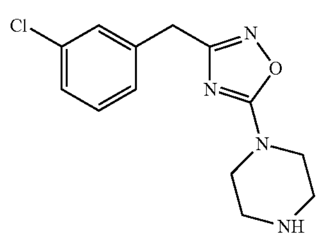 [SMILES: Clc1cccc(Cc2noc(N3CCNCC3)n2)c1] | 1-[3-(3-Chloro-benzyl)-[1,2,4]oxadiazol-5-yl]-piperazine | XII-10 |

TABLE 9-continued

| Intermediate | Scale | Reaction time | Yield | Analysis | Structure | Name | Intermediate |
|---|---|---|---|---|---|---|---|
| VI-11 | 2.448 g | 2.5 h | 51% | ES-MS m/e: 263.5 (M + H$^+$) | 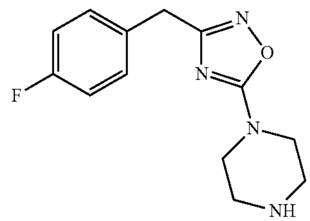 [SMILES: Fc1ccc(Cc2noc(N3CCNCC3)n2)cc1] | 3-(4-fluorobenzyl)-5-(piperazin-1-yl)-1,2,4-oxadiazole | XII-11 |
| VI-13 | 313 mg | 3 h | 68% | ES-MS m/e: 281.2 (M + H+) | 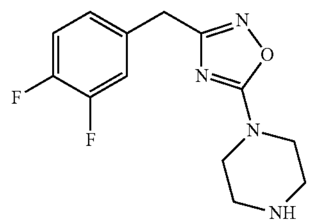 [SMILES: Fc1ccc(Cc2noc(N3CCNCC3)n2)cc1F] | 1-[3-(3,4-Difluoro-benzyl)-[1,2,4]oxadiazol-5-yl]-piperazine | XII-13 |
| VI-16 | 1.50 g | 7 h | 20% | ES-MS m/e: 291.1 (M + H+) | 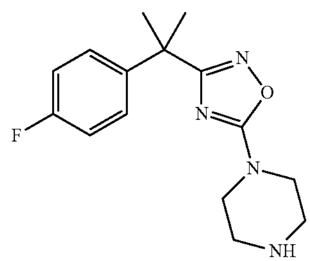 [SMILES: CC(C)(c1ccc(F)cc1)c1noc(N2CCNCC2)n1] | 1-{3-[1-(4-Fluoro-phenyl)-1-methyl-ethyl]-[1,2,4]oxadiazol-5-yl}-piperazine | XII-16 |
| VI-17 | 5.13 g | o/n | 47% over 2 steps | ES-MS m/e: 271.3 (M + H+) | 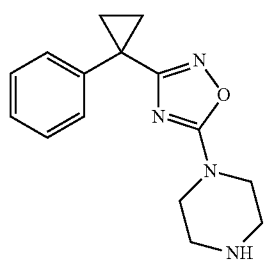 [SMILES: c1ccc(C2(c3noc(N4CCNCC4)n3)CC2)cc1] | 1-[3-(1-Phenyl-cyclopropyl)-[1,2,4]oxadiazol-5-yl]-piperazine | XII-17 |
| VI-18 | 2.54 g | o/n | 68% | ES-MS m/e: 305.1 (M + H+) | 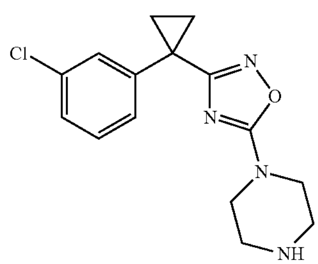 [SMILES: Clc1cccc(C2(c3noc(N4CCNCC4)n3)CC2)c1] | 1-{3-[1-(3-Chloro-phenyl)-cyclopropyl]-[1,2,4]oxadiazol-5-yl}-piperazine | XII-18 |
| VI-19 | 1.74 g | 5 h | 49% | ES-MS m/e: 305.1 (M + H+) | 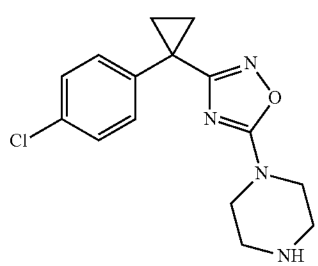 [SMILES: Clc1ccc(C2(c3noc(N4CCNCC4)n3)CC2)cc1] | 1-{3-[1-(4-Chloro-phenyl)-cyclopropyl]-[1,2,4]oxadiazol-5-yl}-piperazine | XII-19 |

TABLE 9-continued

| Intermediate | Scale | Reaction time | Yield | Analysis | Structure | Name | Intermediate |
|---|---|---|---|---|---|---|---|
| VI-20 | 1.18 g | 1 h | 89% | ES-MS m/e: 315.0 (M + H+) | 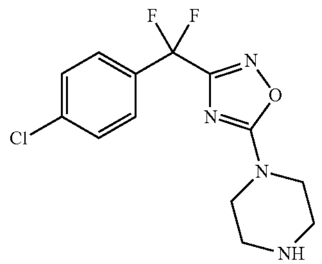 [SMILES: FC(F)(c1ccc(Cl)cc1)c1noc(N2CCNCC2)n1] | 1-{3-[(4-Chloro-phenyl)-difluoro-methyl]-[1,2,4]oxadiazol-5-yl}-piperazine | XII-20 |
| VI-21 | 0.55 g | 2 h | 89% | ES-MS m/e: 299.1 (M + H+) | 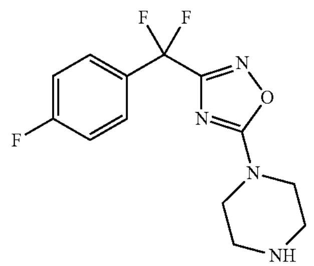 [SMILES: Fc1ccc(C(F)(F)c2noc(N3CCNCC3)n2)cc1] | 1-{3-[Difluoro-(4-fluoro-phenyl)-methyl]-[1,2,4]oxadiazol-5-yl}-piperazine | XII-21 |
| VI-22 | 0.93 g | 4 h | 15% | ES-MS m/e: 307.2 (M + H+) | 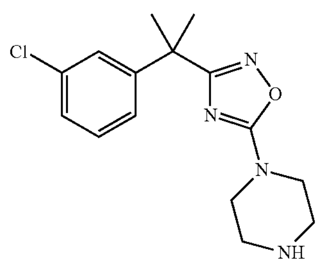 [SMILES: CC(C)(c1cccc(Cl)c1)c1noc(N2CCNCC2)n1] | 1-{3-[1-(3-Chloro-phenyl)-1-methyl-ethyl]-[1,2,4]oxadiazol-5-yl}-piperazine | XII-22 |
| VI-23 | 2.94 g | 15 min | 59% | ES-MS m/e: 281.1 (M + H+) | 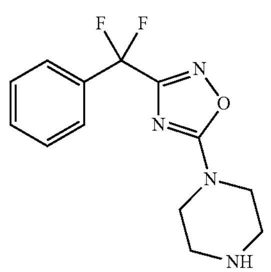 [SMILES: FC(F)(c1ccccc1)c1noc(N2CCNCC2)n1] | 1-[3-(Difluoro-phenyl-methyl)-[1,2,4]oxadiazol-5-yl]-piperazine | XII-23 |
| VI-24 | 1.5 g | 4 h | 20% | | 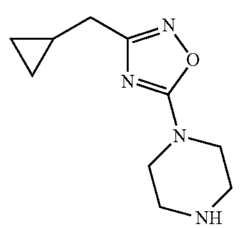 [SMILES: C1CN(c2nc(CC3CC3)no2)CCN1] | 3-(cyclopropylmethyl)-5-(piperazin-1-yl)-1,2,4-oxadiazole | XII-24 |
| VI-25 | 1.31 g | 4 h (+o/n at 50° C.) | 43% | Light yellow oil | 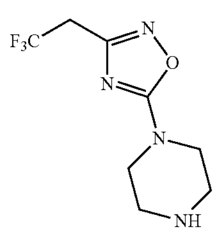 [SMILES: FC(F)(F)Cc1noc(N2CCNCC2)n1] | 5-(piperazin-1-yl)-3-(2,2,2-trifluoroethyl)-1,2,4-oxadiazole | XII-25 |

TABLE 9-continued

| Intermediate | Scale | Reaction time | Yield | Analysis | Structure | Name | Intermediate |
|---|---|---|---|---|---|---|---|
| VI-26 | 320 mg | 5 h | 18% | ES-MS m/e: 260.1 (M + H+) | 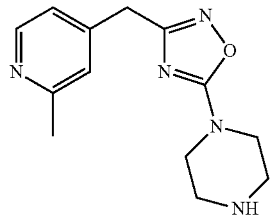 [SMILES: Cc1cc(Cc2noc(N3CCNCC3)n2)ccn1] | 1-[3-(2-Methyl-pyridin-4-ylmethyl)-[1,2,4]oxadiazol-5-yl]-piperazine | XII-26 |
| VI-27 | 2.6 g | 1 h | 65% | Light yellow oil | 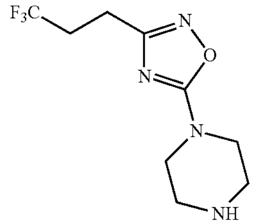 [SMILES: FC(F)(F)CCc1noc(N2CCNCC2)n1] | 5-(piperazin-1-yl)-3-(3,3,3-trifluoropropyl)-1,2,4-oxadiazole | XII-27 |
| VI-29 | 1.2 g | 30 min | 37% | Yellow oil | 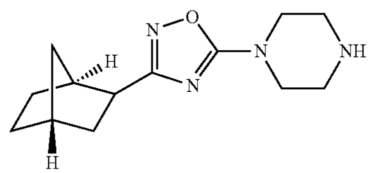 [SMILES: C1CN(c2nc(C3C[C@@H]4CC[C@H]3C4)no2)CCN1] | 3-((1S,4R)-bicyclo[2.2.1]heptan-2-yl)-5-(piperazin-1-yl)-1,2,4-oxadiazole | XII-29 |
| VI-30 | 700 mg | 2 h | 35% | ES-MS m/e: 195.3 (M + H+) | 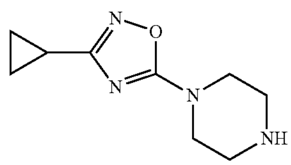 [SMILES: C1CN(c2nc(C3CC3)no2)CCN1] | 3-cyclopropyl-5-(piperazin-1-yl)-1,2,4-oxadiazole | XII-30 |
| VI-32 | 1.16 g | 4 h | 7% | ES-MS m/e: 272.1 (M + H+) | 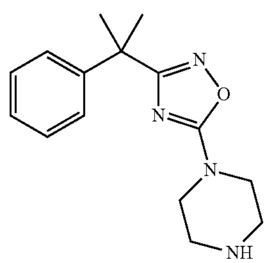 [SMILES: CC(C)(c1ccccc1)c1noc(N2CCNCC2)n1] | 1-[3-(1-Methyl-1-phenyl-ethyl)-[1,2,4]oxadiazol-5-yl]-piperazine | XII-32 |

Intermediate XII-33; Ethyl 5-(piperazin-1-yl)-1,2,4-oxadiazole-3-carboxylate

In a 100 mL round-bottomed flask, ethyl 5-(trichloromethyl)-1,2,4-oxadiazole-3-carboxylate VI-33 (2.2 g, 7.63 mmol) and piperazine (3.94 g, 45.8 mmol) were combined with DMF (20 ml) to give a solution. The reaction mixture was heated to 60° C. and stirred for 30 min. The reaction mixture was poured into 300 mL EtOAc and extracted with water and brine (1×100 mL). The organic layers were dried over Na$_2$SO$_4$ and concentrated in vacuo. Filtration on SiO$_2$ pad gave 200 mg (11%) of title product.

The following intermediates of formula XII were prepared according to the same procedure from intermediates VI previously described as shown in Table 10:

TABLE 10

| Intermediate | Scale | Reaction time | Yield | Analysis | Structure | Name | Intermediate |
|---|---|---|---|---|---|---|---|
| VI-34 | 967 mg | 1 h | 34% | ES-MS m/e: 197.2 (M + H+) | 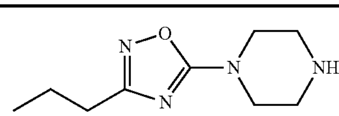 | 5-(piperazin-1-yl)-3-propyl-1,2,4-oxadiazole | XII-34 |

TABLE 10-continued

| Intermediate | Scale | Reaction time | Yield | Analysis | Structure | Name | Intermediate |
|---|---|---|---|---|---|---|---|
| VI-35 | 1.05 g | 30 min | 31% | ES-MS m/e: 211.2(M + H+) | 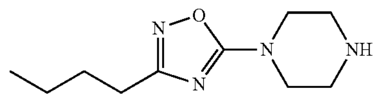 | 3-butyl-5-(piperazin-1-yl)-1,2,4-oxadiazole | XII-35 |
| VI-36 | 540 mg | 30 min | 49% | ES-MS m/e: 211.2(M + H+) | 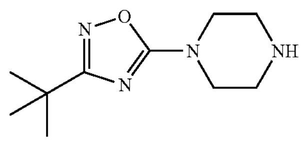 | 3-(tert-butyl)-5-(piperazin-1-yl)-1,2,4-oxadiazole | XII-36 |
| VI-37 | 480 mg | 30 min | 52% | | 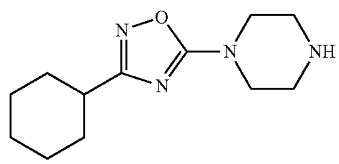 [SMILES: C1CCC(c2noc(N3CCNCC3)n2)CC1] | 3-cyclohexyl-5-(piperazin-1-yl)-1,2,4-oxadiazole | XII-37 |
| VI-38 | 280 mg | 30 min | | ES-MS m/e: 197.2(M + H+) | 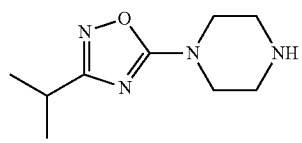 | 3-isopropyl-5-(piperazin-1-yl)-1,2,4-oxadiazole | XII-38 |
| VI-39 | 300 mg | 30 min | 53% | ES-MS m/e: 213.2 (M + H+) | 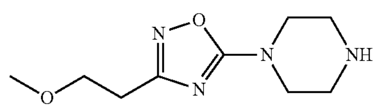 | 3-(2-methoxyethyl)-5-(piperazin-1-yl)-1,2,4-oxadiazole | XII-39 |

Intermediate XIIa-31; 3-(2-(2-Methylpyridin-4-yl)propan-2-yl)-5-(piperazin-1-yl)-1,2,4-oxadiazole

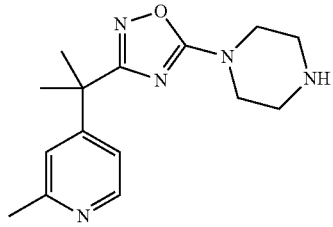 [SMILES: Cc1cc(C(C)(C)c2noc(N3CCNCC3)n2)ccn1]

To a 10 mL microwave vial was added 3-(2-(2-methylpyridin-4-yl)propan-2-yl)-5-(trichloromethyl)-1,2,4-oxadiazole VI-31 (110 mg, 343 µmol) and piperazine (296 mg, 3.43 mmol) in DMF. The vial was capped and heated in the microwave to 130° C. for 10 min. The solvent was then evaporated and the residue poured into water and extracted with EtOAc. The organic layers were dried over Na₂SO₄ and concentrated in vacuo. The crude residue was then purified by column chromatography (silica, CH₂Cl₂/MeOH 95:5-8:2) to yield 3-(2-(2-methylpyridin-4-yl)propan-2-yl)-5-(piperazin-1-yl)-1,2,4-oxadiazole (35 mg, 122 µmol, 35.5% yield). ES-MS m/e: 288 (M+H+).

Process for Preparation Intermediates of Formula XIII

Intermediate XIII-11; 3-(4-Fluorobenzyl)-5-(2,7-diazaspiro[3.5]nonan-2-yl)-1,2,4-oxadiazole bis(2,2,2-trifluoroacetate)

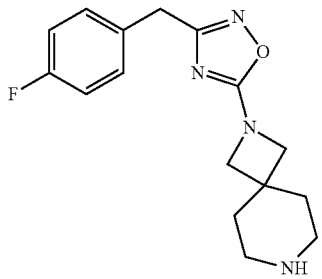 [SMILES: Fc1ccc(Cc2noc(N3CC4(CCNCC4)C3)n2)cc1]

In a 50 mL pear-shaped flask, tert-butyl 2,7-diazaspiro[3.5]nonane-7-carboxylate (300 mg, 1.33 mmol) and 3-(4-fluorobenzyl)-5-(trichloromethyl)-1,2,4-oxadiazole VI-11 (470 mg, 1.59 mmol) were combined with DMF (8.84 ml) to give a light yellow solution. The reaction mixture was stirred for 18 h. iPr₂NEt (171 mg, 232 µl, 1.33 mmol) was added. The reaction mixture was poured into 150 mL EtOAc and extracted with sat NaHCO₃ (1×50 mL). The organic layers were dried over Na₂SO₄ and concentrated in vacuo. The crude material was purified by flash chromatography (silica gel, 50 g, 0-100% EtOAc in heptane) to give 83 mg (16%) of tert-butyl 2-(3-(4-fluorobenzyl)-1,2,4-oxadiazol-5-yl)-2,7-diazaspiro[3.5]nonane-7-carboxylate.

This compound was dissolved in CH$_2$Cl$_2$ (0.33 mL) and TFA (111 μL, 1.44 mmol) and the reaction mixture was stirred overnight. The crude reaction mixture was concentrated in vacuo, to give 104.6 g 3-(4-fluorobenzyl)-5-(2,7-diazaspiro[3.5]nonan-2-yl)-1,2,4-oxadiazole XIII-11, TFA salt (97% yield). ES-MS m/e: 303.3 (M+H+).

Intermediate XIII-25; 5-(2,7-Diazaspiro[3.5]nonan-2-yl)-3-(2,2,2-trifluoroethyl)-1,2,4-oxadiazole

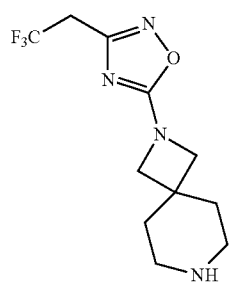 [SMILES: FC(F)(F)Cc1noc(N2CC3(CCNCC3)C2)n1]

In a 5 ml screw cap reactor, 5-(trichloromethyl)-3-(2,2,2-trifluoroethyl)-1,2,4-oxadiazole VI-25 (150 mg, 0.557 mmol), tert-butyl 2,7-diazaspiro[3.5]nonane-2-carboxylate (189 mg, 0.835 mmol) and iPr$_2$NEt (1.67 mmol, 216 mg, Eq:3) were combined with DMF. The reaction mixture was heated to 50° C. and stirred for 75 min. The crude material was purified by preparative HPLC to give 163 mg of Boc-protected material which was then stirred in CH$_2$Cl$_2$/TFA (4/1 ratio) at RT for 20 minutes. The solvent was evaporated under high vacuum to give title compound, which was used in the next step without further purification.

Intermediate XIII-39; 3-(2-Methoxyethyl)-5-(2,7-diazaspiro[3.5]nonan-2-yl)-1,2,4-oxadiazole

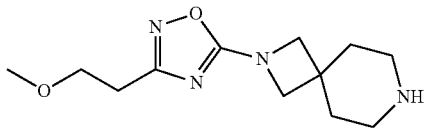 [SMILES: COCCc1noc(N2CC3(CCNCC3)C2)n1]

3-(2-Methoxyethyl)-5-(2,7-diazaspiro[3.5]nonan-2-yl)-1,2,4-oxadiazole was prepared following the same method as Intermediate XIII-25, starting from intermediate VI-39.

Process for Preparation Compounds of Formula I

General Procedure A

To a stirred solution of a piperazine intermediate XII (0.1 mmol) in CH$_2$Cl$_2$ (1 ml) at RT were added ethyl-diisopropyl-amine (0.2 mmol) and a sulfonyl chloride of formula ArSO$_2$Cl (1.1 mmol). Stirring was continued until completion of the reaction. The reaction mixture was then concentrated under vacuo and purification by flash chromatography on SiO$_2$ or preparative HPLC afforded final compounds formula (I).

General Procedure B

To a stirred solution of a piperazine intermediate XII (0.13 μmol, 1 eq) in DMF (1 ml) at RT were added a derivative of formula III (0.195 μmol, 1.5 eq), ethyl-diisopropyl-amine (0.26 μmol, 2.0 eq). The reaction mixture was heated to 50° C. until completion of the reaction. The reaction mixture was then concentrated under vacuo and purification by flash chromatography on SiO$_2$ or preparative HPLC afforded final compounds of formula (I).

General Procedure C

To a stirred solution of a piperazine intermediate XII (0.08 mmol) in DMF (1 mL) at RT were added ethyl-diisopropyl-amine (10 eq) and a sulfonyl chloride of formula ArSO$_2$Cl (1.1 mmol). Stirring was continued until completion of the reaction. The reaction mixture was then concentrated under vacuo and purification by flash chromatography on SiO$_2$ or preparative HPLC afforded final compounds of formula (I).

Example 1; 5-(4-(2-Chlorobenzyl)piperazin-1-yl)-3-phenyl-1,2,4-oxadiazole 5-(4-(2-Chlorobenzyl)piperazin-1-yl)-3-phenyl-1,2,4-oxadiazole was prepared according to general procedure B by reacting piperazine intermediate XII-1 and 1-(bromomethyl)-2-chlorobenzene overnight.

Example 2; 5-(4-(4-Methylbenzyl)piperazin-1-yl)-3-phenyl-1,2,4-oxadiazole 5-(4-(4-methylbenzyl)piperazin-1-yl)-3-phenyl-1,2,4-oxadiazole was prepared according to general procedure B by reacting piperazine intermediate XII-1 and 1-(bromomethyl)-4-methylbenzene overnight. ES-MS m/e: 335.3 (M+H$^+$).

Example 3; 5-(4-(4-Chlorophenethyl)piperazin-1-yl)-3-phenyl-1,2,4-oxadiazole 5-(4-(4-Chlorophenethyl)piperazin-1-yl)-3-phenyl-1,2,4-oxadiazole was prepared according to general procedure B by reacting piperazine intermediate XII-1 and 1-(2-bromoethyl)-4-chlorobenzene overnight. ES-MS m/e: 369.2 (M+H$^+$)

Example 4; 5-(4-(2-(2-Methoxypyridin-4-yl)ethyl)piperazin-1-yl)-3-phenyl-1,2,4-oxadiazole 15-(4-(2-(2-methoxypyridin-4-yl)ethyl)piperazin-1-yl)-3-phenyl-1,2,4-oxadiazole was prepared according to general procedure B by reacting piperazine intermediate XII-1 and 4-(2-bromoethyl)-2-methoxypyridine. ES-MS m/e: 366.2 (M+H$^+$).

Example 5; 4-{2-[4-(3-Phenyl-[1,2,4]oxadiazol-5-yl)-piperazin-1-yl]-ethyl}-morpholine 4-{2-[4-(3-Phenyl-[1,2,4]oxadiazol-5-yl)-piperazin-1-yl]-ethyl}-morpholine was prepared according to general procedure B by reacting piperazine intermediate XII-1 and 4-(2-chloroethyl)morpholine hydrochloride. ES-MS m/e: 344.1 (M+H$^+$).

Example 6; 5-(4-Isopentylpiperazin-1-yl)-3-phenyl-1,2,4-oxadiazole 5-(4-Isopentylpiperazin-1-yl)-3-phenyl-1,2,4-oxadiazole was prepared according to general procedure B by reacting piperazine intermediate XII-1 and 1-bromo-3-methylbutane. ES-MS m/e: 301.2 (M+H$^+$).

Example 7; 5-(4-(Benzo[d][1,3]dioxol-5-ylmethyl) piperazin-1-yl)-3-(p-tolyl)-1,2,4-oxadiazole To a solution of 5-chloro-3-p-tolyl-[1,2,4]oxadiazole (as described in the synthesis of intermediate XII-2) (0.95 g, 4.88 mmol) (19.5 mg, 100 μmol) in N-Methyl-2-pyrrolidinone (1 mL) was added iPr₂NEt (25.8 mg, 19.1 μl, 200 μmol) and 1-(benzo[d][1,3]dioxol-5-ylmethyl)piperazine (33 mg, 150 μmol). The reaction mixture was stirred at 175° C. for 20 minutes. After cooling down, the reaction mixture was directly purified by preparative HPLC to give 29.8 mg (78.7%) of the title product as light brown solid. ES-MS m/e: 379.4 (M+H⁺).

Example 8; 5-(4-(4-Chlorobenzyl)piperazin-1-yl)-3-(p-tolyl)-1,2,4-oxadiazole 5-(4-(4-Chlorobenzyl)piperazin-1-yl)-3-(p-tolyl)-1,2,4-oxadiazole was prepared by coupling 5-chloro-3-p-tolyl-1,2,4-oxadiazole (as described in the synthesis of intermediate XII-2) with 1-(4-chlorobenzyl)piperazine as described in Example 7. ES-MS m/e: 397.3 (M+H⁺).

Example 9; 5-(4-(3-Methoxyphenethyl)piperazin-1-yl)-3-(p-tolyl)-1,2,4-oxadiazole 5-(4-(3-Methoxyphenethyl)piperazin-1-yl)-3-(p-tolyl)-1,2,4-oxadiazole was prepared according to general procedure B by reacting piperazine intermediate XII-2 and 3-methoxy-1-(2-bromoethyl)benzene. ES-MS m/e: 379.4 (M+H⁺).

Example 10; 5-(4-(2-Methylbenzyl)piperazin-1-yl)-3-(p-tolyl)-1,2,4-oxadiazole 5-(4-(2-Methylbenzyl)piperazin-1-yl)-3-(p-tolyl)-1,2,4-oxadiazole was prepared according to general procedure B by reacting piperazine intermediate XII-2 and 2-methylbenzyl chloride. ES-MS m/e: 349.3 (M+H⁺).

Example 11; 5-(4-((4-(Oxazol-5-yl)phenyl)sulfonyl) piperazin-1-yl)-3-(p-tolyl)-1,2,4-oxadiazole 5-(4-((4-(Oxazol-5-yl)phenyl)sulfonyl)piperazin-1-yl)-3-(p-tolyl)-1,2,4-oxadiazole was prepared in 46% yield according to general procedure C by reacting piperazine intermediate XII-2 with 4-(oxazol-5-yl)benzene-1-sulfonyl chloride overnight. ES-MS m/e: 452.1 (M+H⁺).

Example 12; 5-(4-((4-(difluoromethoxy)phenyl) sulfonyl)piperazin-1-yl)-3-(p-tolyl)-1,2,4-oxadiazole 5-(4-((4-(Difluoromethoxy)phenyl)sulfonyl)piperazin-1-yl)-3-(p-tolyl)-1,2,4-oxadiazole was prepared in 53% yield according to general procedure C by reacting piperazine intermediate XII-2 with 4-(difluoromethoxy)benzene-1-sulfonyl chloride overnight. ES-MS m/e: 451.3 (M+H⁺).

Example 13; 3-(p-Tolyl)-5-(4-((4-(trifluoromethoxy) phenyl)sulfonyl)piperazin-1-yl)-1,2,4-oxadiazole 3-(p-Tolyl)-5-(4-((4-(trifluoromethoxy)phenyl)sulfonyl) piperazin-1-yl)-1,2,4-oxadiazole was prepared in 42% yield according to general procedure C by reacting piperazine intermediate XII-2 with 4-(trifluoromethoxy)benzene-1-sulfonyl chloride overnight. ES-MS m/e: 469.2 (M+H+).

Example 14; 5-(4-((4-Fluorophenyl)sulfonyl)piperazin-1-yl)-3-(p-tolyl)-1,2,4-oxadiazole 5-(4-((4-Fluorophenyl)sulfonyl)piperazin-1-yl)-3-(p-tolyl)-1,2,4-oxadiazole was prepared in 59% yield according to general procedure C by reacting piperazine intermediate XII-2 with 4-fluorobenzene-1-sulfonyl chloride overnight. ES-MS m/e: 403.3 (M+H+).

Example 15; 5-(4-((4-Isopropylphenyl)sulfonyl) piperazin-1-yl)-3-(p-tolyl)-1,2,4-oxadiazole 5-(4-((4-Isopropylphenyl)sulfonyl)piperazin-1-yl)-3-(p-tolyl)-1,2,4-oxadiazole was prepared in 56% yield according to general procedure C by reacting piperazine intermediate XII-2 with 4-isopropylbenzene-1-sulfonyl chloride overnight. ES-MS m/e: 427.3 (M+H+).

Example 16; 3-(p-Tolyl)-5-(4-((4-(trifluoromethyl) phenyl)sulfonyl)piperazin-1-yl)-1,2,4-oxadiazole 3-(p-Tolyl)-5-(4-((4-(trifluoromethyl)phenyl)sulfonyl) piperazin-1-yl)-1,2,4-oxadiazole was prepared in 57% yield according to general procedure C by reacting piperazine intermediate XII-2 with 4-(trifluoromethyl)benzene-1-sulfonyl chloride overnight. ES-MS m/e: 453.2 (M+H+).

Example 17; 1-(4-((4-(3-(p-Tolyl)-1,2,4-oxadiazol-5-yl)piperazin-1-yl)sulfonyl)phenyl)pyrrolidin-2-one 1-(4-((4-(3-(p-Tolyl)-1,2,4-oxadiazol-5-yl)piperazin-1-yl)sulfonyl)phenyl)pyrrolidin-2-one was prepared in 30% yield according to general procedure C by reacting piperazine intermediate XII-2 with 4-(2-oxopyrrolidin-1-yl)benzene-1-sulfonyl chloride overnight. ES-MS m/e: 468.3 (M+H+).

Example 18; 5-(4-((4-Methoxyphenyl)sulfonyl)piperazin-1-yl)-3-(p-tolyl)-1,2,4-oxadiazole 5-(4-((4-Methoxyphenyl)sulfonyl)piperazin-1-yl)-3-(p-tolyl)-1,2,4-oxadiazole was prepared in 62% yield according to general procedure C by reacting piperazine intermediate XII-2 with 4-methoxybenzene-1-sulfonyl chloride overnight. ES-MS m/e: 415.2 (M+H+).

Example 19; 5-(4-(4-Chlorophenethyl)piperazin-1-yl)-3-(4-chlorophenyl)-1,2,4-oxadiazole 5-(4-(4-Chlorophenethyl)piperazin-1-yl)-3-(4-chlorophenyl)-1,2,4-oxadiazole was prepared to according general procedure B by reacting piperazine intermediate XII-3 with 1-(2-bromoethyl)-4-chlorobenzene. ES-MS m/e: 403.3 (M+H⁺).

Example 20; 3-(4-chlorophenyl)-5-(4-phenethylpiperazin-1-yl)-1,2,4-oxadiazole 3-(4-Chlorophenyl)-5-(4-phenethylpiperazin-1-yl)-1,2,4-oxadiazole was prepared according to general procedure B by reacting piperazine intermediate XII-3 with (2-bromoethyl)-benzene. ES-MS m/e: 369.2 (M+H⁺).

Example 21; 3-(4-Chlorophenyl)-5-(4-(3-methoxyphenethyl)piperazin-1-yl)-1,2,4-oxadiazole 3-(4-Chlorophenyl)-5-(4-(3-methoxyphenethyl)piperazin-1-yl)-1,2,4-oxadiazole was prepared according to general procedure B by reacting piperazine intermediate XII-3 with 1-(2-bromo-ethyl)-3-methoxy-benzene. ES-MS m/e: 399.2 (M+H$^+$).

Example 22; 3-(4-Chlorophenyl)-5-(4-(2-methylbenzyl)piperazin-1-yl)-1,2,4-oxadiazole 3-(4-Chlorophenyl)-5-(4-(2-methylbenzyl)piperazin-1-yl)-1,2,4-oxadiazole was prepared according to general procedure B by reacting piperazine intermediate XII-3 with 2-methylbenzyl chloride. ES-MS m/e: 369.1 (M+H$^+$).

Example 23; 3-(4-Chlorophenyl)-5-(4-(2-(2-methoxypyridin-4-yl)ethyl)piperazin-1-yl)-1,2,4-oxadiazole 3-(4-Chlorophenyl)-5-(4-(2-(2-methoxypyridin-4-yl)ethyl)piperazin-1-yl)-1,2,4-oxadiazole was prepared according to general procedure B by reacting piperazine intermediate XII-3 with 4-(2-bromoethyl)-2-methoxypyridine. ES-MS m/e: 400.1 (M+H$^+$).

Example 24; 5-(4-(4-Chlorophenethyl)piperazin-1-yl)-3-(3-chlorophenyl)-1,2,4-oxadiazole 5-(4-(4-Chlorophenethyl)piperazin-1-yl)-3-(3-chlorophenyl)-1,2,4-oxadiazole was prepared according to general procedure B by reacting piperazine intermediate XII-4 with 1-(2-bromoethyl)-4-chlorobenzene. ES-MS m/e: 403.3 (M+H$^+$).

Example 25; 3-(3-Chlorophenyl)-5-(4-(2-(2-methoxypyridin-4-yl)ethyl)piperazin-1-yl)-1,2,4-oxadiazole 3-(3-Chlorophenyl)-5-(4-(2-(2-methoxypyridin-4-yl)ethyl)piperazin-1-yl)-1,2,4-oxadiazole was prepared according to general procedure B by reacting piperazine intermediate XII-4 with 4-(2-bromoethyl)-2-methoxypyridine. ES-MS m/e: 400.1 (M+H$^+$).

Example 26; 3-(3-Chlorophenyl)-5-(4-(2-methylbenzyl)piperazin-1-yl)-1,2,4-oxadiazole 3-(3-Chlorophenyl)-5-(4-(2-methylbenzyl)piperazin-1-yl)-1,2,4-oxadiazole was prepared according to general procedure B by reacting piperazine intermediate XII-4 with 2-methylbenzyl chloride. ES-MS m/e: 369.1 (M+H$^+$).

Example 27; 5-(4-(2-Chlorobenzyl)piperazin-1-yl)-3-(3-chlorophenyl)-1,2,4-oxadiazole 5-(4-(2-Chlorobenzyl)piperazin-1-yl)-3-(3-chlorophenyl)-1,2,4-oxadiazole was prepared according to general procedure B by reacting piperazine intermediate XII-4 with 1-(bromomethyl)-2-chlorobenzene. ES-MS m/e: 389.2 (M+H$^+$).

Example 28; 2-{4-[3-(3-Chloro-phenyl)-[1,2,4]oxadiazol-5-yl]-piperazin-1-ylmethyl}-benzonitrile 2-{4-[3-(3-Chloro-phenyl)-[1,2,4]oxadiazol-5-yl]-piperazin-1-ylmethyl}-benzonitrile was prepared according to general procedure B by reacting piperazine intermediate XII-4 with 2-(bromomethyl)benzonitrile. ES-MS m/e: 380.3 (M+H$^+$).

Example 29; 5-(4-(2-Chlorobenzyl)piperazin-1-yl)-3-(3-fluorophenyl)-1,2,4-oxadiazole 5-(4-(2-Chlorobenzyl)piperazin-1-yl)-3-(3-fluorophenyl)-1,2,4-oxadiazole was prepared according to general procedure B by reacting piperazine intermediate XII-5 with 1-(bromomethyl)-2-chlorobenzene. ES-MS m/e: 373.1 (M+H$^+$).

Example 30; 3-(3-Fluorophenyl)-5-(4-(4-methylbenzyl)piperazin-1-yl)-1,2,4-oxadiazole 3-(3-Fluorophenyl)-5-(4-(4-methylbenzyl)piperazin-1-yl)-1,2,4-oxadiazole was prepared according to general procedure B by reacting piperazine intermediate XII-5 with 1-(bromomethyl)-4-methylbenzene.

Example 31; 5-(4-(4-Chlorophenethyl)piperazin-1-yl)-3-(3-fluorophenyl)-1,2,4-oxadiazole 5-(4-(4-Chlorophenethyl)piperazin-1-yl)-3-(3-fluorophenyl)-1,2,4-oxadiazole was prepared according to general procedure B by reacting piperazine intermediate XII-5 with 1-(2-bromoethyl)-4-chlorobenzene. ES-MS m/e: 387.2 (M+H$^+$).

Example 32; 3-(3-Fluorophenyl)-5-(4-(2-(2-methoxypyridin-4-yl)ethyl)piperazin-1-yl)-1,2,4-oxadiazole 3-(3-Fluorophenyl)-5-(4-(2-(2-methoxypyridin-4-yl)ethyl)piperazin-1-yl)-1,2,4-oxadiazole was prepared according to general procedure B by reacting piperazine intermediate XII-5 with 4-(2-bromoethyl)-2-methoxypyridine. ES-MS m/e: 384.2 (M+H$^+$).

Example 33; 4-(2-(4-(3-(3-Fluorophenyl)-1,2,4-oxadiazol-5-yl)piperazin-1-yl)ethyl)morpholine 4-(2-(4-(3-(3-Fluorophenyl)-1,2,4-oxadiazol-5-yl)piperazin-1-yl)ethyl)morpholine was prepared according to general procedure B by reacting piperazine intermediate XII-5 and 4-(2-chloroethyl)morpholine hydrochloride.

Example 34; 3-(3-Fluorophenyl)-5-(4-isopentylpiperazin-1-yl)-1,2,4-oxadiazole 3-(3-Fluorophenyl)-5-(4-isopentylpiperazin-1-yl)-1,2,4-oxadiazole was prepared according to general procedure B by reacting piperazine intermediate XII-5 and 1-bromo-3-methylbutane. ES-MS m/e: 319.1 (M+H$^+$).

Example 35; 5-(4-(2-Chlorobenzyl)piperazin-1-yl)-3-(3,4-difluorophenyl)-1,2,4-oxadiazole 5-(4-(2-Chlorobenzyl)piperazin-1-yl)-3-(3,4-difluorophenyl)-1,2,4-oxadiazole was prepared according to general procedure B by reacting piperazine intermediate XII-6 and 1-(bromomethyl)-2-chlorobenzene. ES-MS m/e: 391.1 (M+H$^+$).

Example 36; 1-[2-(4-Chloro-phenyl)-ethyl]-4-[3-(3,4-difluoro-phenyl)-[1,2,4]oxadiazol-5-yl]-piperazine 1-[2-(4-Chloro-phenyl)-ethyl]-4-[3-(3,4-difluoro-phenyl)-[1,2,4]oxadiazol-5-yl]-piperazine was prepared accord-

Example 37; 1-(3-Benzyl-[1,2,4]oxadiazol-5-yl)-4-(4-methoxy-benzenesulfonyl)-piperazine ing to general procedure B by reacting piperazine intermediate XII-6 and 1-(2-bromoethyl)-4-chlorobenzene. ES-MS m/e: 405.3 (M+H$^+$).

Example 37; 1-(3-Benzyl-[1,2,4]oxadiazol-5-yl)-4-(4-methoxy-benzenesulfonyl)-piperazine 1-(3-Benzyl-[1,2,4]oxadiazol-5-yl)-4-(4-methoxy-benzenesulfonyl)-piperazine was prepared according to general procedure A by reacting piperazine intermediate XII-7 and 4-methoxy-benzenesulfonyl chloride. ES-MS m/e: 415.3 (M+H$^+$).

Example 38; 1-(3-Benzyl-[1,2,4]oxadiazol-5-yl)-4-(4-ethoxy-benzenesulfonyl)-piperazine 1-(3-Benzyl-[1,2,4]oxadiazol-5-yl)-4-(4-ethoxy-benzenesulfonyl)-piperazine was prepared according to general procedure A by reacting piperazine intermediate XII-7 and 4-ethoxy-benzenesulfonyl chloride. ES-MS m/e: 429.3 (M+H$^+$).

Example 39; 1-(3-Benzyl-[1,2,4]oxadiazol-5-yl)-4-(4-difluoromethoxy-benzenesulfonyl)-piperazine 1-(3-Benzyl-[1,2,4]oxadiazol-5-yl)-4-(4-difluoromethoxy-benzenesulfonyl)-piperazine was prepared according to general procedure A by reacting piperazine intermediate XII-7 and 4-difluoromethoxy-benzenesulfonyl chloride. ES-MS m/e: 451.2 (M+H$^+$).

Example 40; 1-Benzo[1,3]dioxol-5-ylmethyl-4-(3-benzyl-[1,2,4]oxadiazol-5-yl)-piperazine 1-Benzo[1,3]dioxol-5-ylmethyl-4-(3-benzyl-[1,2,4]oxadiazol-5-yl)-piperazine was prepared according to general procedure B by reacting piperazine intermediate XII-7 and 5-chloromethyl-benzo[1,3]dioxole. ES-MS m/e: 379.4 (M+H$^+$).

Example 41; 1-(3-Benzyl-[1,2,4]oxadiazol-5-yl)-4-(2-methyl-benzyl)-piperazine 1-(3-Benzyl-[1,2,4]oxadiazol-5-yl)-4-(2-methyl-benzyl)-piperazine was prepared according to general procedure B by reacting piperazine intermediate XII-7 and 2-methylbenzyl chloride. ES-MS m/e: 350.4 (M+H$^+$).

Example 42; 1-(3-Benzyl-[1,2,4]oxadiazol-5-yl)-4-[2-(3-methoxy-phenyl)-ethyl]-piperazine 1-(3-Benzyl-[1,2,4]oxadiazol-5-yl)-4-[2-(3-methoxy-phenyl)-ethyl]-piperazine was prepared according to general procedure B by reacting piperazine intermediate XII-7 and 1-(2-bromo-ethyl)-3-methoxy-benzene. ES-MS m/e: 379.4 (M+H$^+$).

Example 43; 5-((4-(3-benzyl-1,2,4-oxadiazol-5-yl)piperazin-1-yl)sulfonyl)benzo[d]oxazol-2(3H)-one 5-((4-(3-benzyl-1,2,4-oxadiazol-5-yl)piperazin-1-yl)sulfonyl)benzo[d]oxazol-2(3H)-one was prepared according to general procedure B by reacting for 2 h at 40° C. piperazine intermediate XII-7 and 2-oxo-2,3-dihydro-1,3-benzoxazole-5-sulfonyl chloride. 38% yield.

Example 44; 5-(4-((4-Methoxyphenyl)sulfonyl)piperazin-1-yl)-3-(1-phenylpropyl)-1,2,4-oxadiazole 5-(4-((4-Methoxyphenyl)sulfonyl)piperazin-1-yl)-3-(1-phenylpropyl)-1,2,4-oxadiazole was prepared according to general procedure A by reacting piperazine intermediate XII-8 and 4-methoxy-benzenesulfonyl chloride. ES-MS m/e: 443.3 (M+H$^+$).

Example 45; 1-(4-Ethoxy-benzenesulfonyl)-4-[3-(1-phenyl-propyl)-[1,2,4]oxadiazol-5-yl]-piperazine 1-(4-Ethoxy-benzenesulfonyl)-4-[3-(1-phenyl-propyl)-[1,2,4]oxadiazol-5-yl]-piperazine was prepared according to general procedure A by reacting piperazine intermediate XII-8 and 4-ethoxy-benzenesulfonyl chloride. ES-MS m/e: 457.4 (M+H$^+$).

Example 46; 1-(4-Difluoromethoxy-benzenesulfonyl)-4-[3-(1-phenyl-propyl)-[1,2,4]oxadiazol-5-yl]-piperazine 1-(4-Difluoromethoxy-benzenesulfonyl)-4-[3-(1-phenyl-propyl)-[1,2,4]oxadiazol-5-yl]-piperazine was prepared according to general procedure A by reacting piperazine intermediate XII-8 and 4-difluoromethoxy-benzenesulfonyl chloride. ES-MS m/e: 479.2 (M+H$^+$).

Example 47; 5-(4-(Benzo[d][1,3]dioxol-5-ylmethyl)piperazin-1-yl)-3-(1-phenylpropyl)-1,2,4-oxadiazole 5-(4-(Benzo[d][1,3]dioxol-5-ylmethyl)piperazin-1-yl)-3-(1-phenylpropyl)-1,2,4-oxadiazole was prepared in 57% yield according to general procedure B by reacting for 20 h at 75° C. piperazine intermediate XII-8 and 5-(chloromethyl)benzo[d][1,3]dioxole.

Example 48; 5-(4-(2-Methylbenzyl)piperazin-1-yl)-3-(1-phenylpropyl)-1,2,4-oxadiazole 5-(4-(2-Methylbenzyl)piperazin-1-yl)-3-(1-phenylpropyl)-1,2,4-oxadiazole was prepared in 29% yield according to general procedure B by reacting for 20 h at 75° C. piperazine intermediate XII-8 and 2-methylbenzyl chloride.

Example 49; 5-(4-(3-Methoxyphenethyl)piperazin-1-yl)-3-(1-phenylpropyl)-1,2,4-oxadiazole 5-(4-(3-Methoxyphenethyl)piperazin-1-yl)-3-(1-phenylpropyl)-1,2,4-oxadiazole was prepared in 44% yield according to general procedure B by reacting for 20 h at 75° C. piperazine intermediate XII-8 and 1-(2-bromoethyl)-3-methoxybenzene.

Examples 50 and 51; 1-(4-Methoxy-benzenesulfonyl)-4-[3-((S)-1-phenyl-propyl)-[1,2,4]oxadiazol-5-yl]-piperazine and 1-(4-Methoxy-benzenesulfonyl)-4-[3-((R)-1-phenyl-propyl)-[1,2,4]oxadiazol-5-yl]-piperazine The two optically pure enantiomers were obtained after resolution of the racemic mixture (prepared herein above, Example 44) by preparative chiral HPLC. Column: Chiralpak AD; Solvent 40% Ethanol/Heptane. ES-MS m/e: 443.3 (M+H$^+$) and ES-MS m/e: 443.3 (M+H$^+$).

Example 52; 1-[3-(4-Chloro-benzyl)-[1,2,4]oxadiazol-5-yl]-4-(4-methoxy-benzenesulfonyl)-piperazine 1-[3-(4-Chloro-benzyl)-[1,2,4]oxadiazol-5-yl]-4-(4-methoxy-benzenesulfonyl)-piperazine was prepared according to general procedure A by reacting piperazine intermediate XII-9 and 4-methoxy-benzenesulfonyl chloride. ES-MS m/e: 449.2 (M+H$^+$).

Example 53; 1-[3-(4-Chloro-benzyl)-[1,2,4]oxadiazol-5-yl]-4-(4-ethoxy-benzenesulfonyl)-piperazine 1-[3-(4-Chloro-benzyl)-[1,2,4]oxadiazol-5-yl]-4-(4-ethoxy-benzenesulfonyl)-piperazine was prepared according to general procedure A by reacting piperazine intermediate XII-9 and 4-ethoxy-benzenesulfonyl chloride. ES-MS m/e: 463.2 (M+H$^+$).

Example 54; 1-[3-(4-Chloro-benzyl)-[1,2,4]oxadiazol-5-yl]-4-(4-difluoromethoxy-benzenesulfonyl)-piperazine 1-[3-(4-Chloro-benzyl)-[1,2,4]oxadiazol-5-yl]-4-(4-difluoromethoxy-benzenesulfonyl)-piperazine was prepared according to general procedure A by reacting piperazine intermediate XII-9 and 4-difluoromethoxy-benzenesulfonyl chloride. ES-MS m/e: 485.2 (M+H$^+$).

Example 55; 1-Benzo[1,3]dioxol-5-ylmethyl-4-[3-(4-chloro-benzyl)-[1,2,4]oxadiazol-5-yl]-piperazine 1-Benzo[1,3]dioxol-5-ylmethyl-4-[3-(4-chloro-benzyl)-[1,2,4]oxadiazol-5-yl]-piperazine was prepared according to general procedure B by reacting piperazine intermediate XII-9 and 5-chloromethyl-benzo[1,3]dioxole. ES-MS m/e: 413.2 (M+H$^+$).

Example 56; 1-[3-(4-Chloro-benzyl)-[1,2,4]oxadiazol-5-yl]-4-[2-(3-methoxy-phenyl)-ethyl]-piperazine 1-[3-(4-Chloro-benzyl)-[1,2,4]oxadiazol-5-yl]-4-[2-(3-methoxy-phenyl)-ethyl]-piperazine was prepared according to general procedure B by reacting piperazine intermediate XII-9 and 1-(2-bromo-ethyl)-3-methoxy-benzene. ES-MS m/e: 413.4 (M+H$^+$).

Example 57; 5-((4-(3-(4-Chlorobenzyl)-1,2,4-oxadiazol-5-yl)piperazin-1-yl)sulfonyl)benzo[d]oxazol-2(3H)-one 5-((4-(3-(4-Chlorobenzyl)-1,2,4-oxadiazol-5-yl)piperazin-1-yl)sulfonyl)benzo[d]oxazol-2(3H)-one was prepared in 10% yield according to general procedure A by reacting for 2 h at 40° C. piperazine intermediate XII-9 and 2-oxo-2,3-dihydro-1,3-benzoxazole-5-sulfonyl chloride.

Example 58; 1-[3-(4-Chloro-benzyl)-[1,2,4]oxadiazol-5-yl]-4-(2-methyl-benzyl)-piperazine 1-[3-(4-Chloro-benzyl)-[1,2,4]oxadiazol-5-yl]-4-(2-methyl-benzyl)-piperazine was prepared according to general procedure B by reacting piperazine intermediate XII-9 and 2-methylbenzyl chloride. ES-MS m/e: 383.4 (M+H$^+$).

Example 59; 1-[3-(4-Chloro-benzyl)-[1,2,4]oxadiazol-5-yl]-4-[2-(4-chloro-phenyl)-ethyl]-piperazine 1-[3-(4-Chloro-benzyl)-[1,2,4]oxadiazol-5-yl]-4-[2-(4-chloro-phenyl)-ethyl]-piperazine was prepared according to general procedure B by reacting piperazine intermediate XII-9 and 1-(2-bromoethyl)-4-chlorobenzene. ES-MS m/e: 417.3 (M+H$^+$).

Example 60; 1-[3-(4-Chloro-benzyl)-[1,2,4]oxadiazol-5-yl]-4-[2-(6-methoxy-pyridin-3-yl)-ethyl]-piperazine 1-[3-(4-Chloro-benzyl)-[1,2,4]oxadiazol-5-yl]-4-[2-(6-methoxy-pyridin-3-yl)-ethyl]-piperazine was prepared according to general procedure B by reacting piperazine intermediate XII-9 and 5-(2-bromoethyl)-2-methoxypyridine. ES-MS m/e: 414.3 (M+H$^+$).

Example 61; 3-(4-chlorobenzyl)-5-(4-(2-fluorobenzyl)piperazin-1-yl)-1,2,4-oxadiazole 3-(4-chlorobenzyl)-5-(4-(2-fluorobenzyl)piperazin-1-yl)-1,2,4-oxadiazole was prepared according to general procedure B by reacting piperazine intermediate XII-9 and 1-(bromomethyl)-2-fluorobenzene.

Example 62; 1-(2-Chloro-benzyl)-4-[3-(4-chloro-benzyl)-[1,2,4]oxadiazol-5-yl]-piperazine 1-(2-Chloro-benzyl)-4-[3-(4-chloro-benzyl)-[1,2,4]oxadiazol-5-yl]-piperazine was prepared in 24% yield according to general procedure B by reacting piperazine intermediate XII-9 and 1-(bromomethyl)-2-chlorobenzene. ES-MS m/e: 403.3 (M+H$^+$).

Example 63; 1-[3-(4-Chloro-benzyl)-[1,2,4]oxadiazol-5-yl]-4-(4-methyl-benzyl)-piperazine 1-[3-(4-Chloro-benzyl)-[1,2,4]oxadiazol-5-yl]-4-(4-methyl-benzyl)-piperazine was prepared in 25% yield according to general procedure B by reacting piperazine intermediate XII-9 and 1-(bromomethyl)-4-methylbenzene. ES-MS m/e: 383.2 (M+H$^+$).

Example 64; 4-{4-[3-(4-Chloro-benzyl)-[1,2,4]oxadiazol-5-yl]-piperazin-1-yl}-butyronitrile 4-{4-[3-(4-Chloro-benzyl)-[1,2,4]oxadiazol-5-yl]-piperazin-1-yl}-butyronitrile was prepared in 14% yield according to general procedure B by reacting piperazine intermediate XII-9 and 4-bromobutanenitrile. ES-MS m/e: 346.2 (M+H$^+$).

Example 65; 1-[3-(4-Chloro-benzyl)-[1,2,4]oxadiazol-5-yl]-4-(2-ethoxy-ethyl)-piperazine 1-[3-(4-Chloro-benzyl)-[1,2,4]oxadiazol-5-yl]-4-(2-ethoxy-ethyl)-piperazine was prepared in 15% yield according to general procedure B by reacting piperazine intermediate XII-9 and 1-bromo-2-ethoxyethane. ES-MS m/e: 351.3 (M+H$^+$).

Example 66; 1-[3-(4-Chloro-benzyl)-[1,2,4]oxadiazol-5-yl]-4-propyl-piperazine 1-[3-(4-Chloro-benzyl)-[1,2,4]oxadiazol-5-yl]-4-propyl-piperazine was prepared in 10% yield according to general procedure B by reacting piperazine intermediate XII-9 and 1-bromopropane. ES-MS m/e: 321.2 (M+H$^+$).

Example 67; 3-(4-Chlorobenzyl)-5-(4-isopentylpiperazin-1-yl)-1,2,4-oxadiazole 3-(4-Chlorobenzyl)-5-(4-isopentylpiperazin-1-yl)-1,2,4-oxadiazole was prepared in 44% yield according to general procedure B by reacting piperazine intermediate XII-9 and 1-bromo-3-methylbutane.

Example 68; 1-[3-(4-Chloro-benzyl)-[1,2,4]oxadiazol-5-yl]-4-(4,4,4-trifluoro-butyl)-piperazine 1-[3-(4-Chloro-benzyl)-[1,2,4]oxadiazol-5-yl]-4-(4,4,4-trifluoro-butyl)-piperazine was prepared in 10% yield according to general procedure B by reacting piperazine intermediate XII-9 and 4-bromo-1,1,1-trifluorobutane. ES-MS m/e: 389.2 (M+H$^+$).

Example 69; 3-(4-Chlorobenzyl)-5-(4-((tetrahydro-2H-pyran-4-yl)methyl)piperazin-1-yl)-1,2,4-oxadiazole 3-(4-Chlorobenzyl)-5-(4-((tetrahydro-2H-pyran-4-yl)methyl)piperazin-1-yl)-1,2,4-oxadiazole was prepared in 25% yield according to general procedure B by reacting piperazine intermediate XII-9 and 4-(bromomethyl)tetrahydro-2H-pyran.

Example 70; 4-(2-(4-(3-(4-Chlorobenzyl)-1,2,4-oxadiazol-5-yl)piperazin-1-yl)ethyl)morpholine 4-(2-(4-(3-(4-Chlorobenzyl)-1,2,4-oxadiazol-5-yl)piperazin-1-yl)ethyl)morpholine was prepared according to general procedure B by reacting piperazine intermediate XII-9 and 4-(2-chloroethyl)morpholine hydrochloride.

Example 71; 3-(4-Chlorobenzyl)-5-(4-isopropylpiperazin-1-yl)-1,2,4-oxadiazole 3-(4-Chlorobenzyl)-5-(4-isopropylpiperazin-1-yl)-1,2,4-oxadiazole was prepared according to general procedure B by reacting overnight at 80° C. piperazine intermediate XII-9 and 2-bromopropane. ES-MS m/e: 321.2 (M+H$^+$).

Example 72; 1-[3-(3-Chloro-benzyl)-[1,2,4]oxadiazol-5-yl]-4-(4-methoxy-benzenesulfonyl)-piperazine 1-[3-(3-Chloro-benzyl)-[1,2,4]oxadiazol-5-yl]-4-(4-methoxy-benzenesulfonyl)-piperazine was prepared according to general procedure A by reacting piperazine intermediate XII-10 and 4-methoxy-benzenesulfonyl chloride. ES-MS m/e: 449.2 (M+H$^+$).

Example 73; 1-[3-(3-Chloro-benzyl)-[1,2,4]oxadiazol-5-yl]-4-(4-ethoxy-benzenesulfonyl)-piperazine 1-[3-(3-Chloro-benzyl)-[1,2,4]oxadiazol-5-yl]-4-(4-ethoxy-benzenesulfonyl)-piperazine was prepared according to general procedure A by reacting piperazine intermediate XII-10 and 4-ethoxy-benzenesulfonyl chloride. ES-MS m/e: 463.2 (M+H$^+$).

Example 74; 1-[3-(3-Chloro-benzyl)-[1,2,4]oxadiazol-5-yl]-4-(4-difluoromethoxy-benzenesulfonyl)-piperazine 1-[3-(3-Chloro-benzyl)-[1,2,4]oxadiazol-5-yl]-4-(4-difluoromethoxy-benzenesulfonyl)-piperazine was prepared according to general procedure A by reacting piperazine intermediate XII-10 and 4-difluoromethoxy-benzenesulfonyl chloride. ES-MS m/e: 485.3 (M+H$^+$).

Example 75; 1-[3-(3-Chloro-benzyl)-[1,2,4]oxadiazol-5-yl]-4-(2-methyl-benzyl)-piperazine 1-[3-(3-Chloro-benzyl)-[1,2,4]oxadiazol-5-yl]-4-(2-methyl-benzyl)-piperazine was prepared according to general procedure B by reacting piperazine intermediate XII-10 and 2-methylbenzyl chloride. ES-MS m/e: 383.2 (M+H$^+$).

Example 76; 1-[3-(3-Chloro-benzyl)-[1,2,4]oxadiazol-5-yl]-4-[2-(3-methoxy-phenyl)-ethyl]-piperazine 1-[3-(3-Chloro-benzyl)-[1,2,4]oxadiazol-5-yl]-4-[2-(3-methoxy-phenyl)-ethyl]-piperazine was prepared according to general procedure B by reacting piperazine intermediate XII-10 and 1-(2-bromo-ethyl)-3-methoxy-benzene. ES-MS m/e: 413.4 (M+H$^+$).

Example 77; 5-{4-[3-(3-Chloro-benzyl)-[1,2,4]oxadiazol-5-yl]-piperazine-1-sulfonyl}-3H-benzooxazol-2-one 5-{4-[3-(3-Chloro-benzyl)-[1,2,4]oxadiazol-5-yl]-piperazine-1-sulfonyl}-3H-benzooxazol-2-one was prepared according to general procedure A by reacting piperazine intermediate XII-10 and 2-oxo-2,3-dihydro-1,3-benzoxazole-5-sulfonyl chloride. ES-MS m/e: 476.3 (M+H$^+$).

Example 78; 4-(3-(3-Chlorobenzyl)-1,2,4-oxadiazol-5-yl)-N,N-dimethylpiperazine-1-sulfonamide 4-(3-(3-chlorobenzyl)-1,2,4-oxadiazol-5-yl)-N,N-dimethylpiperazine-1-sulfonamide was prepared in 40% yield according to general procedure A by reacting piperazine intermediate XII-10 and dimethylsulfamoyl chloride.

Example 79; 4-(3-(3-Chlorobenzyl)-1,2,4-oxadiazol-5-yl)-N,N-diethylpiperazine-1-sulfonamide 4-(3-(3-Chlorobenzyl)-1,2,4-oxadiazol-5-yl)-N,N-diethylpiperazine-1-sulfonamide was prepared in 17% yield according to general procedure A by reacting piperazine intermediate XII-10 and diethylsulfamoyl chloride.

Example 80; 4-((4-(3-(3-Chlorobenzyl)-1,2,4-oxadiazol-5-yl)piperazin-1-yl)sulfonyl)morpholine 4-((4-(3-(3-Chlorobenzyl)-1,2,4-oxadiazol-5-yl)piperazin-1-yl)sulfonyl)morpholine was prepared in 30% yield according to general procedure A by reacting piperazine intermediate XII-10 and morpholine-4-sulfonyl chloride.

Example 81; 3-(3-Chlorobenzyl)-5-(4-(pyrrolidin-1-ylsulfonyl)piperazin-1-yl)-1,2,4-oxadiazole 3-(3-Chlorobenzyl)-5-(4-(pyrrolidin-1-ylsulfonyl)piperazin-1-yl)-1,2,4-oxadiazole was prepared in 27% yield according to general procedure A by reacting piperazine intermediate XII-10 and pyrrolidine-1-sulfonyl chloride.

Example 82; 5-(4-(Azepan-1-ylsulfonyl)piperazin-1-yl)-3-(3-chlorobenzyl)-1,2,4-oxadiazole 5-(4-(Azepan-1-ylsulfonyl)piperazin-1-yl)-3-(3-chlorobenzyl)-1,2,4-oxadiazole was prepared in 9% yield according to general procedure A by reacting piperazine intermediate XII-10 and azepane-1-sulfonyl chloride.

Example 83; 3-(3-Chlorobenzyl)-5-(4-((4-methoxypiperidin-1-yl)sulfonyl)piperazin-1-yl)-1,2,4-oxadiazole 3-(3-Chlorobenzyl)-5-(4-((4-methoxypiperidin-1-yl)sulfonyl)piperazin-1-yl)-1,2,4-oxadiazole was prepared according to general procedure A by reacting piperazine intermediate XII-10 and 4-methoxypiperidine-1-sulfonyl chloride.

Example 84; 1-[3-(3-Fluoro-benzyl)-[1,2,4]oxadiazol-5-yl]-4-(4-methoxy-benzenesulfonyl)-piperazine 1-[3-(3-Fluoro-benzyl)-[1,2,4]oxadiazol-5-yl]-4-(4-methoxy-benzenesulfonyl)-piperazine was prepared according to general procedure A by reacting piperazine intermediate XII-12 and 4-methoxy-benzenesulfonyl chloride. ES-MS m/e: 433.1 (M+H$^+$).

Example 85; 1-(4-Fluoro-benzenesulfonyl)-4-[3-(3-fluoro-benzyl)-[1,2,4]oxadiazol-5-yl]-piperazine 1-(4-Fluoro-benzenesulfonyl)-4-[3-(3-fluoro-benzyl)-[1,2,4]oxadiazol-5-yl]-piperazine was prepared according to general procedure A by reacting piperazine intermediate XII-12 and 4-fluoro-benzenesulfonyl chloride. ES-MS m/e: 421.2 (M+H$^+$).

Example 86; N-(4-{4-[3-(3-Fluoro-benzyl)-[1,2,4]oxadiazol-5-yl]-piperazine-1-sulfonyl}-phenyl)-acetamide N-(4-{4-[3-(3-Fluoro-benzyl)-[1,2,4]oxadiazol-5-yl]-piperazine-1-sulfonyl}-phenyl)-acetamide was prepared according to general procedure A by reacting piperazine intermediate XII-12 and 4-acetylamino-benzenesulfonyl chloride. ES-MS m/e: 460.2 (M+H$^+$).

Example 87; 1-[3-(3-Fluoro-benzyl)-[1,2,4]oxadiazol-5-yl]-4-(4-trifluoromethoxy-benzenesulfonyl)-piperazine 1-[3-(3-Fluoro-benzyl)-[1,2,4]oxadiazol-5-yl]-4-(4-trifluoromethoxy-benzenesulfonyl)-piperazine was prepared according to general procedure A by reacting piperazine intermediate XII-12 and 4-trifluoromethoxy-benzenesulfonyl chloride. ES-MS m/e: 487.1 (M+H$^+$).

Example 88; 1-[3-(3-Fluoro-benzyl)-[1,2,4]oxadiazol-5-yl]-4-(3-trifluoromethyl-benzenesulfonyl)-piperazine 1-[3-(3-Fluoro-benzyl)-[1,2,4]oxadiazol-5-yl]-4-(3-trifluoromethyl-benzenesulfonyl)-piperazine was prepared according to general procedure A by reacting piperazine intermediate XII-12 and 3-trifluoromethyl-benzenesulfonyl. ES-MS m/e: 471.1 (M+H$^+$).

Example 89; 1-[3-(3-Fluoro-benzyl)-[1,2,4]oxadiazol-5-yl]-4-(3-methyl-benzyl)-piperazine To a solution of 1-[3-(3-fluoro-benzyl)-[1,2,4]oxadiazol-5-yl]-piperazine XII-12 (20 mg, 76.3 µmol) in DMF (1 mL) was added sodium hydride (4.03 mg, 83.9 µmol). The reaction mixture was stirred at room temperature for 5 minutes, then 1-(bromomethyl)-3-methylbenzene (21.1 mg, 114 µmol) was added. The reaction mixture was stirred at 50° C. overnight. After cooling down, the reaction mixture was quenched with 200 µl water. The reaction mixture was filtrated over Decalite. The crude material was purified by preparative HPLC to give 5.8 mg (20.7%) of the title product. ES-MS m/e: 367.2 (M+H$^+$).

Example 90; 1-[3-(3-Fluoro-benzyl)-[1,2,4]oxadiazol-5-yl]-4-[2-(3-methoxy-phenyl)-ethyl]-piperazine 1-[3-(3-Fluoro-benzyl)-[1,2,4]oxadiazol-5-yl]-4-[2-(3-methoxy-phenyl)-ethyl]-piperazine was prepared according to general procedure B by reacting piperazine intermediate XII-12 and 1-(2-bromoethyl)-3-methoxybenzene. ES-MS m/e: 397.3 (M+H$^+$).

Example 91; 1-(4-Ethoxy-benzenesulfonyl)-4-[3-(3-fluoro-benzyl)-[1,2,4]oxadiazol-5-yl]-piperazine 1-(4-Ethoxy-benzenesulfonyl)-4-[3-(3-fluoro-benzyl)-[1,2,4]oxadiazol-5-yl]-piperazine was prepared according to general procedure A by reacting piperazine intermediate XII-12 and 4-ethoxy-benzenesulfonyl chloride. ES-MS m/e: 447.3 (M+H$^+$).

Example 92; 1-(4-Difluoromethoxy-benzenesulfonyl)-4-[3-(3-fluoro-benzyl)-[1,2,4]oxadiazol-5-yl]-piperazine 1-(4-Difluoromethoxy-benzenesulfonyl)-4-[3-(3-fluoro-benzyl)-[1,2,4]oxadiazol-5-yl]-piperazine was prepared according to general procedure A by reacting piperazine intermediate XII-12 and 4-difluoromethoxy-benzenesulfonyl chloride. ES-MS m/e: 469.2 (M+H$^+$).

Example 93; 1-[3-(3-Fluoro-benzyl)-[1,2,4]oxadiazol-5-yl]-4-(4-isopropoxy-benzenesulfonyl)-piperazine 1-[3-(3-Fluoro-benzyl)-[1,2,4]oxadiazol-5-yl]-4-(4-isopropoxy-benzenesulfonyl)-piperazine was prepared according to general procedure A by reacting piperazine intermediate XII-12 and 4-isopropoxy-benzenesulfonyl chloride. ES-MS m/e: 461.2 (M+H$^+$).

Example 94; 3-(4-((4-(3-(3-Fluorobenzyl)-1,2,4-oxadiazol-5-yl)piperazin-1-yl)sulfonyl)phenoxy)propanenitrile 3-(4-((4-(3-(3-Fluorobenzyl)-1,2,4-oxadiazol-5-yl)piperazin-1-yl)sulfonyl)phenoxy)propanenitrile was prepared in 28% yield according to general procedure A by reacting piperazine intermediate XII-12 and 4-(2-cyanoethoxy)benzene-1-sulfonyl chloride.

Example 95; 1-(2,3-Dihydro-benzofuran-5-sulfonyl)-4-[3-(3-fluoro-benzyl)-[1,2,4]oxadiazol-5-yl]-piperazine 1-(2,3-Dihydro-benzofuran-5-sulfonyl)-4-[3-(3-fluoro-benzyl)-[1,2,4]oxadiazol-5-yl]-piperazine was prepared according to general procedure A by reacting piperazine

Example 96; 3-(3-Fluorobenzyl)-5-(4-((4-isopropoxyphenyl)sulfonyl)piperazin-1-yl)-1,2,4-oxadiazole 3-(3-Fluorobenzyl)-5-(4-((4-isopropoxyphenyl)sulfonyl)piperazin-1-yl)-1,2,4-oxadiazole was prepared in 29% yield according to general procedure A by reacting piperazine intermediate XII-12 and 4-isopropoxybenzene-1-sulfonyl chloride.

Example 97; 1-(4-Chloro-benzyl)-4-[3-(3,4-difluoro-benzyl)-[1,2,4]oxadiazol-5-yl]-piperazine a) 3-(3,4-Difluoro-benzyl)-4H-[1,2,4]oxadiazol-5-one

To a solution of 2-(3,4-difluorophenyl)-N'-(hydroxy)acetamidine V-13 (1.1 g, 5.49 mmol) in dichloromethane (5 mL), was added dropwise a solution of ethyl chloroformate (538 µl, 5.6 mmol) and triethylamine (1.15 mL, 8.24 mmol). The reaction mixture was stirred at room temperature for 30 minutes. Then, it was extracted with water and dichloromethane. The organic phase was dried over $Na_2SO_4$ and concentrated under vacuo. The obtained white solid was then dissolved in toluene (10 mL). The reaction mixture was heated to reflux for 20 hours. The volatiles were removed under vacuo and a column chromatography (EtOAc/Heptane 1/1) gave the title product. ES-MS m/e: 211.1 (M–H$^+$).

b) 1-(4-Chloro-benzyl)-4-[3-(3,4-difluoro-benzyl)-[1,2,4]oxadiazol-5-yl]-piperazine To a solution of 3-(3,4-difluoro-benzyl)-4H-[1,2,4]oxadiazol-5-one (50 mg, 236 µmol) in DMF (1 mL) was added iPr$_2$NEt (60.9 mg, 82.3 µl, 471 µmol), (1H-benzo[d][1,2,3]triazol-1-yloxy)tris(dimethylamino)phosphonium hexafluorophosphate(V) (115 mg, 259 µmol) and 1-(4-chlorobenzyl)piperazine (99.2 mg, 471 µmol). The reaction mixture was stirred at 70° C. for 2 days. The volatiles were removed under vacuo, and the residue taken up in EtOAC and washed with a saturated aqueous solution of NaHCO$_3$, followed by a HCl 0.1N solution. The organic phase was dried over Na$_2$SO$_4$, concentrated under vacuo, and a column chromatography (EtOAc/Heptane 1/2) gave the title product. ES-MS m/e: 405.3 (M+H$^+$).

Example 98; 1-[3-(3,4-Difluoro-benzyl)-[1,2,4]oxadiazol-5-yl]-4-[2-(3-methoxy-phenyl)-ethyl]-piperazine 1-[3-(3,4-Difluoro-benzyl)-[1,2,4]oxadiazol-5-yl]-4-[2-(3-methoxy-phenyl)-ethyl]-piperazine was prepared according to general procedure B by reacting piperazine intermediate XII-13 and 1-(2-bromoethyl)-3-methoxybenzene. ES-MS m/e: 415.4 (M+H$^+$).

Example 99; 1-[3-(3,4-Difluoro-benzyl)-[1,2,4]oxadiazol-5-yl]-4-(4-methoxy-benzenesulfonyl)-piperazine 1-[3-(3,4-Difluoro-benzyl)-[1,2,4]oxadiazol-5-yl]-4-(4-methoxy-benzenesulfonyl)-piperazine was prepared according to general procedure A by reacting piperazine intermediate XII-13 and 4-methoxy-benzenesulfonyl chloride. ES-MS m/e: 451.1 (M+H$^+$).

Example 100; 1-[3-(3,4-Difluoro-benzyl)-[1,2,4]oxadiazol-5-yl]-4-(4-ethoxy-benzenesulfonyl)-piperazine 1-[3-(3,4-Difluoro-benzyl)-[1,2,4]oxadiazol-5-yl]-4-(4-ethoxy-benzenesulfonyl)-piperazine was prepared according to general procedure A by reacting piperazine intermediate XII-13 and 4-ethoxy-benzenesulfonyl chloride. ES-MS m/e: 465.3 (M+H$^+$).

Example 101; 1-[3-(3,4-Difluoro-benzyl)-[1,2,4]oxadiazol-5-yl]-4-(4-difluoromethoxy-benzenesulfonyl)-piperazine 1-[3-(3,4-Difluoro-benzyl)-[1,2,4]oxadiazol-5-yl]-4-(4-difluoromethoxy-benzenesulfonyl)-piperazine was prepared according to general procedure A by reacting piperazine intermediate XII-13 and 4-difluoromethoxy-benzenesulfonyl chloride. ES-MS m/e: 487.2 (M+H$^+$).

Example 102; 1-[2-(4-Chloro-phenyl)-ethyl]-4-[3-(3,4-difluoro-benzyl)-[1,2,4]oxadiazol-5-yl]-piperazine 1-[2-(4-Chloro-phenyl)-ethyl]-4-[3-(3,4-difluoro-benzyl)-[1,2,4]oxadiazol-5-yl]-piperazine was prepared according to general procedure B by reacting piperazine intermediate XII-13 and 1-(2-bromoethyl)-4-chlorobenzene. ES-MS m/e: 419.2 (M+H$^+$).

Example 103; 1-[3-(3,4-Difluoro-benzyl)-[1,2,4]oxadiazol-5-yl]-4-[2-(6-methoxy-pyridin-3-yl)-ethyl]-piperazine 1-[3-(3,4-Difluoro-benzyl)-[1,2,4]oxadiazol-5-yl]-4-[2-(6-methoxy-pyridin-3-yl)-ethyl]-piperazine was prepared according to general procedure B by reacting piperazine intermediate XII-13 and 4-(2-bromoethyl)-2-methoxypyridine. ES-MS m/e: 416.3 (M+H$^+$).

Example 104; 1-[3-(3,4-Difluoro-benzyl)-[1,2,4]oxadiazol-5-yl]-4-(2-methyl-benzyl)-piperazine 1-[3-(3,4-Difluoro-benzyl)-[1,2,4]oxadiazol-5-yl]-4-(2-methyl-benzyl)-piperazine was prepared according to general procedure B by reacting piperazine intermediate XII-13 and 2-methylbenzyl chloride. ES-MS m/e: 385.2 (M+H$^+$).

Example 105; 1-{3-[1-(4-Fluoro-phenyl)-cyclopropyl]-[1,2,4]oxadiazol-5-yl}-4-(4-methoxy-benzenesulfonyl)-piperazine 1-{3-[1-(4-Fluoro-phenyl)-cyclopropyl]-[1,2,4]oxadiazol-5-yl}-4-(4-methoxy-benzenesulfonyl)-piperazine was prepared according to general procedure A by reacting piperazine intermediate XII-15 and 4-methoxy-benzenesulfonyl chloride. ES-MS m/e: 459.2 (M+H$^+$).

Example 106; 1-(4-Ethoxy-benzenesulfonyl)-4-{3-[1-(4-fluoro-phenyl)-cyclopropyl]-[1,2,4]oxadiazol-5-yl}-piperazine 1-(4-Ethoxy-benzenesulfonyl)-4-{3-[1-(4-fluoro-phenyl)-cyclopropyl]-[1,2,4]oxadiazol-5-yl}-piperazine was prepared according to general procedure A by reacting piperazine intermediate XII-15 and 4-ethoxy-benzenesulfonyl chloride. ES-MS m/e: 473.2 (M+H$^+$).

Example 107; 3-(1-(4-Fluorophenyl)cyclopropyl)-5-(4-((4-(trifluoromethoxy)phenyl)sulfonyl) piperazin-1-yl)-1,2,4-oxadiazole 3-(1-(4-Fluorophenyl)cyclopropyl)-5-(4-((4-(trifluoromethoxy)phenyl)sulfonyl)piperazin-1-yl)-1,2,4-oxadiazole was prepared according to general procedure A by reacting piperazine intermediate XII-15 and 4-(trifluoromethoxy)benzene-1-sulfonyl chloride.

Example 108; 3-(1-(4-Fluorophenyl)cyclopropyl)-5-(4-(2-methylbenzyl)piperazin-1-yl)-1,2,4-oxadiazole 3-(1-(4-Fluorophenyl)cyclopropyl)-5-(4-(2-methylbenzyl)piperazin-1-yl)-1,2,4-oxadiazole was prepared according to general procedure B by reacting piperazine intermediate XII-15 and 1-(chloromethyl)-2-methylbenzene.

Example 109; 3-(1-(4-Fluorophenyl)cyclopropyl)-5-(4-(3-methoxyphenethyl)piperazin-1-yl)-1,2,4-oxadiazole 3-(1-(4-Fluorophenyl)cyclopropyl)-5-(4-(3-methoxyphenethyl)piperazin-1-yl)-1,2,4-oxadiazole was prepared according to general procedure B by reacting piperazine intermediate XII-15 and 1-(2-bromoethyl)-3-methoxybenzene.

Example 110; 1-{3-[1-(4-Fluoro-phenyl)-cyclopropyl]-[1,2,4]oxadiazol-5-yl}-4-(4-methylsulfanyl-benzenesulfonyl)-piperazine 1-{3-[1-(4-Fluoro-phenyl)-cyclopropyl]-[1,2,4]oxadiazol-5-yl}-4-(4-methylsulfanyl-benzenesulfonyl)-piperazine was prepared according to general procedure A by reacting piperazine intermediate XII-15 and 4-methylsulfanyl-benzenesulfonyl chloride. ES-MS m/e: 475.3 (M+H$^+$).

Example 111; 5-(4-(4-Chlorophenethyl)piperazin-1-yl)-3-(1-(4-fluorophenyl)cyclopropyl)-1,2,4-oxadiazole 5-(4-(4-Chlorophenethyl)piperazin-1-yl)-3-(1-(4-fluorophenyl)cyclopropyl)-1,2,4-oxadiazole was prepared according to general procedure B by reacting piperazine intermediate XII-15 and 1-(2-bromoethyl)-4-chlorobenzene.

Example 112; 5-(4-((2,2-Difluorobenzo[d][1,3]dioxol-5-yl)methyl)piperazin-1-yl)-3-(1-(4-fluorophenyl)cyclopropyl)-1,2,4-oxadiazole 5-(4-((2,2-Difluorobenzo[d][1,3]dioxol-5-yl)methyl)piperazin-1-yl)-3-(1-(4-fluorophenyl)cyclopropyl)-1,2,4-oxadiazole was prepared according to general procedure B by reacting piperazine intermediate XII-15 and 5-(bromomethyl)-2,2-difluorobenzo[d][1,3]dioxole.

Example 113; 1-{3-[1-(4-Fluoro-phenyl)-1-methyl-ethyl]-[1,2,4]oxadiazol-5-yl}-4-(4-methoxy-benzenesulfonyl)-piperazine 1-{3-[1-(4-Fluoro-phenyl)-1-methyl-ethyl]-[1,2,4]oxadiazol-5-yl}-4-(4-methoxy-benzenesulfonyl)-piperazine was prepared according to general procedure A by reacting piperazine intermediate XII-16 and 4-methoxy-benzenesulfonyl chloride. ES-MS m/e: 461.3 (M+H$^+$).

Example 114; 1-(4-Difluoromethoxy-benzenesulfonyl)-4-{3-[1-(4-fluoro-phenyl)-1-methyl-ethyl]-[1,2,4]oxadiazol-5-yl}-piperazine 1-(4-Difluoromethoxy-benzenesulfonyl)-4-{3-[1-(4-fluoro-phenyl)-1-methyl-ethyl]-[1,2,4]oxadiazol-5-yl}-piperazine was prepared according to general procedure A by reacting piperazine intermediate XII-16 and 4-difluoromethoxy-benzenesulfonyl chloride. ES-MS m/e: 497.2 (M+H$^+$).

Example 115; 1-(4-Ethoxy-benzenesulfonyl)-4-{3-[1-(4-fluoro-phenyl)-1-methyl-ethyl]-[1,2,4]oxadiazol-5-yl}-piperazine 1-(4-Ethoxy-benzenesulfonyl)-4-{3-[1-(4-fluoro-phenyl)-1-methyl-ethyl]-[1,2,4]oxadiazol-5-yl}-piperazine was prepared according to general procedure A by reacting piperazine intermediate XII-16 and 4-ethoxy-benzenesulfonyl chloride. ES-MS m/e: 475.2 (M+H$^+$).

Example 116; 1-{3-[1-(4-Fluoro-phenyl)-1-methyl-ethyl]-[1,2,4]oxadiazol-5-yl}-4-(4-methylsulfanyl-benzenesulfonyl)-piperazine 1-{3-[1-(4-Fluoro-phenyl)-1-methyl-ethyl]-[1,2,4]oxadiazol-5-yl}-4-(4-methylsulfanyl-benzenesulfonyl)-piperazine was prepared according to general procedure A by reacting piperazine intermediate XII-16 and 4-methylsulfanyl-benzenesulfonyl chloride. ES-MS m/e: 477.1 (M+H$^+$).

Example 117; 3-(2-(4-Fluorophenyl)propan-2-yl)-5-(4-(2-methylbenzyl)piperazin-1-yl)-1,2,4-oxadiazole 3-(2-(4-Fluorophenyl)propan-2-yl)-5-(4-(2-methylbenzyl)piperazin-1-yl)-1,2,4-oxadiazole was prepared according to general procedure B by reacting piperazine intermediate XII-16 and 2-methylbenzyl chloride.

Example 118; 3-(2-(4-Fluorophenyl)propan-2-yl)-5-(4-(3-methoxyphenethyl)piperazin-1-yl)-1,2,4-oxadiazole 3-(2-(4-Fluorophenyl)propan-2-yl)-5-(4-(3-methoxyphenethyl)piperazin-1-yl)-1,2,4-oxadiazole was prepared according to general procedure B by reacting piperazine intermediate XII-16 and 1-(2-bromoethyl)-3-methoxybenzene.

Example 119; 5-(4-(Benzo[d][1,3]dioxol-5-ylmethyl)piperazin-1-yl)-3-(2-(4-fluorophenyl)propan-2-yl)-1,2,4-oxadiazole 5-(4-(Benzo[d][1,3]dioxol-5-ylmethyl)piperazin-1-yl)-3-(2-(4-fluorophenyl)propan-2-yl)-1,2,4-oxadiazole was prepared according to general procedure B by reacting piperazine intermediate XII-16 and 5-(bromomethyl)benzo[d][1,3]dioxole.

Example 120; 1-(4-Methoxy-benzenesulfonyl)-4-[3-(1-phenyl-cyclopropyl)-[1,2,4]oxadiazol-5-yl]-piperazine 1-(4-Methoxy-benzenesulfonyl)-4-[3-(1-phenyl-cyclopropyl)-[1,2,4]oxadiazol-5-yl]-piperazine was prepared according to general procedure A by reacting piperazine intermediate XII-17 and 4-methoxy-benzenesulfonyl chloride. ES-MS m/e: 441.3 (M+H⁺).

Example 121; 1-(4-Ethoxy-benzenesulfonyl)-4-[3-(1-phenyl-cyclopropyl)-[1,2,4]oxadiazol-5-yl]-piperazine 1-(4-Ethoxy-benzenesulfonyl)-4-[3-(1-phenyl-cyclopropyl)-[1,2,4]oxadiazol-5-yl]-piperazine was prepared according to general procedure A by reacting piperazine intermediate XII-17 and 4-ethoxy-benzenesulfonyl chloride. ES-MS m/e: 455.4 (M+H⁺).

Example 122; 1-(4-Difluoromethoxy-benzenesulfonyl)-4-[3-(1-phenyl-cyclopropyl)-[1,2,4]oxadiazol-5-yl]-piperazine 1-(4-Difluoromethoxy-benzenesulfonyl)-4-[3-(1-phenyl-cyclopropyl)-[1,2,4]oxadiazol-5-yl]-piperazine was prepared according to general procedure A by reacting piperazine intermediate XII-17 and 4-difluoromethoxy-benzenesulfonyl chloride. ES-MS m/e: 477.3 (M+H⁺).

Example 123; 5-(4-(2-Methylbenzyl)piperazin-1-yl)-3-(1-phenylcyclopropyl)-1,2,4-oxadiazole 5-(4-(2-Methylbenzyl)piperazin-1-yl)-3-(1-phenylcyclopropyl)-1,2,4-oxadiazole was prepared according to general procedure B by reacting piperazine intermediate XII-17 and 2-methylbenzyl chloride.

Example 124; 5-(4-(Benzo[d][1,3]dioxol-5-ylmethyl)piperazin-1-yl)-3-(1-phenylcyclopropyl)-1,2,4-oxadiazole 5-(4-(Benzo[d][1,3]dioxol-5-ylmethyl)piperazin-1-yl)-3-(1-phenylcyclopropyl)-1,2,4-oxadiazole was prepared according to general procedure B by reacting piperazine intermediate XII-17 and 5-(bromomethyl)benzo[d][1,3]dioxole.

Example 125; 5-(4-(3-Methoxyphenethyl)piperazin-1-yl)-3-(1-phenylcyclopropyl)-1,2,4-oxadiazole 5-(4-(3-Methoxyphenethyl)piperazin-1-yl)-3-(1-phenylcyclopropyl)-1,2,4-oxadiazole was prepared according to general procedure B by reacting piperazine intermediate XII-17 and 1-(2-bromoethyl)-3-methoxybenzene.

Example 126; 1-(4-Methylsulfanyl-benzenesulfonyl)-4-[3-(1-phenyl-cyclopropyl)-[1,2,4]oxadiazol-5-yl]-piperazine 1-(4-Methylsulfanyl-benzenesulfonyl)-4-[3-(1-phenyl-cyclopropyl)-[1,2,4]oxadiazol-5-yl]-piperazine was prepared according to general procedure A by reacting piperazine intermediate XII-17 and 4-methylsulfanyl-benzenesulfonyl chloride. ES-MS m/e: 457.3 (M+H⁺).

Example 127; 5-(4-(4-Chlorophenethyl)piperazin-1-yl)-3-(1-phenylcyclopropyl)-1,2,4-oxadiazole 5-(4-(4-Chlorophenethyl)piperazin-1-yl)-3-(1-phenylcyclopropyl)-1,2,4-oxadiazole was prepared according to general procedure B by reacting piperazine intermediate XII-17 and 1-(2-bromoethyl)-4-chlorobenzene.

Example 128; 5-(4-((2,2-Difluorobenzo[d][1,3]dioxol-5-yl)methyl)piperazin-1-yl)-3-(1-phenylcyclopropyl)-1,2,4-oxadiazole 5-(4-((2,2-Difluorobenzo[d][1,3]dioxol-5-yl)methyl)piperazin-1-yl)-3-(1-phenylcyclopropyl)-1,2,4-oxadiazole was prepared according to general procedure B by reacting piperazine intermediate XII-17 and 5-(bromomethyl)-2,2-difluorobenzo[d][1,3]dioxole.

Example 129; 5-(4-(2-Chlorobenzyl)piperazin-1-yl)-3-(1-phenylcyclopropyl)-1,2,4-oxadiazole 5-(4-(2-Chlorobenzyl)piperazin-1-yl)-3-(1-phenylcyclopropyl)-1,2,4-oxadiazole was prepared according to general procedure B by reacting piperazine intermediate XII-17 and 1-(bromomethyl)-2-chlorobenzene.

Example 130; 5-(4-(4-Methylbenzyl)piperazin-1-yl)-3-(1-phenylcyclopropyl)-1,2,4-oxadiazole 5-(4-(4-Methylbenzyl)piperazin-1-yl)-3-(1-phenylcyclopropyl)-1,2,4-oxadiazole was prepared according to general procedure B by reacting piperazine intermediate XII-17 and 1-(bromomethyl)-4-methylbenzene.

Example 131; 5-(4-(2-(2-Methoxypyridin-4-yl)ethyl)piperazin-1-yl)-3-(1-phenylcyclopropyl)-1,2,4-oxadiazole 5-(4-(2-(2-Methoxypyridin-4-yl)ethyl)piperazin-1-yl)-3-(1-phenylcyclopropyl)-1,2,4-oxadiazole was prepared according to general procedure B by reacting piperazine intermediate XII-17 and 4-(2-bromoethyl)-2-methoxypyridine.

Example 132; 4-(2-(4-(3-(1-Phenylcyclopropyl)-1,2,4-oxadiazol-5-yl)piperazin-1-yl)ethyl)morpholine 4-(2-(4-(3-(1-Phenylcyclopropyl)-1,2,4-oxadiazol-5-yl)piperazin-1-yl)ethyl)morpholine was prepared according to general procedure B by reacting piperazine intermediate XII-17 and 4-(2-chloroethyl)morpholine hydrochloride.

Example 133; 5-(4-Isopentylpiperazin-1-yl)-3-(1-phenylcyclopropyl)-1,2,4-oxadiazole 5-(4-Isopentylpiperazin-1-yl)-3-(1-phenylcyclopropyl)-1,2,4-oxadiazole was prepared according to general procedure B by reacting piperazine intermediate XII-17 and 1-bromo-3-methylbutane.

Example 134; 1-{3-[1-(3-Chloro-phenyl)-cyclopropyl]-[1,2,4]oxadiazol-5-yl}-4-(4-methoxy-benzenesulfonyl)-piperazine 1-{3-[1-(3-Chloro-phenyl)-cyclopropyl]-[1,2,4]oxadiazol-5-yl}-4-(4-methoxy-benzenesulfonyl)-piperazine was prepared according to general procedure A by reacting

239 piperazine intermediate XII-18 and 4-methoxy-benzenesulfonyl chloride. ES-MS m/e: 475.3 (M+H$^+$).

Example 135; 1-{3-[1-(3-Chloro-phenyl)-cyclopropyl]-[1,2,4]oxadiazol-5-yl}-4-(4-ethoxy-benzenesulfonyl)-piperazine 1-{3-[1-(3-Chloro-phenyl)-cyclopropyl]-[1,2,4]oxadiazol-5-yl}-4-(4-ethoxy-benzenesulfonyl)-piperazine was prepared according to general procedure A by reacting piperazine intermediate XII-18 and 4-ethoxy-benzenesulfonyl chloride. ES-MS m/e: 489.3 (M+H$^+$).

Example 136; 1-{3-[1-(3-Chloro-phenyl)-cyclopropyl]-[1,2,4]oxadiazol-5-yl}-4-(4-difluoromethoxy-benzenesulfonyl)-piperazine 1-{3-[1-(3-Chloro-phenyl)-cyclopropyl]-[1,2,4]oxadiazol-5-yl}-4-(4-difluoromethoxy-benzenesulfonyl)-piperazine was prepared according to general procedure A by reacting piperazine intermediate XII-18 and 4-difluoromethoxy-benzenesulfonyl chloride. ES-MS m/e: 511.2 (M+H$^+$).

Example 137; 1-{3-[1-(3-Chloro-phenyl)-cyclopropyl]-[1,2,4]oxadiazol-5-yl}-4-(4-methylsulfanyl-benzenesulfonyl)-piperazine 1-{3-[1-(3-Chloro-phenyl)-cyclopropyl]-[1,2,4]oxadiazol-5-yl}-4-(4-methylsulfanyl-benzenesulfonyl)-piperazine was prepared according to general procedure A by reacting piperazine intermediate XII-18 and 4-methylsulfanyl-benzenesulfonyl chloride. ES-MS m/e: 491.2 (M+H$^+$).

Example 138; 1-{3-[1-(4-Chloro-phenyl)-cyclopropyl]-[1,2,4]oxadiazol-5-yl}-4-(4-methoxy-benzenesulfonyl)-piperazine 1-{3-[1-(4-Chloro-phenyl)-cyclopropyl]-[1,2,4]oxadiazol-5-yl}-4-(4-methoxy-benzenesulfonyl)-piperazine was prepared according to general procedure A by reacting piperazine intermediate XII-19 and 4-methoxy-benzenesulfonyl chloride. ES-MS m/e: 475.3 (M+H$^+$).

Example 139; 1-{3-[1-(4-Chloro-phenyl)-cyclopropyl]-[1,2,4]oxadiazol-5-yl}-4-(4-ethoxy-benzenesulfonyl)-piperazine 1-{3-[1-(4-Chloro-phenyl)-cyclopropyl]-[1,2,4]oxadiazol-5-yl}-4-(4-ethoxy-benzenesulfonyl)-piperazine was prepared according to general procedure A by reacting piperazine intermediate XII-19 and 4-ethoxy-benzenesulfonyl chloride. ES-MS m/e: 489.3 (M+H$^+$).

Example 140; 1-{3-[1-(4-Chloro-phenyl)-cyclopropyl]-[1,2,4]oxadiazol-5-yl}-4-(4-difluoromethoxy-benzenesulfonyl)-piperazine 1-{3-[1-(4-Chloro-phenyl)-cyclopropyl]-[1,2,4]oxadiazol-5-yl}-4-(4-difluoromethoxy-benzenesulfonyl)-piperazine was prepared according to general procedure A by reacting piperazine intermediate XII-19 and 4-difluoromethoxy-benzenesulfonyl chloride. ES-MS m/e: 511.3 (M+H$^+$).

240

Example 141; 1-{3-[1-(4-Chloro-phenyl)-cyclopropyl]-[1,2,4]oxadiazol-5-yl}-4-(4-methylsulfanyl-benzenesulfonyl)-piperazine 1-{3-[1-(4-Chloro-phenyl)-cyclopropyl]-[1,2,4]oxadiazol-5-yl}-4-(4-methylsulfanyl-benzenesulfonyl)-piperazine was prepared according to general procedure A by reacting piperazine intermediate XII-19 and 4-methylsulfanyl-benzenesulfonyl chloride. ES-MS m/e: 491.2 (M+H$^+$).

Example 142; 1-{3-[(4-Chloro-phenyl)-difluoro-methyl]-[1,2,4]oxadiazol-5-yl}-4-(4-methoxy-benzenesulfonyl)-piperazine 1-{3-[(4-Chloro-phenyl)-difluoro-methyl]-[1,2,4]oxadiazol-5-yl}-4-(4-methoxy-benzenesulfonyl)-piperazine was prepared according to general procedure A by reacting piperazine intermediate XII-20 and 4-methoxy-benzenesulfonyl chloride. ES-MS m/e: 485.2 (M+H$^+$).

Example 143; 1-{3-[(4-Chloro-phenyl)-difluoro-methyl]-[1,2,4]oxadiazol-5-yl}-4-(4-ethoxy-benzenesulfonyl)-piperazine 1-{3-[(4-Chloro-phenyl)-difluoro-methyl]-[1,2,4]oxadiazol-5-yl}-4-(4-ethoxy-benzenesulfonyl)-piperazine was prepared according to general procedure A by reacting piperazine intermediate XII-20 and 4-ethoxy-benzenesulfonyl chloride. ES-MS m/e: 499.2 (M+H$^+$).

Example 144; 1-{3-[(4-Chloro-phenyl)-difluoro-methyl]-[1,2,4]oxadiazol-5-yl}-4-(4-difluoromethoxy-benzenesulfonyl)-piperazine 1-{3-[(4-Chloro-phenyl)-difluoro-methyl]-[1,2,4]oxadiazol-5-yl}-4-(4-difluoromethoxy-benzenesulfonyl)-piperazine was prepared according to general procedure A by reacting piperazine intermediate XII-20 and 4-difluoromethoxy-benzenesulfonyl chloride. ES-MS m/e: 521.2 (M+H$^+$).

Example 145; 1-{3-[(4-Chloro-phenyl)-difluoro-methyl]-[1,2,4]oxadiazol-5-yl}-4-(4-methylsulfanyl-benzenesulfonyl)-piperazine 1-{3-[(4-Chloro-phenyl)-difluoro-methyl]-[1,2,4]oxadiazol-5-yl}-4-(4-methylsulfanyl-benzenesulfonyl)-piperazine was prepared according to general procedure A by reacting piperazine intermediate XII-20 and 4-methylsulfanyl-benzenesulfonyl chloride. ES-MS m/e: 501.2 (M+H$^+$).

Example 146; 1-{3-[Difluoro-(4-fluoro-phenyl)-methyl]-[1,2,4]oxadiazol-5-yl}-4-(4-methoxy-benzenesulfonyl)-piperazine 1-{3-[Difluoro-(4-fluoro-phenyl)-methyl]-[1,2,4]oxadiazol-5-yl}-4-(4-methoxy-benzenesulfonyl)-piperazine was prepared according to general procedure A by reacting piperazine intermediate XII-21 and 4-methoxy-benzenesulfonyl chloride. ES-MS m/e: 469.3 (M+H$^+$).

Example 147; 1-{3-[Difluoro-(4-fluoro-phenyl)-methyl]-[1,2,4]oxadiazol-5-yl}-4-(4-ethoxy-benzenesulfonyl)-piperazine 1-{3-[Difluoro-(4-fluoro-phenyl)-methyl]-[1,2,4]oxadiazol-5-yl}-4-(4-ethoxy-benzenesulfonyl)-piperazine was prepared according to general procedure A by reacting piperazine intermediate XII-21 and 4-ethoxy-benzenesulfonyl chloride. ES-MS m/e: 483.3 (M+H⁺).

Example 148; 1-{3-[Difluoro-(4-fluoro-phenyl)-methyl]-[1,2,4]oxadiazol-5-yl}-4-(4-difluoromethoxy-benzenesulfonyl)-piperazine 1-{3-[Difluoro-(4-fluoro-phenyl)-methyl]-[1,2,4]oxadiazol-5-yl}-4-(4-difluoromethoxy-benzenesulfonyl)-piperazine was prepared according to general procedure A by reacting piperazine intermediate XII-21 and 4-difluoromethoxy-benzenesulfonyl chloride. ES-MS m/e: 505.3 (M+H⁺).

Example 149; 5-(4-(Benzo[d][1,3]dioxol-5-ylmethyl)piperazin-1-yl)-3-(difluoro(4-fluorophenyl)methyl)-1,2,4-oxadiazole 5-(4-(Benzo[d][1,3]dioxol-5-ylmethyl)piperazin-1-yl)-3-(difluoro(4-fluorophenyl)methyl)-1,2,4-oxadiazole was prepared according to general procedure B by reacting piperazine intermediate XII-21 and 5-(bromomethyl)benzo[d][1,3]dioxole.

Example 150; 3-(Difluoro(4-fluorophenyl)methyl)-5-(4-(3-methoxyphenethyl)piperazin-1-yl)-1,2,4-oxadiazole 3-(difluoro(4-fluorophenyl)methyl)-5-(4-(3-methoxyphenethyl)piperazin-1-yl)-1,2,4-oxadiazole was prepared according to general procedure B by reacting piperazine intermediate XII-21 and 1-(2-bromo-ethyl)-3-methoxy-benzene.

Example 151; 1-{3-[Difluoro-(4-fluoro-phenyl)-methyl]-[1,2,4]oxadiazol-5-yl}-4-(4-methylsulfanyl-benzenesulfonyl)-piperazine 1-{3-[Difluoro-(4-fluoro-phenyl)-methyl]-[1,2,4]oxadiazol-5-yl}-4-(4-methylsulfanyl-benzenesulfonyl)-piperazine was prepared according to general procedure A by reacting piperazine intermediate XII-21 and 4-methylsulfanyl-benzenesulfonyl chloride. ES-MS m/e: 485.3 (M+H⁺).

Example 152; 1-{3-[1-(3-Chloro-phenyl)-1-methyl-ethyl]-[1,2,4]oxadiazol-5-yl}-4-(4-methoxy-benzenesulfonyl)-piperazine 1-{3-[1-(3-Chloro-phenyl)-1-methyl-ethyl]-[1,2,4]oxadiazol-5-yl}-4-(4-methoxy-benzenesulfonyl)-piperazine was prepared according to general procedure A by reacting piperazine intermediate XII-22 and 4-methoxy-benzenesulfonyl chloride. ES-MS m/e: 477.0 (M+H⁺).

Example 153; 1-{3-[1-(3-Chloro-phenyl)-1-methyl-ethyl]-[1,2,4]oxadiazol-5-yl}-4-(4-ethoxy-benzenesulfonyl)-piperazine 1-{3-[1-(3-Chloro-phenyl)-1-methyl-ethyl]-[1,2,4]oxadiazol-5-yl}-4-(4-ethoxy-benzenesulfonyl)-piperazine was prepared according to general procedure A by reacting piperazine intermediate XII-22 and 4-ethoxy-benzenesulfonyl chloride. ES-MS m/e: 491.3 (M+H⁺).

Example 154; 1-{3-[1-(3-Chloro-phenyl)-1-methyl-ethyl]-[1,2,4]oxadiazol-5-yl}-4-(4-difluoromethoxy-benzenesulfonyl)-piperazine 1-{3-[1-(3-Chloro-phenyl)-1-methyl-ethyl]-[1,2,4]oxadiazol-5-yl}-4-(4-difluoromethoxy-benzenesulfonyl)-piperazine was prepared according to general procedure A by reacting piperazine intermediate XII-22 and 4-difluoromethoxy-benzenesulfonyl chloride. ES-MS m/e: 513.0 (M+H⁺).

Example 155; 1-{3-[1-(3-Chloro-phenyl)-1-methyl-ethyl]-[1,2,4]oxadiazol-5-yl}-4-(4-methylsulfanyl-benzenesulfonyl)-piperazine 1-{3-[1-(3-Chloro-phenyl)-1-methyl-ethyl]-[1,2,4]oxadiazol-5-yl}-4-(4-methylsulfanyl-benzenesulfonyl)-piperazine was prepared according to general procedure A by reacting piperazine intermediate XII-22 and 4-methylsulfanyl-benzenesulfonyl chloride. ES-MS m/e: 493.2 (M+H⁺).

Example 156; 1-[3-(Difluoro-phenyl-methyl)-[1,2,4]oxadiazol-5-yl]-4-(4-methoxy-benzenesulfonyl)-piperazine 1-[3-(Difluoro-phenyl-methyl)-[1,2,4]oxadiazol-5-yl]-4-(4-methoxy-benzenesulfonyl)-piperazine was prepared according to general procedure A by reacting piperazine intermediate XII-23 and 4-methoxy-benzenesulfonyl chloride. ES-MS m/e: 450.9 (M+H⁺).

Example 157; 1-[3-(Difluoro-phenyl-methyl)-[1,2,4]oxadiazol-5-yl]-4-(4-methylsulfanyl-benzenesulfonyl)-piperazine 1-[3-(Difluoro-phenyl-methyl)-[1,2,4]oxadiazol-5-yl]-4-(4-methylsulfanyl-benzenesulfonyl)-piperazine was prepared according to general procedure A by reacting piperazine intermediate XII-23 and 4-methylsulfanyl-benzenesulfonyl chloride. ES-MS m/e: 467.5 (M+H⁺).

Example 158; 1-(4-Difluoromethoxy-benzenesulfonyl)-4-[3-(difluoro-phenyl-methyl)-[1,2,4]oxadiazol-5-yl]-piperazine 1-(4-Difluoromethoxy-benzenesulfonyl)-4-[3-(difluoro-phenyl-methyl)-[1,2,4]oxadiazol-5-yl]-piperazine was prepared according to general procedure A by reacting piperazine intermediate XII-23 and 4-difluoromethoxy-benzenesulfonyl chloride. ES-MS m/e: 487.2 (M+H⁺).

Example 159; 3-(Cyclopropylmethyl)-5-(4-((4-methoxyphenyl)sulfonyl)piperazin-1-yl)-1,2,4-oxadiazole 3-(Cyclopropylmethyl)-5-(4-((4-methoxyphenyl)sulfonyl)piperazizin-1-yl)-1,2,4-oxadiazole was prepared in 21% yield according to general procedure A by reacting piperazine intermediate XII-24 and 4-methoxy-benzenesulfonyl chloride.

Example 160; 3-(Cyclopropylmethyl)-5-(4-((4-(difluoromethoxy)phenyl)sulfonyl)piperazin-1-yl)-1,2,4-oxadiazole 3-(Cyclopropylmethyl)-5-(4-((4-(difluoromethoxy)phenyl)sulfonyl)piperazin-1-yl)-1,2,4-oxadiazole was prepared in 38% yield according to general procedure A by reacting piperazine intermediate XII-24 and 4-difluoromethoxy-benzenesulfonyl chloride.

Example 161; 3-(Cyclopropylmethyl)-5-(4-((4-(methylthio)phenyl)sulfonyl)piperazin-1-yl)-1,2,4-oxadiazole 3-(Cyclopropylmethyl)-5-(4-((4-(methylthio)phenyl)sulfonyl)piperazin-1-yl)-1,2,4-oxadiazole was prepared in 48% yield according to general procedure A by reacting piperazine intermediate XII-24 and 4-methylsulfanyl-benzenesulfonyl chloride.

Example 162; 3-(Cyclopropylmethyl)-5-(4-((4-ethoxyphenyl)sulfonyl)piperazin-1-yl)-1,2,4-oxadiazole 3-(Cyclopropylmethyl)-5-(4-((4-ethoxyphenyl)sulfonyl)piperazin-1-yl)-1,2,4-oxadiazole was prepared in 12% yield according to general procedure A by reacting piperazine intermediate XII-24 and 4-ethoxy-benzenesulfonyl chloride.

Example 163; 5-(4-(3-Methoxyphenethyl)piperazin-1-yl)-3-(2,2,2-trifluoroethyl)-1,2,4-oxadiazole 5-(4-(3-Methoxyphenethyl)piperazin-1-yl)-3-(2,2,2-trifluoroethyl)-1,2,4-oxadiazole was prepared according to general procedure B by reacting piperazine intermediate XII-25 and 1-(2-bromo-ethyl)-3-methoxy-benzene.

Example 164; 5-(4-(4-Chlorophenethyl)piperazin-1-yl)-3-(2,2,2-trifluoroethyl)-1,2,4-oxadiazole 5-(4-(4-Chlorophenethyl)piperazin-1-yl)-3-(2,2,2-trifluoroethyl)-1,2,4-oxadiazole was prepared according to general procedure B by reacting piperazine intermediate XII-25 and 1-(2-bromoethyl)-4-chlorobenzene.

Example 165; 5-(4-((4-Methoxyphenyl)sulfonyl)piperazin-1-yl)-3-(2,2,2-trifluoroethyl)-1,2,4-oxadiazole 5-(4-((4-Methoxyphenyl)sulfonyl)piperazin-1-yl)-3-(2,2,2-trifluoroethyl)-1,2,4-oxadiazole was prepared in 27% yield according to general procedure A by reacting piperazine intermediate XII-25 and 4-methoxy-benzenesulfonyl chloride.

Example 166; 5-(4-((4-Ethoxyphenyl)sulfonyl)piperazin-1-yl)-3-(2,2,2-trifluoroethyl)-1,2,4-oxadiazole 5-(4-((4-Ethoxyphenyl)sulfonyl)piperazin-1-yl)-3-(2,2,2-trifluoroethyl)-1,2,4-oxadiazole was prepared in 16% yield according to general procedure A by reacting piperazine intermediate XII-25 and 4-ethoxy-benzenesulfonyl chloride.

Example 167; 5-(4-((4-(Difluoromethoxy)phenyl)sulfonyl)piperazin-1-yl)-3-(2,2,2-trifluoroethyl)-1,2,4-oxadiazole 5-(4-((4-(Difluoromethoxy)phenyl)sulfonyl)piperazin-1-yl)-3-(2,2,2-trifluoroethyl)-1,2,4-oxadiazole was prepared in 12% yield according to general procedure A by reacting piperazine intermediate XII-25 and 4-difluoromethoxy-benzenesulfonyl chloride.

Example 168; 5-(4-((4-(Methylthio)phenyl)sulfonyl)piperazin-1-yl)-3-(2,2,2-trifluoroethyl)-1,2,4-oxadiazole 5-(4-((4-(Methylthio)phenyl)sulfonyl)piperazin-1-yl)-3-(2,2,2-trifluoroethyl)-1,2,4-oxadiazole was prepared in 30% yield according to general procedure A by reacting piperazine intermediate XII-25 and 4-methylsulfanyl-benzenesulfonyl chloride.

Example 169; 1-(4-Methoxy-benzenesulfonyl)-4-[3-(2-methyl-pyridin-4-ylmethyl)-[1,2,4]oxadiazol-5-yl]-piperazine 1-(4-Methoxy-benzenesulfonyl)-4-[3-(2-methyl-pyridin-4-ylmethyl)-[1,2,4]oxadiazol-5-yl]-piperazine was prepared according to general procedure A by reacting piperazine intermediate XII-26 and 4-methoxy-benzenesulfonyl chloride. ES-MS m/e: 430.3 (M+H$^+$).

Example 170; 5-(4-(4-Chlorophenethyl)piperazin-1-yl)-3-((2-methylpyridin-4-yl)methyl)-1,2,4-oxadiazole 5-(4-(4-Chlorophenethyl)piperazin-1-yl)-3-((2-methylpyridin-4-yl)methyl)-1,2,4-oxadiazole was prepared according to general procedure B by reacting piperazine intermediate XII-26 and 1-(2-bromoethyl)-4-chlorobenzene.

Example 171; 5-(4-((4-Methoxyphenyl)sulfonyl)piperazin-1-yl)-3-(3,3,3-trifluoropropyl)-1,2,4-oxadiazole 5-(4-((4-Methoxyphenyl)sulfonyl)piperazin-1-yl)-3-(3,3,3-trifluoropropyl)-1,2,4-oxadiazole was prepared according to general procedure A by reacting piperazine intermediate XII-27 and 4-methoxy-benzenesulfonyl chloride.

Example 172; 5-(4-((4-(Methylthio)phenyl)sulfonyl)piperazin-1-yl)-3-(3,3,3-trifluoropropyl)-1,2,4-oxadiazole 5-(4-((4-(Methylthio)phenyl)sulfonyl)piperazin-1-yl)-3-(3,3,3-trifluoropropyl)-1,2,4-oxadiazole was prepared according to general procedure A by reacting piperazine intermediate XII-27 and 4-methylsulfanyl-benzenesulfonyl chloride.

Example 173; 5-(4-((4-(Difluoromethoxy)phenyl)sulfonyl)piperazin-1-yl)-3-(3,3,3-trifluoropropyl)-1,2,4-oxadiazole 5-(4-((4-(Difluoromethoxy)phenyl)sulfonyl)piperazin-1-yl)-3-(3,3,3-trifluoropropyl)-1,2,4-oxadiazole was prepared according to general procedure A by reacting piperazine intermediate XIIa-27 and 4-difluoromethoxy-benzenesulfonyl chloride.

Example 174; 5-(4-(4-Chlorophenethyl)piperazin-1-yl)-3-(3,3,3-trifluoropropyl)-1,2,4-oxadiazole 5-(4-(4-Chlorophenethyl)piperazin-1-yl)-3-(3,3,3-trifluoropropyl)-1,2,4-oxadiazole was prepared according to general procedure B by reacting piperazine intermediate XII-27 and 1-(2-bromoethyl)-4-chlorobenzene.

Example 175; 5-(4-(2-(2-Methoxypyridin-4-yl)ethyl)piperazin-1-yl)-3-(3,3,3-trifluoropropyl)-1,2,4-oxadiazole 5-(4-(2-(2-Methoxypyridin-4-yl)ethyl)piperazin-1-yl)-3-(3,3,3-trifluoropropyl)-1,2,4-oxadiazole was prepared according to general procedure B by reacting piperazine intermediate XII-27 and 4-(2-bromoethyl)-2-methoxypyridine.

Example 176; 5-(4-(2-Methylbenzyl)piperazin-1-yl)-3-(3,3,3-trifluoropropyl)-1,2,4-oxadiazole 5-(4-(2-Methylbenzyl)piperazin-1-yl)-3-(3,3,3-trifluoropropyl)-1,2,4-oxadiazole was prepared according to general procedure B by reacting piperazine intermediate XII-27 and 2-methylbenzyl chloride.

Example 177; 5-(4-(2-Chlorobenzyl)piperazin-1-yl)-3-(3,3,3-trifluoropropyl)-1,2,4-oxadiazole 5-(4-(2-Chlorobenzyl)piperazin-1-yl)-3-(3,3,3-trifluoropropyl)-1,2,4-oxadiazole was prepared according to general procedure B by reacting piperazine intermediate XII-27 and 1-(bromomethyl)-2-chlorobenzene.

Example 178; 2-((4-(3-(3,3,3-Trifluoropropyl)-1,2,4-oxadiazol-5-yl)piperazin-1-yl)methyl)benzonitrile 2-((4-(3-(3,3,3-Trifluoropropyl)-1,2,4-oxadiazol-5-yl)piperazin-1-yl)methyl)benzonitrile was prepared according to general procedure B by reacting piperazine intermediate XII-27 and 2-(bromomethyl)benzonitrile.

Example 179; 5-(4-Isopentylpiperazin-1-yl)-3-(3,3,3-trifluoropropyl)-1,2,4-oxadiazole 5-(4-Isopentylpiperazin-1-yl)-3-(3,3,3-trifluoropropyl)-1,2,4-oxadiazole was prepared according to general procedure B by reacting piperazine intermediate XII-27 and 1-bromo-3-methylbutane.

Example 180; 4-(2-(4-(3-(3,3,3-Trifluoropropyl)-1,2,4-oxadiazol-5-yl)piperazin-1-yl)ethyl)morpholine 4-(2-(4-(3-(3,3,3-Trifluoropropyl)-1,2,4-oxadiazol-5-yl)piperazin-1-yl)ethyl)morpholine was prepared according to general procedure B by reacting piperazine intermediate XII-27 and 4-(2-chloroethyl)morpholine hydrochloride.

Example 181; 4-(4-(3-(3,3,3-Trifluoropropyl)-1,2,4-oxadiazol-5-yl)piperazin-1-yl)butanenitrile 4-(4-(3-(3,3,3-Trifluoropropyl)-1,2,4-oxadiazol-5-yl)piperazin-1-yl)butanenitrile was prepared according to general procedure B by reacting piperazine intermediate XII-27 and 4-bromobutanenitrile.

Example 182; 5-(4-((6-Methylpyridin-2-yl)methyl)piperazin-1-yl)-3-(3,3,3-trifluoropropyl)-1,2,4-oxadiazole 5-(4-((6-Methylpyridin-2-yl)methyl)piperazin-1-yl)-3-(3,3,3-trifluoropropyl)-1,2,4-oxadiazole was prepared according to general procedure B by reacting piperazine intermediate XII-27 and 2-(chloromethyl)-6-methylpyridine.

Example 183; 1-[2-(4-Chloro-phenyl)-ethyl]-4-[3-(4-trifluoromethyl-phenyl)-[1,2,4]oxadiazol-5-yl]-piperazine 1-[2-(4-Chloro-phenyl)-ethyl]-4-[3-(4-trifluoromethyl-phenyl)-[1,2,4]oxadiazol-5-yl]-piperazine was prepared according to general procedure B by reacting piperazine intermediate XII-28 and 1-(2-bromoethyl)-4-chlorobenzene. ES-MS m/e: 437.1 (M+H$^+$).

Example 184; 3-((1S,4R)-bicyclo[2.2.1]heptan-2-yl)-5-(4-(2-chlorobenzyl)piperazin-1-yl)-1,2,4-oxadiazole 3-((1S,4R)-bicyclo[2.2.1]heptan-2-yl)-5-(4-(2-chlorobenzyl)piperazin-1-yl)-1,2,4-oxadiazole was prepared according to general procedure B by reacting piperazine intermediate XII-29 and 1-(bromomethyl)-2-chlorobenzene.

Example 185; 3-((1S,4R)-bicyclo[2.2.1]heptan-2-yl)-5-(4-(4-methylbenzyl)piperazin-1-yl)-1,2,4-oxadiazole 3-((1 S,4R)-bicyclo[2.2.1]heptan-2-yl)-5-(4-(4-methylbenzyl)piperazin-1-yl)-1,2,4-oxadiazole was prepared according to general procedure B by reacting piperazine intermediate XII-29 and 1-(bromomethyl)-4-methylbenzene.

Example 186; 3-((1S,4R)-bicyclo[2.2.1]heptan-2-yl)-5-(4-(4-chlorophenethyl)piperazin-1-yl)-1,2,4-oxadiazole 3-((1S,4R)-bicyclo[2.2.1]heptan-2-yl)-5-(4-(4-chlorophenethyl)piperazin-1-yl)-1,2,4-oxadiazole was prepared according to general procedure B by reacting piperazine intermediate XII-29 and 1-(2-bromoethyl)-4-chlorobenzene.

Example 187; 3-((1S,4R)-bicyclo[2.2.1]heptan-2-yl)-5-(4-(2-(2-methoxypyridin-4-yl)ethyl)piperazin-1-yl)-1,2,4-oxadiazole 3-((1 S,4R)-bicyclo[2.2.1]heptan-2-yl)-5-(4-(2-(2-methoxypyridin-4-yl)ethyl)piperazin-1-yl)-1,2,4-oxadiazole was prepared according to general procedure B by reacting piperazine intermediate XIIa-29 and 4-(2-bromoethyl)-2-methoxypyridine.

Example 188; 4-(2-(4-(3-((1S,4R)-bicyclo[2.2.1]heptan-2-yl)-1,2,4-oxadiazol-5-yl)piperazin-1-yl)ethyl)morpholine 4-(2-(4-(3-((1S,4R)-bicyclo[2.2.1]heptan-2-yl)-1,2,4-oxadiazol-5-yl)piperazin-1-yl)ethyl)morpholine was prepared according to general procedure B by reacting piperazine intermediate XII-29 and 4-(2-chloroethyl)morpholine hydrochloride.

Example 189; 3-((1S,4R)-bicyclo[2.2.1]heptan-2-yl)-5-(4-isopentylpiperazin-1-yl)-1,2,4-oxadiazole 3-((1S,4R)-bicyclo[2.2.1]heptan-2-yl)-5-(4-isopentylpiperazin-1-yl)-1,2,4-oxadiazole was prepared according to general procedure B by reacting piperazine intermediate XII-29 and 1-bromo-3-methylbutane.

Example 190; 3-((1S,4R)-bicyclo[2.2.1]heptan-2-yl)-5-(4-((4-methoxyphenyl)sulfonyl)piperazin-1-yl)-1,2,4-oxadiazole 3-((1 S,4R)-bicyclo[2.2.1]heptan-2-yl)-5-(4-((4-methoxyphenyl)sulfonyl)piperazin-1-yl)-1,2,4-oxadiazole was prepared according to general procedure C by reacting piperazine intermediate XII-29 and 4-methoxybenzene-1-sulfonyl chloride.

Example 191; 3-((1S,4R)-bicyclo[2.2.1]heptan-2-yl)-5-(4-((4-(methylthio)phenyl)sulfonyl) piperazin-1-yl)-1,2,4-oxadiazole 3-((1 S,4R)-bicyclo[2.2.1]heptan-2-yl)-5-(4-((4-(methylthio)phenyl)sulfonyl)piperazin-1-yl)-1,2,4-oxadiazole was prepared according to general procedure C by reacting piperazine intermediate XII-29 and 4-(methylthio)benzene-1-sulfonyl chloride.

Example 192; 3-((1 S,4R)-bicyclo[2.2.1]heptan-2-yl)-5-(4-((4-(difluoromethoxy)phenyl)sulfonyl) piperazin-1-yl)-1,2,4-oxadiazole 3-((1 S,4R)-bicyclo[2.2.1]heptan-2-yl)-5-(4-((4-(difluoromethoxy)phenyl)sulfonyl)piperazin-1-yl)-1,2,4-oxadiazole was prepared according to general procedure C by reacting piperazine intermediate XII-29 and 4-(difluoromethoxy)benzene-1-sulfonyl chloride.

Example 193; 3-Cyclopropyl-5-(4-((4-ethoxyphenyl)sulfonyl)piperazin-1-yl)-1,2,4-oxadiazole 3-Cyclopropyl-5-(4-((4-ethoxyphenyl)sulfonyl)piperazin-1-yl)-1,2,4-oxadiazole was prepared in 49% yield according to general procedure A by reacting piperazine intermediate XII-30 and 4-ethoxybenzene-1-sulfonyl chloride. ES-MS m/e: 379 (M+H$^+$).

Example 194; 3-Cyclopropyl-5-(4-((4-methoxyphenyl)sulfonyl)piperazin-1-yl)-1,2,4-oxadiazole 3-Cyclopropyl-5-(4-((4-methoxyphenyl)sulfonyl)piperazin-1-yl)-1,2,4-oxadiazole was prepared in 51% yield according to general procedure A by reacting piperazine intermediate XII-30 and 4-methoxybenzene-1-sulfonyl chloride. ES-MS m/e: 365 (M+H$^+$).

Example 195; 5-(4-((4-Methoxyphenyl)sulfonyl) piperazin-1-yl)-3-(2-(2-methylpyridin-4-yl)propan-2-yl)-1,2,4-oxadiazole 5-(4-((4-Methoxyphenyl)sulfonyl)piperazin-1-yl)-3-(2-(2-methylpyridin-4-yl)propan-2-yl)-1,2,4-oxadiazole was prepared in 5% yield according to general procedure A by reacting piperazine intermediate XII-31 and 4-methoxybenzene-1-sulfonyl chloride. ES-MS m/e: 458 (M+H$^+$).

Example 196; 1-(4-Difluoromethoxy-benzenesulfonyl)-4-[3-(1-methyl-1-phenyl-ethyl)-[1,2,4]oxadiazol-5-yl]-piperazine 1-(4-Difluoromethoxy-benzenesulfonyl)-4-[3-(1-methyl-1-phenyl-ethyl)-[1,2,4]oxadiazol-5-yl]-piperazine was prepared according to general procedure A by reacting piperazine intermediate XII-32 and 4-difluoromethoxy-benzenesulfonyl chloride. ES-MS m/e: 479.4 (M+H$^+$).

Example 197; 1-(4-Methoxy-benzenesulfonyl)-4-[3-(1-methyl-1-phenyl-ethyl)-[1,2,4]oxadiazol-5-yl]-piperazine 1-(4-Methoxy-benzenesulfonyl)-4-[3-(1-methyl-1-phenyl-ethyl)-[1,2,4]oxadiazol-5-yl]-piperazine was prepared according to general procedure A by reacting piperazine intermediate XII-32 and 4-methoxy-benzenesulfonyl chloride. ES-MS m/e: 443.3 (M+H$^+$).

Example 198; (5-(4-((4-Methoxyphenyl)sulfonyl) piperazin-1-yl)-1,2,4-oxadiazol-3-yl)methanol In a 50 mL pear-shaped flask, ethyl 5-(piperazin-1-yl)-1,2,4-oxadiazole-3-carboxylate IIa-33 (200 mg, 884 µmol), iPr$_2$NEt (137 mg, 185 µl, 1.06 mmol) and 4-methoxybenzene-1-sulfonyl chloride (192 mg, 928 µmol) were combined with CH$_2$Cl$_2$ (10 ml) to give a colorless solution. The reaction mixture was stirred for 2 h at RT. The reaction mixture was poured into 50 mL CH$_2$Cl$_2$ and extracted with water (1×25 mL). The organic layers were dried over Na$_2$SO$_4$ and concentrated in vacuo. The crude material was purified by chromatography (silica gel, factor 50, EtOAc/Heptane=1/1 (rf=0.2)) to give 78 mg of ethyl 5-(4-((4-methoxyphenyl)sulfonyl)piperazin-1-yl)-1,2,4-oxadiazole-3-carboxylate. ES-MS m/e: 397.2 (M+H$^+$).

This carboxylate was combined with THF (4 ml) to give a colorless solution. The solution was cooled down to 0° C. under inert conditions. Lithium aluminum hydride (7.18 mg, 189 µmol) was added portion-wise over 30 min. Reaction was quenched with water and the reaction mixture was poured into 25 mL EtOAc and extracted with water (1×15 mL). The organic layers were dried over Na$_2$SO$_4$ and concentrated in vacuo. The crude was triturated in diethyl ether (2×) and the mother liquors were removed to give 40 mg (60%) of title compounds as a white powder. ES-MS m/e: 355.2 (M+H+).

Example 199; 3-(Methoxymethyl)-5-(4-((4-methoxyphenyl)sulfonyl)piperazin-1-yl)-1,2,4-oxadiazole In a 5 mL round-bottomed flask, (5-(4-(4-methoxyphenylsulfonyl)piperazin-1-yl)-1,2,4-oxadiazol-3-yl)methanol (Example 198, 35 mg, 98.8 µmol) was combined with DMF (2 ml) to give a colorless solution. It was cooled down to 0° C. under inert conditions. Sodium hydride (4.98 mg, 104 µmol) was added. The reaction mixture was stirred for 3 min; then, iodomethane (15.4 mg, 6.79 µl, 109 µmol) was added. After 30 min, the reaction mixture was poured into 20 mL CH$_2$Cl$_2$ and extracted with water (1×15 mL). The organic layers were dried over Na$_2$SO$_4$ and concentrated in vacuo. The crude was taken in diethyl ether/heptane (5/1) and sonicated. The mother liquors were removed and the remaining white solid was dried under high vacuum to give 28 mg (77%) of title compound as a white powder. ES-MS m/e: 369.2 (M+H+).

Example 200; 3-((4-Chlorophenoxy)methyl)-5-(4-((4-methoxyphenyl)sulfonyl)piperazin-1-yl)-1,2,4-oxadiazole In a 5 mL screw cap reactor, triphenylphosphine on resin (57.0 mg, 217 µmol) was combined with THF (0.5 mL) to give a yellow suspension. A solution of 4-chlorophenol (19 mg, 148 µmol) and di-tert-butyl azodicarboxylate (36.4 mg, 158 µmol, Eq: 1.6) in THF (0.5 mL) was added. After 3 min, a clear solution of (5-(4-(4-methoxyphenylsulfonyl)piperazin-1-yl)-1,2,4-oxadiazol-3-yl)methanol (Example 198, 35 mg, 98.8 µmol) in THF (2 mL) was added. The reaction mixture was stirred at room temperature over the night. The reaction mixture was filtered and the filtrate was concentrated under vacuum. The crude material was then taken in DMF and purified by Prep. HPLC to give title compound.

Example 201; 3-((3-Chlorophenoxy)methyl)-5-(4-((4-methoxyphenyl)sulfonyl)piperazin-1-yl)-1,2,4-oxadiazole 3-((3-Chlorophenoxy)methyl)-5-(4-((4-methoxyphenyl)sulfonyl)piperazin-1-yl)-1,2,4-oxadiazole was prepared as described for example 200 replacing 4-chlorophenol by 3-chlorophenol.

Example 202; 5-(4-((4-Methoxyphenyl)sulfonyl)piperazin-1-yl)-3-(phenoxymethyl)-1,2,4-oxadiazole 5-(4-((4-Methoxyphenyl)sulfonyl)piperazin-1-yl)-3-(phenoxymethyl)-1,2,4-oxadiazole was prepared as described for example 200 replacing 4-chlorophenol by phenol.

Example 203; 3-((Cyclopropylmethoxy)methyl)-5-(4-((4-methoxyphenyl)sulfonyl)piperazin-1-yl)-1,2,4-oxadiazole (5-(4-(4-Methoxyphenylsulfonyl)piperazin-1-yl)-1,2,4-oxadiazol-3-yl)methanol (Example 198, 20 mg, 56 µmol) was dissolved in acetone (1.5 mL) and lithium chloride was added (9.5 mg, 226 µmol). The mixture was stirred at room temperature overnight to give 3-(chloromethyl)-5-(4-((4-methoxyphenyl)sulfonyl)piperazin-1-yl)-1,2,4-oxadiazole.

In a 5 mL round-bottomed flask, cyclopropylmethanol (4.04 mg, 56.1 µmol) and sodium hydride (2.94 mg, 61.2 µmol) were combined with DMF (1 ml) to give a suspension. After 2 min, a solution of 3-(chloromethyl)-5-(4-(4-methoxyphenylsulfonyl)piperazin-1-yl)-1,2,4-oxadiazole (19 mg, 51.0 µmol) in 0.5 mL DMF was added. The reaction mixture was stirred at RT for 60 min. The reaction was quenched with water. The reaction mixture was poured into 15 mL EtOAc and extracted with sat NH$_4$Cl (1×15 mL). The organic layers were dried over Na$_2$SO$_4$ and concentrated in vacuo. The crude material was purified by chromatography (silica gel, factor 70, EtOAc/Heptane=1/2) to give (8 mg, 36%) of title compound as a white solid. ES-MS m/e: 409.3 (M+H+).

Example 204; 5-(4-((4-Methoxyphenyl)sulfonyl)piperazin-1-yl)-3-((pyridin-3-yloxy)methyl)-1,2,4-oxadiazole 5-(4-((4-Methoxyphenyl)sulfonyl)piperazin-1-yl)-3-((pyridin-3-yloxy)methyl)-1,2,4-oxadiazole was prepared as described for example 200 replacing 4-chlorophenol by pyridin-3-ol.

Example 205; 4-((5-(4-((4-Methoxyphenyl)sulfonyl)piperazin-1-yl)-1,2,4-oxadiazol-3-yl)methoxy)benzonitrile 4-((5-(4-((4-Methoxyphenyl)sulfonyl)piperazin-1-yl)-1,2,4-oxadiazol-3-yl)methoxy)benzonitrile was prepared as described for example 200 replacing 4-chlorophenol by 4-hydroxybenzonitrile.

Example 206; 3-((4-Fluorophenoxy)methyl)-5-(4-((4-methoxyphenyl)sulfonyl)piperazin-1-yl)-1,2,4-oxadiazole 3-((4-Fluorophenoxy)methyl)-5-(4-((4-methoxyphenyl)sulfonyl)piperazin-1-yl)-1,2,4-oxadiazole was prepared as described for example 200 replacing 4-chlorophenol by 4-fluorophenol.

Example 207; 5-(4-((4-Methoxyphenyl)sulfonyl)piperazin-1-yl)-3-propyl-1,2,4-oxadiazole 5-(4-((4-Methoxyphenyl)sulfonyl)piperazin-1-yl)-3-propyl-1,2,4-oxadiazole was prepared in 68% yield according to general procedure A by reacting piperazine intermediate XII-34 and 4-methoxybenzene-1-sulfonyl chloride. ES-MS m/e: 367.2 (M+H+).

Example 208; 3-Butyl-5-(4-((4-methoxyphenyl)sulfonyl)piperazin-1-yl)-1,2,4-oxadiazole 3-Butyl-5-(4-((4-methoxyphenyl)sulfonyl)piperazin-1-yl)-1,2,4-oxadiazole was prepared in 77% yield according to general procedure A by reacting piperazine intermediate XII-35 and 4-methoxybenzene-1-sulfonyl chloride. ES-MS m/e: 381.3 (M+H+).

Example 209; 3-(Tert-butyl)-5-(4-((4-methoxyphenyl)sulfonyl)piperazin-1-yl)-1,2,4-oxadiazole 3-(Tert-butyl)-5-(4-((4-methoxyphenyl)sulfonyl)piperazin-1-yl)-1,2,4-oxadiazole was prepared in 74% yield according to general procedure A by reacting piperazine intermediate XII-36 and 4-methoxybenzene-1-sulfonyl chloride. ES-MS m/e: 381.3 (M+H+).

Example 210; 3-Cyclohexyl-5-(4-((4-methoxyphenyl)sulfonyl)piperazin-1-yl)-1,2,4-oxadiazole 3-Cyclohexyl-5-(4-((4-methoxyphenyl)sulfonyl)piperazin-1-yl)-1,2,4-oxadiazole was prepared in 52% yield according to general procedure A by reacting piperazine intermediate XII-37 and 4-methoxybenzene-1-sulfonyl chloride. ES-MS m/e: 407.3 (M+H+).

Example 211; 3-Isopropyl-5-(4-((4-methoxyphenyl)sulfonyl)piperazin-1-yl)-1,2,4-oxadiazole 3-Isopropyl-5-(4-((4-methoxyphenyl)sulfonyl)piperazin-1-yl)-1,2,4-oxadiazole was prepared in 43% yield according to general procedure A by reacting piperazine intermediate XII-38 and 4-methoxybenzene-1-sulfonyl chloride. ES-MS m/e: 367.2 (M+H+).

Example 212; 3-(2-Methoxyethyl)-5-(4-((4-methoxyphenyl)sulfonyl)piperazin-1-yl)-1,2,4-oxadiazole 3-(2-Methoxyethyl)-5-(4-((4-methoxyphenyl)sulfonyl)piperazin-1-yl)-1,2,4-oxadiazole was prepared in 27% yield according to general procedure A by reacting piperazine intermediate XII-39 and 4-methoxybenzene-1-sulfonyl chloride. ES-MS m/e: 383.2 (M+H+).

Example 213; 3-(1-(4-Fluorophenyl)cyclopropyl)-5-(7-((4-methoxyphenyl)sulfonyl)-2,7-diazaspiro[3.5]nonan-2-yl)-1,2,4-oxadiazole In a 50 mL pear-shaped flask, tert-butyl 2,7-diazaspiro[3.5]nonane-2-carboxylate (2.5 g, 11.0 mmol), 4-methoxybenzene-1-sulfonyl chloride (2.28 g, 11.0 mmol) and iPr$_2$NEt (2.14 g, 2.84 ml, 16.6 mmol) were combined with CH$_2$Cl$_2$ (73.6 ml). The reaction mixture was stirred for 1 h. The reaction mixture was then poured into CH$_2$Cl$_2$ and extracted with water. The organic layers were dried over Na$_2$SO$_4$ and concentrated in vacuo. The crude material was purified by flash chromatography (silica gel, 120 g, 10% to 50% EtOAc in heptane) to give 2.965 g(68%) of tert-butyl 7-(4-methoxyphenylsulfonyl)-2,7-diazaspiro[3.5]nonane-2-carboxylate. ES-MS m/e: 397.3 (M+H+).

In a 250 mL pear-shaped flask, tert-butyl 7-(4-methoxyphenylsulfonyl)-2,7-diazaspiro[3.5]nonane-2-carboxylate (2.965 g, 7.48 mmol) was combined with CH$_2$Cl$_2$ (18 ml). TFA (8.53 g, 5.73 ml, 74.8 mmol) was added and the reaction mixture was stirred for 90 min. The crude reaction mixture was concentrated in vacuo.

Diethyl ether was added and evaporated to give 7-(4-methoxyphenylsulfonyl)-2,7-diazaspiro[3.5]nonane 2,2,2-trifluoroacetate as a white solid. ES-MS m/e: 297.4 (M+H+).

In a 5 mL round-bottomed flask, intermediate VIII-15 (40 mg, 182 µmol), 7-(4-methoxyphenylsulfonyl)-2,7-diazaspiro[3.5]nonane 2,2,2-trifluoroacetate (149 mg, 363 µmol) and iPr$_2$NEt (168 mg, 228 µl, 1.3 mmol) were combined with DMF (1.38 ml) to give a colorless solution. After 5 min stirring at RT, BOP (159 mg, 358 µmol) was added. The reaction mixture was heated to 50° C. and stirred for 2 h. The reaction mixture was poured into 50 mL EtOAc and extracted with sat NaHCO$_3$ (1×15 mL). The organic layers were washed with sat NH$_4$Cl (1×10 mL). The organic layers were dried over Na$_2$SO$_4$ and concentrated in vacuo. The crude material was purified by prep. HPLC to give 9.4 mg (10%) of title compound as a white powder. ES-MS m/e: 499.1 (M+H+).

Example 214; 5-(7-((4-Methoxyphenyl)sulfonyl)-2,7-diazaspiro[3.5]nonan-2-yl)-3-(2,2,2-trifluoroethyl)-1,2,4-oxadiazole 5-(7-((4-Methoxyphenyl)sulfonyl)-2,7-diazaspiro[3.5]nonan-2-yl)-3-(2,2,2-trifluoroethyl)-1,2,4-oxadiazole was prepared according to general procedure A by reacting intermediate XIII-25 and 4-methoxybenzene-1-sulfonyl chloride. ES-MS m/e: 447.2 (M+H+).

Example 215; 5-(7-((4-(Methylthio)phenyl)sulfonyl)-2,7-diazaspiro[3.5]nonan-2-yl)-3-(2,2,2-trifluoroethyl)-1,2,4-oxadiazole 5-(7-((4-(Methylthio)phenyl)sulfonyl)-2,7-diazaspiro[3.5]nonan-2-yl)-3-(2,2,2-trifluoroethyl)-1,2,4-oxadiazole was prepared according to general procedure A by reacting intermediate XIII-25 and 4-(methylthio)benzene-1-sulfonyl chloride. ES-MS m/e: 463.2 (M+H+).

Example 216; 5-(7-((4-Ethoxyphenyl)sulfonyl)-2,7-diazaspiro[3.5]nonan-2-yl)-3-(2,2,2-trifluoroethyl)-1,2,4-oxadiazole 5-(7-((4-Ethoxyphenyl)sulfonyl)-2,7-diazaspiro[3.5]nonan-2-yl)-3-(2,2,2-trifluoroethyl)-1,2,4-oxadiazole was prepared according to general procedure A by reacting intermediate XIII-25 and 4-ethoxybenzene-1-sulfonyl chloride. ES-MS m/e: 461.3 (M+H+).

Example 217; 5-(7-((4-(Difluoromethoxy)phenyl)sulfonyl)-2,7-diazaspiro[3.5]nonan-2-yl)-3-(2,2,2-trifluoroethyl)-1,2,4-oxadiazole 5-(7-((4-(Difluoromethoxy)phenyl)sulfonyl)-2,7-diazaspiro[3.5]nonan-2-yl)-3-(2,2,2-trifluoroethyl)-1,2,4-oxadiazole was prepared according to general procedure A by reacting intermediate XIII-25 and 4-(difluoromethoxy)benzene-1-sulfonyl chloride. ES-MS m/e: 483.2 (M+H+).

Example 218; (3-(4-Fluorobenzyl)-1,2,4-oxadiazol-5-yl)(7-((4-methoxyphenyl)sulfonyl)-2,7-diazaspiro[3.5]nonan-2-yl)methanone In a 25 mL pear-shaped flask, 7-(4-methoxyphenylsulfonyl)-2,7-diazaspiro[3.5]nonane TFA (as prepared in example 213, 300 mg, 731 µmol) and iPr$_2$NEt (283 mg, 383 µl, 2.19 mmol) were combined with EtOH (4 ml) to give a white suspension. 3-(4-fluorobenzyl)-5-(trichloromethyl)-1,2,4-oxadiazole (VI-11, 216 mg, 731 µmol) was added. The reaction mixture was heated to 70° C. and stirred for 6 h.

On heating the cloudy suspension changed to a clear solution and then to an orange solution. A further 0.5 eq (80 mg) oxadiazole was added and the reaction was stirred at RT overnight. A further 0.5 eq (80 mg) oxadiazole was added and the reaction was stirred at RT for 3 h and then at 700 for 1.5 h. The reaction mixture was poured into EtOAc and extracted with water. The organic layers were dried over Na$_2$SO$_4$ and concentrated in vacuo to give 710 mg of dark brown semisolid. The crude material was purified by flash chromatography (silica gel, 20 g, 15% to 70% EtOAc in heptane to give 81 mg (22%) of (3-(4-fluorobenzyl)-1,2,4-oxadiazol-5-yl)(7-((4-methoxyphenylsulfonyl)-2,7-diazaspiro[3.5]nonan-2-yl)methanone. ES-MS m/e: 501.2 (M+H+).

Example 219; 3-(4-Fluorobenzyl)-5-(7-((4-methoxyphenyl)sulfonyl)-2,7-diazaspiro[3.5]nonan-2-yl)-1,2,4-oxadiazole 3-(4-Fluorobenzyl)-5-(7-((4-methoxyphenyl)sulfonyl)-2,7-diazaspiro[3.5]nonan-2-yl)-1,2,4-oxadiazole was prepared in 21% yield according to general procedure A by reacting intermediate XIII-11 and 4-methoxybenzene-1-sulfonyl chloride. ES-MS m/e: 473.2 (M+H+).

Example 220; 3-(2-Methoxyethyl)-5-(7-((4-methoxyphenyl)sulfonyl)-2,7-diazaspiro[3.5]nonan-2-yl)-1,2,4-oxadiazole 3-(2-Methoxyethyl)-5-(7-((4-methoxyphenyl)sulfonyl)-2,7-diazaspiro[3.5]nonan-2-yl)-1,2,4-oxadiazole was prepared according to general procedure A by reacting intermediate XIII-39 and 4-methoxybenzene-1-sulfonyl chloride. ES-MS m/e: 383.0 (M+H+).

Example 221; Use of a Rat Insulinoma Cell Line Exposed to Extracellular Stressors as a Model for Beta Cell Stress/Apoptosis The INS-1E cell line, a rat insulinoma cell line, has been characterized extensively. INS-1E cells respond to glucose by secreting insulin and, unlike most other immortalized β-cell lines, they do this in a consistent manner over time. The cells are sensitive to hyperglycemia-, free fatty acid (FFA)-, and cytokine-induced stress. Prolonged stress ultimately leads to induction of apoptotic pathways and, if stress is not counter-acted, to apoptosis. Caspase-3 and -7 play a central role downstream where various apoptotic pathways merge. As such, activation (i.e. cleavage) of these caspases forms a relevant primary read-out to evaluate protective activity of compounds against stress-induced apoptosis.

To evaluate the efficacy of different compounds to prevent induction of apoptosis, an in vitro screen was developed in which INS-1E cells were exposed to a cytokine mix (IFN-γ, 5 ng/ml; IL-1β, 20 pg/ml; TNF-α, 0.25 ng/ml). The degree of induction of apoptosis was evaluated using a substrate for cleaved caspase-3 and -7, i.e. a proluminescent caspase-3/7 DEVD aminoluciferin substrate with a thermostable luciferase (Caspase-Glo® 3/7 assay; Promega, cat. G8092).

Experimental Procedure:

On day 0, INS-1E cells were plated in a white-walled 96-well microplate (Greiner, cat. 655098) at 20,000 cells per well in 100 µl complete medium (RPMI containing 11 mM glucose supplemented with 5% FCS, 100 IU/ml penicillin, 100 µg/ml streptomycin, 10 mM HEPES, 1 mM Sodium Pyruvate and 50 µM 2-Mercapto-ethanol). On day 2, 100 µl medium containing cytokines and compound dissolved in DMSO was added to the cells. Wells without cytokines containing DMSO and wells with cytokines and DMSO were included to evaluate the degree of caspase 3/7 activation by the cytokine mix. After 24 hours exposure to cytokines and/or compound, Caspase-Glo® 3/7 reagent was added to the cells and caspase activity was determined by measuring luminescence.

To evaluate compound efficacy, the "toxicity window" was calculated by subtracting caspase activity of wells without stressor from activity of wells with stressor but without compound. The amount of caspase activity in the latter wells was normalized to 1 and used as reference. Subsequently, caspase activity in the wells with stressor and varying concentrations of compound was calculated relative to the wells without compound. Plotting caspase activity vs the log 10 of the concentration of compound permitted calculation of the $EC_{50}$ values for the compounds which typically lied between 0.0001 and 10 µM. Compounds with an $EC_{50}$<10 µM were considered active.

The $EC_{50}$ values of compounds of the invention on the stress induced beta cells apoptosis model are shown in Table 11 as "CYT $EC_{50}$".

TABLE 11

| Compound | CYT $EC_{50}$ (µM) |
| --- | --- |
| Cmpd105 | 0.027 |
| Cmpd106 | 0.099 |
| Cmpd110 | 0.010 |
| Cmpd113 | 0.001 |
| Cmpd116 | 0.026 |
| Cmpd120 | 0.040 |
| Cmpd121 | 0.186 |
| Cmpd122 | 0.043 |
| Cmpd126 | 0.028 |
| Cmpd134 | 0.016 |
| Cmpd135 | 0.129 |
| Cmpd136 | 0.024 |
| Cmpd137 | 0.009 |
| Cmpd141 | 0.019 |
| Cmpd145 | 0.082 |
| Cmpd146 | 0.075 |
| Cmpd151 | 0.041 |
| Cmpd157 | 0.498 |

TABLE 11-continued

| Compound | CYT $EC_{50}$ (µM) |
| --- | --- |
| Cmpd191 | 0.554 |
| Cmpd195 | 0.052 |
| Cmpd203 | 0.153 |
| Cmpd206 | 0.189 |
| Cmpd213 | 0.010 |
| Cmpd214 | 0.055 |
| Cmpd215 | 0.145 |

Example 222; Use of α-Synuclein Expressing Cells as a Model for Neuronal Degeneration Construction of an α-Synuclein Over-Expressing Cell Line A α-synuclein expression plasmid was constructed by subcloning the NcoI/XhoI fragment from 212T-SYN(WT) (Griffioen et al., Biochem Biophys Acta (2006) 1762(3): 312-318) containing the cDNA of human wild type α-synuclein correspondingly into a standard mammalian expression vector pcDNA3.1 resulting in plasmid pcDNA3.1-SYNwt. Plasmids pcDNA3.1 and pcDNA3.1-SYNwt were transfected into human neuroblastoma cells (BE-M17; ATCC No. CRL-2267™) using lipofectamine reagent and subsequently, independent clonal cell lines with the plasmids stably integrated into the genome were selected by antibiotic resistance selection (Geneticin (G418)), resulting in cell lines M17.pcDNA3 and M17_3SYN. Overexpression of α-synuclein in the M17_3SYN cell line was confirmed by Western blot analysis.

Use of α-Synuclein Expressing Cells as a Model for Neuronal Degeneration

Due to the high levels of α-synuclein, M17_3SYN cells were sensitive to paraquat, a well-known risk factor Parkinson's disease and of synuclein-dependent neuronal degeneration. Cytotoxicity of cells was measured by quantification of lactate dehydrogenase (LDH) levels. In dead cells, LDH leaked out of the cells into the medium due to a loss of plasma-membrane integrity.

Experimental Procedure:

Three days preceding the experiment, primary pre-cultures of M17.pcDNA3 (as possible control) and M17_3SYN cells were prepared, starting from a stock culture, at a density of 20.000-40.000 cells/cm2 in culture medium (Opti-MEM® Reduced Serum Medium with Phenol Red (Invitrogen, Cat. 31985-047) supplemented with 10% FCS, 1 mM sodium pyruvate, 1×NEAA, 500 µg/ml G418 and 0.5×antibiotic/antimycotic (ABAM)). 3 days later these primary pre-cultures were used as a starting point to make secondary pre-cultures at a density of 50.000-100.000 cells/cm$^2$. At the day of the experiment these secondary precultures were diluted to ~0.5·106 cells/ml in detection medium (Opti-MEM® Reduced-Serum Medium without Phenol Red (Invitrogen, Cat. 11085-021) supplemented with 10% FCS, 1 mM sodium pyruvate, 1×NEAA, 500 µg/ml G418 and 0.5×ABAM) and 60 µL of this suspension was dispensed per well into a 96-well microtiter plate. After 3 hours of incubation at 37° C./5% $CO_2$ an equal volume of detection medium containing a final concentration of 6 mM Paraquat was added and subsequently incubated for 2 days at 37° C./5% $CO_2$. Then LDH activity was determined using the Promega Cytotox 96 Non-Radioactive cytotoxicity assay (Promega, Cat. G1780), according to the manufacturer's instructions. Cytotoxicity was defined as the ratio of LDH relative to the total LDH in the cells and supernatant.

Use of the Neuroblastoma α-Synucleinopathy Model to Screen Compounds

The assay described above using the M17_3SYN cell line allowed screening compounds for their ability to decrease cytotoxicity in PQ-challenged cells. Compounds of the invention were tested for their ability to decrease toxicity at different concentrations, ranging from low non-effective concentrations to high effective concentrations. Afterwards, a dose-dependent inhibition curve was used to calculate the $EC_{50}$. A compound was considered to be active in this test when it inhibited toxicity by more than 20% relative to untreated M17_3SYN cells at a concentration of 10 µM or lower.

The $EC_{50}$ values of toxicity inhibition of the compounds of the invention using the M17_3SYN cells are shown in Table 12 as "SYN $EC_{50}$".

TABLE 12

| Compound | SYN $EC_{50}$ (µM) |
| --- | --- |
| Cmpd016 | 0.009 |
| Cmpd037 | 0.003 |
| Cmpd038 | 0.013 |
| Cmpd039 | 0.011 |
| Cmpd044 | 0.015 |
| Cmpd045 | 0.018 |
| Cmpd046 | 0.059 |
| Cmpd050 | 0.068 |
| Cmpd051 | 0.046 |
| Cmpd052 | 0.024 |
| Cmpd053 | 0.031 |
| Cmpd054 | 0.019 |
| Cmpd072 | 0.003 |
| Cmpd073 | 0.033 |
| Cmpd074 | 0.010 |
| Cmpd077 | 0.139 |
| Cmpd084 | 0.005 |
| Cmpd085 | 0.250 |
| Cmpd086 | 0.522 |
| Cmpd087 | 0.497 |
| Cmpd088 | 1.838 |
| Cmpd091 | 0.057 |
| Cmpd092 | 0.047 |
| Cmpd093 | 0.326 |
| Cmpd095 | 0.089 |
| Cmpd096 | 0.289 |
| Cmpd099 | 0.016 |
| Cmpd100 | 0.130 |
| Cmpd101 | 0.050 |
| Cmpd105 | 0.009 |
| Cmpd106 | 0.065 |
| Cmpd110 | 0.030 |
| Cmpd113 | 0.008 |
| Cmpd114 | 0.017 |
| Cmpd115 | 0.054 |
| Cmpd116 | 0.007 |
| Cmpd120 | 0.004 |
| Cmpd121 | 0.010 |
| Cmpd122 | 0.009 |
| Cmpd126 | 0.007 |
| Cmpd134 | 0.002 |
| Cmpd135 | 0.028 |
| Cmpd136 | 0.008 |
| Cmpd137 | 0.007 |
| Cmpd138 | 0.039 |
| Cmpd139 | 0.356 |
| Cmpd140 | 0.044 |
| Cmpd141 | 0.012 |
| Cmpd142 | 0.024 |
| Cmpd143 | 0.025 |
| Cmpd144 | 0.145 |
| Cmpd145 | 0.015 |
| Cmpd146 | 0.008 |
| Cmpd147 | 0.022 |
| Cmpd148 | 0.034 |
| Cmpd151 | 0.013 |
| Cmpd152 | 0.001 |

TABLE 12-continued

| Compound | SYN $EC_{50}$ (µM) |
| --- | --- |
| Cmpd153 | 0.005 |
| Cmpd154 | 0.007 |
| Cmpd155 | 0.002 |
| Cmpd156 | 0.005 |
| Cmpd157 | 0.004 |
| Cmpd158 | 0.031 |
| Cmpd159 | 0.095 |
| Cmpd160 | 0.148 |
| Cmpd161 | 0.023 |
| Cmpd162 | 0.224 |
| Cmpd165 | 0.032 |
| Cmpd166 | 0.368 |
| Cmpd167 | 10.000 |
| Cmpd168 | 0.198 |
| Cmpd169 | 0.034 |
| Cmpd171 | 0.248 |
| Cmpd172 | 0.166 |
| Cmpd173 | 0.438 |
| Cmpd190 | 0.215 |
| Cmpd191 | 0.109 |
| Cmpd192 | 0.164 |
| Cmpd195 | 0.070 |
| Cmpd196 | 0.008 |
| Cmpd197 | 0.002 |
| Cmpd200 | 0.022 |
| Cmpd201 | 0.011 |
| Cmpd202 | 0.011 |
| Cmpd203 | 0.008 |
| Cmpd204 | 0.065 |
| Cmpd206 | 0.022 |
| Cmpd207 | 0.406 |
| Cmpd208 | 0.098 |
| Cmpd209 | 0.296 |
| Cmpd210 | 0.327 |
| Cmpd213 | 0.360 |
| Cmpd214 | 0.164 |
| Cmpd215 | 0.274 |

Example 223; Use of TAU Expressing Cells as a Model for Neuronal Degeneration

Construction of a TAU Gene Over-Expressing Cell Line

A TAU expression plasmid was constructed by subcloning the cDNA encoding for human TAU-P301L protein, wherein proline at position 301 was substituted by a leucine residue, into mammalian expression vector pcDNA3.1 resulting in the plasmid pcDNA3.1-TAUP301L. Plasmid pcDNA3.1-TAU P301L was transfected into human neuroblastoma cells (BE-M17; ATCC No. CRL-2267™) using lipofectamine reagent and subsequently, independent clonal cell lines with the plasmids stably integrated into the genome were selected by antibiotic resistance selection (Geneticin (G418)), resulting in cell line M17_3TAUP301L. Expression of the TAUP301L gene in the M17_3TAUP301L cells was confirmed by Western blot analysis.

Use of TAU Expressing Cells as a Model of Neuronal Degeneration

M17_3TAU(P301L) cells were treated chronically with retinoic acid (RA) in low serum conditions to induce Alzheimer's disease-like intracellular signaling deregulation leading to increased TAU levels and subsequent cell death. Cytotoxicity of cells was measured by quantification of lactate dehydrogenase (LDH) levels. In dead cells LDH leaked out of the cells into the medium due to a loss of plasma-membrane integrity.

Experimental Procedure:

3 days preceding the experiment, a pre-culture of M17_3TAU(P301L) cells was prepared, starting from a stock culture, at a density of 50.000-100.000 cells/cm² in culture medium (Optimem Reduced Serum with phenol red (Invitrogen, Cat. 31985-047)) supplemented with 10% fetal calf serum (FCS), 1 mM sodium pyruvate, 1×non-essential amino acids (NEAA), 500 μg/ml G418 and 0.5×(ABAM). At the day of the experiment these precultures were diluted to $\sim 0.1 \cdot 10^6$ cells/ml in detection medium (Optimem Reduced Serum without phenol red (Gibco, Cat.11058-021) supplemented with 1% fetal calf serum (FCS), 1 mM sodium pyruvate, 1×non-essential amino acids (NEAA), 500 μg/ml G418 and 0.5×ABAM) and 60 μL of this suspension was dispensed per well into a 96-well microtiter plate. After 3 hours of incubation at 37° C./5% $CO_2$ an equal volume of detection medium (without FCS) containing 3.75 μM RA was added and subsequently incubated for 7 days at 37° C./5% $CO_2$. Then LDH activity was determined using the Promega Cytotox 96 Non-Radioactive cytotoxicity assay (Cat. G1780), according to the manufacturer's instructions. Cytotoxicity was defined as the ratio of LDH relative the total LDH in the cells and supernatant.

Use of the Neuroblastoma Tauopathy Model to Screen Compounds

The assay described above using the M17_3TAU(P301L) cell line allowed to screen compounds for their ability to decrease cytotoxicity in RA-challenged cells. Compounds of the invention were tested for their ability to decrease toxicity at different concentrations, ranging from low non-effective concentrations to high potent concentrations. Afterwards, the dose-dependent inhibition curve was used to calculate their $EC_{50}$. A compound was considered to be active in this test when it inhibited toxicity by more than 20% relative to untreated M17_3TAU(P301L) cells at a concentration of 10 μM or lower.

The $EC_{50}$ values of toxicity inhibition of the compounds of the invention using the M17_3TAU(P301L) cells are shown in Table 13 as "TAU $EC_{50}$".

TABLE 13

| Compound | TAU $EC_{50}$ (μM) |
| --- | --- |
| Cmpd001 | 0.027 |
| Cmpd002 | 0.008 |
| Cmpd003 | 0.012 |
| Cmpd004 | 0.036 |
| Cmpd005 | 0.041 |
| Cmpd006 | 0.008 |
| Cmpd007 | 0.352 |
| Cmpd008 | 0.182 |
| Cmpd009 | 0.039 |
| Cmpd010 | 0.306 |
| Cmpd019 | 0.112 |
| Cmpd020 | 0.010 |
| Cmpd021 | 0.005 |
| Cmpd022 | 0.035 |
| Cmpd023 | 0.018 |
| Cmpd024 | 0.119 |
| Cmpd025 | 0.014 |
| Cmpd026 | 0.088 |
| Cmpd027 | 0.074 |
| Cmpd028 | 0.048 |
| Cmpd029 | 0.097 |
| Cmpd030 | 0.013 |
| Cmpd031 | 0.031 |
| Cmpd032 | 0.008 |
| Cmpd034 | 0.002 |
| Cmpd035 | 0.024 |
| Cmpd036 | 0.022 |
| Cmpd040 | 0.064 |
| Cmpd041 | 0.055 |
| Cmpd042 | 0.003 |
| Cmpd047 | 0.063 |
| Cmpd049 | 0.010 |
| Cmpd055 | 0.452 |

TABLE 13-continued

| Compound | TAU $EC_{50}$ (μM) |
| --- | --- |
| Cmpd056 | 0.075 |
| Cmpd058 | 0.177 |
| Cmpd059 | 0.220 |
| Cmpd060 | 0.074 |
| Cmpd061 | 0.685 |
| Cmpd062 | 0.002 |
| Cmpd063 | 0.174 |
| Cmpd064 | 0.054 |
| Cmpd065 | 0.763 |
| Cmpd066 | 0.145 |
| Cmpd067 | 0.022 |
| Cmpd068 | 0.151 |
| Cmpd069 | 0.161 |
| Cmpd071 | 0.133 |
| Cmpd075 | 0.238 |
| Cmpd076 | 0.006 |
| Cmpd089 | 0.485 |
| Cmpd090 | 0.037 |
| Cmpd097 | 0.486 |
| Cmpd098 | 0.003 |
| Cmpd102 | 0.017 |
| Cmpd103 | 0.010 |
| Cmpd104 | 0.037 |
| Cmpd108 | 0.758 |
| Cmpd109 | 0.487 |
| Cmpd111 | 0.237 |
| Cmpd118 | 0.105 |
| Cmpd123 | 0.849 |
| Cmpd125 | 0.103 |
| Cmpd127 | 0.059 |
| Cmpd128 | 0.617 |
| Cmpd130 | 0.185 |
| Cmpd131 | 0.135 |
| Cmpd133 | 0.030 |
| Cmpd149 | 0.849 |
| Cmpd150 | 0.199 |
| Cmpd163 | 0.418 |
| Cmpd164 | 0.306 |
| Cmpd170 | 0.640 |
| Cmpd174 | 0.024 |
| Cmpd175 | 0.105 |
| Cmpd176 | 0.169 |
| Cmpd177 | 0.172 |
| Cmpd179 | 0.046 |
| Cmpd180 | 0.222 |
| Cmpd181 | 0.584 |
| Cmpd182 | 0.282 |
| Cmpd183 | 0.057 |
| Cmpd184 | 0.135 |
| Cmpd185 | 0.071 |
| Cmpd186 | 0.017 |
| Cmpd187 | 0.047 |
| Cmpd188 | 0.004 |
| Cmpd189 | 0.003 |

Example 224; In Vivo Evaluation of Compounds

For in vivo evaluation of compound efficacy, male BKS.Cg-+Leprdb/Leprdb/OlaHsd mice (db/db mice—Harlan) were used. The db/db phenotype results from a mutation in the leptin receptor gene, leading to a splice variant (Chen, Charlat et al. 1996; Lee, Proenca et al. 1996). The development of type 2 diabetes in db/db mice is associated with reduced insulin levels due to progressive β-cell failure following an initial period of hypersecretion of insulin. Since these mice develop type 2 diabetes in a manner related to pathology development in humans, and the model is accepted as in vivo model for evaluation of novel antidiabetic treatments by the Food and Drug Administration (FDA, US), it is a highly relevant model for testing candidate drugs for efficacy.

Compounds were administered intraperitoneal (IP) or oral (PO) at a dose of maximally 50 mg/kg. Mice were subjected to metabolic analysis weekly or bi-weekly. These tests included but were not limited to determination of fasting (5 hrs) and non-fasting blood glucose levels, plasma insulin levels, % glycated hemoglobin (HbA1c) levels, glucose tolerance test and insulin sensitivity test.

Treatment with cmpd110 at 15 mg/kg IP increased weight gain (FIG. 1A). Fasted blood glucose levels were significantly lower in animals treated with cmpd110 (FIG. 1B). Plasma insulin levels remained significantly higher after 6 weeks of treatment in animals treated with cmpd110 vs vehicle-treated animals (FIG. 1C). Time indications are weeks of treatment. *$p<0.05$; **$p<0.01$; n=5-8. p values are compound vs vehicle.

The invention claimed is:

1. A compound of formula (I); or a stereoisomer, enantiomer, racemic, or tautomer thereof, or a solvate, hydrate, or pharmaceutically acceptable salt thereof,

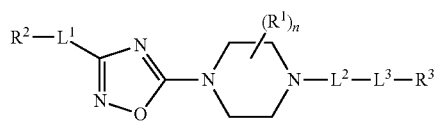

(I)

wherein, n is an integer selected from 0 or 1;

$R^1$ is selected from the group consisting of $C_{1-6}$alkyl, halo, halo$C_{1-6}$alkyl, and halo$C_{1-6}$alkyloxy;

$R^2$ is $C_{6-12}$aryl, wherein said $C_{6-12}$aryl can be unsubstituted or substituted with one or more $Z^1$;

$R^3$ is selected from the group consisting of $C_{6-12}$aryl heterocyclyl, and heteroaryl wherein said $C_{6-12}$aryl, heterocyclyl, or heteroaryl can be unsubstituted or substituted with one or more $Z^2$;

$L^1$ is a single bond, or is a group of formula (i);

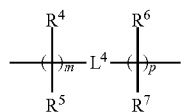

(i)

wherein the left side of the group of formula (i) is attached to $R^2$ and the right side thereof is attached to the oxadiazole ring; and wherein, m is an integer selected from 0, 1, or 2;

p is an integer selected from 0, 1, or 2;

$L^4$ is a single bond;

$R^4$ is selected from the group consisting of hydrogen, $C_{1-6}$alkyl, halo, halo$C_{1-6}$alkyl, and halo$C_{1-6}$alkyloxy;

$R^5$ is selected from the group consisting of hydrogen, $C_{1-6}$alkyl, halo, halo$C_{1-6}$alkyl, and halo$C_{1-6}$alkyloxy;

or $R^4$ and $R^5$ together with the carbon atom to which they are attached form a saturated 3-, 4-, 5-, or 6-membered carbocyclic ring;

$R^6$ is selected from the group consisting of hydrogen, $C_{1-6}$alkyl, halo, halo$C_{1-6}$alkyl, and halo$C_{1-6}$alkyloxy;

$R^7$ is selected from the group consisting of hydrogen, $C_{1-6}$alkyl, halo, halo$C_{1-6}$alkyl, and halo$C_{1-6}$alkyloxy;

or $R^6$ and $R^7$ together with the carbon atom to which they are attached form a saturated 3-, 4-, 5-, or 6-membered carbocyclic ring;

$L^2$ is $—SO_2—$;

$L^3$ is a single bond;

each $R^{15}$ is independently selected from the group consisting of $C_{1-6}$alkyl and cyano$C_{1-6}$alkyl;

each $R^{16}$ is independently selected from the group consisting of hydrogen, $C_{1-6}$alkyl, and cyano$C_{1-6}$ alkyl;

each $Z^1$ is independently selected from the group consisting of halo, hydrogen, $C_{1-6}$alkyl, halo$C_{1-6}$alkyl, and halo$C_{1-6}$alkyloxy;

each $Z^2$ is independently selected from the group consisting of halo, hydrogen, $C_{1-6}$alkyl, halo$C_{1-6}$alkyl, halo$C_{1-6}$ alkyloxy, heterocyclyl, heteroaryl, hydroxyl, $—OR^{15}$, and $—SR^{16}$;

wherein said heteroaryl group is selected from the group consisting of pyridyl, 1,3-benzodioxolyl, benzo[d]oxazol-2(3H)-one, 2,3-dihydro-benzofuranyl, oxazolyl, isoxazolyl, imidazolyl, benzimidazolyl, and thiazolyl; and wherein at least one carbon atom of said benzodioxolyl or 2,3-dihydro-benzofuranyl can be oxidized to form at least one C=O;

wherein the group heterocyclyl is selected from the group consisting of piperidinyl, 2,3-dihydro-1,3-benzoxazol-5-yl, succinimidyl, 1-pyrrolidinyl, 2-pyrrolidinyl, 3-pyrrolidinyl, azepanyl, piperazinyl, homopiperazinyl, tetrahydropyranyl, tetrahydrofuranyl, thiomorpholin-4-yl, and morpholin-4-yl; and wherein at least one carbon atom of said piperidinyl, 2,3-dihydro-1,3-benzoxazol-5-yl, succinimidyl, 1-pyrrolidinyl, 2-pyrrolidinyl, 3-pyrrolidinyl, azepanyl, piperazinyl, homopiperazinyl, tetrahydropyranyl, tetrahydrofuranyl, thiomorpholin-4-yl and morpholin-4-yl can be oxidized to form at least one C=O;

and with the proviso that said compound is not 5-[4-(4-methoxyphenyl)sulfonylpiperazin-1-yl]-3-phenyl-1,2, 4-oxadiazole.

2. The compound according to claim 1, having structural formula (IA),

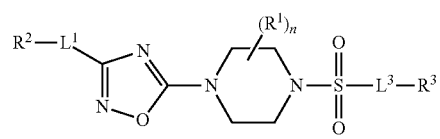

(IA)

wherein $L^1$, $L^3$, n, $R^1$, $R^2$ and $R^3$ have the same meaning as that defined in claim 1.

3. The compound according to claim 1, having structural formula (IC),

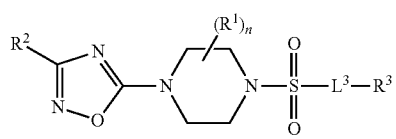

(IC)

wherein, $L^3$, n, $R^1$, $R^2$ and $R^3$ have the same meaning as defined in claim 1.

4. The compound according to claim 1, having structural formula (ID), (ID)

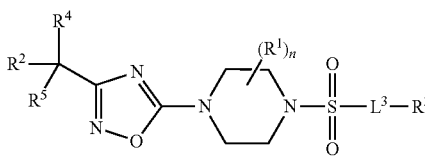

wherein, $L^3$, n, $R^1$, $R^2$, $R^3$, $R^4$, and $R^5$, have the same meaning as defined in claim 1.

5. The compound according to claim 1, having structural formula (IF), (IF)

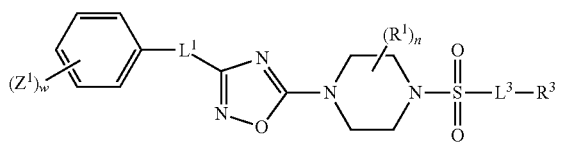

wherein, $L^1$, $L^3$, n, $R^1$, $R^3$, and $Z^1$ have the same meaning as that defined in claim 1; and
wherein w is an integer selected from 1, 2, or 3.

6. The compound according to claim 1, having structural formula (IH), (IH)

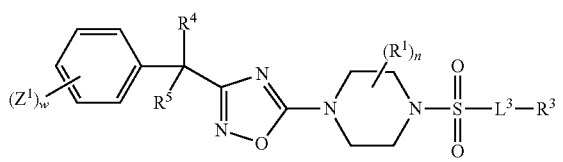

wherein, $L^3$, n, $R^1$, $R^3$, $R^4$, $R^5$, and $Z^1$ and w have the same meaning as defined in claim 1, and wherein w is an integer selected from 1, 2, or 3.

7. A compound selected from the group consisting of 5-(4-((4-(Oxazol-5-yl)phenyl)sulfonyl)piperazin-1-yl)-3-(p-tolyl)-1,2,4-oxadiazole; 5-(4-((4-(Difluoromethoxy)phenyl)sulfonyl)piperazin-1-yl)-3-(p-tolyl)-1,2,4-oxadiazole; 3-(p-Tolyl)-5-(4-((4-(trifluoromethoxy)phenyl)sulfonyl)piperazin-1-yl)-1,2,4-oxadiazole; 5-(4-((4-Fluorophenyl)sulfonyl)piperazin-1-yl)-3-(p-tolyl)-1,2,4-oxadiazole; 5-(4-((4-Isopropylphenyl)sulfonyl)piperazin-1-yl)-3-(p-tolyl)-1,2,4-oxadiazole; 3-(p-Tolyl)-5-(4-((4-(trifluoromethyl)phenyl)sulfonyl)piperazin-1-yl)-1,2,4-oxadiazole; 1-(4-((4-(3-(p-Tolyl)-1,2,4-oxadiazol-5-yl)piperazin-1-yl)sulfonyl)phenyl)pyrrolidin-2-one; 5-(4-((4-Methoxyphenyl)sulfonyl)piperazin-1-yl)-3-(p-tolyl)-1,2,4-oxadiazole; 1-(3-Benzyl-[1,2,4]oxadiazol-5-yl)-4-(4-methoxy-benzenesulfonyl)-piperazine; 1-(3-Benzyl-[1,2,4]oxadiazol-5-yl)-4-(4-ethoxy-benzenesulfonyl)-piperazine; 1-(3-Benzyl-[1,2,4]oxadiazol-5-yl)-4-(4-difluoromethoxy-benzenesulfonyl)-piperazine; 5-((4-(3-Benzyl-1,2,4-oxadiazol-5-yl)piperazin-1-yl)sulfonyl)benzo[d]oxazol-2(3H)-one; 5-(4-((4-Methoxyphenyl)sulfonyl)piperazin-1-yl)-3-(1-phenylpropyl)-1,2,4-oxadiazole; 1-(4-Ethoxy-benzenesulfonyl)-4-[3-(1-phenyl-propyl)-[1,2,4]oxadiazol-5-yl]-piperazine; 1-(4-Difluoromethoxy-benzenesulfonyl)-4-[3-(1-phenyl-propyl)-[1,2,4]oxadiazol-5-yl]-piperazine; 1-(4-Methoxy-benzenesulfonyl)-4-[3-((S)-1-phenyl-propyl)-[1,2,4]oxadiazol-5-yl]-piperazine; 1-(4-Methoxy-benzenesulfonyl)-4-[3-((R)-1-phenyl-propyl)-[1,2,4]oxadiazol-5-yl]-piperazine; 1-[3-(4-Chloro-benzyl)-[1,2,4]oxadiazol-5-yl]-4-(4-methoxy-benzenesulfonyl)-piperazine; 1-[3-(4-Chloro-benzyl)-[1,2,4]oxadiazol-5-yl]-4-(4-ethoxy-benzenesulfonyl)-piperazine; 1-[3-(4-Chloro-benzyl)-[1,2,4]oxadiazol-5-yl]-4-(4-difluoromethoxy-benzenesulfonyl)-piperazine; 5-((4-(3-(4-Chlorobenzyl)-1,2,4-oxadiazol-5-yl)piperazin-1-yl)sulfonyl)benzo[d]oxazol-2(3H)-one; 1-[3-(3-Chloro-benzyl)-[1,2,4]oxadiazol-5-yl]-4-(4-methoxy-benzenesulfonyl)-piperazine; 1-[3-(3-Chloro-benzyl)-[1,2,4]oxadiazol-5-yl]-4-(4-ethoxy-benzenesulfonyl)-piperazine; 1-[3-(3-Chloro-benzyl)-[1,2,4]oxadiazol-5-yl]-4-(4-difluoromethoxy-benzenesulfonyl)-piperazine; 5-{4-[3-(3-Chloro-benzyl)-[1,2,4]oxadiazol-5-yl]-piperazine-1-sulfonyl}-3H-benzooxazol-2-one; 4-(3-(3-Chlorobenzyl)-1,2,4-oxadiazol-5-yl)-N,N-dimethylpiperazine-1-sulfonamide; 4-((4-(3-(3-Chlorobenzyl)-1,2,4-oxadiazol-5-yl)piperazin-1-yl)sulfonyl)morpholine; 3-(3-Chlorobenzyl)-5-(4-(pyrrolidin-1-ylsulfonyl)piperazin-1-yl)-1,2,4-oxadiazole; 5-(4-(Azepan-1-ylsulfonyl)piperazin-1-yl)-3-(3-chlorobenzyl)-1,2,4-oxadiazole; 3-(3-Chlorobenzyl)-5-(4-((4-methoxypiperidin-1-yl)sulfonyl)piperazin-1-yl)-1,2,4-oxadiazole; 1-[3-(3-Fluoro-benzyl)-[1,2,4]oxadiazol-5-yl]-4-(4-methoxy-benzenesulfonyl)-piperazine; 1-(4-Fluoro-benzenesulfonyl)-4-[3-(3-fluoro-benzyl)-[1,2,4]oxadiazol-5-yl]-piperazine; N-(4-{1-[3-(3-Fluoro-benzyl)-[1,2,4]oxadiazol-5-yl]-piperazine-1-sulfonyl}-phenyl)-acetamide; 1-[3-(3-Fluoro-benzyl)-[1,2,4]oxadiazol-5-yl]-4-(4-trifluoromethoxy-benzenesulfonyl)-piperazine; 1-[3-(3-Fluoro-benzyl)-[1,2,4]oxadiazol-5-yl]-4-(3-trifluoromethyl-benzenesulfonyl)-piperazine; 1-(4-Ethoxy-benzenesulfonyl)-4-[3-(3-fluoro-benzyl)-[1,2,4]oxadiazol-5-yl]-piperazine; 1-(4-Difluoromethoxy-benzenesulfonyl)-4-[3-(3-fluoro-benzyl)-[1,2,4]oxadiazol-5-yl]-piperazine; 1-[3-(3-Fluoro-benzyl)-[1,2,4]oxadiazol-5-yl]-4-(4-isopropoxy-benzenesulfonyl)-piperazine; 3-(4-((4-(3-(3-Fluorobenzyl)-1,2,4-oxadiazol-5-yl)piperazin-1-yl)sulfonyl)phenoxy)propanenitrile; 1-(2,3-Dihydro-benzofuran-5-sulfonyl)-4-[3-(3-fluoro-benzyl)-[1,2,4]oxadiazol-5-yl]-piperazine; 3-(3-Fluorobenzyl)-5-(4-((4-isopropoxyphenyl)sulfonyl)piperazin-1-yl)-1,2,4-oxadiazole; 1-[3-(3,4-Difluoro-benzyl)-[1,2,4]oxadiazol-5-yl]-4-(4-methoxy-benzenesulfonyl)-piperazine; 1-[3-(3,4-Difluoro-benzyl)-[1,2,4]oxadiazol-5-yl]-4-(4-ethoxy-benzenesulfonyl)-piperazine; 1-[3-(3,4-Difluoro-benzyl)-[1,2,4]oxadiazol-5-yl]-4-(4-difluoromethoxy-benzenesulfonyl)-piperazine; 1-{3-[1-(4-Fluoro-phenyl)-cyclopropyl]-[1,2,4]oxadiazol-5-yl}-4-(4-methoxy-benzenesulfonyl)-piperazine; 1-(4-Ethoxy-benzenesulfonyl)-4-{3-[1-(4-fluoro-phenyl)-cyclopropyl]-[1,2,4]oxadiazol-5-yl}-piperazine; 3-(1-(4-Fluorophenyl)cyclopropyl)-5-(4-((4-(trifluoromethoxy)phenyl)sulfonyl)piperazin-1-yl)-1,2,4-oxadiazole; 1-{3-[1-(4-Fluoro-phenyl)-cyclopropyl]-[1,2,4]oxadiazol-5-yl}-4-(4-methylsulfanyl-benzenesulfonyl)-piperazine; 1-{3-[1-(4-Fluoro-phenyl)-1-methyl-ethyl]-[1,2,4]oxadiazol-5-yl}-4-(4-methoxy-benzenesulfonyl)-piperazine; 1-(4-Difluoromethoxy-benzenesulfonyl)-4-{3-[1-(4-fluoro-phenyl)-1-methyl-ethyl]-[1,2,4]oxadiazol-5-yl}-piperazine; 1-(4-Ethoxy-benzenesulfonyl)-4-{3-[1-(4-fluoro-phenyl)-1-methyl-ethyl]-[1,2,4]oxadiazol-5-yl}-piperazine; 1-{3-[1-(4-Fluoro-phenyl)-1-methyl-ethyl]-[1,2,4]oxadiazol-5-yl}-4-(4-methylsulfanyl-benzenesulfonyl)-piperazine; 1-(4-Methoxy-benzenesulfonyl)-4-[3-(1-phenyl-cyclopropyl)-[1,2,4]oxadiazol-5-yl]-piperazine; 1-(4-Ethoxy-benzenesulfonyl)-4-[3-(1-phenyl-cyclopropyl)-[1,2,4]

oxadiazol-5-yl]-piperazine; 1-(4-Difluoromethoxy-benzenesulfonyl)-4-[3-(1-phenyl-cyclopropyl)-[1,2,4]oxadiazol-5-yl]-piperazine; 1-(4-Methylsulfanyl-benzenesulfonyl)-4-[3-(1-phenyl-cyclopropyl)-[1,2,4]oxadiazol-5-yl]-piperazine; 1-{3-[1-(3-Chloro-phenyl)-cyclopropyl]-[1,2,4]oxadiazol-5-yl}-4-(4-methoxy-benzenesulfonyl)-piperazine; 1-{3-[1-(3-Chloro-phenyl)-cyclopropyl]-[1,2,4]oxadiazol-5-yl}-4-(4-ethoxy-benzenesulfonyl)-piperazine; 1-{3-[1-(3-Chloro-phenyl)-cyclopropyl]-[1,2,4]oxadiazol-5-yl}-4-(4-difluoromethoxy-benzenesulfonyl)-piperazine; 1-{3-[1-(3-Chloro-phenyl)-cyclopropyl]-[1,2,4]oxadiazol-5-yl}-4-(4-methylsulfanyl-benzenesulfonyl)-piperazine; 1-{3-[1-(4-Chloro-phenyl)-cyclopropyl]-[1,2,4]oxadiazol-5-yl}-4-(4-methoxy-benzenesulfonyl)-piperazine; 1-{3-[1-(4-Chloro-phenyl)-cyclopropyl]-[1,2,4]oxadiazol-5-yl}-4-(4-ethoxy-benzenesulfonyl)-piperazine; 1-{3-[1-(4-Chloro-phenyl)-cyclopropyl]-[1,2,4]oxadiazol-5-yl}-4-(4-difluoromethoxy-benzenesulfonyl)-piperazine; 1-{3-[1-(4-Chloro-phenyl)-cyclopropyl]-[1,2,4]oxadiazol-5-yl}-4-(4-methylsulfanyl-benzenesulfonyl)-piperazine; 1-{3-[(4-Chloro-phenyl)-difluoro-methyl]-[1,2,4]oxadiazol-5-yl}-4-(4-methoxy-benzenesulfonyl)-piperazine; 1-{3-[(4-Chloro-phenyl)-difluoro-methyl]-[1,2,4]oxadiazol-5-yl}-4-(4-ethoxy-benzenesulfonyl)-piperazine; 1-{3-[(4-Chloro-phenyl)-difluoro-methyl]-[1,2,4]oxadiazol-5-yl}-4-(4-difluoromethoxy-benzenesulfonyl)-piperazine; 1-{3-[(4-Chloro-phenyl)-difluoro-methyl]-[1,2,4]oxadiazol-5-yl}-4-(4-methylsulfanyl-benzenesulfonyl)-piperazine; 1-{3-[Difluoro-(4-fluoro-phenyl)-methyl]-[1,2,4]oxadiazol-5-yl}-4-(4-methoxy-benzenesulfonyl)-piperazine; 1-{3-[Difluoro-(4-fluoro-phenyl)-methyl]-[1,2,4]oxadiazol-5-yl}-4-(4-ethoxy-benzenesulfonyl)-piperazine; 1-{3-[Difluoro-(4-fluoro-phenyl)-methyl]-[1,2,4]oxadiazol-5-yl}-4-(4-difluoromethoxy-benzenesulfonyl)-piperazine; 1-{3-[Difluoro-(4-fluoro-phenyl)-methyl]-[1,2,4]oxadiazol-5-yl}-4-(4-methylsulfanyl-benzenesulfonyl)-piperazine; 1-{3-[1-(3-Chloro-phenyl)-1-methyl-ethyl]-[1,2,4]oxadiazol-5-yl}-4-(4-methoxy-benzenesulfonyl)-piperazine; 1-{3-[1-(3-Chloro-phenyl)-1-methyl-ethyl]-[1,2,4]oxadiazol-5-yl}-4-(4-ethoxy-benzenesulfonyl)-piperazine; 1-{3-[1-(3-Chloro-phenyl)-1-methyl-ethyl]-[1,2,4]oxadiazol-5-yl}-4-(4-difluoromethoxy-benzenesulfonyl)-piperazine; 1-{3-[1-(3-Chloro-phenyl)-1-methyl-ethyl]-[1,2,4]oxadiazol-5-yl}-4-(4-methylsulfanyl-benzenesulfonyl)-piperazine; 1-[3-(Difluoro-phenyl-methyl)-[1,2,4]oxadiazol-5-yl]-4-(4-methoxy-benzenesulfonyl)-piperazine; 1-[3-(Difluoro-phenyl-methyl)-[1,2,4]oxadiazol-5-yl]-4-(4-methylsulfanyl-benzenesulfonyl)-piperazine; 1-(4-Difluoromethoxy-benzenesulfonyl)-4-[3-(difluoro-phenyl-methyl)-[1,2,4]oxadiazol-5-yl]-piperazine; 1-(4-Difluoromethoxy-benzenesulfonyl)-4-[3-(1-methyl-1-phenyl-ethyl)-[1,2,4]oxadiazol-5-yl]-piperazine; and 1-(4-Methoxy-benzenesulfonyl)-4-[3-(1-methyl-1-phenyl-ethyl)-[1,2,4]oxadiazol-5-yl]-piperazine; or a solvate, hydrate, or pharmaceutically acceptable salt thereof.

8. A pharmaceutical composition comprising one or more pharmaceutically excipients and a therapeutically effective amount of a compound according to claim 1; or a solvate, hydrate, or pharmaceutically acceptable salt thereof.

9. A pharmaceutical composition comprising one or more pharmaceutically excipients and a therapeutically effective amount of a compound according to claim 7, or a solvate, hydrate, or pharmaceutically acceptable salt thereof.

* * * * *